United States Patent
Edmunds et al.

(10) Patent No.: US 11,229,208 B2
(45) Date of Patent: *Jan. 25, 2022

(54) PESTICIDALLY ACTIVE BI- OR TRICYCLIC HETEROCYCLES WITH SULFUR CONTAINING SUBSTITUENTS

(71) Applicant: SYNGENTA PARTICIPATIONS AG, Basel (CH)

(72) Inventors: Andrew Edmunds, Stein (CH); Michel Muehlebach, Stein (CH); André Stoller, Stein (CH); Olivier Loiseleur, Stein (CH); Anke Buchholz, Stein (CH); Ottmar Franz Hueter, Stein (CH); Aurelien Bigot, Stein (CH); Roger Graham Hall, Stein (CH); Daniel Emery, Stein (CH); Pierre Joseph Marcel Jung, Stein (CH); Long Lu, Shanghai (CN); Yaming Wu, Shanghai (CN); Ruifang Chen, Shanghai (CN)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/068,334

(22) Filed: Oct. 12, 2020

(65) Prior Publication Data

US 2021/0037827 A1     Feb. 11, 2021

Related U.S. Application Data

(63) Continuation of application No. 14/898,597, filed as application No. PCT/EP2014/062946 on Jun. 19, 2014, now Pat. No. 10,939,682.

(30) Foreign Application Priority Data

Jul. 2, 2013   (EP) .................................... 13174698
Jul. 12, 2013   (EP) .................................... 13176263
Dec. 13, 2013   (EP) .................................... 13197069

(51) Int. Cl.
    *A01N 43/90*      (2006.01)
    *C07D 471/04*     (2006.01)
            (Continued)

(52) U.S. Cl.
    CPC ............ *A01N 43/90* (2013.01); *C07D 471/04* (2013.01); *C07D 471/12* (2013.01); *C07D 487/04* (2013.01); *C07D 498/04* (2013.01)

(58) Field of Classification Search
None
See application file for complete search history.

(56) References Cited

U.S. PATENT DOCUMENTS

| 4,603,139 | A | ‡ | 7/1986 | King | .................... | C07D 471/04 |
|---|---|---|---|---|---|---|
| | | | | | | 514/337 |
| 10,081,641 | B2 | ‡ | 9/2018 | Stoller | ................. | C07D 471/04 |
| 10,364,243 | B2 | ‡ | 7/2019 | Fischer | ................ | C07D 471/04 |

FOREIGN PATENT DOCUMENTS

WO    2009131237 A1    10/2009
WO    2010125985 A1    11/2010
(Continued)

OTHER PUBLICATIONS

International Search Report for International Patent Application No. PCT/EP2014/062946 dated Nov. 10, 2014.‡
(Continued)

*Primary Examiner* — Alton N Pryor
(74) *Attorney, Agent, or Firm* — Bakerhostetler; Toni-Junell Herbert

(57) ABSTRACT

Compounds of formula I

A-B                                      (I), wherein A is a radical selected from the group consisting of formulae $A_1$ to $A_8$:

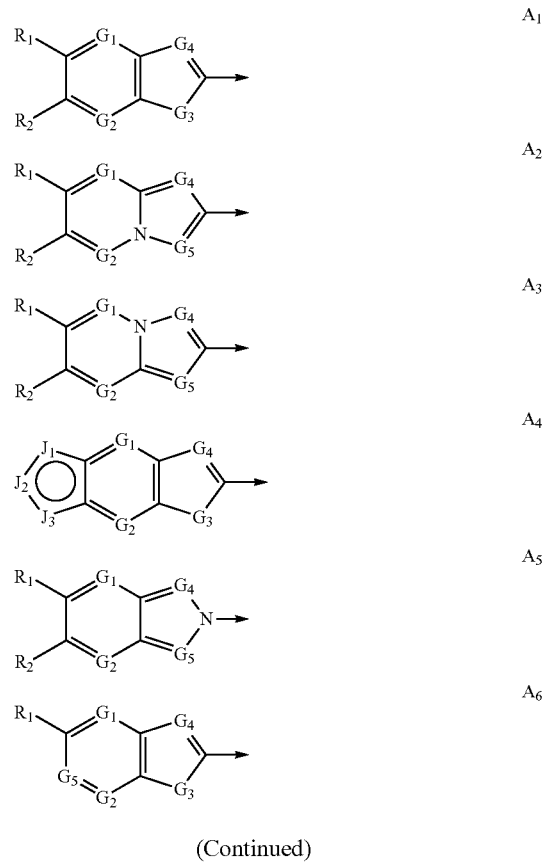

(Continued)

-continued

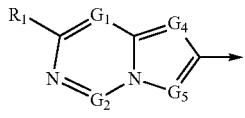
A₇

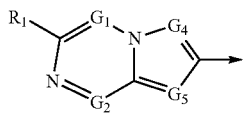
A₈ wherein the arrow denotes the point of attachment to the radical B; and

B is a radical selected from the group consisting of formulae B₁ to B₁₁:

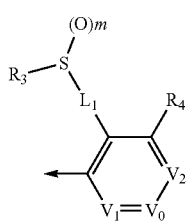
B₁

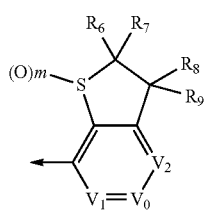
B₂

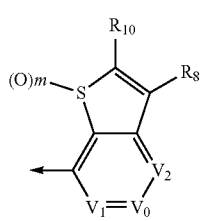
B₃

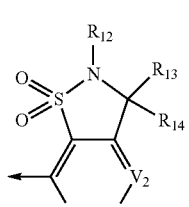
B₄

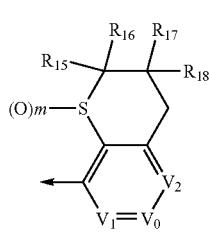
B₅

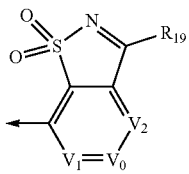
B₆

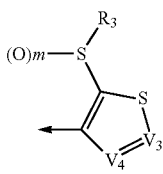
B₇

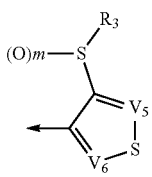
B₈

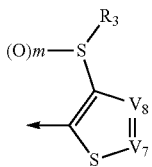
B₉

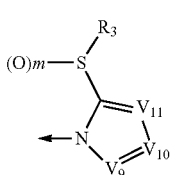
B₁₀

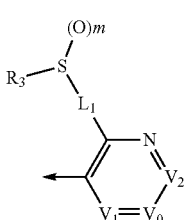
B₁₁ wherein the arrow denotes the point of attachment to the radical A; and wherein the substituents are as defined in claim 1, and the agrochemically acceptable salts and all stereoisomers and tautomeric forms of the compounds of formula I can be used as insecticides and can be prepared in a manner known per se.

22 Claims, No Drawings

(51) Int. Cl.
  *C07D 471/12* (2006.01)
  *C07D 487/04* (2006.01)
  *C07D 498/04* (2006.01)

(56) References Cited

FOREIGN PATENT DOCUMENTS

| WO | 2011040629 A1 | | 4/2011 |
|---|---|---|---|
| WO | 2011043404 A1 | | 4/2011 |
| WO | 2012086848 A1 | | 6/2012 |
| WO | WO-2012/086848 A1 | ‡ | 6/2012 |
| WO | 2013018928 A1 | | 2/2013 |
| WO | WO-2013/018928 A1 | ‡ | 2/2013 |
| WO | 2013180193 A1 | | 12/2013 |
| WO | 2013180194 A1 | | 12/2013 |
| WO | 2013191113 A1 | | 12/2013 |
| WO | WO-2013/180193 | ‡ | 12/2013 |
| WO | WO-2013/180194 | ‡ | 12/2013 |
| WO | 2014142292 A1 | | 3/2014 |
| WO | WO-2014/142292 | ‡ | 3/2014 |
| WO | 2014132971 A1 | | 9/2014 |
| WO | 2014132972 A1 | | 9/2014 |
| WO | WO-2014/132971 | ‡ | 9/2014 |
| WO | WO-2014/132972 | ‡ | 9/2014 |
| WO | 2015121136 A1 | | 8/2015 |
| WO | WO-2015/121136 | ‡ | 8/2015 |
| WO | WO-2013/191113 | ‡ | 5/2016 |

OTHER PUBLICATIONS

Ex. 1019—Bayer EP14155372 Priority and translation, PGR2020-00058.‡
Ex. 1020—Cudley, PGR2020-00058.‡
Ex. 1018—Wang Discovery of azabenzimidazoles, PGR2020-00058.‡
Ex. 1017—Yadav mini review 1-s2.0-S0223523414010940-main, PGR2020-00058.‡
Ex. 1023—Printout of Chemistry msu.edu—Heterocyclic webpage, PGR2020-0005 8.‡
Ex. 1025—Robinson, PK, Essays Biochem, Nov. 15, 2015, PGR2020-00058.‡
Ex. 1024—Walsh, PGR2020-00058.‡
Ex. 1022—Williams, Chirality in Agrochemicals Ref, PGR2020-00058.‡
Ex. 1021—Mori Insect Pheromone Chirality NK003-20170213001, PGR2020-00058.‡
Ex. 1013—Suiter Scharf Insecticide Basics for Pest Mgmt Profl B 1352 3sm, PGR2020-00058.‡
Ex. 1012—Walter structure-based design of agrochem b100919 open, PGR2020-00058.‡
Ex. 1015—Kar AQM17-24-203, PGR2020-00058.‡
Ex. 1016—Liszekova SAR of JH analogs pone.0006001 1.. 15, PGR2020-00058.‡
Ex. 1014—McKinney scanned gp, PGR2020-00058.‡
Ex. 1003—Prestwich Dec—Public Version, PGR2020-00058.‡
Ex. 1011—Winter Dec for Syngenta Testing—Public Version, PGR2020-00058.‡
Aug. 13, 2020—Bayer—PO Preliminary Response, PGR2020-00058.‡
Apr. 30, 2020—Syngenta—Petition for Post-Grant Review, PGR2020-00058—Public Version.‡
Ex. 1025—Robinson, PK, Essays Biochem, Nov. 1, 2015, PGR2020-00058.

‡ imported from a related application

PESTICIDALLY ACTIVE BI- OR TRICYCLIC HETEROCYCLES WITH SULFUR CONTAINING SUBSTITUENTS

CROSS-REFERENCE TO RELATED APPLICATIONS

This application is a continuation of U.S. application Ser. No. 14/898,597, filed Dec. 15, 2015, which is a 371 National Stage application of International Application No. PCT/EP2014/062946, filed Jun. 19, 2014, which claims priority to EP 13174698.4, filed Jul. 2, 2013, EP 13176263.5, filed Jul. 12, 2013, EP 13197069.1, filed Dec. 13, 2013; and International Patent Application No. PCT/CN2014/076736, filed May 4, 2014, the contents of which applications are herein incorporated by reference.

The present invention relates to insecticidally active heterocyclic sulfur containing derivatives, to processes for their preparation, to compositions comprising those compounds, and to their use for controlling animal pests (including arthropods and in particular insects or representatives of the order *Acarina*).

Heterocyclic compounds with pesticidal action are known and described, for example, in WO 2009/131237, WO 2011/043404, WO 2011/040629, WO 2010/125985, WO 2012/086848, WO 2013/018928, WO 2013/191113, WO 2013/180193 and WO 2013/180194.

There have now been found novel heterocyclic derivatives with pesticidal properties.

The present invention accordingly relates to compounds of formula I,

A-B (I), wherein A is a radical selected from the group consisting of formulae $A_1$ to $A_8$:

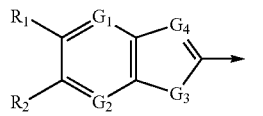
$A_1$

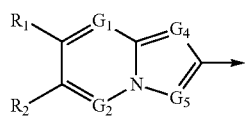
$A_2$

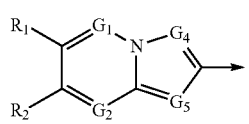
$A_3$

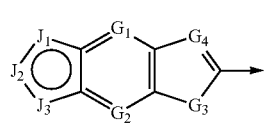
$A_4$

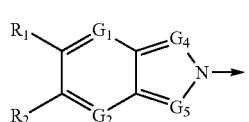
$A_5$

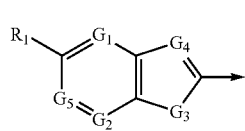
$A_6$

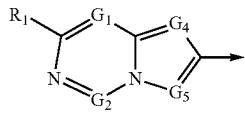
$A_7$

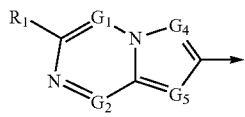
$A_8$ wherein the arrow denotes the point of attachment to the radical B; and B is a radical selected from the group consisting of formulae $B_1$ to $B_{11}$:

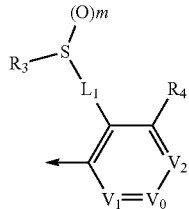
$B_1$

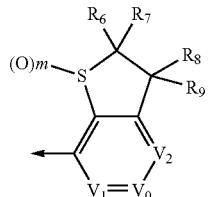
$B_2$

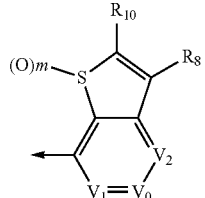
$B_3$

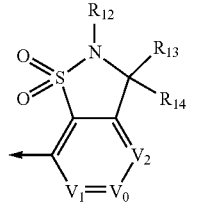
$B_4$

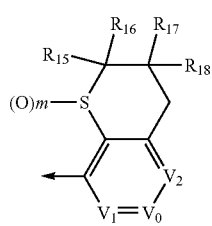
$B_5$

-continued

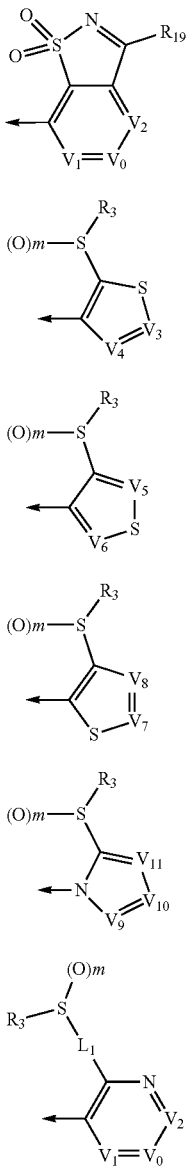

wherein the arrow denotes the point of attachment to the radical A;
wherein
L₁ is methylene or a direct bond;
V₀ nitrogen or CR₅;
V₁ is nitrogen or CR₂₀; V₂ is nitrogen or CR₂₁; V₃ is nitrogen or CR₂₂; V₄ is nitrogen or CR₂₃;
V₅ is nitrogen or CR₂₄; V₆ is nitrogen or CR₂₅; V₇ is nitrogen or CR₂₆; Vg is nitrogen or CR₂₇;
V₉ is nitrogen, or CR₂₈ V₁₀ is nitrogen or CR₂₉; is nitrogen or CR₃₀;
G₁ is nitrogen or CR₃₁;
G₂ is nitrogen or CR₃₂;
G₃ is —NR₃₅, an oxygen atom or a sulfur atom;
G₄ is nitrogen or CR₃₃;
G₅ is nitrogen or CR₃₄;
J₁, J₂, J₃ together form together a 5 membered heterocyclic ring, which can be saturated or unsaturated, containing one or two atoms selected from the group consisting of nitrogen, oxygen and sulfur, which ring can be mono- or polysubstituted by substituents selected from the group consisting of C₁-C₆alkyl, halogen and or C₁-C₆haloalkyl, with the proviso that if the ring contains two oxygen atoms, or two sulfur atoms, they are separated by one carbon atom;
R₁ and R₂ are the same or different and each represents hydrogen, halogen, C₁-C₆alkyl or C₁-C₆haloalkyl;
R₃ is a C₁-C₆alkyl, C₂-C₆alkenyl or C₂-C₆alkynyl group which can be mono- or polysubstituted by substituents selected from the group consisting of C₁-C₆alkoxy, C₁-C₆haloalkoxy, C₂-C₆alkenyloxy, C₂-C₆haloalkenyloxy, C₂-C₆alkynyloxy, C₂-C₆haloalkynyloxy, C₁-C₆alkylsulphanyl, C₁-C₆haloalkylsulfanyl, C₁-C₆alkylsulfinyl, C₁-C₆haloalkylsulfinyl, C₁-C₆alkylsulfonyl, C₁-C₆haloalkylsulfonyl, C₂-C₆alkylcarbonyl, C₂-C₆haloalkylcarbonyl, C₂-C₆alkoxycarbonyl, C₂-C₆haloalkoxycarbonyl, cyano, hydroxy, halogen, C₃-C₆cycloalkyl, said C₃-C₆cycloalkyl itself can be mono- or polysubstituted by substituents selected from halogen and C₁-C₃alkyl; and by a 5- or 6-membered heterocyclic group, which can be mono- or polysubstituted by substituents selected from the group consisting of C₁-C₆alkyl, C₁-C₆haloalkyl, C₁-C₆alkoxy, C₁-C₆haloalkoxy, C₁-C₆alkylsulfanyl, C₁-C₆haloalkylsulfanyl, C₁-C₆alkylsulfinyl, C₁-C₆haloalkylsulfinyl, C₁-C₆alkylsulfonyl, C₁-C₆haloalkylsulfonyl, C₂-C₆alkylcarbonyl, C₂-C₆haloalkylcarbonyl, C₂-C₆alkoxycarbonyl, C₂-C₆haloalkoxycarbonyl, C₁-C₆alkylamino, C₁-C₆haloalkylamino, C₂-C₈dialkylamino, C₂-C₈halodialkylamino, halogen, cyano and nitro;
or R₃ is —CO₂R₃₆, —C(O)R₃₆ or hydrogen;
or R₃ is C₃-C₆cycloalkyl, which can be mono- or polysubstituted by substituents selected from the group consisting of C₁-C₆alkyl, C₁-C₆haloalkyl, C₁-C₆alkoxy, C₁-C₆haloalkoxy, C₂-C₆alkenyloxy, C₂-C₆haloalkenyloxy, C₂-C₆alkynyloxy, C₂-C₆haloalkynyloxy and halogen;
or R₃ is a 5- or 6-membered heterocyclic group, which can be mono- or polysubstituted by substituents selected from the group consisting of C₁-C₆alkyl, C₁-C₆haloalkyl, C₁-C₆alkoxy, C₁-C₆haloalkoxy, C₁-C₆alkylsulfanyl, C₁-C₆haloalkylsulfanyl, C₁-C₆alkylsulfinyl, C₁-C₆haloalkylsulfinyl, C₁-C₆alkylsulfonyl, C₁-C₆haloalkylsulfonyl, C₂-C₆alkylcarbonyl, C₂-C₆haloalkylcarbonyl, C₂-C₆alkoxycarbonyl, C₂-C₆haloalkoxycarbonyl, C₁-C₆alkylamino, C₁-C₆haloalkylamino, C₂-C₈dialkylamino, C₂-C₈halodialkylamino, halogen, cyano and nitro;
R₃₅ is hydrogen, C₁-C₆alkyl which can be mono- or polysubstituted by substituents selected from the group consisting of C₁-C₆alkoxy, C₁-C₆haloalkoxy, C₂-C₆alkenyloxy, C₂-C₆haloalkenyloxy, C₂-C₆ alkynyloxy, C₂-C₆haloalkynyloxy, C₁-C₆alkylsulphanyl, C₁-C₆haloalkylsulfanyl, C₁-C₆haloalkylsulfinyl, C₁-C₆alkylsulfonyl, C₁-C₆haloalkylsulfonyl, C₂-C₆alkylcarbonyl, C₂-C₆alkoxycarbonyl, cyano, hydroxy, halogen and C₃-C₆cycloalkyl, said C₃-C₆cycloalkyl itself can be mono- or polysubstituted by substituents selected from halogen and C₁-C₃alkyl; or an N-oxide thereof;
R₄, R₅, R₂₀, R₂₁, R₂₂, R₂₃, R₂₄, R₂₅, R₂₆, R₂₇, R₂₈, R₂₉ and R₃₀ are the same or different and represents cyano, nitro, halogen, hydroxy, C₁-C₆alkenyloxy, C₁-C₆haloalkoxy, —C(O)R₃₆—C(O)R₃₆ or hydrogen; or
C₁-C₆alkyl which can be mono- or polysubstituted by substituents selected from the group consisting of cyano, halogen, hydroxy, C₁-C₆alkoxy, C₁-C₆haloalkoxy, C₂-C₆alkenyloxy, C₂-C₆haloalkenyloxy, C₂-C₆alkynyloxy, $C_2$-$C_6$haloalkynyloxy, $C_1$-$C_6$alkylsulfanyl, $C_1$-$C_6$haloalkylsulfanyl, $C_1$-$C_6$haloalkylsulfinyl, $C_1$-$C_6$alkylsulfonyl, $C_1$-$C_6$haloalkylsulfonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl, said cycloalkyl itself can be substituted by substituents selected from the group consisting of halogen and $C_1$-$C_3$alkyl, or represents a phenyl group which can be mono or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulfanyl, $C_1$-$C_6$haloalkylsulfanyl, $C_1$-$C_6$haloalkylsulfinyl, $C_1$-$C_6$alkylsulfonyl, $C_1$-$C_6$haloalkylsulfonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ and $R_{19}$ are the same or different and represents $C_1$-$C_6$alkyl, $C_1$-$C_6$haloalkyl or hydrogen, and the group $CR_{13}R_{14}$ can additionally be a carbonyl group C=O;

$R_{31}$, $R_{32}$, $R_{33}$, $R_{34}$ and $R_{40}$ are the same or different and represents $C_1$-$C_6$ alkyl, $C_1$-$C_6$haloalkyl, —$OR_7$, —$S(O)_nR_{36}$, —$NR_{36}R_{37}$, —$CO_2R_{36}$, —$C(O)R_{36}$, cyano, nitro, halogen or hydrogen;

$R_{36}$ and $R_{37}$ are the same or different and represents hydrogen, $C_1$-$C_6$alkyl which can be mono- or polysubstituted by substituents selected from $C_1$-$C_6$alkoxy, $C_1$-$C_6$haloalkoxy, $C_2$-$C_6$ alkenyloxy, $C_2$-$C_6$haloalkenyloxy, $C_2$-$C_6$alkynyloxy, $C_2$-$C_6$haloalkynyloxy, $C_1$-$C_6$ alkylsulfanyl, $C_1$-$C_6$haloalkylsulfanyl, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$ cycloalkyl, wherein said $C_3$-$C_6$ cycloalkyl can be mono- or polysubstituted by substituents selected from the group consisting of halogen and $C_1$-$C_3$alkyl; or $R_{36}$ and $R_{37}$ are the same or different and represents a phenyl group which can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulfanyl, $C_1$-$C_6$haloalkylsulfanyl, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro;

each m independently represents 0, 1 or 2, and n represents 0, 1 or 2, with the provisos that:
a) in —$S(O)_nR_{36}$, $R_{36}$ is hydrogen when n is 0;
b) if B is $B_1$, then A is different from $A_2$, $A_3$ and $A_5$;
c) if A is $A_1$, then B is different from B1, B7, $B_8$, $B_9$ and $B_{10}$;
d) if A is $A_5$, then B is different from $B_{10}$;
as well as agrochemically acceptable salts, enantiomers, diastereomers, tautomers, and N-oxides of those compounds.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulphinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

"5-membered heterocyclic" in the present invention means a 5-membered aromatic heterocyclic group or 5-membered non-aromatic heterocyclic group, and the "6-membered heterocyclic" means a 6-membered aromatic heterocyclic group or a. 6-membered non-aromatic heterocyclic group. Accordingly, a "5- or 6-membered heterocyclic group" in the present invention means a 5- or 6-membered aromatic heterocyclic group, or a 5- or 6-membered non-aromatic heterocyclic group.

"5- or 6-membered heterocyclic group, which can be substituted" in the present invention means a heterocyclic group, wherein the hydrogen atom(s) bound to the carbon atom(s), nitrogen atom(s) and/or sulfur atom(s) is/are optionally substituted by one or more atoms or groups selected from a pre-defined list, wherein the group has two or more atoms or groups selected from a pre-defined list, these atoms or groups are the same or different from each other. In context of an N atom or S atom, when it's oxidized to form an N oxide or sulfone and sulfoxide respectively, the oxidised analog is not substituted; however, such an analog is within the scope of the invention.

Examples of 5- or 6-membered heterocyclic group, which can be substituted include pyrrolidin-1-yl group, a 3,3,4,4-tetrafluoropyrrolidin-1-yl group, a tetrahydrofuran-2-yl group, a piperidyl group, a morpholyl group, a thiomorpholyl group, and the like.

Examples of a 5- or 6-membered aromatic heterocyclic groups, which can be substituted, are 2-pyrroly, 2-furyl group, 3-furyl group, 5-pyrazolyl, a 4-pyrazolyl, 1-pyrroly, l-methyl-2-pyrroly, 2-methylsulfanyl-l-pyrroly, 2-methylsulfinyl-1-pyrroly, 2-methylsulfonyl-l-pyrroly, a 2-methylamino-l-pyrroly group, a 2-dimethylamino-l-pyrroly group, a 5-bromo-2-furyl, a 5-nitro-2-furyl group, a 5-cyano-2-furyl group, a 5-methoxy-2-furyl group, a 5-acetyl-2-furyl, a 5-methoxycarbonyl-2-furyl group, a 2-methyl-3-furyl group, a 2, 5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1, 3-dimethyl-4-pyrazolyl group, pyrazol-l-yl group, a 3-chloro-pyrazol-l-yl group, a 3-bromopyrazol-l-yl group, a 4-chloropyrazol-l-yl group, a.4-bromopyrazol-l-yl group, an imidazole-l-yl group, a 1,2,4-triazol-l-yl group, a 3-chloro-l, 2,4-triazol-l-yl group, a 1, 2, 3, 4-tetrazol-l-yl group, a 1,2,3,5-tetrazol-l-yl group, a 2-thienyl group, a 3-thienyl group, a 3-trifluoromethyl-1,2,4-triazol-l-yl group, a 4-trifluoromethyl pyrazol-l-yl group, pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and the like.

In a preferred embodiment of the invention, $R_{35}$ is $C_1$-$C_6$alkyl which can be mono- or polysubstituted by substituents selected from the group consisting of $C_1$-$C_6$alkoxy, $C_1$-$C_6$haloalkoxy, $C_2$-$C_6$alkenyloxy, $C_2$-$C_6$haloalkenyloxy, $C_2$-$C_6$ alkynyloxy, $C_2$-$C_6$haloalkynyloxy, $C_1$-$C_6$alkylsulfanyl, $C_1$-$C_6$haloalkylsulfanyl, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_2$-$C_6$alkylcarbonyl, $C_2$-$C_6$alkoxycarbonyl, cyano, hydroxy, halogen and $C_3$-$C_6$cycloalkyl, said $C_3$-$C_6$cycloalkyl itself can be mono- or polysubstituted by substituents selected from halogen and $C_1$-$C_3$alkyl; or an N-oxide thereof.

Preferably $R_4$, $R_5$, $R_{20}$, $R_{21}$, $R_{22}$, $R_{23}$, $R_{24}$, $R_{25}$, $R_{26}$, $R_{27}$, $R_{28}$, $R_{29}$, and $R_{30}$ are the same or different and represents cyano, nitro, halogen, hydroxy, —C(O)$R_{36}$ or hydrogen; or
$C_1$-$C_6$alkyl which can be mono- or polysubstituted by substituents selected from the group consisting of cyano, halogen, hydroxy, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$ alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl, said cycloalkyl itself can be substituted by substituents selected from the group consisting of halogen and $C_1$-$C_3$alkyl; or represents
a phenyl group which can be mono or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro.

Compounds of formula (I) are made up of a combination of a radical selected from group A and a radical selected from group B.

Accordingly, in an embodiment of the invention, the compound of formula (I) is a radical selected from A and any one radical selected from group B, such as
   a) radical $A_1$ is combined with one radical selected from the group consisting of the radicals $B_1$ to $B_{11}$;
   b) radical $A_2$ is combined with one radical selected from the group consisting of the radicals $B_1$ to $B_{11}$;
   c) radical $A_3$ is combined with one radical selected from the group consisting of the radicals $B_1$ to $B_{11}$;
   d) radical $A_4$ is combined with one radical selected from the group consisting of the radicals $B_1$ to $B_{11}$;
   e) radical $A_5$ is combined with one radical selected from the group consisting of the radicals $B_1$ to $B_{11}$;

f) radical A₆ is combined with one radical selected from the group consisting of the radicals B₁ to B₁₁;

g) radical A₇ is combined with one radical selected from the group consisting of the radicals B₁ to B₁₁; or h) radical A₈ is combined with one radical selected from the group consisting of the radicals B₁ to B₁₁.

Similarly, in another embodiment, the compound of formula (I) is a radical selected from B and any one radical selected from group A, such as a) radical B₁ is combined with one radical selected from the group consisting of the radicals A₁ to A₈;

b) radical B₂ is combined with one radical selected from the group consisting of the radicals A₁ to A₈;

c) radical B₃ is combined with one radical selected from the group consisting of the radicals A₁ to A₈;

d) radical B₄ is combined with one radical selected from the group consisting of the radicals A₁ to A₈;

e) radical B₅ is combined with one radical selected from the group consisting of the radicals A₁ to A₈;

f) radical B₆ is combined with one radical selected from the group consisting of the radicals A₁ to A₈;

g) radical B₇ is combined with one radical selected from the group consisting of the radicals A₁ to A₈;

e) radical B₈ is combined with one radical selected from the group consisting of the radicals A₁ to A₈;

f) radical B₉ is combined with one radical selected from the group consisting of the radicals A₁ to A₈;

g) radical B₁₀ is combined with one radical selected from the group consisting of the radicals A₁ to A₈; or h) radical B₁₁ is combined with one radical selected from the group consisting of the radicals A₁ to A₈.

In a further embodiment, radical A is selected from any one of the following more specific radicals $Q_1$ to $Q_{11}$ from $A_1$ to $A_8$, wherein $R_1$ is as defined in the first aspect:

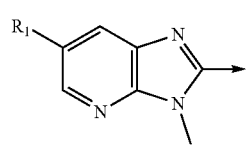

Q₁

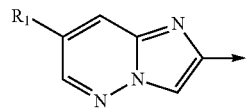

Q₂

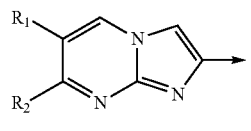

Q₃

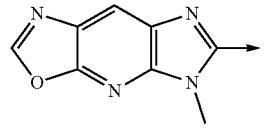

Q₄

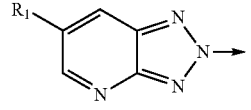

Q₅

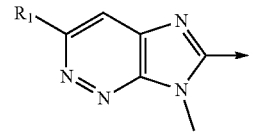

Q₆

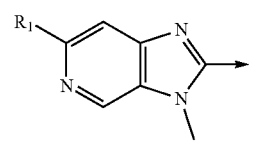

Q₇

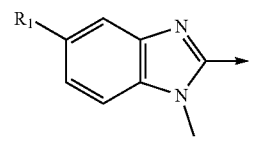

Q₈

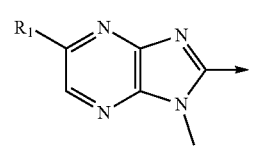

Q₉

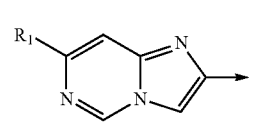

Q₁₀

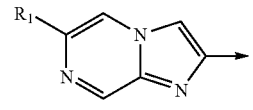

Q₁₁

Further embodiments of the first aspect are set-out in Table Z below:

TABLE Z

Combinations of A and B for formula (I)

| Embodiment E | A group | B group |
| --- | --- | --- |
| E1 | A₁ | B₁ |
| E2 | A₁ | B₂ |
| E3 | A₁ | B₃ |
| E4 | A₁ | B₄ |
| E5 | A₁ | B₅ |
| E6 | A₁ | B₆ |
| E7 | A₁ | B₇ |
| E8 | A₁ | B₈ |
| E9 | A₁ | B₉ |
| E10 | A₁ | B₁₀ |
| E11 | A₁ | B₁₁ |
| E12 | A₂ | B₁ |
| E13 | A₂ | B₂ |
| E14 | A₂ | B₃ |
| E15 | A₂ | B₄ |
| E16 | A₂ | B₅ |
| E17 | A₂ | B₆ |
| E18 | A₂ | B₇ |
| E19 | A₂ | B₈ |
| E20 | A₂ | B₉ |
| E21 | A₂ | B₁₀ |
| E22 | A₂ | B₁₁ |
| E23 | A₃ | B₁ |
| E24 | A₃ | B₂ |
| E25 | A₃ | B₃ |
| E26 | A₃ | B₄ |
| E27 | A₃ | B₅ |
| E28 | A₃ | B₆ |

TABLE Z-continued

Combinations of A and B for formula (I)

| Embodiment E | A group | B group |
|---|---|---|
| E29 | $A_3$ | $B_7$ |
| E30 | $A_3$ | $B_8$ |
| E31 | $A_3$ | $B_9$ |
| E32 | $A_3$ | $B_{10}$ |
| E33 | $A_3$ | $B_{11}$ |
| E34 | $A_4$ | $B_1$ |
| E35 | $A_4$ | $B_2$ |
| E36 | $A_4$ | $B_3$ |
| E37 | $A_4$ | $B_4$ |
| E38 | $A_4$ | $B_5$ |
| E39 | $A_4$ | $B_6$ |
| E40 | $A_4$ | $B_7$ |
| E41 | $A_4$ | $B_8$ |
| E42 | $A_4$ | $B_9$ |
| E43 | $A_4$ | $B_{10}$ |
| E44 | $A_4$ | $B_{11}$ |
| E45 | $A_5$ | $B_1$ |
| E46 | $A_5$ | $B_2$ |
| E47 | $A_5$ | $B_3$ |
| E48 | $A_5$ | $B_4$ |
| E49 | $A_5$ | $B_5$ |
| E50 | $A_5$ | $B_6$ |
| E51 | $A_5$ | $B_7$ |
| E52 | $A_5$ | $B_8$ |
| E53 | $A_5$ | $B_9$ |
| E54 | $A_5$ | $B_{10}$ |
| E55 | $A_5$ | $B_{11}$ |
| E56 | $A_6$ | $B_1$ |
| E57 | $A_6$ | $B_2$ |
| E58 | $A_6$ | $B_3$ |
| E59 | $A_6$ | $B_4$ |
| E60 | $A_6$ | $B_5$ |
| E61 | $A_6$ | $B_6$ |
| E62 | $A_6$ | $B_7$ |
| E63 | $A_6$ | $B_8$ |
| E64 | $A_6$ | $B_9$ |
| E65 | $A_6$ | $B_{10}$ |
| E66 | $A_6$ | $B_{11}$ |
| E67 | $A_7$ | $B_1$ |
| E68 | $A_7$ | $B_7$ |
| E69 | $A_7$ | $B_8$ |
| E70 | $A_7$ | $B_9$ |
| E71 | $A_7$ | $B_{10}$ |
| E72 | $A_7$ | $B_{11}$ |
| E73 | $A_8$ | $B_1$ |
| E74 | $A_8$ | $B_7$ |
| E75 | $A_8$ | $B_8$ |
| E76 | $A_8$ | $B_9$ |
| E77 | $A_8$ | $B_{10}$ |
| E78 | $A_8$ | $B_{11}$ |

In an embodiment of the present invention, a preferred radical A is $A_1$, $A_6$, or $A_4$; especially preferred is $A_1$ and $A_6$; in particular $A_1$.

In another preferred embodiment of the present invention, a preferred radical B is $B_1$, $B_2$, $B_{11}$, $B_7$, $B_8$, $B_9$, $B_{10}$, $B_3$ or $B_6$; especially preferred is $B_1$, $B_2$, $B_{11}$, $B_7$, $B_8$, $B_9$, or $B_{10}$, in particular $B_1$, $B_2$, $B_{11}$, $B_7$, $B_8$ or $B_9$; such as $B_1$, $B_2$ or $B_{11}$.

Accordingly, formula (I) preferably consists of the following combinations of radicals A and B:

| A group | B group | A group | B group | A group | B group |
|---|---|---|---|---|---|
| $A_1$ | $B_1$ | $A_6$ | $B_1$ | $A_4$ | $B_1$ |
| $A_1$ | $B_2$ | $A_6$ | $B_2$ | $A_4$ | $B_2$ |
| $A_1$ | $B_{11}$ | $A_6$ | $B_{11}$ | $A_4$ | $B_{11}$ |
| $A_1$ | $B_7$ | $A_6$ | $B_7$ | $A_4$ | $B_7$ |
| $A_1$ | $B_8$ | $A_6$ | $B_8$ | $A_4$ | $B_8$ |
| $A_1$ | $B_9$ | $A_6$ | $B_9$ | $A_4$ | $B_9$ |
| $A_1$ | $B_{10}$ | $A_6$ | $B_{10}$ | $A_4$ | $B_{10}$ |
| $A_1$ | $B_3$ | $A_6$ | $B_3$ | $A_4$ | $B_3$ |

In an embodiment of the present invention, if $V_0$ in $B_1$ is $CR_5$, A is different from $A_1$. In a preferred embodiment, $V_0$ in $B_1$ is $CR_5$ and A is selected from $A_2$, $A_3$, $A_4$, $A_5$ and $A_6$, especially selected from $A_4$ and $A_6$.

In an embodiment of the present invention, $L_1$, in reference to each of B, is a direct bond.

In another embodiment of the present invention, $R_1$, in reference to each of A, is the same or different and each represents hydrogen, halogen, $C_1$-$C_3$alkyl or $C_1$-$C_3$ haloalkyl; preferably hydrogen, bromine, chlorine, methyl, difluoromethyl or trifluoromethyl.

In another embodiment of the present invention, $R_2$, in reference to each of A, is the same or different and each represents, hydrogen, halogen, $C_1$-$C_3$alkyl or $C_1$-$C_3$haloalkyl; preferably hydrogen.

In another embodiment of the present invention, $R_3$, in reference to each of B, is the same or different and each represents $C_1$-$C_3$alkyl or $C_1$-$C_3$haloalkyl; preferably methyl or ethyl.

In another embodiment of the present invention, $R_4$, in reference to each of B, is the same or different and each represents, hydrogen or $C_1$-$C_3$alkyl; preferably hydrogen or methyl.

Also preferred are compounds of formula I, represented by a combination of the 4 "another embodiment" groups mentioned above.

In another embodiment of the present invention, m, in reference to each of B, is the same or different and each represents 0, 1 or 2; preferably 2.

In another embodiment of the present invention, $R_6$ and $R_7$, in reference to each of B, is the same or different and each represents $C_1$-$C_3$alkyl or $C_1$-$C_3$haloalkyl; preferably methyl.

In another embodiment of the present invention, $R_{10}$ and $R_{11}$, in reference to each of B, is the same or different and each represents, hydrogen, $C_1$-$C_3$alkyl or $C_1$-$C_3$haloalkyl; preferably hydrogen or methyl. In a preferred embodiment, $R_{11}$ is hydrogen and $R_{10}$ is methyl.

In another embodiment of the present invention, $R_{12}$, $R_{13}$, and $R_{14}$, in reference to each of B, is the same or different and each represents, hydrogen, $C_1$-$C_3$ alkyl or $C_1$-$C_3$haloalkyl; preferably hydrogen or methyl. In a preferred embodiment, $R_{13}$, and $R_{14}$ are each hydrogen and $R_{12}$ is methyl.

In another embodiment of the present invention, $R_{15}$, $R_{16}$, $R_{17}$ and $R_{18}$, in reference to each of B, is the same or different and each represents, hydrogen, $C_1$-$C_3$ alkyl or $C_1$-$C_3$haloalkyl; preferably hydrogen or methyl. In a preferred embodiment, $R_{15}$, $R_{16}$, $R_{17}$ and $R_{18}$ are each hydrogen.

In another embodiment of the present invention, $R_{19}$, in reference to each of B, is the same or different and represents, hydrogen, $C_1$-$C_4$ alkyl or $C_1$-$C_4$ haloalkyl; preferably hydrogen or tert-butyl.

In another embodiment of the present invention, $V_1$, in reference to each of B, is the same or different and represents CH or N.

In another embodiment of the present invention, $V_0$, in reference to each of B, is the same or different and represents CH or N.

In another embodiment of the present invention, $V_2$, in reference to each of B, is the same or different and represents, $CR_{21'}$, where $R_{21'}$, in reference to each of B, is the same or different and represents, hydrogen, halogen, $C_1$-$C_3$ alkyl, $C_1$-$C_3$ haloalkyl, or phenyl or 4-trifluoromethylphenyl, preferably hydrogen, chlorine, bromine or trifluoromethyl.

In another embodiment of the present invention, $V_3$, in reference to each of B, is the same or different and represents, $CR_{22'}$, where $R_{22'}$, in reference to each of B, is the same or different and represents, hydrogen, halogen, $C_1$-$C_3$alkyl or $C_1$-$C_3$haloalkyl, preferably hydrogen, chlorine, bromine or trifluoromethyl.

In another embodiment of the present invention, $V_4$, in reference to each of B, is the same or different and represents, N or $CR_{23'}$, where $R_{23'}$, in reference to each of B, is the same or different and represents, hydrogen, halogen, $C_1$-$C_3$alkyl or $C_1$-$C_3$haloalkyl; preferably $V_4$ represents N or CH.

In another embodiment of the present invention, $V_5$, in reference to each of B, is the same or different and represents, N or $CR_{24'}$, where $R_{24'}$, in reference to each of B, is the same or different and represents, hydrogen, halogen, $C_1$-$C_3$alkyl or $C_1$-$C_3$haloalkyl; preferably $V_5$ represents CH.

In another embodiment of the present invention, $V_6$, in reference to each of B, is the same or different and represents, N or $CR_{25'}$, where $R_{25'}$, in reference to each of B, is the same or different and represents, hydrogen, halogen, $C_1$-$C_3$alkyl or $C_1$-$C_3$haloalkyl; preferably $V_6$ represents N or CH.

In another embodiment of the present invention, $V_7$, in reference to each of B, is the same or different and represents, N or $CR_{26'}$, where $R_{26'}$, in reference to each of B, is the same or different and represents, hydrogen, halogen, $C_1$-$C_3$alkyl or $C_1$-$C_3$haloalkyl; preferably $V_7$ represents N, CH, C-chlorine, C-bromine or C—$CF_3$.

In another embodiment of the present invention, $V_8$, in reference to each of B, is the same or different and represents, N or $CR_{27'}$, where $R_{27'}$, in reference to each of B, is the same or different and represents, hydrogen, halogen, $C_1$-$C_3$alkyl or $C_1$-$C_3$haloalkyl; preferably $V_8$ represents CH.

In another embodiment of the present invention, $V_9$, in reference to each of B, is the same or different and represents, N or $CR_{28'}$, where $R_{28'}$, in reference to each of B, is the same or different and represents, hydrogen, halogen, $C_1$-$C_3$alkyl or $C_1$-$C_3$haloalkyl; preferably $V_9$ represents N or CH.

In another embodiment of the present invention, $V_{10}$, in reference to each of B, is the same or different and represents, N or $CR_{29'}$, where $R_{29'}$, in reference to each of B, is the same or different and represents, hydrogen, halogen, $C_1$-$C_3$alkyl or $C_1$-$C_3$haloalkyl; preferably $V_9$ represents N or CH.

In another embodiment of the present invention, $V_{11}$, in reference to each of B, is the same or different and represents N or $CR_{30'}$, where $R_{30'}$, in reference to each of B, is the same or different and represents hydrogen, halogen, $C_1$-$C_3$alkyl or $C_1$-$C_3$haloalkyl; preferably $V_9$ represents N or CH.

In another embodiment of the present invention, $G_1$, in reference to each of A, is the same or different and represents N or $CR_{31'}$, where $R_{31'}$, in reference to each of A, is the same or different and represents hydrogen, halogen, $C_1$-$C_3$alkyl or $C_1$-$C_3$haloalkyl; preferably $G_1$ represents N or CH.

In another embodiment of the present invention, $G_2$, in reference to each of A, is the same or different and represents N or $CR_{32'}$, where $R_{32'}$, in reference to each of A, is the same or different and represents hydrogen, halogen, $C_1$-$C_3$alkyl or $C_1$-$C_3$haloalkyl; preferably $G_2$ represents N or CH.

In another embodiment of the present invention, $G_3$, in reference to each of A, is the same or different and represents oxygen, sulfur or $NR_{35'}$, where $R_{35}$ is N-methyl, in reference to each of A, is the same or different and represents $C_1$-$C_3$alkyl or $C_1$-$C_3$haloalkyl; preferably $G_3$ represents oxygen, sulfur, or N—$CH_3$.

In another embodiment of the present invention, $G_4$, in reference to each of A, is the same or different and represents N or $CR_{33'}$, where $R_{33'}$, in reference to each of A, is the same or different and represents $C_1$-$C_3$alkyl or $C_1$-$C_3$haloalkyl; preferably $G_4$ represents N or N—$CH_3$.

In another embodiment of the present invention, $G_5$, in reference to each of A, is the same or different and represents N or $CR_{34'}$, where $R_{34'}$, in reference to each of A, is the same or different and represents hydrogen, $C_1$-$C_3$alkyl or $C_1$-$C_3$haloalkyl; preferably $G_5$ represents N or N—$CH_3$.

In another embodiment of the present invention, $J_1$, in reference to each of radical $A_4$, is N.

In another embodiment of the present invention, $J_2$, in reference to each of radical $A_4$, is CH, $C_1$-$C_3$ alkyl or $C_1$-$C_3$ haloalkyl, such as CH, C—$CH_3$, or C—$CF_3$.

In another embodiment of the present invention, $J_3$, in reference to each of radical $A_4$, is oxygen or sulfur.

The process according to the invention for preparing compounds of formula (I) is carried out in principle by methods known to those skilled in the art, or described for example in WO 2009/131237, WO 2011/043404, WO 2011/040629, WO 2010/125985, WO 2012/086848, WO 2013/018928, WO 2013/191113, WO 2013/180193 and WO 2013/180194, and involves reaction of a compound of formula II,

(II)

wherein Q is the radical $B_1$, $B_2$, $B_3$, $B_4$, $B_5$, $B_6$, $B_7$, $B_8$, $B_9$ and $B_{11}$, wherein $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $V_0$, $V_1$, $V_2$, $V_3$, $V_4$, $V_5$, $V_6$, $V_7$, $V_8$ and $L_1$ are as described in formula I, and the arrows in the radicals $B_1$-$B_9$ and $B_{11}$ show the point of attachment to the carbonyl atom of the carboxyl group In formula II, with a compounds of formula III, IV, or V;

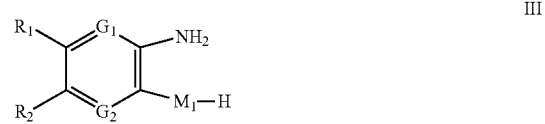

III

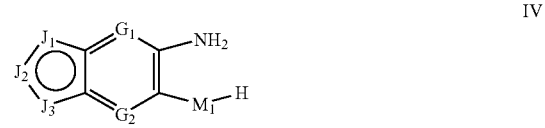

IV

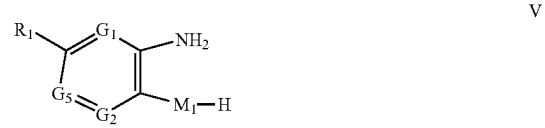

V wherein $R_1$, $R_2$, $G_1$, $G_2$, and $G_5$ are as described in formula (I) and $M_1$ is oxygen, sulfur, or $NR_{35}$, in the presence of a dehydrating agent such as polyphosphoric acid at temperature between 150° C. to 200° C., to yield compounds of formula Ia, Ib, and Ic, wherein the substituents are as described for formula (I).

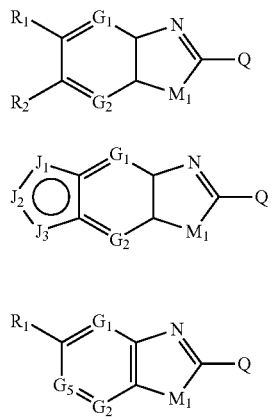

Such processes are well known and have been described for example in WO 2011/040629 or WO 2009131237 ($M_1$ is oxygen), WO 2011088990 or *Inorg. Chimica Acta,* 358(9), 2701-2710; 2005 ($M_1$ is sulfur) and *J. Am. Chem. Soc.,* 132(5), 1545-1557, 2010 or WO 2008128968 ($M_1$ is $NR_{35}$). The process is summarized in scheme 1 for compounds of formula Ia:

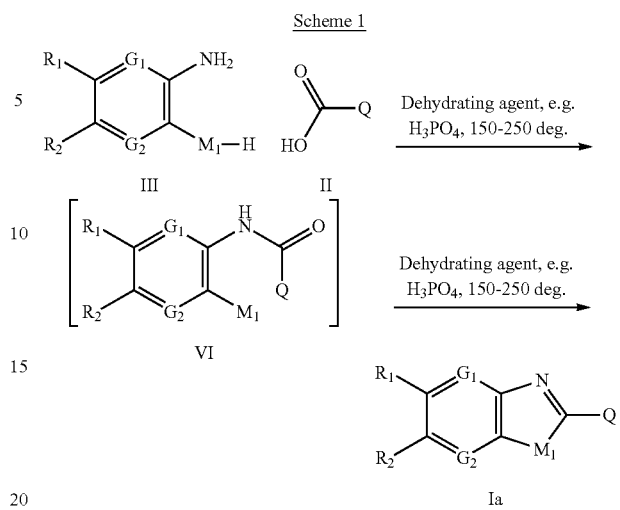

As can be seen in scheme 1, the formation of Ia occurs through the intermediacy of a compound of formula VI. It is in many cases advantageous to thus prepare compounds of formula (I) through such intermediates. This is illustrated for compounds of formula Ia in scheme 2.

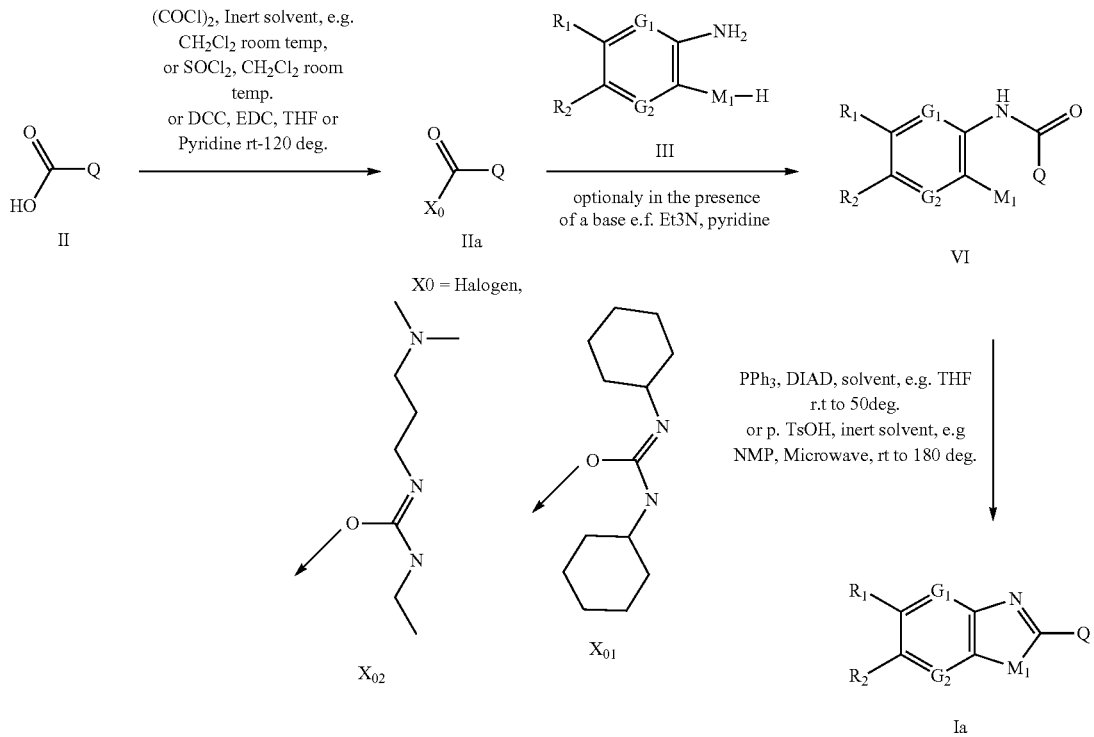

In scheme 2 compounds of formula II wherein Q is as previously described, are activated to compounds of formula IIa by methods known to those skilled in the art and described in for example *Tetrahedron,* 61 (46), 10827-10852, 2005. For example compounds where $X_0$ is halogen are formed by treatment with for example, oxallyl chloride or thionyl chloride in the presence of catalytic quantities of DMF in inert solvents such as methylene chloride or THF at temperatures between 20° C. to 100° C., preferably 25° C. Treatment of IIa with compounds of formula III, optionally in the presence of a base, e.g. triethylamine or pyridine leads to compounds of formula VI. Alternatively, compounds of formula VI can be prepared by treatment of compounds of formula II with dicyclohexyl carbodiimide (DCC) or 1-Ethyl-3-(3-dimethylaminopropyl)carbodiimide (EDC) to give the activated species IIa, wherein $X_O$ is $X_{O1}$ and $X_{O2}$ respectively, in an inert solvent, e.g. pyridine, or THF optionally in the presence of a base, e.g. triethylamine, at temperatures between 50-180° C. Compounds of Formula VI so obtained can then be converted to compounds of formula Ia by dehydration, eg. by heating the compounds in a microwave, in the presence of an acid catalyst, for example methane sulfonic acid, or para-toluene sulfonic acid, in an inert solvent such as N-methyl pyrrolidine at temperatures between 25-180° C., preferably 130-170° C. Such processes have been described previously in WO 2010125985. Alternatively, compounds of formula VI can be converted to compounds of formula Ia (wherein $M_1$ is O) using triphenyl phosphine, di-isopropyl azo dicarboxylate in an inert solvent such as THF at temperatures between 25-50° C. Such Mitsunobu conditions have been previously described for such transformations (see WO2009131237). Application of such methods in the reaction of compounds of formula II respectively IIa with compounds of formula IV and V, leads to compounds Ib and Ic via the intermediates VII and VIII respectively.

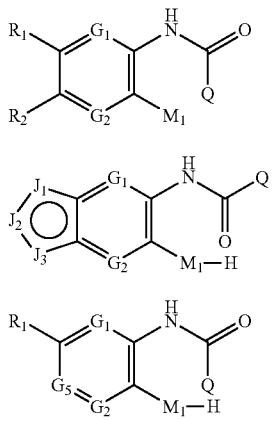

Alternatively, compounds of formula (I) can be prepared by reacting compounds of formula IX, X, XI, XII, and XIII;

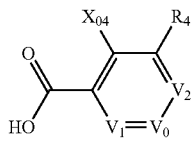

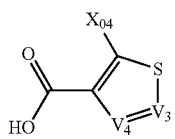

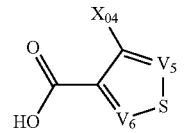

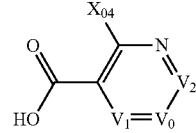

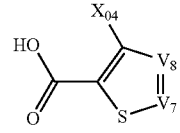

wherein $V_0$, $V_1$, $V_2$, $V_3$, $V_4$, $V_5$, $V_6$, $V_7$, $V_8$ and $R_4$ are as defined for formula (I) and $X_{04}$ is halogen, with compounds of formula III, IV and V as described in schemes 2 and 3 to give compounds of formula XIV, XV, XVI, XVII, XVIII, XIX, XX, XXI, XXII, XXIII, XIV, XV, XVI, XVII, and XVIII;

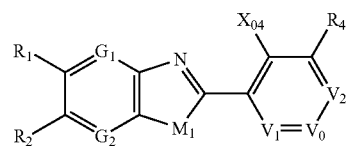

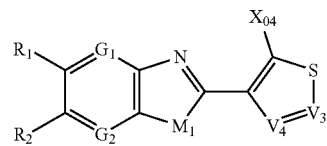

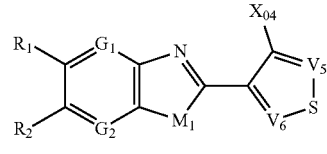

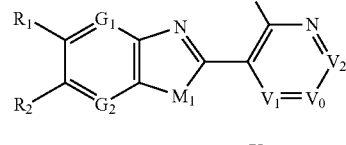

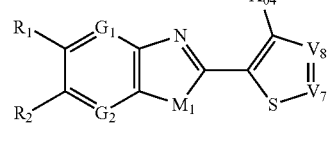

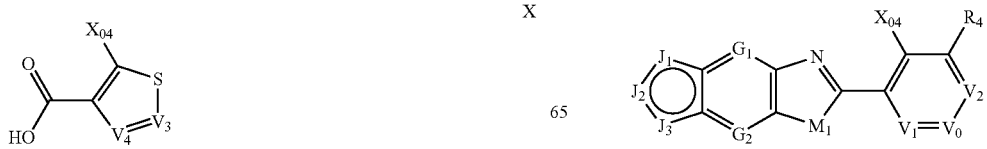

-continued

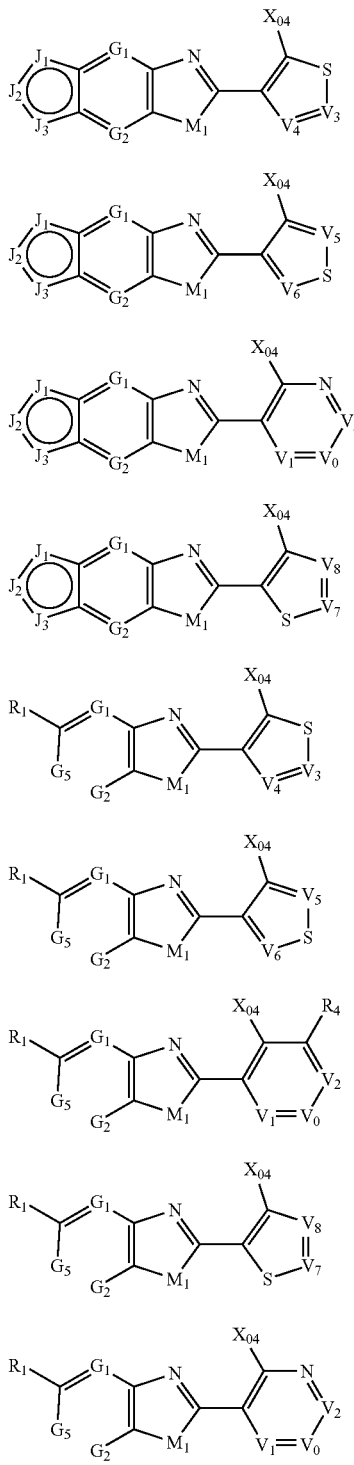

wherein $R_1$, $R_2$, $R_4$, $G_1$, $G_2$, $G_5$, $V_0$, $V_1$, $V_2$, $V_3$, $V_4$, $V_5$, $V_6$, $V_7$, $V_8$, $J_1$, $J_2$ and $J_3$ are as defined in formula I, $M_1$ is oxygen, sulfur, or $NR_{35}$, and $X_{04}$ is halogen. Compounds of formula XIV, XV, XVI, XVII, XVIII, XIX, XX, XXI, XXII, XXIII, XXIV, XXV, XXVI, XXVII, and XXVIII can be reacted with compounds of formula XXIX $$R_3\text{—SH} \quad \text{(XXIX)}$$

wherein $R_3$ is as described in formula I, in the presence of a suitable base, such as alkali metal carbonates, for example sodium carbonate and potassium carbonate or alkali metal hydrides such as sodium hydride, in a suitable solvent, at temperatures between 25-120° C. to give compounds of formula Id, Ie, If, Ig, I h, Ii, Ij, Ik, Il, Im, In, Io, Ip, Iq and Ir:

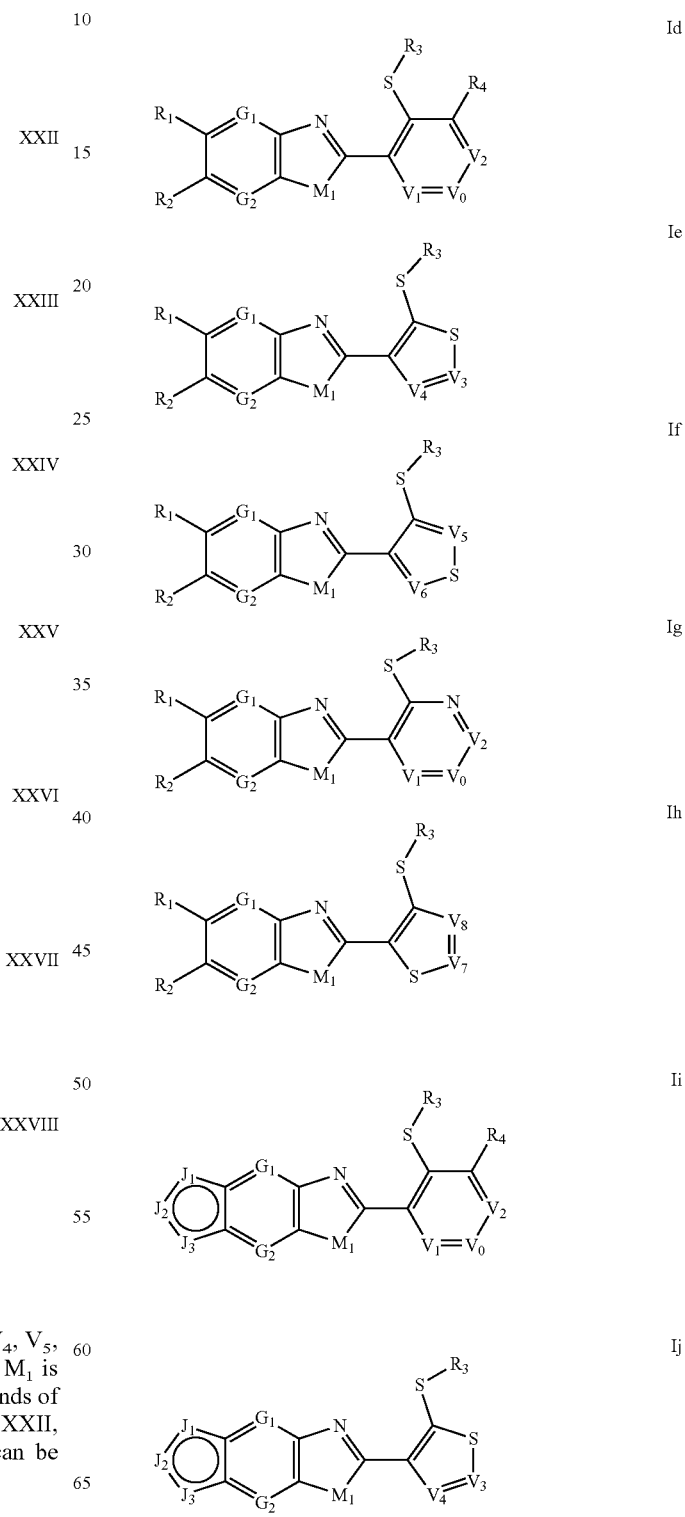

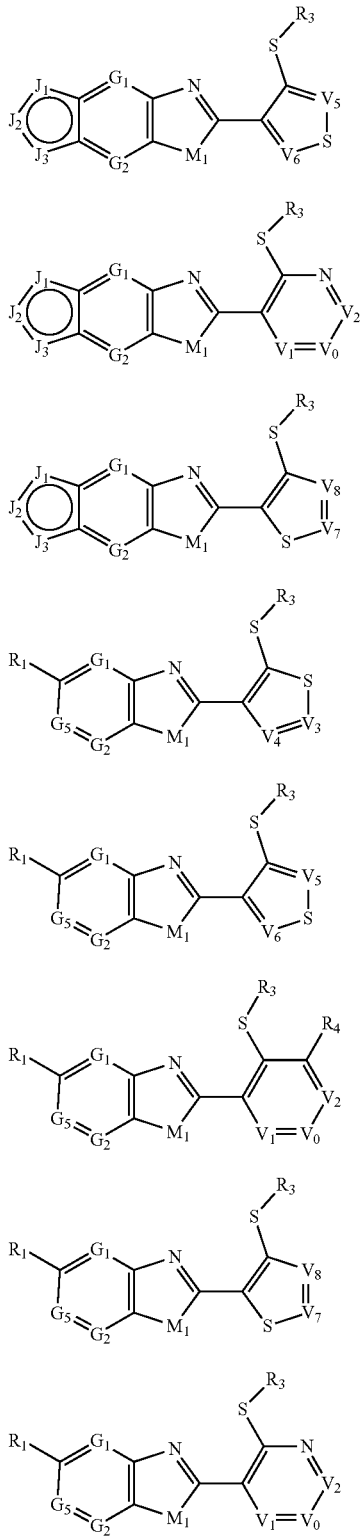

Examples of the solvent to be used in the reaction include ethers such as THF, ethylene glycol dimethyl ether, tert-butylmethyl ether, and 1,4-dioxane, aromatic hydrocarbons such as toluene and xylene, nitriles such as acetonitrile. Similar chemistry has been previously described, as for example in WO 2013018928. Alternatively, the reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al in *Tetrahedron*, 61, 5253-5259, 2005.

Compounds represented by the formula (I) wherein m is 1 or 2 can be produced by oxidizing the compounds of formula Id, Ie, If, Ig, I h, Ii, Ij, Ik, Il, Im, In, Io, Ip, Iq and Ir. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. Examples of the oxidant to be used in the reaction include sodium periodate and m-chloroperbenzoic acid. The amount of the oxidant to be used in the reaction is generally 1 to 3 moles, preferably 1 to 1.2 moles, relative to 1 mole of the compounds Id, Ie, If, Ig, I h, Ii, Ij, Ik, Il, Im, In, Io, Ip, Iq and Ir to produce compounds of formula (I) where m=1, and preferably 2 to 2.2 moles of oxidant, preferably metachloroperbenzoic acid, relative to 1 mole of the compounds Id, Ie, If, Ig, I h, Ii, Ij, Ik, Il, Im, In, Io, Ip, Iq and Ir to produce compounds of formula (I) wherein m=2.

Compounds of formula I, wherein B is $B_{10}$, can be prepared by reacting a compound of formula XXX:

$$Q_1\text{-}X_{05} \qquad (XXX),$$

wherein $Q_1$ is $A_1, A_2, A_3, A_4$, and $A_8$ and $X_{05}$ is a halogen or a leaving group $OSO_2R_{38}$, and the arrows in the substituents in $A_1, A_2, A_3, A_4$, and $A_6$ show the point attachment of the radical A to the substituent $X_{04}$, and wherein $R_{38}$, is $C_1$-$C_6$alkyl, $C_1$-$C_6$haloalkyl, or phenyl optionally substituted by nitro or $C_1$-$C_3$alkyl, with a compound of formula XXXI;

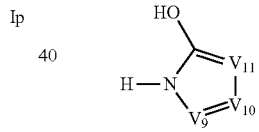

(XXXI)

wherein $V_9$, $V_{10}$, and $V_{11}$, are as described in formula I, in the presence of a suitable base, such as sodium hydride or cesium carbonate, in an inert solvent such as dimethyl formamide, N-methylpyrollidine, or acetonitrile, at temperatures between 20-150° C., to yield compounds of formula XXXII:

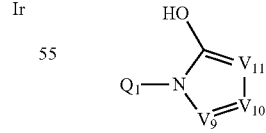

(XXXII)

Alternatively compounds of formula XXXII can be obtained by reacting compounds of formula XXX with compounds of formula XXXI in an inert solvent such as dioxane, in the presence of a catalytic amount of copper iodide and catalytic amount of a diamine, for example N,N-dimethylethylenediamine or racemic trans-N,N-dimethylcyclohexanediamine, with a base, for example potassium carbonate or potassium phosphate at temperatures between 50-120° C., preferably 90-110° C. Such reactions are well precedented in the literature and described for example in *J. Org. Chem.*, 68, 2609-2617, 2003, and *Org. Letts.*, 9, 643-646, 2007. Compounds of formula XXXII can be reacted with a halogenating reagent such as phosphorus oxychloride, phosphorus trichloride or tribromide, phosphorus pentachloride or pentabromide, or thionyl chloride, optionally in an inert solvent at temperatures between 25-120° C., to give compounds of formula XXXIII, wherein $X_{06}$ is halogen:

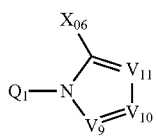

(XXXIII)

Compounds of formula XXXIII can subsequently be treated with compounds of formula XXIX;

R$_3$—SH       (XXIX)

wherein $R_3$ is as described in formula I, in the presence of a suitable base, such as an alkaline earth metal hydride, for example sodium hydride and a polar aprotic solvent, such as dimethyl formamide, at temperatures between 25-120° C. to give compounds of formula Is:

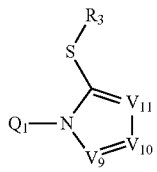

(Is)

Oxidation of compound Is by methods known to those skilled in the art, for example using sodium periodate to prepare compounds of formula It, where m=1, or at least two equivalents of meta-chloroperbenozoic (MCPBA) in an inert solvent such as methylene chloride, leads to compounds of formula It where m=2.

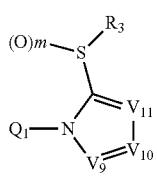

(It)

The synthesis is summarized in scheme 3.

Scheme 3

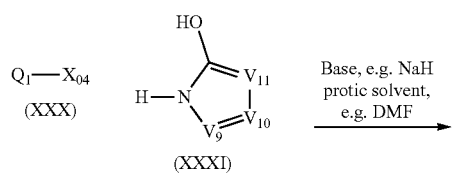

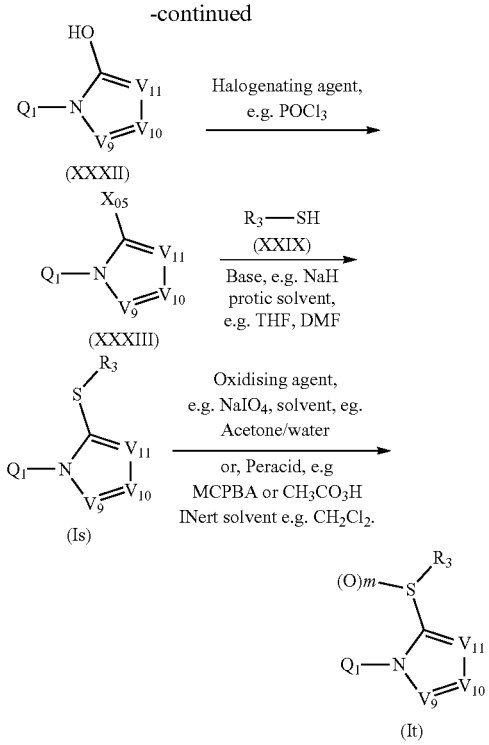

The subgroup of compounds of formula I, wherein A is $A_2$ and $G_5$ is $CR_{34}$, can be represented by the compounds of formula Iu

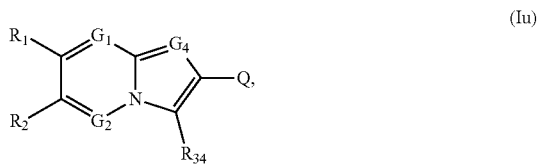

(Iu)

wherein Q is one of the radicals $B_1$, $B_2$, $B_3$, $B_4$, $B_5$, $B_6$, $B_7$, $B_8$, $B_9$ or $B_{11}$, and $R_1$, $R_2$, $G_1$, $G_2$ and $G_4$ are as described in formula (I) and $R_{34}$ is $C_1$-$C_6$alkyl or $C_1$-$C_6$haloalkyl can be prepared by reacting a compound of formula XXXIV

(XXXIV)

wherein $R_1$, $R_2$, $G_1$ and $G_2$ are as described in formula (I) with a compound of formula XXXV

(XXXV)

wherein $X_{07}$ is a halogen or a leaving group $OSO_2R_{38}$ and Q is as defined above, optionally in the presence of a suitable base in an inert solvent.

A further process to prepare compounds of formula Iu, involves reacting a compound of formula XXXIV with a compound of XXXVa

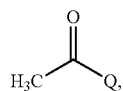
(XXXVa)

In the presence of a Lewis acid, such as Zinc(II)iodide or Indium(III) triflate, in an inert solvent such as chlorobenzene or 1,2,dichlorobenzene, with a catalytic copper(II) salt, such as Cu(II)acetate, under an oxygen or air atmosphere at temperatures between 100-180° C., preferably 110-140° C., to give compounds of formula Iu wherein $R_{34}$ is hydrogen. Such reactions have previously been described in the literature (see *Adv. Synth. Catal.* 2013, 355, 1741-1747, and J. Org. Chem., 2013, 78, 12494-12504). Halogenation of compounds of formula Iu, wherein $R_{34}$ is hydrogen, with a halogenating agent such as N-chlorosuccinamide, N-bromosuccinamide, or N-iodosuccinamide, in a polar aprotic solvent such as acetonitrile or dimethylformamide, at ambient temperature, leads to compounds of formula $Iu_c$

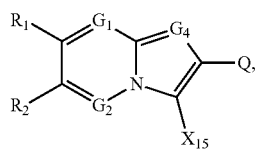
($Iu_c$)

wherein Q, $R_1$, $R_2$, $G_1$, $G_2$ and $G_4$ are as described in formula (I), and $X_{15}$ is halogen. Compounds of formula $Iu_c$ can be reacted with compounds $R_{34}$-$M_0$, wherein $M_0$ is a boronic acid, in the presence of a palladium catalyst to give compounds of formula Iu. When $M_0$ is a boronic acid, the reaction is usually carried out in the presence of a base, for example potassium carbonate, cesium carbonate, or potassium phosphate, in an inert solvent, such as dioxane, optionally in the presence of water, with a palladium(0) catalyst, for example tetrakis(triphenylphosphine)palladium, at a temperature between 80-120° C. Such Suzuki reactions are well precedented in the literature, see for example Masuda, Naoyuki et al, WO 2012133607. Compounds of formula XXXV and XXXVa can be prepared from compounds of formula II by, for example, the methods shown in scheme 4.

Scheme 4

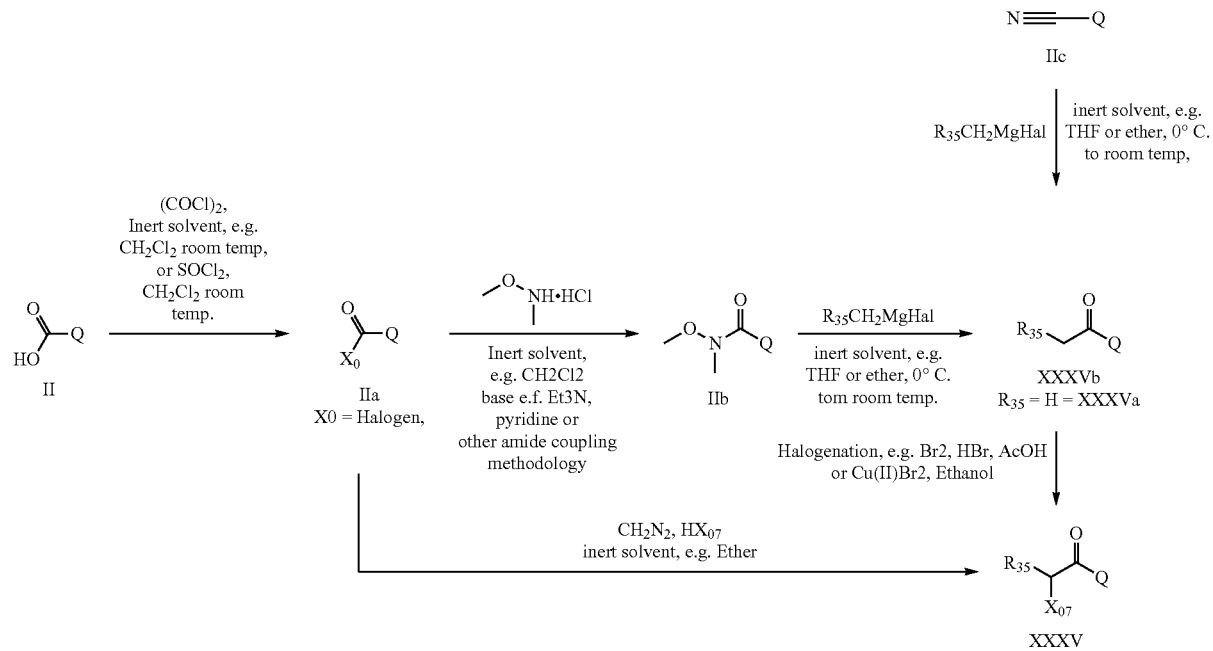

In scheme 4, an acyl halide of formula IIa is converted to a Weinreb amide IIb upon reaction with N,O-Dimethylhydroxylamine by methods known to those skilled in the art and described for example in C. Ferri, "Reaktionen der Organischen Synthese", Georg Thieme Verlag, Stuttgart, 1978, page 223ff. the Weinreb amide of formula IIb is then reacted with a Grignard reagent of formula $R_{35}CH_2MgHal$ according to the method of Weinreb (*Tetrahedron Letters* 1981, 22, 3815-3818) to give compounds of formula XXXVb and XXXVa. Compounds of formula XXXVa and XXXVb can also be prepared by treatment of nitrile compounds of formula IIc, wherein Q is as described in formula I, with a Grignard reagent of formula $R_{35}CH_2MgHal$, followed by acidic hydrolysis (as described in C. Ferri, "Reaktionen der Organischen Synthese", Georg Thieme Verlag, Stuttgart, 1978, page 223ff.).

Compounds of formula XXXVa and XXXVb can be halogenated to compounds of formula XXXV, with for example mixtures of bromine and hydrobromic acid in acetic acid (as described in *Phosphorus, Sulfur and Silicon and the Related Elements*, 2013, 188(12), 1835-1844) or with, for example, copper(II)bromide in an inert solvent, for example chloroform, ethyl acetate and the like, as described in *J. Med. Chem.*, 2013, 56(1), 84-96. Alternatively compounds of formula XXXV where $R_{35}$ is hydrogen, can be prepared directly from compounds of formula IIa by treatment with diazomethane or trimethyl silyl diazomethane and subsequent treatment with an halogen acid, for example, hydrobromic acid or hydrochloric acid in an inert solvent such as diethyl ether. Such procedures are well known in the literature, for example see *Eu. J. Med. Chem.*, 1987, 22(5), 457-62 and WO 2009010455.

In an analogous manner, compounds of formula $Iu_a$

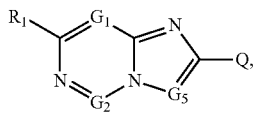
(Iu$_a$)

wherein $R_1$, $G_1$, $G_2$ are as described in formula (I), and $G_5$ is $CR_{34}$ can be prepared by reacting compounds of formula (XXXIVa),

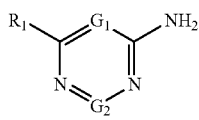
(XXXIVa)

wherein $R_1$, $G_1$, $G_2$, are as described in formula (I) with a compound of formula XXXV or XXXVa analogously to the preparation of compounds of formula Iu. Those skilled in the art will recognize that compounds of formula $Iu_b$

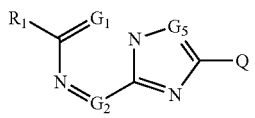
Iu$_b$ can be similarly prepared by reaction of compounds of formula XXXIVb with compounds of formula XXXV or XXXVa, wherein $G_5$ is $CR_{34}$ as described above.

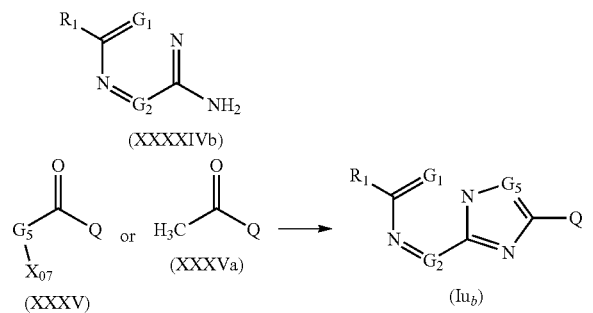
(XXXIVb)
(XXXV)  (XXXVa)
(Iu$_b$)

The subgroup of compounds of formula I, wherein A is $A_2$ and $G_5$ is nitrogen, can be represented by the compounds of formula Iv;

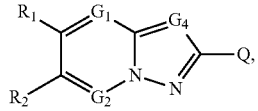
(Iv)

wherein Q is one of the radicals $B_1$, $B_2$, $B_3$, $B_4$, $B_5$, $B_6$, $B_7$, $B_8$, $B_9$ or $B_{11}$, and $R_1$, $R_2$, $G_1$, $G_2$ and $G_4$ are as described in formula I, can be prepared by reacting a compound of formula XXXVI;

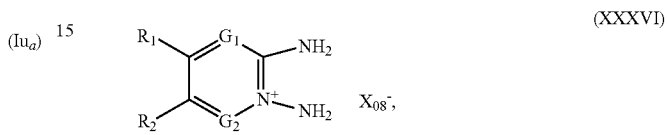
(XXXVI)

wherein $R_1$, $R_2$, $G_1$ and $G_2$ are as described in formula (I) and in which $X_{08}^-$ is a halide ion or an anion of the formula $^-OSO_2R_{38}$ with a compound of formula IIa

(IIa)

wherein $X_0$ is a halogen and Q is as defined above, optionally in the presence of a suitable base in an inert solvent.

Compounds of the formula XXXIV above can be prepared through amino-dehalogenation by reacting a compound of formula XXXVII;

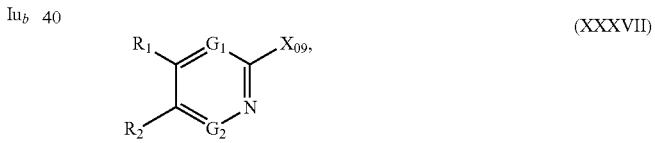
(XXXVII)

wherein $R_1$, $R_2$, $G_1$ and $G_2$ are as described in formula (I) and in which $X_{09}$ is a halogen or a leaving group $OSO_2R_{38}$, with ammonia (either gaseous or aqueous) as a nucleophile. Ammonia may be used in equimolar amounts or in large excess in an appropriate inert solvent, optionally in a pressurised vessel. The reaction may be performed between 0 and 200° C., optionally with microwave irradiation. Ammonia equivalents such as, for example, ammonium hydroxide $NH_4OH$, ammonium acetate $NH_4OAc$, ammonium carbonate (NH4)2CO3 may also be used as a nitrogen source.

Compounds of the formula XXXVII can be prepared by reacting a compound of formula XXXVIII

(XXXVIII)

wherein $R_1$, $R_2$, $G_1$ and $G_2$ are as described in formula (I) with reagents such as, for example, phosphorus oxychloride, phosphorus trichloride or tribromide, phosphorus pentachloride or pentabromide in an inert solvent.

Compounds of the formula XXXVIII are known in the literature. For example, compounds of the formula XXXVIII where $G_2$ is a nitrogen atom and $G_1$ is $CR_{31}$, and wherein $R_1$ and $R_2$ are as described in formula I, are known from or can be prepared in analogy to EP1371638.

Compounds of the formula XXXVI can be prepared via N-amination by reacting a compound of formula XXXIV above with O-mesitylenesulfonylhydroxylamine (MSH) as amination reagent, as described for example by Y. Tamura et al., *J. Heterocyclic Chem.* 1975, 12, 107-110. MSH is also known in form of a precursor as its ethyl-acetohydroxamate; a pre-treatment with for example perchloric acid $HClO_4$ in tetrahydrofurane liberates the required amination reagent MSH. O-mesitylenesulfonyl-hydroxylamine and related aminating reagents have been reviewed: Y. Tamura et al., *Synthesis*, 1-17, 1977.

The subgroup of compounds of formula I, wherein A is $A_3$ and $G_5$ is nitrogen, can be represented by the compounds of formula Iw

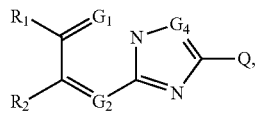

(Iw)

wherein Q is one of the radical $B_1$, $B_2$, $B_3$, $B_4$, $B_5$, $B_6$, $B_7$, $B_8$, $B_9$ or $B_{11}$, and wherein $R_1$, $R_2$, $G_1$, $G_2$ and $G_4$ are as described in formula I.

When $G_4$ is $CR_{33}$ then compounds of the formula Iw can be prepared by reacting a compound of formula XXXIX

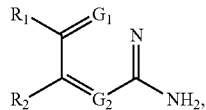

(XXXIX)

wherein $R_1$, $R_2$, $G_1$ and $G_2$ are as described in formula (I) with a compound of formula XL

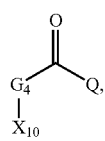

(XL)

wherein $X_{10}$ is a halogen or a leaving group $OSO_2R_{38}$ and Q is as defined above, optionally in the presence of a suitable base in an inert solvent.

Alternatively, when $G_4$ is a nitrogen, compounds of the formula Iw can be prepared by reacting a compound of formula XLI

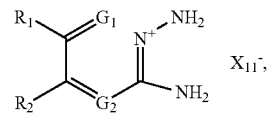

(XLI)

wherein $R_1$, $R_2$, $G_1$ and $G_2$ are as described in formula (I) and in which $X_{11}^-$ is a halide ion or an anion of the formula $^-OSO_2R_{38}$ with a compound of formula IIa

(IIa)

wherein $X_0$ is a halogen and Q is as defined above, optionally in the presence of a suitable base in an inert solvent.

Compounds of the formula XXXIX above can be prepared through amino-dehalogenation by reacting a compound of formula XLII

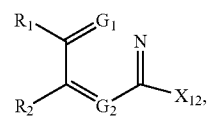

(XLII)

wherein $R_1$, $R_2$, $G_1$ and $G_2$ are as described in formula (I) and in which $X_{12}$ is a halogen or a leaving group $OSO_2R_{38}$ with ammonia (either gaseous or aqueous) as a nucleophile. Ammonia may be used in equimolar amounts or in large excess in an appropriate inert solvent, optionally in a pressurized vessel. The reaction may be performed between 0 and 200° C., optionally with microwave irradiation. Ammonia equivalents such as, for example, ammonium hydroxide $NH_4OH$, ammonium acetate $NH_4OAc$, and ammonium carbonate $(NH_4)_2CO_3$ may also be used as a nitrogen source.

Compounds of the formula XLII can be prepared by reacting a compound of formula XLIII

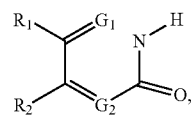

(XLIII)

wherein $R_1$, $R_2$, $G_1$ and $G_2$ are as described in formula (I) with reagents such as, for example, phosphorus oxychloride, phosphorus trichloride or tribromide, phosphorus pentachloride or pentabromide or thionyl chloride in an inert solvent.

Compounds of the formula XL can be prepared, for example, in analogy to EP1371638.

Compounds of the formula XLI can be prepared via N-amination by reacting a compound of formula XXXIX above with O-mesitylenesulfonylhydroxylamine (MSH)—or one of its equivalent—as amination reagent, as described previously for the preparation of compounds of the formula XXXVI. The subgroup of compounds of formula I, wherein A is $A_7$ and both $G_5$ and $G_4$ are nitrogen, can be represented by the compounds of formula Ix

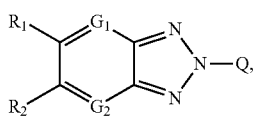

(Ix)

wherein Q is one of the radical $B_1$, $B_2$, $B_3$, $B_4$, $B_5$, $B_6$, $B_7$, $B_8$, $B_9$ or $B_{11}$, and wherein $R_1$, $R_2$, $G_1$ and $G_2$ are as described in formula I.

Compounds of the formula Ic can be prepared by reacting a compound of formula XLIV

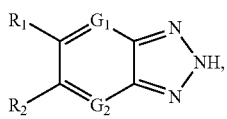

(XLIV)

wherein $R_1$, $R_2$, $G_1$ and $G_2$ are as described in formula (I) with a compound of formula XLV $$X_{13}\text{-}Q \qquad (XLV),$$

wherein $X_{13}$ is a halogen or a leaving group $OSO_2R_{38}$ and Q is as defined above, where the arrows in the radicals $B_1$, $B_2$, $B_3$, $B_4$, $B_5$, $B_6$, $B_7$, $B_8$, $B_9$ or $B_{11}$ show the point of attachment of the substituent $X_{13}$, optionally in the presence of a suitable base in an inert solvent, for example sodium hydride in dimethylformamide, in analogy to, for example, WO10/038081.

Alternatively, compounds of the formula Ix can be prepared by reacting a compound of formula XLIV, with a compound of formula XLV under palladium-catalyzed N-arylation conditions as described, for example, in S. L. Buchwald et al., *Angew. Chem. Int. Ed.*, 50, 8944-8947, 2011. Compounds of the formula XLIV above can be prepared through diazotization by treating a compound of formula XLVI

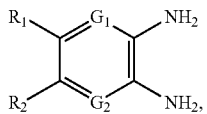

(XLVI)

wherein $R_1$, $R_2$, $G_1$ and $G_2$ are as described in formula I, with either sodium nitrite and hydrohalic acid in water or with an alkyl nitrite (such as, for example, tert-butyl nitrite or isoamyl nitrite) under anhydrous conditions, optionally in presence of an acid (such as, for example, acetic acid) in an inert solvent (such as, for example, tetrahydrofurane) at temperatures between 0 and 130° C. A typical example involving isoamyl nitrite and acetic acid in refluxing tetrahydrofurane may be found in I. Torrini et al., *J. Heterocyclic Chem.*, 23, 1459-1463, 1986.

Compounds of formula (I) wherein $R_{21}$ is $C_1$-$C_6$alkenyloxy, —C(O)$R_{36}$ can be prepared as shown in scheme 5, which is illustrated for radical $A_1$-$B_1$:

Scheme 5.

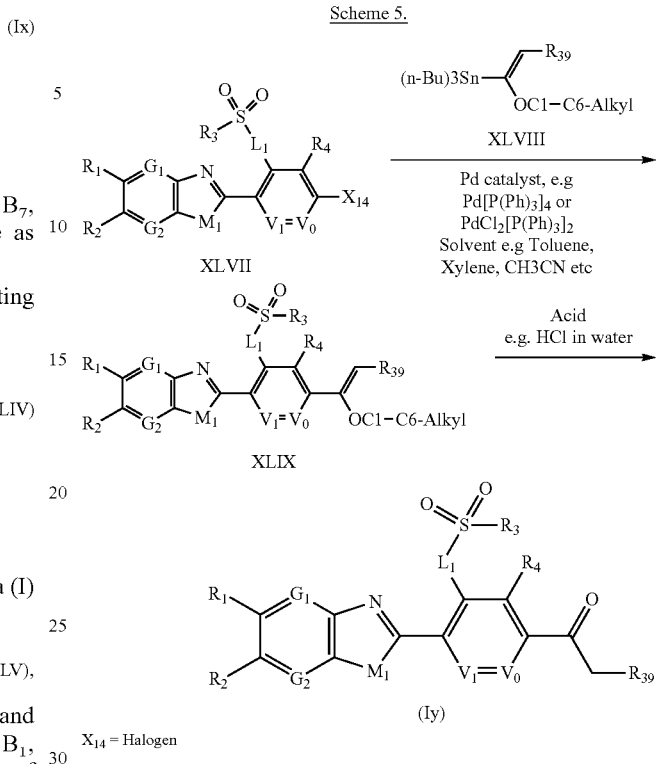

$X_{14}$ = Halogen

In scheme 5, compounds of formula XLVII, wherein $R_1$, $R_2$, $G_1$, $G_2$, $L_1$, $R_3$, $R_4$, $V_1$ and $V_0$ are as described for formula (I), and $X_{14}$ is halogen, preferably bromide, are reacted with compounds of formula XLVIII, wherein $R_{36}$ is $C_1$-$C_5$alkyl which can be mono- or polysubstituted by substituents selected from $C_1$-$C_6$alkoxy, $C_1$-$C_6$haloalkoxy, $C_2$-$C_6$ alkenyloxy, $C_2$-$C_6$haloalkenyloxy, $C_2$-$C_6$alkynyloxy, $C_2$-$C_6$haloalkynyloxy, $C_1$-$C_6$ alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$ cycloalkyl, wherein said $C_3$-$C_6$ cycloalkyl can be mono- or polysubstituted by substituents selected from the group consisting of halogen and $C_1$-$C_3$alkyl, or a phenyl group which can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro, in an inert solvent, such as THF, DMF, dioxane, octane, toluene, and xylene, in the presence of a palladium catalyst, such as tetrakis(triphenylphosphine)palladium(0), or Bis(triphenylphosphine)palladium(II) chloride, in an inert solvent, such as toluene, and xylene, and DMF, or a mixture of these, etc. at temperatures between 25-120° C., preferably 50-90° C. The obtained product XLIX is then treated with a mineral acid, for example aqueous hydrochloric acid, in the presence of an organic co-solvent, for example methanol, acetone, ethanol, THF, etc. to give the product of formula 1y, where the substituents $R_1$, $R_2$, $G_1$, $G_2$, $L_1$, $R_3$, $R_4$, $V_1$, $V_0$ and $R_{39}$ are as previously described. Such processes are well known and have been described previously in for example, Kosugi, Masanori et at *Bull. Chem. Soc. Japan,* 60(2), 767-8, 1987.

Analogous chemistry can be used to introduce such a substituent in $R_4$, $R_5$, $R_{20}$, $R_{22}$, $R_{23}$, $R_{24}$, $R_{25}$, $R_{26}$, $R_{27}$, $R_{28}$, $R_{29}$, and $R_{30}$.

Compounds of formula II are in many cases commercially available, known in the literature, or can be produced analogously to methods described in the literature. For example 3-ethylsulfonyl-5-(trifluoromethyl)pyridine-2-carboxylic acid (WO 2013180194), 3-ethylsulfonylpyridine-2-carboxylic acid (WO 2013180194), 3-ethylsulfonylpyrazine-2-carboxylic acid (WO 2013180194), 3-ethylsulfonylthiophene-2-carboxylic acid (*Synthesis,* 2007, (12), 1827-1832), 3-ethylsulfonyl-5-(trifluoromethyl) thiophene-2-carboxylic acid (WO 2013180193), 2-chloro-6-(trifluoromethyl)pyridine-3-carboxylic acid (WO 2013180194), 5-ethylsulfanylthiazole-4-carboxylic acid (WO 2013180193) 2-ethylsulfanylthiophene-3-carboxylic acid (WO 2013180193), and 4-bromo-2-methyl-1,1-dioxo-2,3-dihydrobenzothiophene-7-carboxylic acid (WO 199909023), In further cases, syntheses for compounds of formula II have been especially developed to prepare compounds of formula I and are shown in the following schemes:

Scheme 6.

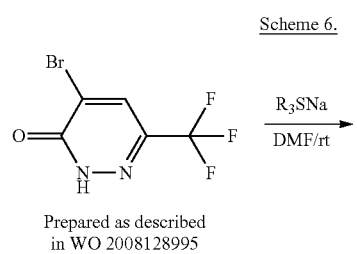

Prepared as described in WO 2008128995

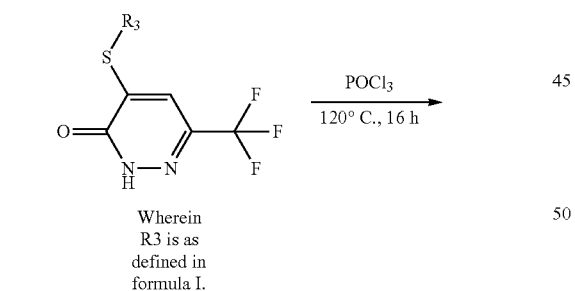

Wherein R3 is as defined in formula I.

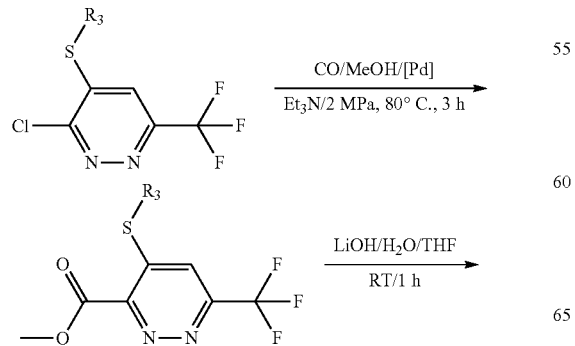

-continued

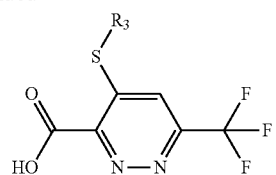

Scheme 7.

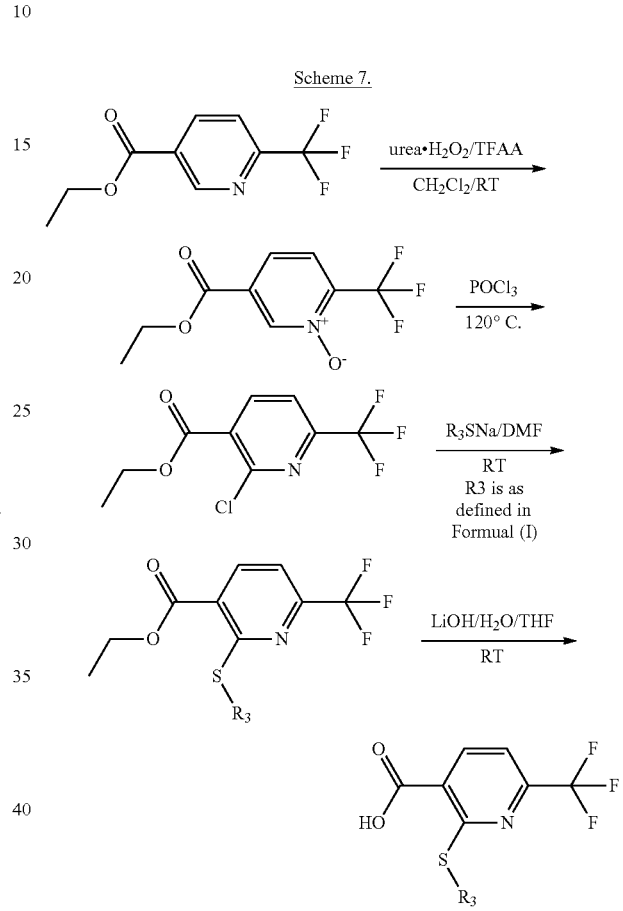

Scheme 8

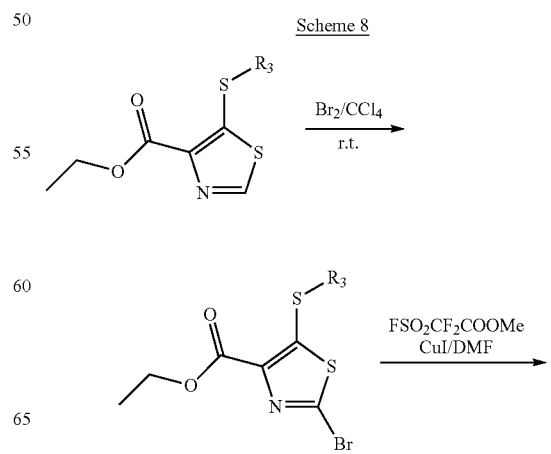

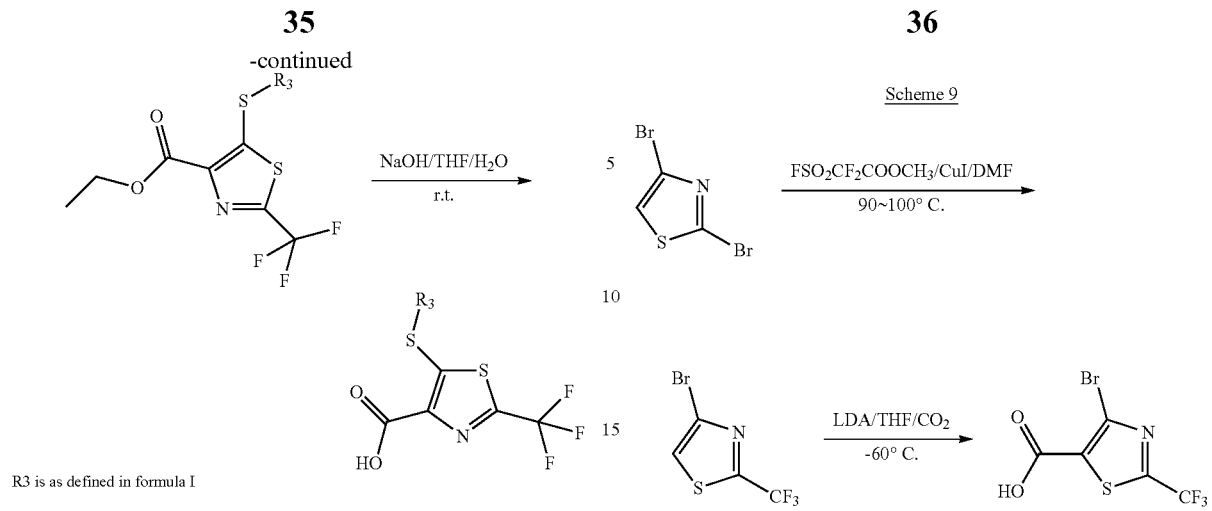
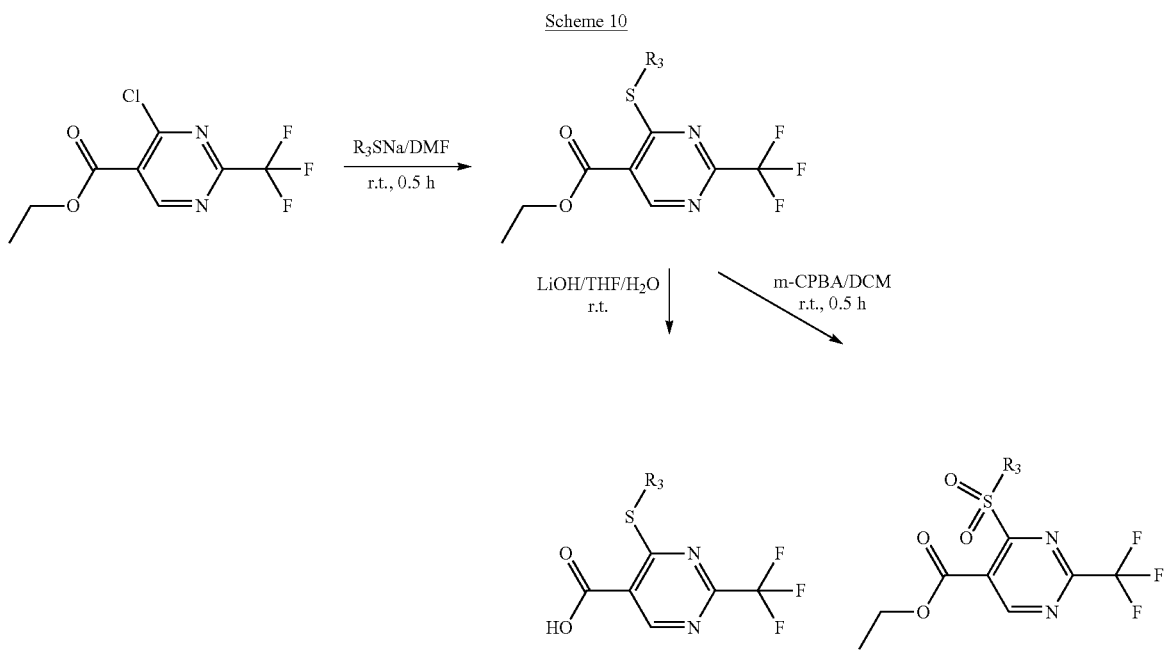
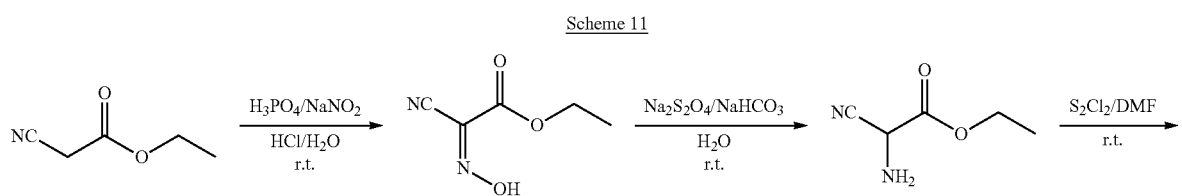

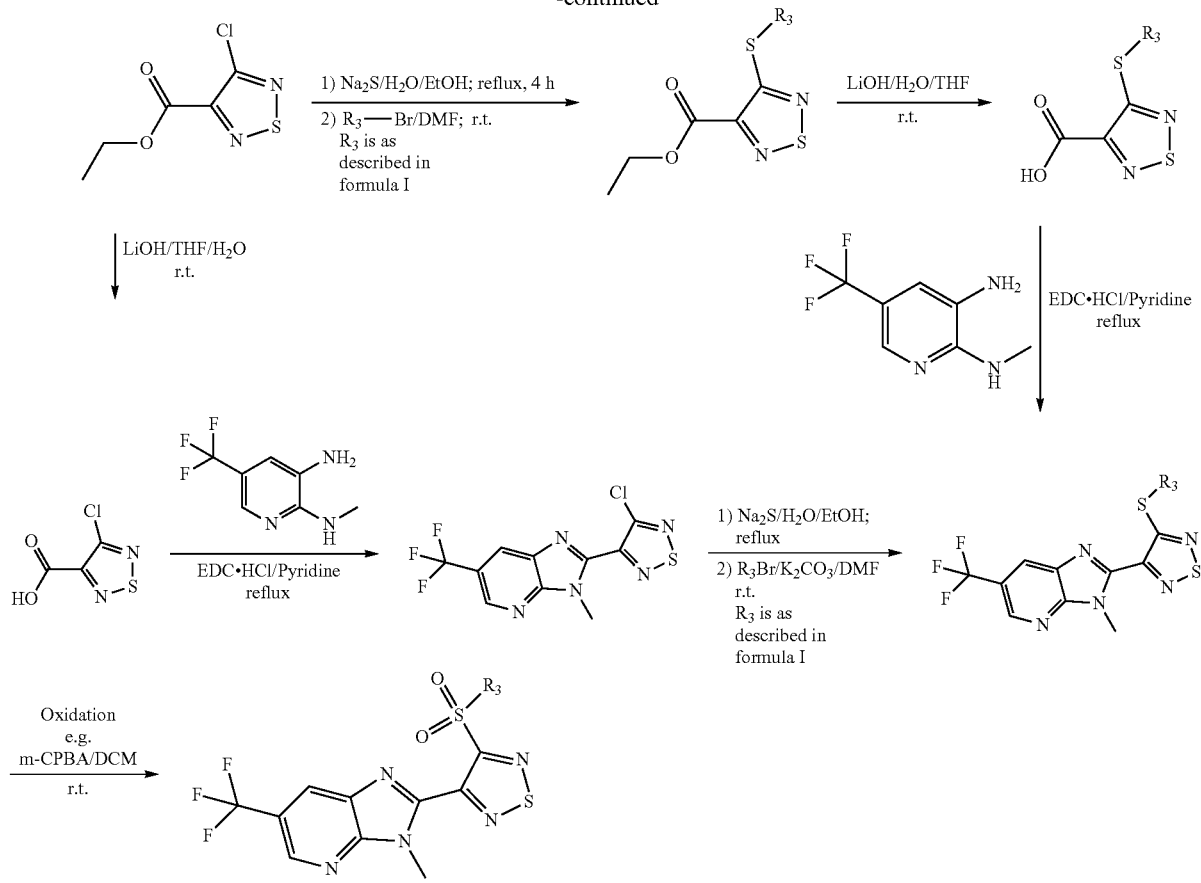

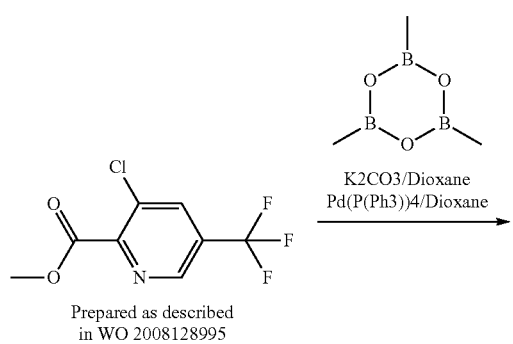

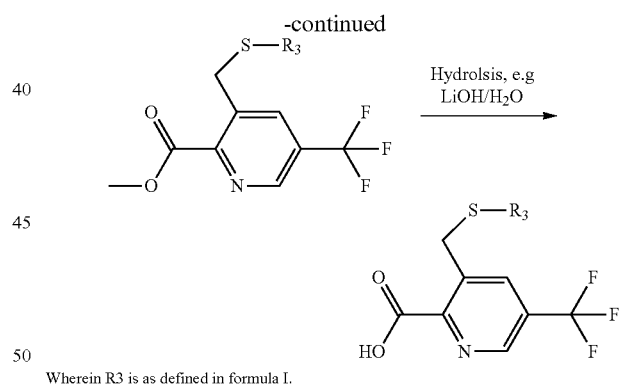

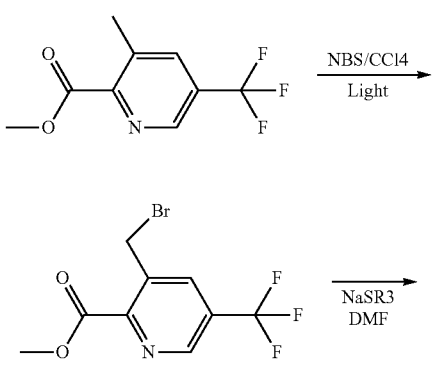

Wherein R3 is as defined in formula I.

Compounds of formula III, IV, and V are commercially available, known in the literature, or can be prepared by analogous methods to those in the literature. For example, N-2-methyl-5-(trifluoromethyl)pyridine-2,3-diamine (WO 2012086848), 6-(trifluoromethyl)pyridine-3,4-diamine (WO 2013/048214), N-3-methyl-6-(trifluoromethyl)pyridine-2,3-diamine (WO 2012/086848), N-5-methyl-2-(trifluoromethyl)pyrimidine-4,5-diamine (CAS [1023817-05-1]), N-1-methyl-4-(trifluoromethyl)benzene-1,2-diamine (WO 2005065680), 3-amino-5-(trifluoromethyl)pyridin-2-ol (WO 2011049222), 3-amino-5-(trifluoromethyl)-2(1H)-Pyridinethione (WO 2011/043404).

In further cases, syntheses for compounds of formula III, IV, and V have been especially developed to prepare compounds of formula I and are shown in the following schemes:
Scheme 13
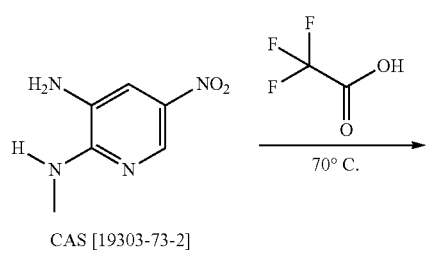
CAS [19303-73-2]
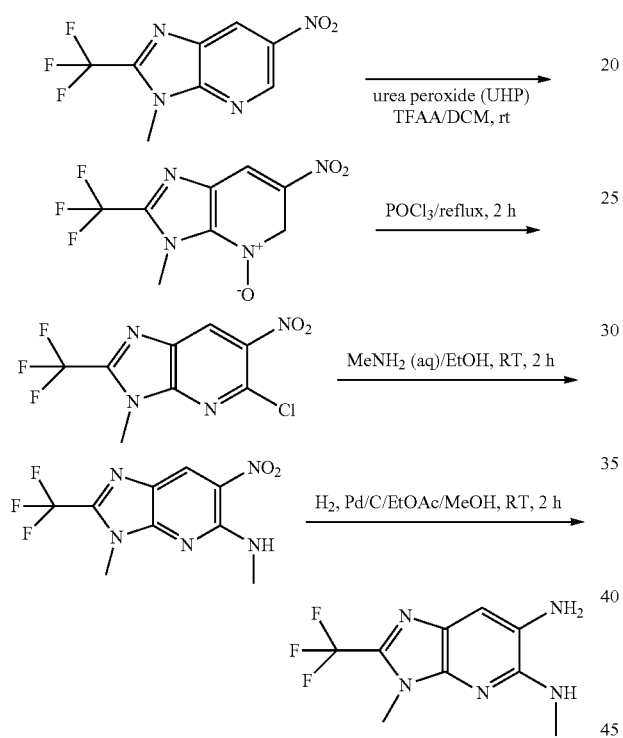
Scheme 14
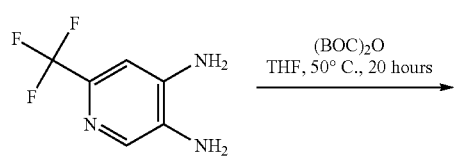
prepared as described in U.S., 7767687
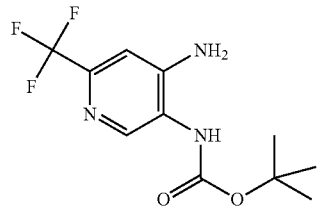
-continued
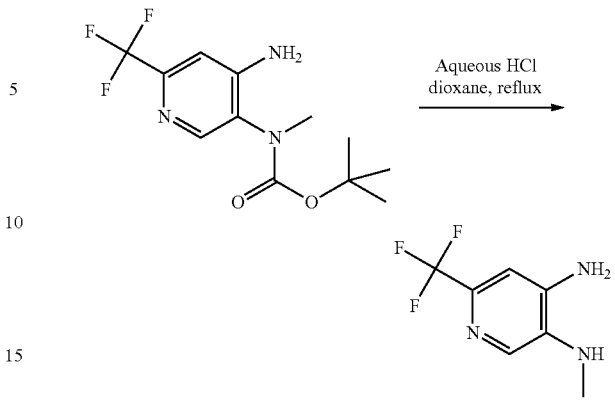
Scheme 15
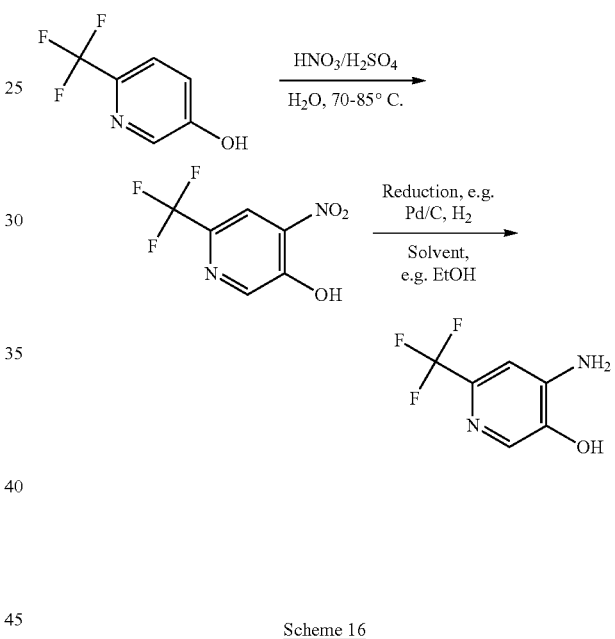
Scheme 16
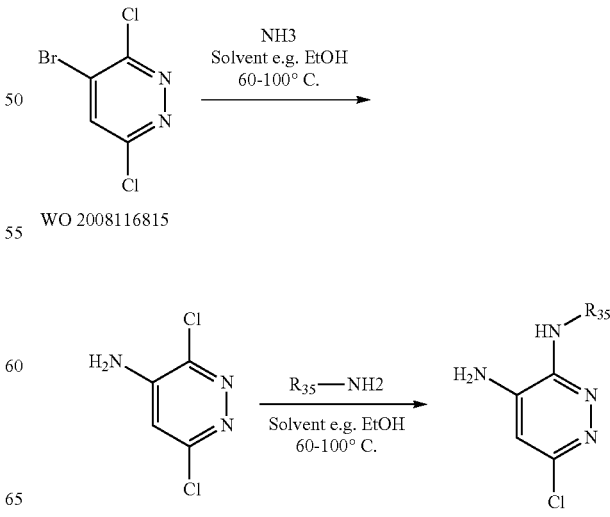
WO 2008116815
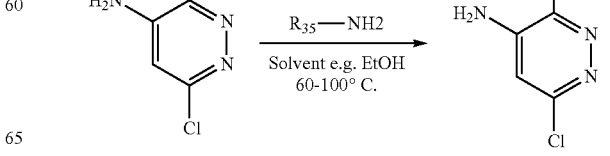

Further syntheses to compounds of formula I are illustrated in the following schemes:

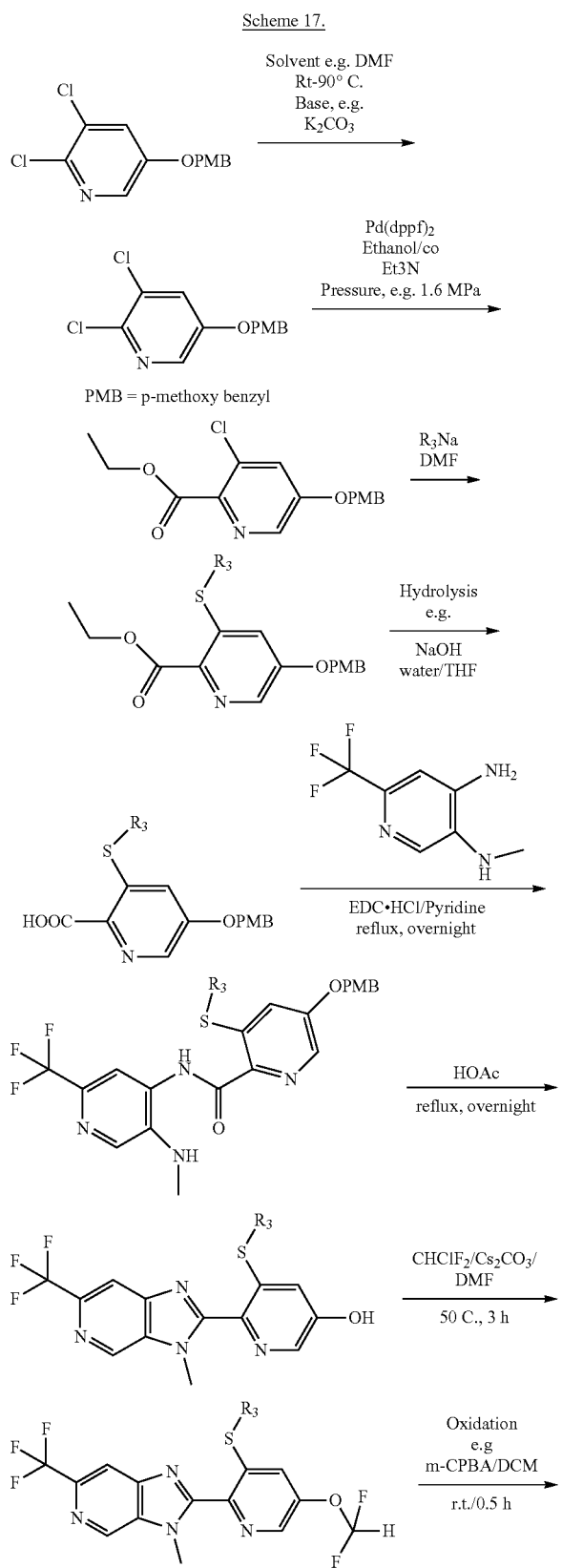

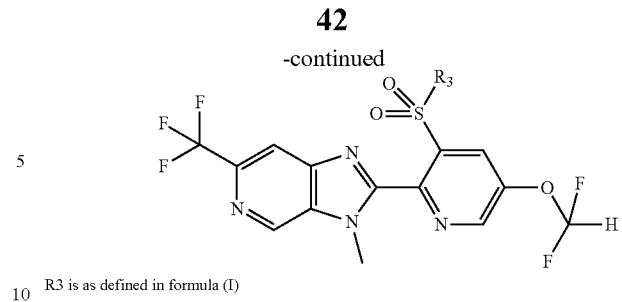

R3 is as defined in formula (I)

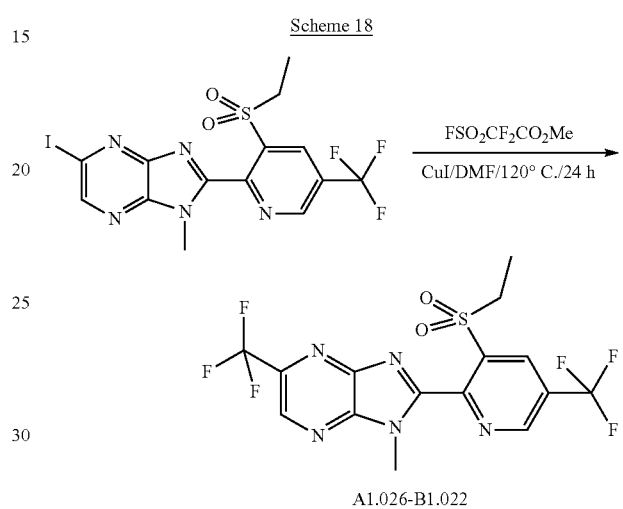

A1.026-B1.022

For preparing all further compounds of the formula (I) functionalized according to the definitions of $A_1$-$A_6$ and $B_1$-$B_{11}$ there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order *Acarina*. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50%.

The compounds of formula I can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula I include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), Lucillia spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Further examples of the above mentioned pests are:

from the order *Acarina*, for example, *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp., *Calipitrimerus* spp., *Chorioptes* spp., *Dermanyssus gallinae, Dermato phagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., Rhizoglyphus spp., *Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order *Diptera*, for example, *Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example, *Acanthocoris scabrator, Acrosternum* spp, *Adelphocoris lineolatus, Amblypelta nitida, Bathycoelia thalassina, Blissus* spp, *Cimex* spp., *Clavigralla to mentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp; *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bacterica cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Per-* egrinus maidis, Perkinsiella spp, Phorodon humuli, Phylloxera spp, Planococcus spp., Pseudaulacaspis spp., Pseudococcus spp., Pseudatomoscelis seriatus, Psylla spp., Pulvinaria aethiopica, Quadraspidiotus spp., Quesada gigas, Recilia dorsalis, Rhopalosiphum spp., Saissetia spp., Scaphoideus spp., Schizaphis spp., Sitobion spp., Sogatella furcifera, Spissistilus festinus, Tarophagus Proserpina, Toxoptera spp, Trialeurodes spp, Tridiscus sporoboli, Trionymus spp, Trioza erytreae, Unaspis citri, Zygina flammigera, Zyginidia scutellaris;

from the order Heteroptera, for example, Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp. and Triatoma spp.;

from the order Homoptera, for example, Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Parlatoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;

from the order Hymenoptera, for example, Acromyrmex, Arge spp, Atta spp., Cephus spp., Diprion spp., Diprionidae, Gilpinia polytoma, Hoplocampa spp., Lasius spp., Monomorium pharaonis, Neodiprion spp., Pogonomyrmex spp, Slenopsis invicta, Solenopsis spp. and Vespa spp.;

from the order Isoptera, for example, Coptotermes spp, Corniternes cumulans, Incisitermes spp, Macrotermes spp, Mastotermes spp, Microtermes spp, Reticulitermes spp.; Solenopsis geminate;

from the order Lepidoptera, for example, Acleris spp., Adoxophyes spp., Aegeria spp., Agrotis spp., Alabama argillaceae, Amylois spp., Anticarsia gemmatalis, Archips spp., Argyresthia spp, Argyrotaenia spp., Autographa spp., Bucculatrix thurberiella, Busseola fusca, Cadra cautella, Carposina nipponensis, Chilo spp., Choristoneura spp., Chrysoteuchia topiaria, Clysia ambiguella, Cnaphalocrocis spp., Cnephasia spp., Cochylis spp., Coleophora spp., Colias lesbia, Cosmophila flava, Crambus spp, Crocidolomia binotalis, Cryptophlebia leucotreta, Cydalima perspectalis, Cydia spp., Diaphania perspectalis, Diatraea spp., Diparopsis castanea, Earias spp., Eldana saccharina, Ephestia spp., Epinotia spp, Estigmene acrea, Etiella zinckinella, Eucosma spp., Eupoecilia ambiguella, Euproctis spp., Euxoa spp., Feltia jaculiferia, Grapholita spp., Hedya nubiferana, Heliothis spp., Hellula undalis, Herpetogramma spp, Hyphantria cunea, Keiferia lycopersicella, Lasmopalpus lignosellus, Leucoptera scitella, Lithocollethis spp., Lobesia botrana, Loxostege bifidalis, Lymantria spp., Lyonetia spp., Malacosoma spp., Mamestra brassicae, Manduca sexta, Mythimna spp, Noctua spp, Operophtera spp., Orniodes indica, Ostrinia nubilalis, Pammene spp., Pandemis spp., Panolis flammea, Papaipema nebris, Pectinophora gossypiela, Perileucoptera coffeella, Pseudaletia unipuncta, Phthorimaea operculella, Pieris rapae, Pieris spp., Plutella xylostella, Prays spp., Pseudoplusia spp, Rachiplusia nu, Richia albicosta, Scirpophaga spp., Sesamia spp., Sparganothis spp., Spodoptera spp., Sylepta derogate, Synanthedon spp., Thaumetopoea spp., Tortrix spp., Trichoplusia ni, Tuta absoluta, and Yponomeuta spp.;

from the order Mallophaga, for example, Damalinea spp. and Trichodectes spp.;

from the order Orthoptera, for example, Blatta spp., Blattella spp., Gryllotalpa spp., Leucophaea maderae, Locusta spp., Neocurtilla hexadactyla, Periplaneta spp., Scapteriscus spp, and Schistocerca spp.;

from the order Psocoptera, for example, Liposcelis spp.;

from the order Siphonaptera, for example, Ceratophyllus spp., Ctenocephalides spp. and Xenopsylla cheopis;

from the order Thysanoptera, for example, Calliothrips phaseoli, Frankliniella spp., Heliothrips spp, Hercinothrips spp., Parthenothrips spp, Scirtothrips aurantii, Sericothrips variabilis, Taeniothrips spp., Thrips spp; and from the order Thysanura, for example, Lepisma saccharina.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, Meloidogyne hapla, Meloidogyne incognita, Meloidogyne javanica, Meloidogyne arenaria and other Meloidogyne species; cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Pin nematodes, Pratylenchus species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; *Deroceras* (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae *Helicigona arbustorum*); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is also to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF (a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (*Diptera*) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium);

NuCOTN 33B® (cotton variety that expresses a CryIA(c) toxin); Bollgard I® (cotton variety that expresses a CryIA(c) toxin); Bollgard II® (cotton variety that expresses a CryIA (c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Crops that exhibit enhanced yield or quality include those with improved flowering or fruit ripening properties (such as delayed ripening); modified oil, starch, amino acid, fatty acid, vitamin, phenolic or other content (such as Vistive™ soybean variety); enhanced nutrient utilisation (such as improved nitrogen assimilation); and enhanced quality plant product (such as higher quality cotton fibre).

Further areas of use of the compounds and compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables AA and BB:

TABLE AA

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
|  | *X. mutilatus* | Hardwoods |
|  | *Tomicus piniperda* | Conifers |

TABLE BB

Examples of native woodborers of economic importance.

| Family | Species | Host or Crop Infested |
|---|---|---|
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chlysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
|  | *Goes tigrinus* | Oak |
|  | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | *Neoptychodes trilineatus* | Fig, Alder, Mulberry, Willow, Netleaf hackberry |
|  | *Oberea ocellata* | Sumac, Apple, Peach, Plum, Pear, Currant, Blackberry |
|  | *Oberea tripunctata* | Dogwood, Viburnum, Elm, Sourwood, Blueberry, Rhododendron, Azalea, Laurel, Poplar, Willow, Mulberry |
|  | *Oncideres cingulata* | Hickory, Pecan, Persimmon, Elm, Sourwood, Basswood, Honeylocust, Dogwood, Eucalyptus, Oak, Hackberry, Maple, Fruit trees |
|  | *Saperda calcarata* | Poplar |
|  | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
|  | *Dendroctonus frontalis* | Pine |
|  | *Dryocoetes betulae* | Birch, Sweetgum, Wild cherry, Beech, Pear |
|  | *Monarthrum fasciatum* | Oak, Maple, Birch, Chestnut, Sweetgum, Blackgum, Poplar, Hickory, Mimosa, Apple, Peach, Pine |
|  | *Phloeotribus liminaris* | Peach, Cherry, Plum, Black cherry, Elm, Mulberry, Mountain-ash |

TABLE BB-continued

Examples of native woodborers of economic importance.

| Family | Species | Host or Crop Infested |
|---|---|---|
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

In the hygiene sector, the compounds and compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order *Diptera* and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds and compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The present invention therefore provides an insecticidal, acaricidal, nematicidal or molluscicidal composition, preferably an insecticidal or acaricidal composition comprising an insecticidally, acaricidally, nematicidally or molluscicidally effective amount of a compound of formula I and a suitable carrier or diluent therefor.

In a further aspect the invention provides a method of combating and controlling pests which comprises applying an insecticidally, acaricidally, nematicidally or molluscicidally effective amount, preferably an insecticidally and acaricidally effective amount of a compound of formula I or a composition comprising a compound of formula I, to a pest, a locus of pest, or to a plant susceptible to attack by a pest, with the exception of a method for treatment of the human or animal body by surgery or therapy and diagnostic methods practised on the human or animal body.

The compounds of formula I are preferably used against insects or acarines.

The term "plant" as used herein includes seedlings, bushes and trees.

The invention also relates to a pesticidal composition, which, in addition to comprising the compound of formula I, comprises formulation adjuvants.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers.

Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo¬lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propy¬lene glycol unit. Examples which may be mentioned are nonylphenoxypolyethoxyethanol, castor oil polyglycol ether, polypropylene glycol/polyethylene oxide adducts, tributylpheno¬xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl) ethyl¬ammonium bromide. Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl¬naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO 01/47356, WO 00/56146, EP-A-0579052 or EP-A-1018299 or are commercially available under their chemical name. Preferred tris-esters of phosphoric acid for use in the new compositions are tris-(2-ethylhexyl) phosphate, tris-n-octyl phosphate and tris-butoxyethyl phosphate, where tris-(2-ethylhexyl) phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tri propylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO 2008/037373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

The term "active ingredient" refers to one of the compounds of formula I, especially the compounds of formula I specifically disclosed in the tables. It also refers to mixtures of the compound of formula I, in particular a compound selected from said Table 1, with other insecticides, fungicides, herbicides, safeners, adjuvants and the like, which mixtures are specifically disclosed below.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO 2008/017388, which can enhance the efficacy of the inventive compounds; or other active ingredients for achieving specific effects, for example ammonium or phosphonium salts, in particular halides, (hydrogen)sulphates, nitrates, (hydrogen)carbonates, citrates, tartrates, formiates and acetates, as described in WO 2007/068427 and WO 2007/068428, which also can enhance the efficacy of the inventive compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries).

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material comprising a compound of formula (I) as defined above are further subjects of the invention. Further methods of application of the compositions according to the invention comprise drip application onto the soil, dipping of parts of plants such as roots bulbs or tubers, drenching the soil, as well as soil injection. These methods are known in the art.

In order to apply a compound of formula I as an insecticide, acaricide, nematicide or molluscicide to a pest, a locus of pest, or to a plant susceptible to attack by a pest, a compound of formula I is usually formulated into a composition which includes, in addition to the compound of formula I, a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting).

As a rule, the compositions comprise 0.1 to 99%, especially 0.1 to 95%, of active ingredient of the formula I and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

When used in a seed dressing, a compound of formula I is used at a rate of 0.0001 g to 10 g (for example 0.001 g or 0.05 g), preferably 0.005 g to 10 g, more preferably 0.005 g to 4 g, per kilogram of seed.

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula I.

Dustable powders (DP) may be prepared by mixing a compound of formula I with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula I with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula I and one or more powdered solid diluents or carriers, or from pre-formed blank granules by absorbing a compound of formula I (or a solution thereof, in a suitable agent) in a porous granular material (such as pumice, attapulgite clays, fuller's earth, kieselguhr, diatomaceous earths or ground corn cobs) or by adsorbing a compound of formula I (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula I in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula I in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula I is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

Oil-based suspension concentrate (OD) may be prepared similarly by suspending finely divided insoluble solid particles of a compound of formula I in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, anti-oxidants, dyestuffs, and/or inert filler materials. An OD is intended and suitable for dilution with water before use to produce a spray solution with sufficient stability to allow spray application through appropriate equipment.

Aerosol formulations comprise a compound of formula I and a suitable propellant (for example n-butane). A compound of formula I may also be dissolved or dispersed in a suitable medium (for example water or a water miscible liquid, such as n-propanol) to provide compositions for use in non-pressurised, hand-actuated spray pumps.

A compound of formula I may be mixed in the dry state with a pyrotechnic mixture to form a composition suitable for generating, in an enclosed space, a smoke containing said compound. Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula I and, optionally, a carrier or diluent therefor. The polymeric shell may be produced by either an interfacial polycondensation reaction or by a coacervation procedure. The compositions may provide for controlled release of the compound of formula I and they may be used for seed treatment. A compound of formula I may also be formulated in a biodegradable polymeric matrix to provide a slow, controlled release of the compound.

A compound of formula I may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above. Compositions for treating seed may include an agent for assisting the adhesion of the composition to the seed (for example a mineral oil or a film-forming barrier).

A composition of the present invention may include one or more additives to improve the biological performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula I may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

A compound of formula I may be used in mixtures with fertilisers (for example nitrogen-, potassium- or phosphorus-containing fertilisers, and more particularly ammonium nitrate and/or urea fertilizers). Suitable formulation types include granules of fertiliser. The mixtures suitably contain up to 25% by weight of the compound of formula I.

Preferred compositions are composed in particular as follows (%=percent by weight):

Emulsifiable Concentrates:
  active ingredient: 1 to 95%, preferably 5 to 20%
  surfactant: 1 to 30%, preferably 10 to 20%
  solvent: 5 to 98%, preferably 70 to 85%

Dusts:
  active ingredient: 0.1 to 10%, preferably 0.1 to 1%
  solid carrier: 99.9 to 90%, preferably 99.9 to 99%

Suspension Concentrates:
  active ingredient: 5 to 75%, preferably 10 to 50%
  water: 94 to 24%, preferably 88 to 30%
  surfactant: 1 to 40%, preferably 2 to 30%

Wettable Powders:
  active ingredient: 0.5 to 90%, preferably 1 to 80%
  surfactant: 0.5 to 20%, preferably 1 to 15%
  solid carrier: 5 to 99%, preferably 15 to 98%

Granulates:
  active ingredient: 0.5 to 30%, preferably 3 to 15%
  solid carrier: 99.5 to 70%, preferably 97 to 85%

PREPARATORY EXAMPLES

"Mpt." means melting point in °C. Free radicals represent methyl groups.

LCMS Methods:

Method (SQD13)

Spectra were recorded on a Mass Spectrometer from Waters (SQD Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method (ZCQ 13):

Spectra were recorded on a Mass Spectrometer from Waters (ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

Method (ZDQ 13):

Spectra were recorded on a Mass Spectrometer from Waters (ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method (ZQ2000):

ZQ2000 Mass Spectrometer from Waters (Single quadrupole mass spectrometer)

Ionisation method: Electrospray

Polarity: positive ions

Capillary (kV) 3.5, Cone (V) 60.00, Extractor (V) 3.00, Source Temperature (° C.) 150, Desolvation Temperature (° C.) 350, Cone Gas Flow (L/Hr) 50, Desolvation Gas Flow (L/Hr) 800

Mass range: 140 to 800 Da

DAD Wavelength range (nm): 210 to 400

Method Waters ACQUITY UPLC with the Following HPLC Gradient Conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

$^1$H and $^{19}$F NMR Measurements: Measured on a Brucker 400 MHz or 300 MHz spectrometer, chemical shifts given in ppm relevant to a TMS standard. Spectra measured in solvents indicated.

Mass Spectroscopy Method MS

LC-20AD Mass Spectrometer from Shimadzu (Single quadrupole mass spectrometer)

Instrument Parameters:

Ionisation method: Electrospray

Polarity: positive and negative ions

Capillary (kV) 1.50

Cone (V) unknown

Extractor (V) 5.00

Source Temperature (° C.) 200

Desolvation Temperature (° C.) 250

Cone gas Flow (l/Hr) 90

Desolvation gas Flow (l/Hr) 90

Mass range: 50 to 1000 Da

Example P1: 2-methyl-7-[3-methyl-6-(trifluoromethyl)imidazo[4,5-b]pyridin-2-yl]-4-(trifluoromethyl)-2,3-dihydrobenzothiophene 1,1-dioxide (Compound A1.014-B2.022)

A1.014-B2.022

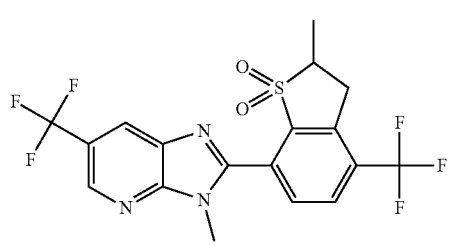

Step A: 2-methyl-N-[2-(methylamino)-5-(trifluoromethyl)-3-pyridyl]-1,1-dioxo-4-(trifluoromethyl)-2,3-dihydrobenzothiophene-7-carboxamide

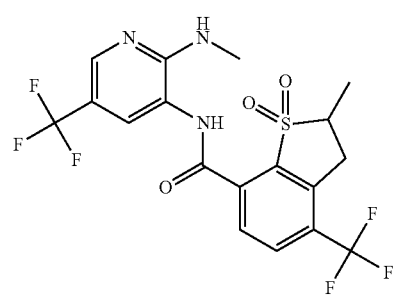 [SMILES: CNc1ncc(C(F)(F)F)cc1NC(=O)c1ccc(C(F)(F)F)c2c1S(=O)(=O)C(C)C2]

A suspension of 2-methyl-1,1-dioxo-4-(trifluoromethyl)-2,3-dihydrobenzothiophene-7-carboxylic acid (308 mg, 1.05 mmol, prepared as described in WO 9909023) and N2-methyl-5-(trifluoromethyl)pyridine-2,3-diamine (200 mg 1.05 mmol, prepared as described in WO 2012/092051) in THF (15 ml) was treated 3-(ethyliminomethyleneamino)-N,N-dimethyl-propan-1-amine (487 mg, 3.14 mmol) and pyridine (100 mg, 1.26 mmol). The reaction mixture was stirred for 18 hours and then diluted with ethyl acetate and 1N HCl. The organic phase was separated and the aqueous phase extracted with ethyl acetate. The combined organic phases were washed with water, dried over anhydrous Na$_2$SO$_4$, filtered and concentrated in vacuo. Purification by flash chromatography eluting with ethyl acetate:cyclohexane 1:1, gave the title product (105 mg, 21%) as a white solid. LCMS (method SQD13): 468 (M+H), retention time 0.97 min.

Step B: 2-methyl-7-[3-methyl-6-(trifluoromethyl)imidazo[4,5-b]pyridin-2-yl]-4-(trifluoromethyl)-2,3-dihydrobenzothiophene 1,1-dioxide (Compound A1.014-B2.022)

A1.014-B2.022

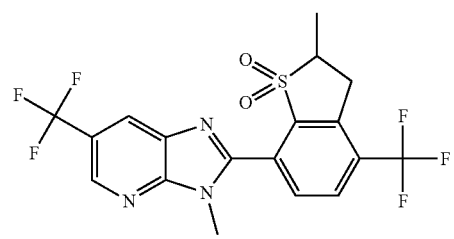

A solution of 2-methyl-N-[2-(methylamino)-5-(trifluoromethyl)-3-pyridyl]-1,1-dioxo-4-(trifluoromethyl)-2,3-dihydrobenzothiophene-7-carboxamide (71 mg, 0.15 mmol) and toluene-4-sulphonic acid (8 mg, 0.05 mmol) dissolved in 1-methylpyrrolidin-2-one (1 ml) was heated at 160° C. for 100 min in the microwave. After this time, the reaction mixture was is poured into water, extracted with ethyl acetate, dried over anhydrous Na$_2$SO$_4$, filtered and concentrated in vacuo. The product obtained was triturated with cyclohexane to give the title compound (45 mg, 66%, as a white solid with mpt. 206° C. LCMS (method SQD13): 450 (M+H), retention time 0.99 min.

¹H NMR (400 MHz, CDCl₃) d' ppm 8.77 (d, J=1.5 Hz, 1H); 8.42 (d, J=1.5 Hz, 1H); 8.05 (d, J=8.1 Hz, 1H); 7.75 (d, J=7.1 Hz, 1H); 3.90 (s, 3H); 3.74 (d, J=16.9, 8.1 Hz, 1H) 3.52-3.68 (m, 1H) 3.19 (dd, J=16.87, 8.1 Hz, 1H); 1.55 ppm (d, J=7.0 Hz, 3H).

Example P2: 4-bromo-2-methyl-7-[3-methyl-6-(trifluoromethyl)imidazo[4,5-b]pyridin-2-yl]-2,3-dihydrobenzothiophene 1,1-dioxide (Compound A1.014-B2.023)

A1.014-B2.023

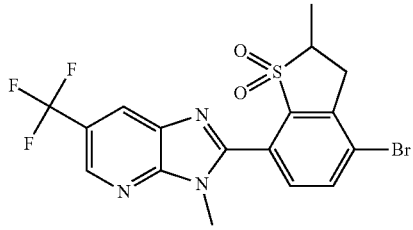

Step A; 4-bromo-2-methyl-N-[2-(methylamino)-5-(trifluoromethyl)-3-pyridyl]-1,1-dioxo-2,3-dihydrobenzothiophene-7-carboxamide

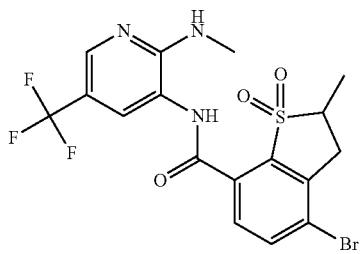 [SMILES: CNc1ncc(C(F)(F)F)cc1NC(=O)c1ccc(Br)c2c1S(=O)(=O)C(C)C2]

A solution of 4-bromo-2-methyl-1,1-dioxo-2,3-dihydrobenzothiophene-7-carboxylic acid (320 mg, 1 mmol, prepared as described in WO 9909023) in dichloromethane (10 ml) was treated with oxallyl chloride (170 mg, 1.3 mmol) and 1-2 drops of DMF at room temperature. After 1 hr, N2-methyl-5-(trifluoromethyl)pyridine-2,3-diamine (200 mg, 1.0 mmol), and triethylamine (100 mg, 1.2 mmol) and were added and the reaction mixture stirred at room temperature until reaction completion. The reaction mixture was diluted with methylene chloride, washed with water, dried over anhydrous Na₂SO₄, filtered and concentrated in vacuo. Purification by flash chromatography eluting with ethyl acetate:cyclohexane 1:1 to give the title compound (240 mg, 48%) as a yellow solid. LCMS (method SQD13): 478/480 (M+H), retention time 0.95 min.

Step B: 4-bromo-2-methyl-7-[3-methyl-6-(trifluoromethyl)imidazo[4,5-b]pyridin-2-yl]-2,3-dihydrobenzothiophene 1,1-dioxide (A1.014-B2.023)

A1.014-B2.023

A solution of 4-bromo-2-methyl-N-[2-(methylamino)-5-(trifluoromethyl)-3-pyridyl]-1,1-dioxo-2,3-dihydrobenzothiophene-7-carboxamide (210 mg, 0.44 mmol) and toluene-4-sulphonic acid (23 mg, 0.13 mmol) dissolved in 1-methylpyrrolidin-2-one (3 ml) was heated at 160° C. for 1 hr in the microwave. After this time, the reaction mixture was poured into water, extracted with ethyl acetate, dried over anhydrous Na₂SO₄, filtered and concentrated in vacuo. Purification by flash chromatography eluting with ethyl acetate:cyclohexane (0/100)->(50/50, gave the title compound as white crystals. LCMS (method SQD13): 460/462 (M+H), retention time 0.97 min.

¹H NMR (400 MHz, CDCl₃) d' ppm 8.76 (d, J=1.10 Hz, 1H); 8.41 (d, J=1.1 Hz, 1H); 8.22 (d, J=7.70 Hz, 1H); 7.73 (d, J=7.70 Hz, 1H); 4.02 (dd, J=17.8, 7.5 Hz, 1H); 3.44-3.60 (m, 1H); 3.35 (dd, J=17.8, 7.5 Hz, 1H); 2.74 (s, 3H) 1.51 ppm (d, J=7.0 Hz, 3H).

Example P3: 2-[4-ethylsulfonyl-6-(trifluoromethyl)pyridazin-3-yl]-3-methyl-6-(trifluoromethyl)imidazo[4,5-b]pyridine (A1.014-B1.058)

A1.014-B1.058

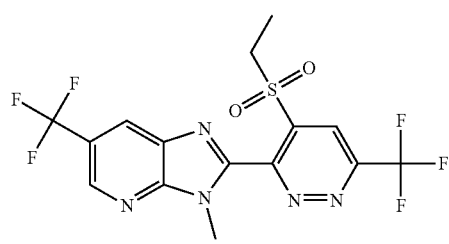

Step A: 5-ethylsulfanyl-3-(trifluoromethyl)-1H-pyridazin-6-one

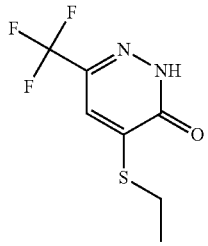

EtSNa (100 mg, 1.2 mmol) was added to a solution of 5-bromo-3-(trifluoromethyl)-1H-pyridazin-6-one (243 mg, 1 mmol, Prepared as described in WO 2008128995) in 10 ml of DMF. After the addition, the mixture was stirred at room temperature for 2 hours. Then the mixture was poured into water and extracted with ethyl acetate three times. The combined organic layers were dried over sodium sulfate, filtered and concentrated under reduced pressure. The residue was purified by column chromatography on silica gel to give 5-ethylsulfanyl-3-(trifluoromethyl)-1H-pyridazin-6-one (182 mg, 81%). $^1$H NMR (300 Mz, DMSO-$d_6$): δ: 1.27 (t, 3H), 3.00 (q, 2H), 7.38 (s, 1H), 13.63 (s, 1H); $^{19}$F NMR (400 MHz, DMSO-$d_6$): δ −65.49 (s, 3F); ESI-MS: 223 (M−H)$^-$.

Step B: 3-chloro-4-ethylsulfanyl-6-(trifluoromethyl) pyridazine

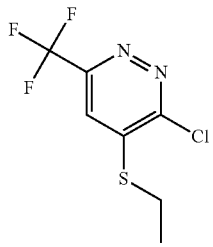

A mixture of 5-ethylsulfanyl-3-(trifluoromethyl)-1H-pyridazin-6-one (5.8 g, 26 mmol) in 25 ml of POCl$_3$ was refluxed for 16 h. Then, the reaction mixture was cooled to room temperature and POCl$_3$ was distilled off under reduced pressure. The residue was poured into water and adjusted to alkaline with sodium hydroxide. The resulting mixture was extracted with ethyl acetate three times. The combined organic layers were dried over sodium sulfate, filtered and concentrated under reduced pressure. The crude product was purified by column chromatography on silica gel to give 3-chloro-4-ethylsulfanyl-6-(trifluoromethyl)pyridazine (4.9 g, 79%). $^1$H NMR (300 Mz, DMSO-$d_6$): δ 1.31 (t, 3H), 3.23 (q, 2H), 8.00 (s, 1H); $^1$F NMR (300 Mz, DMSO-$d_6$): δ −65.19 (s, 3F); ESI-MS(+): 243 (M+H)$^+$.

Step C: methyl 4-ethylsulfanyl-6-(trifluoromethyl) pyridazine-3-carboxylate

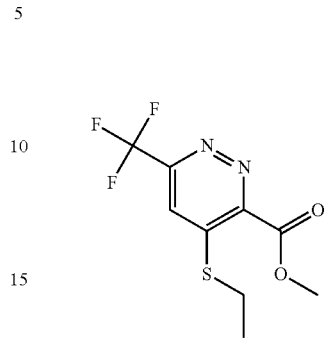

Carbon monoxide gas was introduced to a mixture of 3-chloro-4-ethylsulfanyl-6-(trifluoromethyl)pyridazine (2.5 g, 10 mmol), Pd(OAc)$_2$ (232 mg, 0.1 mmol), dppf (572 mg, 0.1 mmol) and Et$_3$N (3.1 g, 30 mmol) in 30 ml of MeOH, and the internal pressure was increased to 1.5 MPa. Then, the reaction was stirred at 80° C. for 16 h. The reaction mixture was cooled to room temperature and concentrated under reduced pressure. The residue was purified by column chromatography on silica gel to give methyl 4-ethylsulfanyl-6-(trifluoromethyl)pyridazine-3-carboxylate (1.0 g, 37%). $^1$H NMR (300 Mz, DMSO-$d_6$): δ 1.28 (t, 3H), 3.19 (q, 2H), 3.99 (s, 3H), 8.01 (s, 1H); $^{19}$F NMR (300 Mz, DMSO-$d_6$): δ −65.61 (s, 3F); ESI-MS(+): 267 (M+H)$^+$, 289 (M+Na)$^+$.

Step D: 4-ethylsulfanyl-6-(trifluoromethyl) pyridazine-3-carboxylic Acid

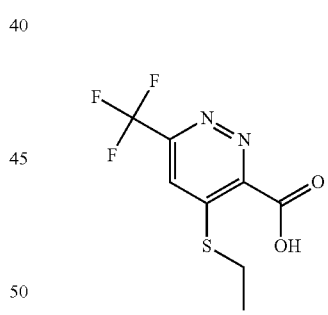

A mixture of methyl 4-ethylsulfanyl-6-(trifluoromethyl)pyridazine-3-carboxylate (532 mg, 2 mmol) and LiOH (96 mg, 4 mmol) in 30 ml of THF and 6 ml of H$_2$O was stirred at room temperature for 30 min. Then the mixture was poured into water and adjusted PH to 3-4 with diluted hydrochloric acid. The resulting mixture was extracted with ethyl acetate three times. The combined organic layers were dried over sodium sulfate, filtered and concentrated under reduced pressure to afford 4-ethylsulfanyl-6-(trifluoromethyl)pyridazine-3-carboxylic acid (398 mg, 79%). $^1$H NMR (300 Mz, DMSO-$d_6$): δ 1.22 (t, 3H), 3.16 (q, 2H), 8.03 (s, 1H); $^{19}$F NMR (300 Mz, DMSO-$d_6$): δ −65.52 (s, 3F); ESI-MS(−): 267 (M−H)$^-$.

Step E: 4-ethylsulfanyl-N-[2-(methylamino)-5-(trifluoromethyl)-3-pyridyl]-6-(trifluoromethyl)pyridazine-3-carboxamide

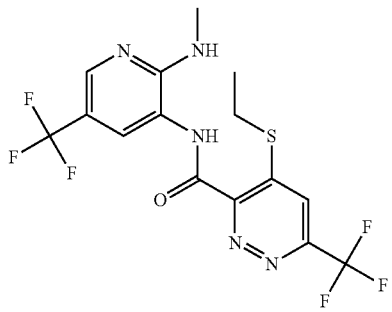 [SMILES: CCSc1cc(C(F)(F)F)nnc1C(=O)Nc1cc(C(F)(F)F)cnc1NC]

A mixture 4-ethylsulfanyl-6-(trifluoromethyl)pyridazine-3-carboxylic acid (230 mg, 0.9 mmol), N2-methyl-5-(trifluoromethyl)pyridine-2,3-diamine (209 mg, 1.1 mmol, prepared as described in WO 2012092051), HATU (520 mg, 1.4 mmol), DIPEA (235 mg, 1.8 mmol) in 20 ml of DMF was stirred at room temperature for 16 h. Then the mixture was poured into water and extracted with ethyl acetate three times. The combined organic layers were dried over sodium sulfate, filtered and concentrated in vacuo. The residue was purified by column chromatography on silica gel to give 4-ethylsulfanyl-N-[2-(methylamino)-5-(trifluoromethyl)-3-pyridyl]-6-(trifluoromethyl)pyridazine-3-carboxamide (369 mg, 95%). $^1$H NMR (300 Mz, DMSO-$d_6$): δ 1.30 (t, 3H), 2.87 (d, 3H), 3.12 (q, 2H), 7.03 (s, 1H), 7.77 (s, 1H), 8.07 (s, 1H), 8.33 (s, 1H), 10.54 (s, 1H); $^{19}$F NMR (300 Mz, DMSO-$d_6$): δ: −65.43 (s, 3F), −58.81 (s, 3F); ESI-MS(+): 426 (M+H)$^+$.

Step D: 2-[4-ethylsulfanyl-6-(trifluoromethyl)pyridazin-3-yl]-3-methyl-6-(trifluoromethyl)imidazo[4,5-b]pyridine (Compound A1.014-B1.050)

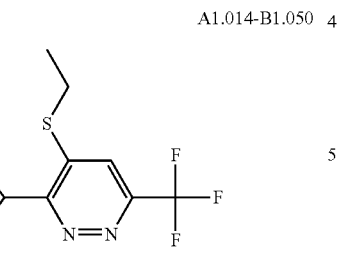

4-ethylsulfanyl-N-[2-(methylamino)-5-(trifluoromethyl)-3-pyridyl]-6-(trifluoromethyl)pyridazine-3-carboxamide (369 mg, 0.9 mmol) in 10 ml of AcOH was refluxed for 2 hours. Then the reaction mixture was concentrated in vacuo. The residue was purified by flash column chromatography on silica gel to give 2-[4-ethylsulfanyl-6-(trifluoromethyl)pyridazin-3-yl]-3-methyl-6-(trifluoromethyl)imidazo[4,5-b]pyridine (compound A1.014-B1.050, 181 mg, 51%). $^1$H NMR (300 Mz, DMSO-$d_6$): δ 1.27 (t, 3H), 3.20 (q, 2H), 4.07 (s, 1H), 8.12 (s, 1H). 8.75 (s, 1H), 8.93 (s, 1H); $^{19}$F NMR (300 Mz, DMSO-$d_6$): δ −66.44 (s, 3F), −58.33 (s, 3F); ESI-MS(+): 408 (M+H)$^+$.)$^+$. Mpt. 149-156° C. LCMS (SQD13) Rt. 1.12 min, 408 (M+H).

Step E: 2-[4-ethylsulfonyl-6-(trifluoromethyl)pyridazin-3-yl]-3-methyl-6-(trifluoromethyl)imidazo[4,5-b]pyridine (A1.014-B1.058)

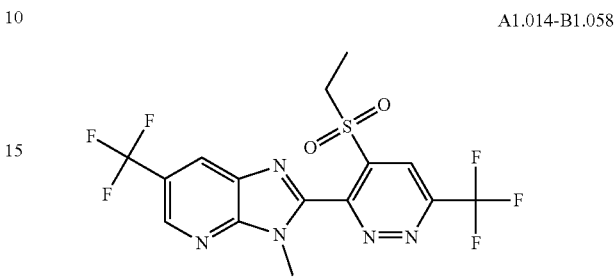

A mixture of 2-[4-ethylsulfanyl-6-(trifluoromethyl)pyridazin-3-yl]-3-methyl-6-(trifluoromethyl)imidazo[4,5-b]pyridine (109 mg, 0.3 mmol) and m-CPBA (232 mg, 1.3 mmol) in 20 ml of CH$_2$Cl$_2$ was stirred at room temperature for 2 h. Then the mixture was washed with saturated sodium sulfite, aqueous sodium bicarbonate and dried over sodium sulfate. After filtration, the solvent was concentrated under reduced pressure. The residue was purified by flash chromatography on silica gel to afford the title compound (compound A1.014-B1.058) (113 mg, 96%). $^1$HNMR (300 Mz, DMSO-$d_6$): δ 1.26 (t, 3H), 3.91 (s, 3H), 3.94 (q, 2H), 8.77 (s, 1H), 8.79 (s, 1H), 8.97 (s, 1H); $^{19}$F-NMR (300 Mz, DMSO-$d_6$): δ −65.30 (s, 3F), −58.32 (s, 3F); ESI-MS(+): 440 (M+H)$^+$.) Mpt. 172-174° C. LCMS (ZCQ13) Rt. 1.06 min, 440 (M+H).

Example P4: 5-ethylsulfonyl-4-[3-methyl-6-(trifluoromethyl)imidazo[4,5-c]pyridin-2-yl]thiazole (V13.05)

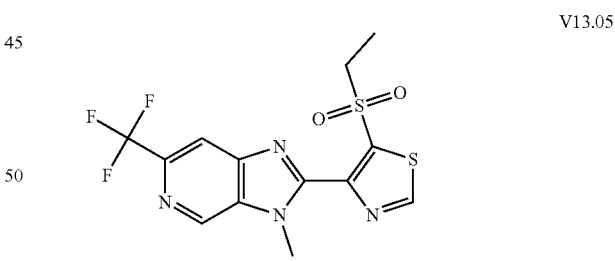

Step A ethyl 5-ethylsulfanylthiazole-4-carboxylate

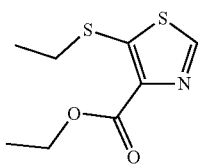

A solution of ethyl isocyanoacetate (5.6 g, 0.05 mol) in 100 ml of THF was added dropwise to a suspension of potassium t-butoxide (6.1 g, 0.055 mol) in 20 ml of THF at −40° C. After the addition, the mixture was cooled to −60° C., carbon disulfide (3.8 g, 0.05 mol) was added dropwise while keeping the temperature below −50° C. Then, the mixture was warmed to 10° C. and ethyl bromide (5.4 g, 0.05 mol) was added. The mixture was stirred for another 2 h and concentrated in vacuo. The residue was purified by column chromatography on silica gel to afford the compound ethyl 5-ethylsulfanylthiazole-4-carboxylate (5.6 g, 52%). $^1$H NMR (300 MHz, DMSO-d$_6$): δ1.27-1.37 (m, 6H), 3.03 (q, 2H), 4.25 (q, 2H), 8.97 (s, 1H); ESI-MS(+): 218 (M+H)$^+$, 240 (M+Na)$^+$.

Step B: 5-ethylsulfanylthiazole-4-carboxylic Acid

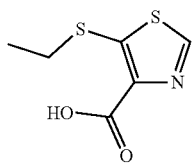

A mixture of ethyl 5-ethylsulfanylthiazole-4-carboxylate (4.6 g, 0.02 mol) and NaOH (1.68 mg, 0.04 mol) in 25 ml of water and 50 ml of THF was stirred at room temperature overnight. Then, the reaction mixture was poured into diluted hydrochloric acid. Then, the deposited precipitate was filtered, washed with water, dried under reduced pressure to obtain the title compound (3.9 g, 90%). $^1$H NMR (300 MHz, DMSO-d$_6$): δ 1.32 (t, 3H), 3.00 (q, 2H), 8.94 (s, 1H), 12.94 (br s, 1H); ESI-MS(+): 190 (M+H)$^+$, 212 (M+Na)$^+$; HPLC: 99.9%.

Step C: tert-butyl N-[4-amino-6-(trifluoromethyl)-3-pyridyl]carbamate

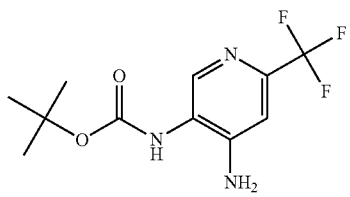

To a solution of 6-(trifluoromethyl)pyridine-3,4-diamine (3.14 g, 17.73 mmol, prepared as described in U.S. Pat. No. 7,767,687) in THF (50 ml) was added tert-butoxycarbonyl tert-butyl carbonate (4.64 g, 21.27 mmol) and the mixture was stirred at 50° C. After 8 hours, a further 1.1 g (5.0 mmol) of tert-butoxycarbonyl tert-butyl carbonate was added, and stirring at 50° C. continued for a further 4 hours. The reaction mixture was then concentrated in vacuo, and the brown residue was suspended in dichloromethane, filtered and dried in vacuo to give the title compound as white crystals. LCMS (method SQD13): Ret. Time 0.79 min, 278 (M+H).

Step D: tert-butyl N-[4-amino-6-(trifluoromethyl)-3-pyridyl]-N-methyl-carbamate

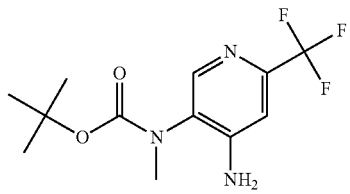 [SMILES: CN(C(=O)OC(C)(C)C)c1cnc(C(F)(F)F)cc1N]

To a stirred suspension of sodium hydride (0.648 g, 14.85 mmol) in 30 ml DMF, tert-butyl N-[4-amino-6-(trifluoromethyl)-3-pyridyl]carbamate (3.92 g, 14.14 mmol) dissolved in 20 ml DMF was added dropwise over a period of 20 min at 20-25° C. After 15 min stirring at RT, iodomethane (2.21 g, 15.55 mmol) was added. After 30 min at ambient temperature the mixture was poured onto 200 ml water, extracted twice with ethyl acetate, and the combined organic fractions washed successively with water and brine, dried over Na$_2$SO$_4$ and concentrated in vacuo. The crude product was recrystallised from Ethyl acetate/Heptane to give the title compound (3.18 g) as white crystals. LCMS (method SQD13): ret. time 0.85 min, 292 (M+H).

Step E:
N3-methyl-6-(trifluoromethyl)pyridine-3,4-diamine

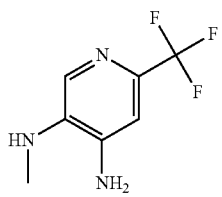

To a clear, colourless solution of tert-butyl N-[4-amino-6-(trifluoromethyl)-3-pyridyl]-N-methyl-carbamate (3.53 g, 12.119 mmol) in dioxan, hydrogen chloride (18 ml of a 2M solution in water, 36.36 mmol) was added and the mixture was heated to reflux. After gas evolution had ceased, the reaction mixture was cooled to room temperature, and treated with solid sodium hydrogen carbonate (3.1 g, 36.9 mmol). The slurry was diluted with water and extracted twice with ethyl acetate. The combined organic layers were washed successively with water and brine, dried over Na$_2$SO$_4$ and concentrated in vacuo to give 2.25 g of the title compound as colourless crystals, Mpt, 138-140° C.; LCMS (method SQD13): ret. Time 0.24 min, 192 (M+H).

Alternatively, N3-methyl-6-(trifluoromethyl)pyridine-3,4-diamine can be obtained by the following procedure:

To a solution of 6-(trifluoromethyl)pyridine-3,4-diamine (2.0 g, 12.2 mmol) and potassium carbonate (3.2 g, 23.1 mmol) in acetonitrile (10 mL) was added iodomethane (0.8 mL). The reaction mixture was stirred at 30° C. overnight. Potassium carbonate was filtered off; the filtrate was dried in vacuo and purified with chromatography column on silica gel (petroleum:EtOAc=4:3) to afford the title compound as a light yellow solid (0.32 g, yield: 37%). $^1$H NMR (400 MHz, DMSO-d$_6$): δ (ppm) 7.57 (s, 1H), 6.83 (s, 1H), 5.82

(s, 2H), 5.23 (d, J=4.8 Hz, 1H), 2.80 (d, J=4.8 Hz, 3H). $^{19}$F NMR (300 MHz, DMSO-d6): δ (ppm) −60.12 (s, 3F). ESI-MS(+): 192 (M+H).

Step F: 5-ethylsulfanyl-4-[3-methyl-6-(trifluoromethyl)imidazo[4,5-c]pyridin-2-yl]thiazole (Compound A6.002-B7.037)

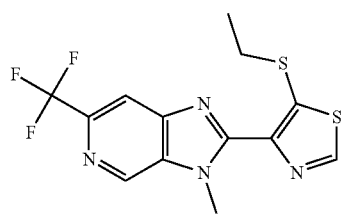

A6.002-B7.037

A mixture of 5-ethylsulfanylthiazole-4-carboxylic acid (567 mg, 3 mmol), N3-methyl-6-(trifluoromethyl)pyridine-3,4-diamine (483 mg, 3 mmol) and N-(3-Dimethylaminopropyl)-N'-ethylcarbodiimide hydrochloride (EDC.HCL) (576 mg, 3.6 mmol) in 20 ml of pyridine was refluxed for 16 h. The reaction mixture was concentrated in vacuo and purified by column chromatography on silica gel to give title compound (120 mg), 5-ethylsulfanyl-N-[5-(methylamino)-2-(trifluoromethyl)-4-pyridyl]thiazole-4-carboxamide (51 mg and), and N-[4-amino-6-(trifluoromethyl)-3-pyridyl]-5-ethylsulfanyl-N-methyl-thiazole-4-carboxamide (162 mg). The latter two compounds were dissolved in 10 ml of AcOH and refluxed for 16 h. Then the mixture was concentrated in vacuo and the residue was purified by column chromatography on silica gel to give additional title compound (140 mg). $^1$H NMR (400 MHz, DMSO-d$_6$): δ 1.34 (t, 3H), 3.08 (q, 2H), 4.23 (s, 3H), 8.20 (s, 1H), 9.17 (s, 1H), 9.27 (s, 1H); $^{19}$F-NMR (400 MHz, DMSO-d$_6$): δ −59.68 (s, 3F); ESI-MS: 345 (M+H)$^+$, 367 (M+Na)$^+$; Mpt. 167-169° C.

Step G: 5-ethylsulfonyl-4-[3-methyl-6-(trifluoromethyl)imidazo[4,5-c]pyridin-2-yl]thiazole (V13.05)

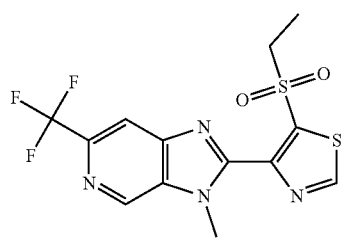

V13.05

5-ethylsulfanyl-4-[3-methyl-6-(trifluoromethyl)imidazo[4,5-c]pyridin-2-yl]thiazole (140 mg, 0.4 mmol) and m-CPBA (280 mg, 1.6 mmol) in 10 ml of dichloromethane was stirred at room temperature for 0.5 h. Then the mixture was poured into a saturated solution of Na$_2$CO$_3$ and Na$_2$SO$_3$ in water, and extracted with ethyl acetate three times. The combined organic layers were dried over sodium sulfate, filtered and concentrated in vacuo. The residue was purified by column chromatography on silica gel to give the title compound (147 mg, 96%). $^1$H NMR (400 MHz, DMSO-d$_6$): δ 1.28 (t, 3H), 4.04 (q, 2H), 4.05 (s, 3H), 8.32 (s, 1H), 9.29 (s, 1H), 9.70 (s, 1H); $^{19}$F-NMR (400 MHz, DMSO-d$_6$): δ −58.84 (s, 3F); ESI-MS(+): 377 (M+H)$^+$, 399 (M+Na)$^+$; LCMS (method SQD13) Rt. 0.85 min 377 (M+H). Mpt. 178-179° C.

Example P5: 2-[5-(difluoromethoxy)-3-ethylsulfonyl-2-pyridyl]-3-methyl-6-(trifluoromethyl)imidazo[4,5-c]pyridine (Compound V12.19)

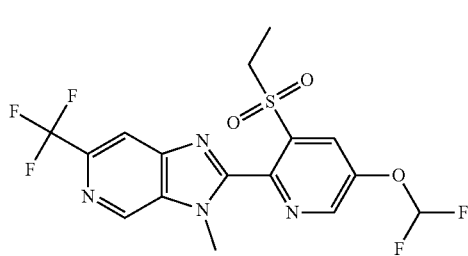

V12.19

Step A: 2,3-Dichloro-5-[(4-methoxyphenyl)methoxy]pyridine

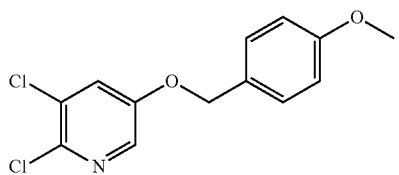 [SMILES: COc1ccc(COc2cnc(Cl)c(Cl)c2)cc1]

A mixture 5,6-dichloropyridin-3-ol (8.2 g, 50 mmol), 4-Methoxybenzylchloride (11.8 g, 75 mmol) and K$_2$CO$_3$ (21.0 g, 150 mmol) in CH$_3$CN (250 ml) was refluxed for 6 h. Then, the mixture was cooled to room temperature and filtered. The filtrate was concentrated under reduced pressure and the residue was purified by column chromatography on silica gel to give the title compound (10.0 g, 70% yield) as a white solid. $^1$H NMR (400 MHz, DMSO-d$_6$): δ 3.72 (s, 3H), 5.09 (s, 2H), 6.92 (d, J=8.8 Hz, 2H), 7.35 (d, J=8.8 Hz, 2H), 7.89 (d, J=2.8 Hz, 1H), 8.15 (d, J=2.8 Hz, 1H); ESI-MS (+): 284 (M+H)$^+$; Mpt.: 124~125° C.

Step B: Ethyl 3-chloro-5-[(4-methoxyphenyl)methoxy]pyridine-2-carboxylate

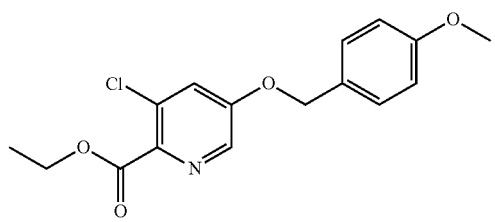 [SMILES: CCOC(=O)c1ncc(OCc2ccc(OC)cc2)cc1Cl]

CO gas was introduced to a mixture of 2,3-dichloro-5-[(4-methoxyphenyl)methoxy]pyridine (10.0 g, 35.2 mmol), dppf (975 mg, 1.8 mmol), Pd(OAc)$_2$ (158 mg, 0.7 mmol) and Et$_3$N (10.2 ml, 70.4 mmol) in 110 ml of EtOH, and the internal pressure was increased to 1.6 MPa. The reaction mixture was stirred at 125° C. for about 7 hours. Then, the mixture was cooled to room temperature and filtered. The filtrate was concentrated under reduced pressure and the residue was purified by column chromatography on silica gel to afford the title compound (6.8 g, 60% yield) as a light yellow solid. ¹H NMR (400 MHz, DMSO-d₆): δ 1.26 (t, J=6.8 Hz, 3H), 3.72 (s, 3H), 4.28 (q, J=6.8 Hz, 2H), 5.15 (s, 2H), 6.92 (d, J=8.0 Hz, 2H), 7.37 (d, J=8.0 Hz, 2H), 7.76 (d, J=2.0 Hz, 1H), 8.32 (d, J=2.0 Hz, 1H); ESI-MS (+): 322 (M+H)⁺, 345 (M+Na)⁺; Mp: 45-46° C.

Step C: Ethyl 3-ethylsulfanyl-5-[(4-methoxyphenyl)methoxy]pyridine-2-carboxylate

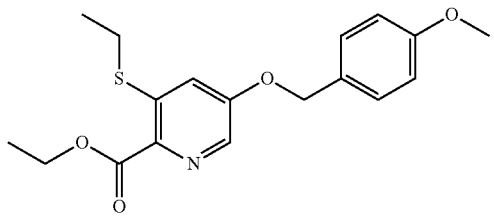 [SMILES: CCOC(=O)c1ncc(OCc2ccc(OC)cc2)cc1SCC]

A mixture of ethyl 3-chloro-5-[(4-methoxyphenyl)methoxy]pyridine-2-carboxylate (6.4 g, 0.02 mol) and EtSNa (3.35 g, 0.04 mol) in 50 ml of DMF was stirred at 90° C. for 4 h. Then, the mixture was poured into water, and extracted with ethyl acetate three times. The combined organic layers were dried over sodium sulfate, filtered and concentrated under reduced pressure. The residue was purified by column chromatography on silica gel to give the title compound (3 g, 43% yield). ¹H NMR (400 MHz, DMSO-d₆): δ 1.22 (t, 3H), 1.29 (t, 3H), 2.97 (q, 2H), 3.76 (s, 3H), 4.27 (q, 2H), 5.24 (s, 2H), 6.96 (d, 2H), 7.34 (d, 1H), 7.41 (d, 2H), 8.15 (d, 1H); ESI-MS(+): 370 (M+Na)⁺.

Step D: 3-Ethylsulfanyl-5-[(4-methoxyphenyl)methoxy]pyridine-2-carboxylic Acid

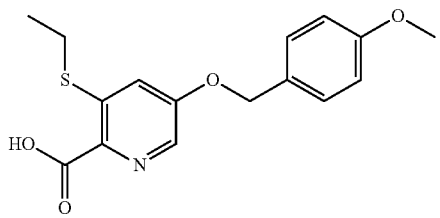 [SMILES: CCSc1cc(OCc2ccc(OC)cc2)cnc1C(=O)O]

A mixture of ethyl-3-ethylsulfanyl-5-[(4-methoxyphenyl)methoxy]pyridine-2-carboxylate (3 g, 0.009 mol) and NaOH (692 mg, 0.017 mol) in 10 ml of water and 30 ml of THF was stirred at room temperature overnight. Then, the reaction mixture was poured into diluted hydrochloric acid and extracted with ethyl acetate three times. The combined organic layers were dried over sodium sulfate, filtered and concentrated in vacuo. The residue was purified by flash column chromatography on silica gel to provide the title compound (2.3 g, 83% yield). ¹H NMR (400 MHz, DMSO-d₆): δ 1.23 (t, 3H), 2.94 (q, 2H), 3.76 (s, 3H), 5.24 (s, 2H), 6.96 (d, 2H), 7.32 (d, 1H), 7.41 (d, 2H), 8.13 (d, 1H), 12.69 (br s, 1H); ESI-MS(+): 320 (M+H)⁺, 342 (M+Na)⁺.

Step E: 3-Ethylsulfanyl-5-[(4-methoxyphenyl)methoxy]-N-[5-(methylamino)-2-(trifluoromethyl)-4-pyridyl]pyridine-2-carboxamide

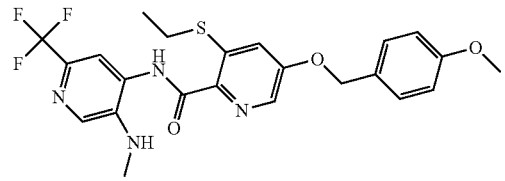 [SMILES: CCSc1cc(OCc2ccc(OC)cc2)cnc1C(=O)Nc1cc(C(F)(F)F)ncc1NC]

A mixture of compound 3-ethylsulfanyl-5-[(4-methoxyphenyl)methoxy]pyridine-2-carboxylic acid (284 mg, 0.89 mmol), N3-methyl-6-(trifluoromethyl)pyridine-3,4-diamine (149 mg, 0.89 mmol, prepared as described in step E, example P4) and EDC.HCl (188 mg, 0.98 mmol) in 10 ml of pyridine was refluxed for 16 h. Then, the mixture was concentrated in vacuo, diluted with water, and extracted with ethyl acetate. The combined organic layers were dried over Na₂SO₄, concentrated under reduced pressure to give crude title product (320 mg), which was directly used for the next step without further purification.

Step F: 5-ethylsulfanyl-6-[3-methyl-6-(trifluoromethyl)imidazo[4,5-c]pyridin-2-yl]pyridin-3-ol

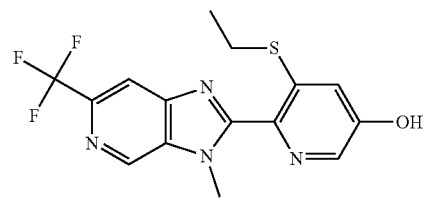 [SMILES: CCSc1cc(O)cnc1-c1nc2cc(C(F)(F)F)ncc2n1C]

3-Ethylsulfanyl-5-[(4-methoxyphenyl)methoxy]-N-[5-(methylamino)-2-(trifluoromethyl)-4-pyridyl]pyridine-2-carboxamide (320 mg) in 10 ml of AcOH was refluxed for 16 h. Then the mixture was concentrated in vacuo and the residue was purified by column chromatography on silica gel to give the title compound (151 mg). ¹H-NMR (400 MHz, DMSO-d₆): δ 1.18 (t, 3H), 2.91 (q, 2H), 3.96 (s, 3H), 7.34 (d, 1H), 8.11 (d, 1H), 8.22 (s, 1H), 9.18 (s, 1H), 10.74 (s, 1H); ¹⁹F-NMR (400 MHz, DMSO-d₆): δ −64.84 (s, 3F); ESI-MS(+): 355 (M+H)⁺.

Step G: 2-[5-(difluoromethoxy)-3-ethylsulfanyl-2-pyridyl]-3-methyl-6-(trifluoromethyl)imidazo[4,5-c]pyridine

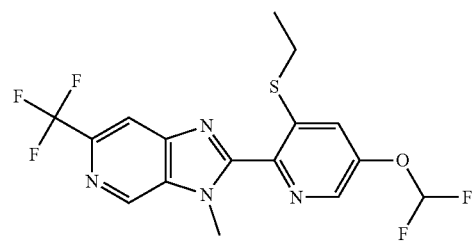 [SMILES: CCSc1cc(OC(F)F)cnc1-c1nc2cc(C(F)(F)F)ncc2n1C]

At 50° C., CHClF₂ gas was introduced to a mixture of 5-ethylsulfanyl-6-[3-methyl-6-(trifluoromethyl)imidazo[4,5-c]pyridin-2-yl]pyridin-3-ol (100 mg, 0.28 mmol) and Cs₂CO₃ (460 mg, 1.41 mmol) in 10 ml of DMF for 2 hours. Then, the mixture was poured into water, and extracted with ethyl acetate three times. The combined organic layers were dried over sodium sulfate, filtered and concentrated in vacuo. The residue was purified by column chromatography on silica gel to give the title product (94 mg, 82%). ¹H NMR (400 MHz, DMSO-d₆): δ 1.35 (t, 3H), 2.93 (q, 2H), 4.07 (s, 3H), 6.67 (t, 1H), 7.52 (d, 1H), 8.19 (s, 1H), 8.36 (d, 1H), 8.95 (s, 1H); ¹⁹F-NMR (400 MHz, DMSO-d₆): δ −81.81 (d, 1F), −66.25 (s, 3F); ESI-MS(+): 405 (M+H)⁺, 427 (M+Na)⁺, 459 (M+MeOH+Na)⁺; HPLC: 98.2%

Step H: 2-[5-(difluoromethoxy)-3-ethylsulfonyl-2-pyridyl]-3-methyl-6-(trifluoromethyl)imidazo[4,5-c]pyridine (Compound V12.19)

V12.19

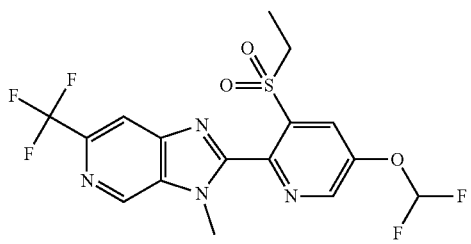

2-[5-(difluoromethoxy)-3-ethylsulfanyl-2-pyridyl]-3-methyl-6-(trifluoromethyl)imidazo[4,5-c]pyridine (80 mg, 0.2 mmol) and m-CPBA (136 mg, 0.8 mmol) in 5 ml of dichloromethane was stirred at room temperature for 0.5 h. Then the mixture was poured into a saturated aqueous solution of Na₂CO₃ and Na₂SO₃, and extracted with ethyl acetate three times. The combined organic layers were dried over sodium sulfate, filtered and concentrated in vacuo. The residue was purified by column chromatography on silica gel to give the title compound (67 mg, 88%). ¹H NMR (400 MHz, DMSO-d₆): δ 1.19 (m, 3H), 3.78 (d, 3H), 3.90 (s, 3H), 6.77 (t, 1H), 8.11 (s, 2H), 8.30 (d, 1H), 8.86 (d, 1H), 9.00 (s, 1H); ¹⁹F-NMR (400 MHz, DMSO-d₆): δ −78.62 (d, 1F), −62.07 (s, 3F); ESI-MS(+): 437 (M+H)⁺. Mpt. 146-148° C.; LCMS (method SQD13): Ret. Time 1.03 mins, 405 (M+H).

Example P6: 6-(2-Ethanesulfonyl-6-trifluoromethyl-pyridin-3-yl)-3-methyl-2-trifluoromethyl-3,5-di-hydro-diimidazo[4,5-b;4',5'-e]pyridine (Compound V26.03)

V26.03

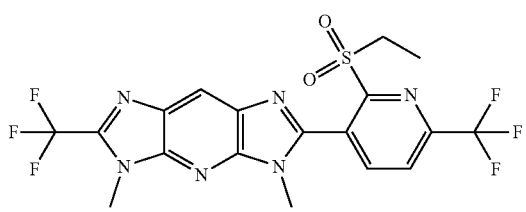

Step A: 3-methyl-6-nitro-2-(trifluoromethyl)imidazo[4,5-b]pyridine

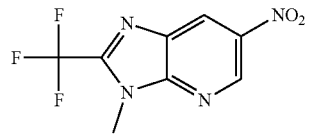 [SMILES: Cn1c(C(F)(F)F)nc2cc([N+](=O)[O-])cnc21]

N2-methyl-5-nitro-pyridine-2,3-diamine (10 g, 59.52 mmol) in TFA (10 mL) was stirred at 70° C. for 16 h. The mixture was purified by chromatography on silica to get the pure title compound (9.81 g, 67%) as yellow solid. ¹HNMR (300 MHz, d6-DMSO): δ 9.46 (d, J=2.4 Hz, 1H), 9.22 (d, J=2.4 Hz, 1H), 4.04 (s, 3H).

Step B: 3-methyl-6-nitro-4-oxido-2-(trifluoromethyl)imidazo[4,5-b]pyridin-4-ium

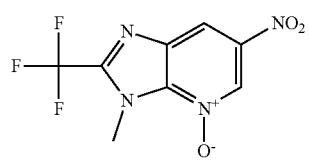 [SMILES: Cn1c(C(F)(F)F)nc2cc([N+](=O)[O-])c[n+]([O-])c21]

To a solution of 3-methyl-6-nitro-2-(trifluoromethyl)imidazo[4,5-b]pyridine (5.3 g, 21.54 mmol) in dichloromethanedichloromethane (60 mL) was added urea hydrogen peroxide (UHP, 6.17 g, 65.7 mmol), cooled with ice bath, and dropwise added TFAA (13.6 g, 65.7 mmol). The mixture was stirred at ambient temperature for 18 hours. TCL showed about 50% of starting material consumed. Another batch of UHP (6.08 g, 64.63 mmol) and TFAA (13.8 g, 64.63 mmol) was added at 0° C. The mixture was stirred at ambient temperature for another 24 hours. The reaction mixture was diluted with water, stirred and for 20 min. The organic phase was separated and the aqueous phase was back extracted with dichloromethane (3 times). The combined organic phases were washed with water and brine, dried over Na₂SO₄, and concentrated in vacuo. The residue was purified by chromatography on silica to give the title compound as a white solid (1.91 g). ¹HNMR (300 MHz, d6-DMSO): δ 9.17 (d, J=1.8 Hz, 1H), 8.83 (d, J=1.8 Hz, 1H), 4.41 (d, J=1.2 Hz, 3H).

Step C: 5-chloro-3-methyl-6-nitro-2-(trifluoromethyl)imidazo[4,5-b]pyridine

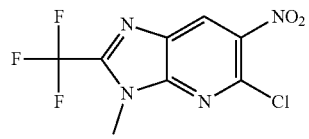 [SMILES: Cn1c(C(F)(F)F)nc2cc([N+](=O)[O-])c(Cl)nc21]

3-methyl-6-nitro-4-oxido-2-(trifluoromethyl)imidazo[4,5-b]pyridin-4-ium (2.8 g, 10.69 mmol) was dissolved in POCl₃ (50 mL), and stirred at reflux for 2 hours. The mixture was poured into ice water, extracted with EtOAc (3 times). The organic phase was washed with NaHCO₃ (aq) and Step D: N5,3-dimethyl-6-nitro-2-(trifluoromethyl)
imidazo[4,5-b]pyridin-5-amine

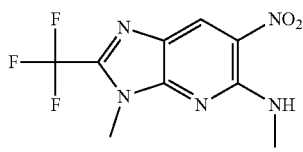 [SMILES: CNc1nc2c(cc1[N+](=O)[O-])nc(C(F)(F)F)n2C]

To a solution of compound 5-chloro-3-methyl-6-nitro-2-(trifluoromethyl)imidazo[4,5-b]pyridine (3.8 g) in ethanol (40 mL) was added MeNH$_2$ (aq, 5 mL). The reaction mixture was stirred at ambient temperature for 18 hours. The mixture was filtered, and dried in vacuo to get the pure title compound (2.3 g) as a white solid. $^1$HNMR (300 MHz, d6-DMSO): δ 8.90 (s, 1H), 8.64-8.62 (m, 1H), 3.79 (d, J=1.2 Hz, 3H), 3.07 (d, J=4.8 Hz, 3H).

Step E: N5,3-dimethyl-2-(trifluoromethyl)imidazo
[4,5-b]pyridine-5,6-diamine

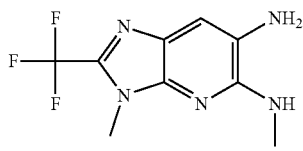 [SMILES: CNc1nc2c(cc1N)nc(C(F)(F)F)n2C]

To a solution of compound N5,3-dimethyl-6-nitro-2-(trifluoromethyl)imidazo[4,5-b]pyridin-5-amine (2.3 g, 8.36 mmol) in EtOAc (30 mL) and methanol (30 mL) was added 200 mg of palladium on carbon under N$_2$. The mixture was hydrogenated using a hydrogen balloon at rt for 4 h. The mixture was filtered through celite and the filtrate was evaporated to dryness. The residue was purified by chromatography on silica to give the title compound (1.6 g, 78%) as a purple solid. $^1$HNMR (300 MHz, d6-DMSO): δ 7.01 (s, 1H), 6.29 (d, J=3.3 Hz, 1H), 4.69 (s, 2H), 3.77 (d, J=1.2 Hz, 3H), 2.92 (d, J=4.5 Hz, 3H).

Step F:
3-bromo-2-chloro-6-(trifluoromethyl)pyridine

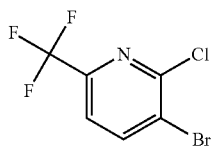

A mixture of compound 2-chloro-6-(trifluoromethyl)pyridin-3-amine (5.88 g, 30 mmol, prepared as described in WO 2009110475), isoamyl nitrite (7.02 g, 60 mmol), p-TsOH (6.19 g, 36 mmol), TBAB (19.32 g, 60 mmol) and CuBr$_2$ (1.40 g, 6 mmol) in 60 ml of MeCN was stirred at room temperature for 4 h. Then, the mixture was concentrated in vacuo and the residue was purified by column chromatography on silica gel to give the title compound (5.85 g, 75%). $^1$H-NMR (300 Mz, DMSO-d$_6$): δ 7.85 (d, 1H), 8.52 (s, 1H); $^{19}$F-NMR (300 Mz, DMSO-d$_6$): δ −65.72 (s, 3F).

Step G: 3-bromo-2-ethylsulfanyl-6-(trifluoromethyl)
pyridine

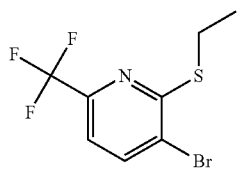

A mixture of 3-bromo-2-chloro-6-(trifluoromethyl)pyridine (5.98 g, 23 mmol) and EtSNa (1.93 g, 23 mmol) in 50 ml of MeCN was stirred for 2 h. Then, the mixture was poured into dilute hydrochloric acid and extracted with ethyl acetate three times. The combined organic layers were dried over sodium sulfate, filtered and concentrated in vacuo. The residue was purified by column chromatography on silica gel to give the title compound (4.06 g, 58%). $^1$H-NMR (300 Mz, DMSO-d$_6$): δ 1.26 (t, 3H), 3.08 (q, 2H), 7.50 (d, 1H), 8.20 (d, 1H); $^{19}$F-NMR (300 Mz, DMSO-d$_6$): δ −65.45 (s, 3F).

Step H: ethyl 2-ethylsulfanyl-6-(trifluoromethyl)
pyridine-3-carboxylate

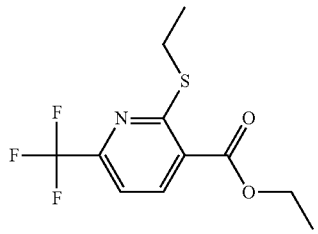 [SMILES: CCOC(=O)c1ccc(C(F)(F)F)nc1SCC]

Carbon monoxide gas was introduced to a mixture of 3-bromo-2-ethylsulfanyl-6-(trifluoromethyl)pyridine (572 mg, 2 mmol), Pd(OAc)$_2$ (90 mg, 0.4 mmol), dppf (444 mg, 0.8 mmol) and Et$_3$N (1.01 g, 10 mmol) in 10 ml of EtOH and 10 ml of DMF and the internal pressure was raised to 2.7 MPa. The mixture was heated at 90° C. for 6 h and cooled to room temperature. Then, it was poured into water and extracted with ethyl acetate three times. The combined organic layers were dried over sodium sulfate, filtered and concentrated in vacuo. The residue was purified by column chromatography on silica gel to give the title compound (795 mg, 88%). $^1$H-NMR (300 Mz, DMSO-d$_6$): δ 1.23 (t, 3H), 1.28 (t, 3H), 3.05 (q, 2H), 4.29 (q, 2H), 7.66 (d, 1H), 8.39 (d, 1H); $^{19}$F-NMR (300 Mz, DMSO-d$_6$): δ −62.88 (s, 3F).

Step I: 2-ethylsulfanyl-6-(trifluoromethyl)pyridine-3-carboxylic Acid

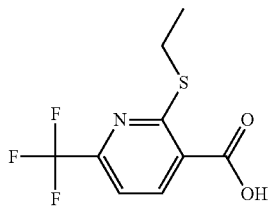 [SMILES: CCSc1nc(C(F)(F)F)ccc1C(=O)O]

A mixture of ethyl 2-ethylsulfanyl-6-(trifluoromethyl) pyridine-3-carboxylate (480 mg, 1.7 mmol) and KOH (482 mg, 8.6 mmol) in 10 ml of water and 10 ml of THF was stirred at room temperature for 16 h. The reaction mixture was poured into diluted hydrochloric acid and extracted with ethyl acetate. The combined organic layers were dried over sodium sulfate, filtered and concentrated in vacuo. The residue was purified by column chromatography on silica gel to provide the title compound (430 mg, 90%). $^1$H-NMR (300 Mz, DMSO-d$_6$): δ 1.23 (t, 3H), 3.02 (q, 2H), 7.64 (d, 1H), 8.37 (d, 1H), 13.85 (br s, 1H); $^{19}$F-NMR (300 Mz, DMSO-d$_6$): δ −62.78 (s, 3F); ESI-MS(−): 250 (M−H)$^-$.

Step J: 2-ethylsulfanyl-N-[3-methyl-5-(methyl-amino)-2-(trifluoromethyl)imidazo[4,5-b]pyridin-6-yl]-6-(trifluoromethyl)pyridine-3-carboxamide

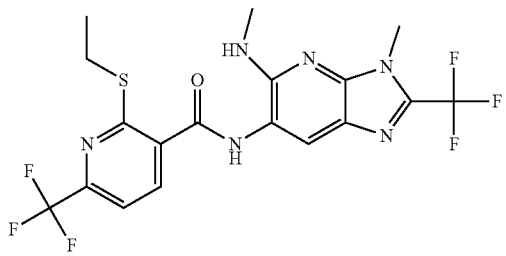 [SMILES: CCSc1nc(C(F)(F)F)ccc1C(=O)Nc1cc2nc(C(F)(F)F)n(C)c2nc1NC]

A mixture of 2-ethylsulfanyl-6-(trifluoromethyl)pyridine-3-carboxylic acid (251 mg, 1 mmol), N5,3-dimethyl-2-(trifluoromethyl)imidazo[4,5-b]pyridine-5,6-diamine (245 mg, 1.0 mmol, product from step E in this example), HATU (570 mg, 1.5 mmol) and DIPEA (258 mg, 2 mmol) in 10 ml of DMF was stirred for 16 h. The mixture was concentrated in vacuo and purified by column chromatography on silica gel to give the title compound (408 mg, 84%). $^1$H NMR (300 Mz, DMSO-d$_6$): δ 1.26 (t, 3H), 2.91 (d, 3H), 3.07 (q, 2H), 3.83 (s, 3H), 6.69 (q, 1H), 7.76 (d, 1H), 7.80 (s, 1H), 8.44 (d, 1H), 9.97 (s, 1H); $^{19}$F NMR (300 Mz, DMSO-d$_6$): δ −62.50 (s, 3F), −57.02 (s, 3F).

Step K: 6-(2-Ethylsulfanyl-6-trifluoromethyl-pyridin-3-yl)-3-methyl-2-trifluoromethyl-3,5-dihydro-diimidazo[4,5-; 4',5'-e]pyridine

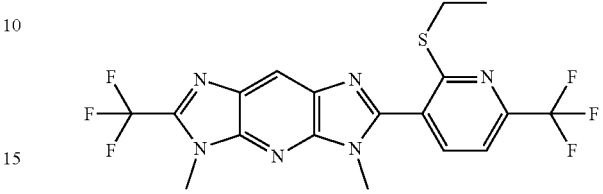

A mixture of 2-ethylsulfanyl-N-[3-methyl-5-(methyl-amino)-2-(trifluoromethyl)imidazo[4,5-b]pyridin-6-yl]-6-(trifluoromethyl)pyridine-3-carboxamide (382 mg, 0.8 mmol) in 10 ml of AcOH was refluxed for 2 h, Then the mixture was concentrated in vacuo and the residue was purified by column chromatography on silica gel to give the title compound (231 mg, 63%). $^1$H-NMR (300 Mz, CDCl$_3$): δ 1.33 (t, 3H), 3.22 (q, 2H), 3.85 (s, 3H), 4.09 (s, 3H), 7.51 (d, 1H), 7.86 (d, 1H), 8.59 (d, 1H); $^{19}$F NMR (300 Mz, CDCl$_3$): δ −68.64 (s, 3F), −63.72 (s, 3F); ESI-MS(+): 461 (M+H)$^+$, 483 (M+Na)$^+$. Mpt. 154-156° C.; LCMS; Ret. Time 1.13 mins, 461 (M+H)

Step L: 6-(2-Ethanesulfonyl-6-trifluoromethyl-pyridin-3-yl)-3-methyl-2-trifluoromethyl-3,5-dihydro-diimidazo[4,5-b: 4',5'-e]pyridine (Compound V26.03)

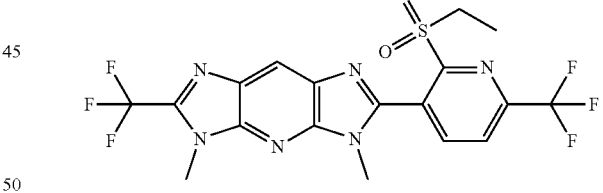

A mixture of 6-(2-ethylsulfanyl-6-trifluoromethyl-pyridin-3-yl)-3-methyl-2-trifluoromethyl-3,5-dihydro-diimidazo[4,5-; 4',5'-e]pyridine (161 mg, 0.35 mmol) and m-CPBA (242 mg, 1.4 mmol) in 10 ml of dichloromethane was stirred at room temperature for 2 h. Then the mixture was poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by column chromatography on silica gel to give the title compound as a white solid (163 mg, 94%). $^1$H NMR (300 Mz, CDCl$_3$): δ 1.30 (t, 3H), 3.53 (q, 2H), 3.85 (s, 3H), 4.09 (s, 3H), 8.08 (d, 1H), 8.30 (d, 1H), 8.54 (s, 1H); $^{19}$F NMR (300 Mz, CDCl$_3$): δ −63.78 (s, 3F), −59.57 (s, 3F); ESI-MS: 493 (M+H)$^+$, 515 (M+Na)$^+$. Mpt. 197-199° C.; LCMS (method SQD13): Ret. Time 0.95 mins, 493 (M+H).

Example P7: 4-Ethylsulfonyl-5-[3-methyl-6-(trifluoromethyl)imidazo[4,5-c]pyridin-2-yl]-2-(trifluoromethyl)thiazole (Compound V14.05)

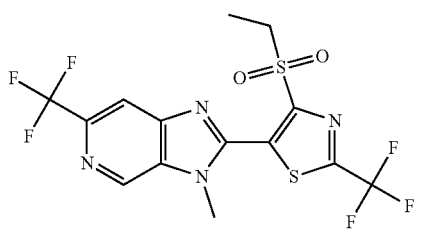

V14.05

Step A: 4-bromo-2-(trifluoromethyl)thiazole

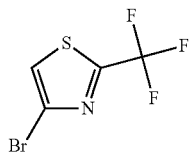

A mixture of 2,4-dibromothiazole (24.3 g, 0.1 mol), $FSO_2CF_2COOCH_3$ (23.0 g, 0.12 mmol) and CuI (19.0 g, 0.1 mol) in 200 ml of DMF was heated for 4 hours at 100° C. Then, the reaction mixture was poured into water and the title compound (22.9 g, 83%) was distilled off at water pump pressure. The product was used without further purification in the next step.

Step B:
4-bromo-2-(trifluoromethyl)thiazole-5-carboxylic Acid

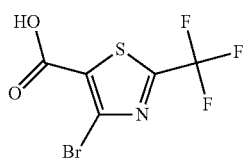 [SMILES: O=C(O)c1sc(C(F)(F)F)nc1Br]

At 60° C., n-BuLi (2.5M in hexane, 62 mmol) was slowly added to i-$Pr_2NH$ (6 g, 59 mmol) in 150 ml of anhydrous THF under a nitrogen atmosphere. After the addition, the mixture was stirred at the same temperature for another 0.5 hours. Then, 4-bromo-2-(trifluoromethyl)thiazole (12 g, 52.0 mmol) was slowly added to the above mixture and stirring was continued for 20 min. The mixture was poured into dry ice and stirred for a further hour. The reaction mixture was allowed to warm to ambient temperature, diluted with ethyl acetate and the organic phase washed successively with water and saturated brine, dried over sodium sulfate, filtered and concentrated under vacuum to give the title product (10.1 g, 71%).

Step C:
4-bromo-2-(trifluoromethyl)thiazole-5-carbonyl Chloride

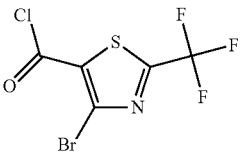 [SMILES: O=C(Cl)c1sc(C(F)(F)F)nc1Br]

A mixture of 4-bromo-2-(trifluoromethyl)thiazole-5-carboxylic acid (276 mg, 1 mmol) in 10 ml of $SOCl_2$ was refluxed for 4 hours. The excess $SOCl_2$ was distilled off to give the crude title product (295 mg) which was directly used in the next step without further purification.

Step D: 4-bromo-5-[3-methyl-6-(trifluoromethyl)imidazo[4,5-c]pyridin-2-yl]-2-(trifluoromethyl)thiazole

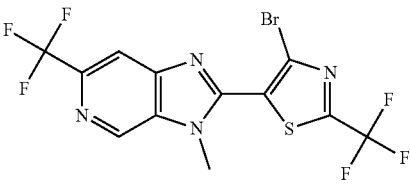 [SMILES: Cn1c(-c2sc(C(F)(F)F)nc2Br)nc2cc(C(F)(F)F)ncc21]

A mixture of 4-bromo-2-(trifluoromethyl)thiazole-5-carbonyl chloride (477 mg, 1.7 mmol) and N3-methyl-6-(trifluoromethyl)pyridine-3,4-diamine (330 mg, 1.7 mmol, prepared as described in step E, example P4) in 10 ml of toluene was refluxed for 16 h. The reaction mixture was then concentrated in vacuo and the residue purified by column chromatography on silica gel to give the title compound (358 mg, 44%). $^1$H NMR (300 Mz, DMSO-$d_6$): δ: 3.98 (s, 3H), 8.30 (s, 1H), 9.28 (s, 1H); $^{19}$F NMR (300 Mz, DMSO-$d_6$): δ −61.58 (s, 3F), −57.88 (s, 3F); ESI-MS: 433 (M+H)$^+$.

Step E: 4-Ethylsulfanyl-5-[3-methyl-6-(trifluoromethyl)imidazo[4,5-c]pyridin-2-yl]-2-(trifluoromethyl)thiazole

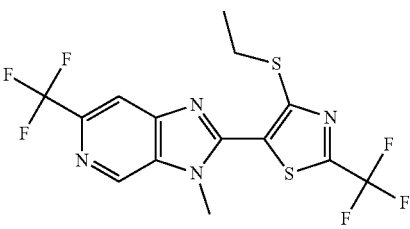 [SMILES: CCSc1nc(C(F)(F)F)sc1-c1nc2cc(C(F)(F)F)ncc2n1C]

EtSNa (123 mg, 1.5 mmol) was added to a mixture of 4-bromo-5-[3-methyl-6-(trifluoromethyl)imidazo[4,5-c]pyridin-2-yl]-2-(trifluoromethyl)thiazole (315 mg, 0.7 mmol) in 10 ml of DMF. After the addition, the mixture was stirred at room temperature for 2 hours. Then the mixture was poured into water and extracted with ethyl acetate three times. The combined organic layers were dried over sodium sulfate, filtered and concentrated under reduced pressure. The crude product was purified by column chromatography on silica gel to give the title compound (176 mg, 58%). $^1$H NMR (300 Mz, DMSO-d$_6$): δ 1.25 (t, 3H), 3.18 (q, 2H), 4.02 (s, 3H), 8.25 (s, 1H), 9.24 (s, 1H); $^{19}$F NMR (300 Mz, DMSO-d$_6$): δ −59.80 (s, 3F), −55.95 (s, 3F); ESI-MS: 413 (M+H)$^+$. LCMS (method SQD13): Rt. 1.12 mins, 413 (M+H) Mpt. 92-94° C.

Step F: 4-ethylsulfonyl-5-[3-methyl-6-(trifluoromethyl)imidazo[4,5-c]pyridin-2-yl]-2-(trifluoromethyl)thiazole (Compound V14.05)

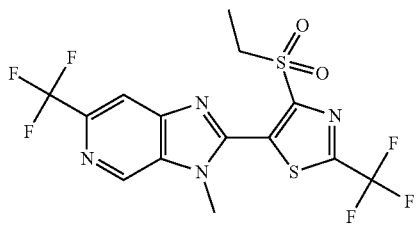

V14.05

A mixture of 4-ethylsulfanyl-5-[3-methyl-6-(trifluoromethyl)imidazo[4,5-c]pyridin-2-yl]-2-(trifluoromethyl)thiazole (109 mg, 0.3 mmol) and m-CPBA (228 mg, 1.3 mmol) in 15 ml of CH$_2$Cl$_2$ was stirred for 2 h at room temperature. The reaction mixture was diluted with saturated sodium sulfite and aqueous sodium bicarbonate, and the organic layer separated, dried over sodium sulfate, filtered and concentrated in vacuo. The residue was purified by flash chromatography on silica gel to give the title compound (71 mg, 61%). $^1$H NMR (300 Mz, DMSO-d$_6$): δ 1.16 (t, 3H), 3.51 (q, 2H), 3.89 (s, 3H), 8.28 (s, 1H), 9.27 (s, 1H); $^{19}$F NMR (300 Mz, DMSO-d$_6$): δ −59.81 (s, 3F), −55.74 (s, 3F); ESI-MS: 445 (M+H)$^+$, 467 (M+Na)$^+$, 499 (M+MeOH+Na)$^+$.

Example P8: 4-ethylsulfonyl-2-(trifluoromethyl)-5-[7-(trifluoromethyl)imidazo[1,2-a]pyridin-2-yl]thiazole (Compound V2.11)

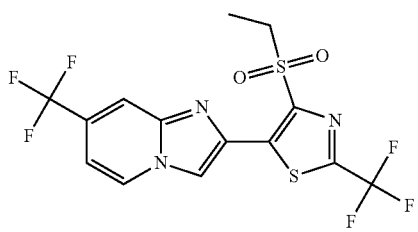

V2.11

Step A: 4-bromo-N-methoxy-N-methyl-2-(trifluoromethyl)thiazole-5-carboxamide

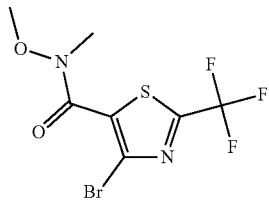 [SMILES: CON(C)C(=O)c1sc(C(F)(F)F)nc1Br]

A mixture of 4-bromo-2-(trifluoromethyl)thiazole-5-carboxylic acid (5.8 g, 21 mmol, prepared as described as described in Step B, example P7), N,O-dimethylhydroxylamine hydrochloride (2.5 g, 25 mmol), HATU (9.6 g, 25 mmol), and DIPEA (5.4 g, 42 mmol) in 35 ml of DMF was stirred at room temperature for 16 h. The mixture was poured into water and extracted with ethyl acetate three times. The combined organic layers were dried over sodium sulfate, filtered and concentrated in vacuo. The residue was purified by column chromatography on silica gel to give the title compound (4.7 g, 70%). $^1$H NMR (300 Mz, DMSO-d$_6$): δ 3.27 (s, 3H), 3.68 (s, 3H); $^{19}$F NMR (300 Mz, DMSO-d$_6$): δ −56.33 (s, 3F); ESI-MS: 341 (M+Na)$^+$.

Step B: 1-[4-bromo-2-(trifluoromethyl)thiazol-5-yl]ethanone

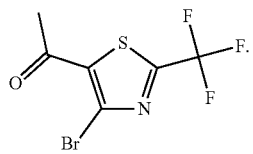

MeMgBr (3M in THF, 15 ml, 45 mmol) was added dropwise to a solution of 4-bromo-N-methoxy-N-methyl-2-(trifluoromethyl)thiazole-5-carboxamide (5.7 g, 21 mmol) in 30 ml of dry THF under nitrogen atmosphere at 0° C. After the addition, the mixture was allowed to warm to ambient temperature and stirred for 30 min. The mixture was then poured into diluted hydrochloric acid and extracted with ethyl acetate three times. The combined organic layers were dried over sodium sulfate, filtered and concentrated in vacuo. The residue was purified by flash chromatography on silica gel to give the title product (4.8 g, 86%). $^1$H NMR (300 Mz, DMSO-d$_6$): δ 2.68 (s, 3H); $^{19}$F NMR (300 Mz, DMSO-d$_6$): δ −66.14 (s, 3F).

Step C: 4-bromo-2-(trifluoromethyl)-5-[7-(trifluoromethyl)imidazo[1,2-a]pyridin-2-yl]thiazole

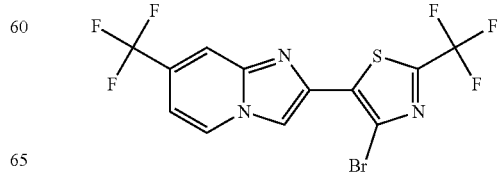

A mixture of 1-[4-bromo-2-(trifluoromethyl)thiazol-5-yl]ethanone (220 mg, 1 mmol), 2-amino-4-(trifluoromethyl)pyridine (193 mg, 1.2 mmol, prepared as described in WO 2011090122), Cu(OAc)$_2$·H$_2$O (12 mg, 0.1 mmol), 1,10-Phenanthroline (18 mg, 0.1 mmol), ZnI$_2$ (32 mg, 0.1 mmol) in 12 ml of dichlorobenzene was stirred at 120° C. for 16 h under an air atmosphere. The mixture was concentrated in vacuo and the residue was purified by column chromatography on silica gel to give the title compound (153 mg, 36%). $^1$H NMR (300 Mz, DMSO-d$_6$): δ 7.25 (d, 1H), 8.12 (s, 1H), 8.84 (d, 1H), 8.96 (s, 1H); $^{19}$F NMR (300 Mz, DMSO-d$_6$): δ −64.34 (s, 3F), −62.89 (s, 3F); ESI-MS(−): 414 (M−H)$^−$; HPLC: 97.7%.

Step D: 4-ethylsulfanyl-2-(trifluoromethyl)-5-[7-(trifluoromethyl)imidazo[1,2-a]pyridin-2-yl]thiazole

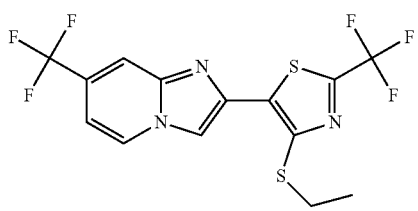 [SMILES: CCSc1nc(C(F)(F)F)sc1-c1cn2ccc(C(F)(F)F)cc2n1]

EtSNa (157 mg, 1.9 mmol) was added to a mixture of 4-bromo-2-(trifluoromethyl)-5-[7-(trifluoromethyl)imidazo[1,2-a]pyridin-2-yl]thiazole (389 mg, 0.9 mmol) in 15 ml of DMF. After the addition, the mixture was stirred at ambient temperature for 2 hours. The reaction mixture was then poured into water and extracted with ethyl acetate three times. The combined organic layers were dried over sodium sulfate, filtered and concentrated in vacuo. The residue was purified by column chromatography on silica gel to give the title compound (281 mg, 76%). $^1$H NMR (300 Mz, DMSO-d$_6$): δ 1.28 (t, 3H), 3.23 (q, 2H), 7.24 (d, 1H), 8.11 (s, 1H), 8.75 (s, 1H), 8.86 (d, 1H); $^{19}$F NMR (300 Mz, DMSO-d$_6$): δ −66.81 (s, 3F), −65.09 (s, 3F); ESI-MS(+): 398 (M+H)$^+$; HPLC: 96.3%.

Step E: 4-ethylsulfonyl-2-(trifluoromethyl)-5-[7-(trifluoromethyl)imidazo[1,2-a]pyridin-2-yl]thiazole (Compound V2.11)

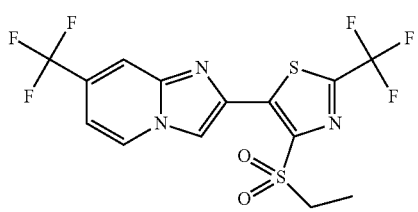

A mixture of 4-ethylsulfanyl-2-(trifluoromethyl)-5-[7-(trifluoromethyl)imidazo[1,2-a]pyridin-2-yl]thiazole (80 mg, 0.2 mmol) and m-CPBA (105 mg, 0.6 mmol) in 10 ml of CH$_2$Cl$_2$ was stirred at ambient temperature for 2 hours. Then the mixture was washed with saturated sodium sulfite and aqueous sodium bicarbonate. The organic layer was dried over sodium sulfate, filtered and concentrated in vacuo. The residue was purified by flash chromatography on silica gel to give the title compound (66 mg, 77%). $^1$H NMR (300 Mz, DMSO-d$_6$): δ 1.22 (t, 3H), 3.57 (q, 2H), 7.27 (d, 1H), 8.16 (s, 1H), 8.94 (d, 2H); $^{19}$F NMR (300 Mz, DMSO-d$_6$): δ −48.60 (s, 3F), −50.52 (s, 3F); ESI-MS(+): 430 (M+H)$^+$; HPLC: 96.9%. Mpt. 126-128° C.

Example P9: 3-methyl-2-[3-methylsulfonyl-5-(trifluoromethyl)-2-pyridyl]-6-(trifluoromethyl)imidazo[4,5-c]pyridine (Compound V12.18)

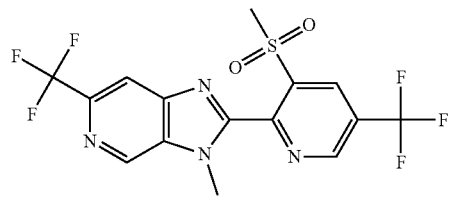

Step A: 3-methylsulfonyl-5-(trifluoromethyl)pyridine-2-carbonyl Chloride

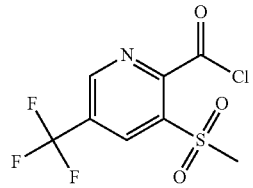 [SMILES: CS(=O)(=O)c1cc(C(F)(F)F)cnc1C(=O)Cl]

3-methylsulfonyl-5-(trifluoromethyl)pyridine-2-carboxylic acid (1.0 g, 3.7 mmol, prepared as described in US 20100234603) was suspended in SOCl$_2$ (5 mL), 1 drop of DMF was added to the mixture. The reaction mixture was heated to reflux, and stirred for 3 h. Then it was evaporated to dryness under reduced pressure to give the title compound as white solid (1.1 g, 100%). The residue was used directly for next step without further purification.

Step B: N-[5-(methylamino)-2-(trifluoromethyl)-4-pyridyl]-3-methylsulfonyl-5-(trifluoromethyl)pyridine-2-carboxamide

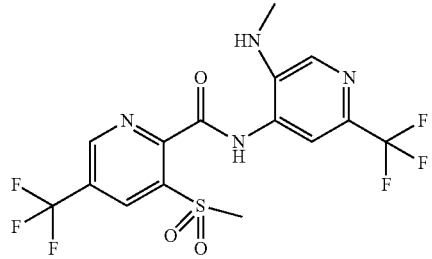 [SMILES: CNc1cnc(C(F)(F)F)cc1NC(=O)c1ncc(C(F)(F)F)cc1S(C)(=O)=O]

To a solution of 3-methylsulfonyl-5-(trifluoromethyl)pyridine-2-carbonyl chloride (80 mg, 0.3 mmol) in 5 ml of toluene was added compound N3-methyl-6-(trifluoromethyl)pyridine-3,4-diamine (60 mg, 1.1 mmol, prepared as described in Step E, example P4), then the reaction mixture was warmed to 100° C. for 5 hours. After that, it was cooled to room temperature and diluted with 15 ml of water and extracted three times with EtOAc. The combined organic layers were dried over sodium sulphate and purified by column chromatography on silica gel (EtOAc:Petroleum ether=1/4) to give the title compound as a white solid (50 mg, 40% yield).

Step C: 3-methyl-2-[3-methylsulfonyl-5-(trifluoromethyl)-2-pyridyl]-6-(trifluoromethyl)imidazo[4,5-c]pyridine (Compound V12.18)

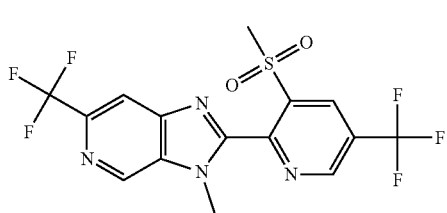

5-methyl-N-[2-methyl-5-(methylamino)-4-pyridyl]-3-methylsulfonyl-pyridine-2-carboxamide (85 mg, 0.2 mmol) was added to 5 ml of acetic acid and the reaction mixture warmed to 100° C. for 12 h. The reaction mixture was cooled to room temperature and diluted with 20 ml of water and extracted three times with EtOAc. The combined organic layers were dried over sodium sulphate and purified by column chromatography on silica gel (EtOAc:Petroleum ether=1/4) to give the title compound as a white solid (40 mg, 50% yield). 1H NMR (300 MHz, CDCl$_3$) δ 3.65 (s, 3H), 3.94 (s, 3H), 8.11 (s, 1H), 8.82 (s, 1H), 9.01 (s, 1H), 9.24 (s, 1H). $^{19}$F NMR (300 Mz, CDCl$_3$) δ −67.27 (s, 3H), δ −63.34 (s, 3H). ESI-MS: 425 (M+1). Mpt. 234-236° C. LCMS (method SQD 13) Rt. 0.93 min, 425 (M+H).

Example P10: 2-[2-ethylsulfonyl-6-(trifluoromethyl)-3-pyridyl]-7-(trifluoromethyl)imidazo[1,2-a]pyridine (Compound V3.05)

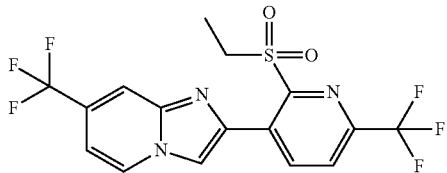

Step A: 2-ethylsulfanyl-6-(trifluoromethyl)pyridine-3-carbonyl Chloride

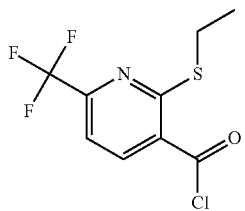 [SMILES: CCSc1nc(C(F)(F)F)ccc1C(=O)Cl]

A mixture of 2-ethylsulfanyl-6-(trifluoromethyl)pyridine-3-carboxylic acid (502 mg, 2 mmol, prepared as described in step I, example P6) in 10 ml of SOCl$_2$ was refluxed for 4 hours. Then, the excess SOCl$_2$ was evaporated to give the title compound (538 mg, 100%), which was directly used for the next step without further purification.

Step B: 2-ethylsulfanyl-N-methoxy-N-methyl-6-(trifluoromethyl)pyridine-3-carboxamide

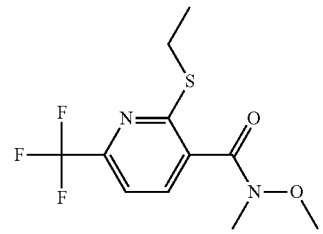 [SMILES: CCSc1nc(C(F)(F)F)ccc1C(=O)N(C)OC]

A mixture of the crude product 2-ethylsulfanyl-6-(trifluoromethyl)pyridine-3-carbonyl chloride (538 mg, 2 mmol), N,O-dimethylhydroxylamine hydrochloride (588 mg, 6 mmol) and K$_2$CO$_3$ (1.66 g, 12 mmol) in 10 ml of THF and 1 ml of water was stirred at room temperature for 10 min. Then, the mixture was poured into water and extracted with ethyl acetate three times. The combined organic layers were dried over sodium sulfate, filtered and concentrated in vacuo. The residue was purified by column chromatography on silica gel to give the title compound (411 mg, y: 70%). $^1$H-NMR (300 Mz, DMSO-d$_6$): δ 1.23 (t, 3H), 3.10 (q, 2H), 3.23 (s, 3H), 3.45 (s, 3H), 7.64 (d, 1H), 7.94 (d, 1H); $^{19}$F NMR (300 Mz, DMSO-d$_6$): δ −62.44 (s, 3F).

Step C: 1-[2-ethylsulfanyl-6-(trifluoromethyl)-3-pyridyl]ethanone

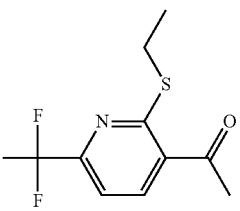

To a solution of 2-ethylsulfanyl-N-methoxy-N-methyl-6-(trifluoromethyl)pyridine-3-carboxamide (411 mg, 1.4 mmol) in 10 ml of THF was added 1.4 ml of MeMgBr (3M in THF) at room temperature and the reaction allowed to stir for 30 min. Then, the mixture was poured into water and extracted with ethyl acetate three times. The combined organic layers were dried over sodium sulfate, filtered and concentrated in vacuo. The residue was purified by column chromatography on silica gel to give the title compound (290 mg, y: 83%). $^1$H-NMR (300 Mz, DMSO-d$_6$): δ 1.22 (t, 3H), 2.60 (s, 3H), 3.02 (q, 2H), 7.71 (d, 1H), 7.52 (d, 1H); $^{19}$F-NMR (300 Mz, DMSO-d$_6$): δ −67.93 (s, 3F).

Step D: 2-[2-ethylsulfanyl-6-(trifluoromethyl)-3-pyridyl]-7-(trifluoromethyl)imidazo[1,2-a]pyridine

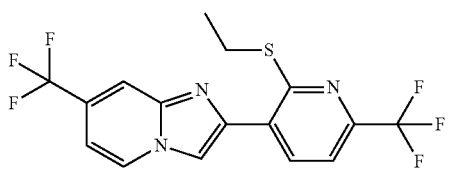 [SMILES: CCSc1nc(C(F)(F)F)ccc1-c1cn2ccc(C(F)(F)F)cc2n1]

A mixture of 1-[2-ethylsulfanyl-6-(trifluoromethyl)-3-pyridyl]ethanone (249 mg, 1 mmol), 4-(trifluoromethyl)pyridin-2-amine (162 mg, 1.2 mmol), Cu(OAc)$_2$.H$_2$O (12 mg, 0.1 mmol), ZnI$_2$ (32 mg, 0.1 mmol) and 1,10-phenanthroline (18 mg, 0.1 mmol) in 5 ml of dichlorobenzene was stirred at 130° C. for 48 h. Then the mixture was concentrated under vacuum and the residue was purified by column chromatography on silica gel to give the title compound (120 mg, y: 30%). $^1$H NMR (300 Mz, CDCl$_3$): δ 1.39 (t, 3H), 3.29 (q, 2H), 7.00 (dd, 1H), 7.46 (d, 1H), 7.94 (s, 1H), 8.27 (d, 1H), 8.42 (s, 1H), 8.47 (d, 1H); $^{19}$F NMR (300 Mz, CDCl$_3$): δ −69.33 (s, 3F), −64.83 (s, 3F); ESI-MS(+): 392 (M+H)$^+$.

Step E: 2-[2-ethylsulfonyl-6-(trifluoromethyl)-3-pyridyl]-7-(trifluoromethyl)imidazo[1,2-a]pyridine (Compound V3.05)

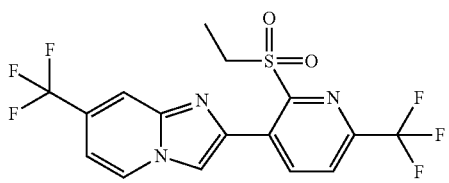

V3.05

A mixture of compound 2-[2-ethylsulfanyl-6-(trifluoromethyl)-3-pyridyl]-7-(trifluoromethyl)imidazo[1,2-a]pyridine (156 mg, 0.4 mmol) and m-CPBA (277 mg, 1.6 mmol) in 10 ml of Ddichloromethane was stirred at ambient temperature for 2 hours. Then the mixture was poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by column chromatography on silica gel to give the title compound (115 mg, y: 68%) $^1$H-NMR (300 Mz, CDCl$_3$): δ 1.50 (t, 3H), 3.74 (q, 2H), 7.01 (dd, 1H), 7.95 (s, 1H), 7.96 (d, 1H), 8.27 (d, 1H), 8.77 (s, 1H), 8.92 (d, 1H); $^{19}$F NMR (300 Mz, CDCl$_3$): δ −73.07 (s, 3F), −69.08 (s, 3F); ESI-MS(+): 424 (M+H)$^+$. Mpt. 188-190° C. LCMS (method SQD 13): Rt. 1.07 mins, 424 (M+H).

Example P11: 3-ethylsulfonyl-4-[3-methyl-6-(trifluoromethyl)imidazo[4,5-b]pyridin-2-yl]-1,2,5-thiadiazole (compound A1.014-B8.012)

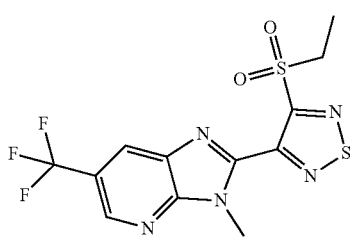

A1-014-B8.012

Step A: ethyl (2Z)-2-cyano-2-hydroxyimino-acetate

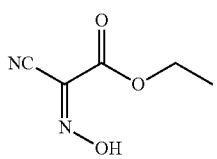

H$_3$PO$_4$ (1.83 mL, 27 mmol) was added to a mixture of ethyl cyanacetate (5 g, 44.2 mmol) and NaNO$_2$ (2.87 g, 41.5 mmol) in 35 mL of water at room temperature. After the addition, the mixture was warmed to 40° C. and stirred for another hour. Then, 3.69 ml of hydrochloric acid was added to the mixture and stirring was continued for 18 hours. The mixture was extracted with diethyl ether three times. The combined organic layers were dried over sodium sulfate, filtered and concentrated under vacuum. The residue was purified by column chromatography on silica gel to give the title compound (4.3 g, y: 69%)$^1$H NMR (300 Mz, DMSO-d$_6$): δ 1.28 (t, 3H), 4.32 (q, 2H).

Step B: ethyl 2-amino-2-cyano-acetate

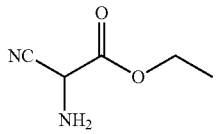

Na$_2$S$_2$O$_4$ (17 g, 105 mmol) was slowly added to a mixture of ethyl (2Z)-2-cyano-2-hydroxyimino-acetate (5 g, 35 mmol) and NaHCO$_3$ (1.5 g, 17 mmol) in 40 ml of water. Then the mixture was stirred at room temperature for 16 h and extracted with chloroform three times. The combined organic layers were dried over sodium sulfate, filtered and concentrated under vacuum to give the title compound (3.18 g, y: 71%). $^1$H NMR (300 Mz, DMSO-d$_6$): δ 1.24 (t, 3H), 3.53 (s, 2H), 4.19 (q, 2H), 4.81 (s, 1H).

Step C: ethyl 4-chloro-1,2,5-thiadiazole-3-carboxylate

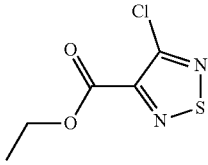

Disulphur dichloride (4.06 g, 30 mmol) was added to a solution of ethyl 2-amino-2-cyano-acetate (1.28 g, 10 mmol) in 10 ml of DMF at ambient temperature. The mixture was stirred at ambient temperature for 16 h and poured into ice, extracted three times with dichloromethane. The combined organic layers were dried over sodium sulfate, filtered and concentrated under vacuum. The residue was purified by column chromatography on silica gel to give the title compound (1.2 g, y: 63%). $^1$H NMR (300 Mz, DMSO-$d_6$): δ 1.35 (t, 3H), 4.39 (q, 2H).

Step D: ethyl 4-ethylsulfanyl-1,2,5-thiadiazole-3-carboxylate

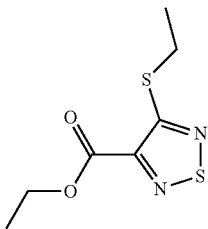

Na$_2$S.9H$_2$O (2.4 g, 10 mmol) in 10 ml of water was added to a solution of ethyl 4-chloro-1,2,5-thiadiazole-3-carboxylate (1.92 g, 10 mmol) in 30 mL of ethanol and the mixture was refluxed for 4 h. Then the mixture was concentrated in vacuo and a solution of bromoethane (3.24 g, 30 mmol) in 10 ml of DMF was added. The reaction mixture was stirred at ambient temperature for 16 hours, poured into dilute hydrochloric acid and extracted with ethyl acetate three times. The combined organic layers were dried over sodium sulfate, filtered and concentrated under vacuum. The residue was purified by column chromatography on silica gel to give the title compound (1.57 g, y: 72%). $^1$H NMR (300 Mz, DMSO-$d_6$): δ 1.34 (t, 3H), 1.36 (t, 3H), 3.19 (q, 2H), 4.37 (q, 2H); ESI-MS (+): 219 (M+H)$^+$, 241 (M+Na)$^+$.

Step E: 4-ethylsulfanyl-1,2,5-thiadiazole-3-carboxylic Acid

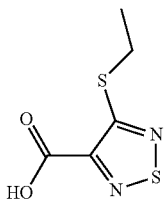

A mixture of ethyl 4-ethylsulfanyl-1,2,5-thiadiazole-3-carboxylate (680 mg, 3.12 mmol) and LiOH (240 mg, 10 mmol) in 5 ml of water and 5 ml of THF was stirred at room temperature for 2 h. Then, the reaction mixture was poured into diluted hydrochloric acid and extracted with ethyl acetate three times. The combined organic layers were dried over sodium sulfate, filtered and concentrated in vacuo. The residue was purified by column chromatography on silica gel to provide product the title compound (550 mg, y: 93%). $^1$H NMR (300 Mz, DMSO-$d_6$): δ 1.35 (t, 3H), 3.12 (q, 2H).

Step F: 3-ethylsulfanyl-4-[3-methyl-6-(trifluoromethyl)imidazo[4,5-b]pyridin-2-yl]-1,2,5-thiadiazole (Compound A1.014-B8.010)

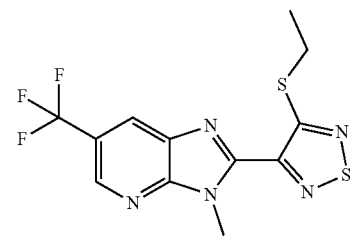

A1.014-B8.010

A mixture of 4-ethylsulfanyl-1,2,5-thiadiazole-3-carboxylic acid (570 mg, 3 mmol), N2-methyl-5-(trifluoromethyl)pyridine-2,3-diamine (669 mg, 3.5 mmol, prepared as described in WO 2012092051) and EDC.HCl (672 mg, 3.5 mmol) in 5 ml of pyridine was refluxed for 16 h. Then, the mixture was concentrated under vacuum and purified by column chromatography on silica gel to give the title compound (621 mg, y: 60%). $^1$H-NMR (300 Mz, DMSO-$d_6$): δ 1.41 (t, 3H), 3.27 (q, 2H), 4.24 (s, 3H), 8.73 (s, 1H), 8.90 (s, 1H); $^{19}$F NMR (300 Mz, DMSO-$d_6$): δ −53.72 (s, 3F); ESI-MS(+): 346 (M+H)$^+$. LCMS (method SQD13): Rt. 1.21 mins, 346 (M+H) Mpt. 188-189° C.

Step G: 3-ethylsulfonyl-4-[3-methyl-6-(trifluoromethyl)imidazo[4,5-b]pyridin-2-yl]-1,2,5-thiadiazole (Compound A1.014-B8.012)

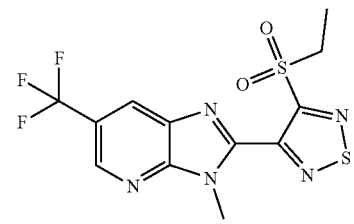

A1.014-B8.012

3-ethylsulfanyl-4-[3-methyl-6-(trifluoromethyl)imidazo[4,5-b]pyridin-2-yl]-1,2,5-thiadiazole (0.87 mmol, 300 mg) and m-CPBA (519 mg, 3 mmol) in 10 ml of DCM was stirred at room temperature for 4 h. Then the mixture was poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by column chromatography on silica gel to give the title compound (245 mg, 75%). ¹H NMR (300 Mz, DMSO-d₆): δ 1.31 (t, 3H), 3.97 (q, 2H), 4.00 (s, 3H), 8.76 (s, 1H), 8.94 (s, 1H); ¹⁹F NMR (300 Mz, DMSO-d₆): δ −53.85 (s, 3F); ESI-MS(+): 378 (M+H)⁺, 400 (M+Na)⁺, 432 (M+Na+MeOH)⁺. LCMS (method SQD13): Rt. 0.93 mins, 378 (M+H) Mpt. 144-146° C.

Example P12: 2-[3-ethylsulfonyl-5-(trifluoromethyl)-2-pyridyl]-7-(trifluoromethyl) [1,2,4]triazolo[1,5-c]pyrimidine (Compound V16.03)

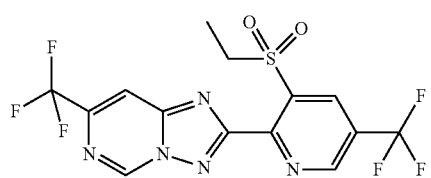

V16.03

Step A: 4-(trifluoromethyl)pyrimidin-1-ium-1,6-diamine, 2,4,6-trimethylbenzenesulfonate Salt (MSH):

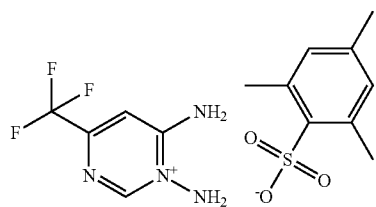

Caution: MSH is explosively unstable as a dry powder and is best handled in dichloromethane solution.

A Microwave tube, equipped with a magnetic stirrer bar, was charged with 2,2,2-trifluoroacetic acid (4.4 g, 2.54 mmol, 2.9 mL). Then, (tert-butoxycarbonylamino) 2,4,6-trimethylbenzenesulfonate (1 g, 2.54 mmol) was added at 0° C. The reaction mixture was stirred at 0° C. for 2 h, ice-water was added and the precipitate was recovered by filtration. The wet cake was washed with water and dissolved in dichloromethane (5 mL) and dried over sodium sulfate. The resulting solution was added dropwise to a stirred solution of 6-(trifluoromethyl)pyrimidin-4-amine (0.3723 g, prepared as in WO2007113558) in dichloromethane (5 mL) at 0° C. After 1 hour at 0° C. and one night at RT (white suspension), the reaction mixture was diluted with diethyl ether (8 mL) and the precipitate was recovered by filtration to afford the title compound (0.791 g, 82%).

Step B: 2-[3-ethylsulfonyl-5-(trifluoromethyl)-2-pyridyl]-7-(trifluoromethyl)-[1,2,4]triazolo[1,5-c]pyrimidine (Compound V16.03)

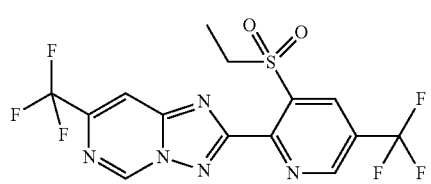

V16.03

4-(trifluoromethyl)pyrimidin-1-ium-1,6-diamine, 2,4,6-trimethylbenzenesulfonate salt (0.3 g, 0.791 mmol), 3-ethylsulfonyl-5-(trifluoromethyl)pyridine-2-carboxylic acid (0.33593 g, 1.1861 mmol) and 3-(ethyliminomethyleneamino)-N,N-dimethyl-propan-1-amine hydrochloride (0.1819098 g, 0.9489 mmol) was dissolved in pyridine (2 mL) and heated for 3 h at 120° C. After this time, the reaction mixture was poured on water, the aqueous layer was extracted three times with EtOAc. The combined organic layer were washed successively with water and brine, dried over Na₂SO₄, filtered and concentrated in vacuo. The crude product was triturated with diethylether, and filtered to give the product as a white powder (110 mg, 33%).

¹H NMR (400 MHz, CDCl3): δ (ppm) 9.31 (d, J=2.2 Hz, 1H), 9.17 (d, J=1.5 Hz, 1H), 8.34-8.53 (m, 1H), 3.23 (q, J=7.5 Hz, 2H), 1.37 (t, J=7.5 Hz, 3H). LCMS (method SQD13): Rt: 0.94 min, 426 (M+H). Mpt.: 190-192° C.

Example P13: 2-[3-ethylsulfonyl-5-(trifluoromethyl)-2-pyridyl]-6-(trifluoromethyl)oxazolo[5,4-c]pyridine (Compound V12.05)

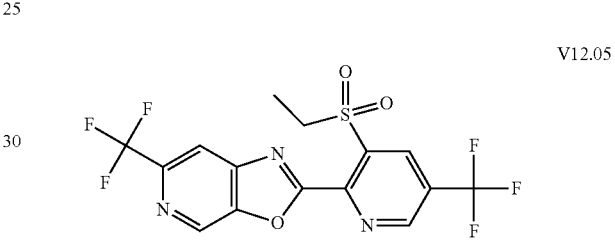

V12.05

Step A: 4-nitro-6-(trifluoromethyl)pyridin-3-ol

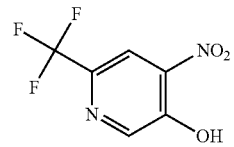 [SMILES: O=[N+]([O-])c1cc(C(F)(F)F)ncc1O]

To a solution of 6-(trifluoromethyl)pyridin-3-ol (5.00 g, 30.7 mmol) in sulfuric acid (92.0 mL) at 0° C. was added Ice (25.0 g, 1390 mmol) keeping the temperature below 10° C. To this solution was added nitric acid (2.97 g, 2.14 mL, 30.7 mmol) and the mixture was heated at 85° C. for 4 hours. A second portion of nitric acid (2.97 g, 2.14 mL, 30.7 mmol) was added and the reaction was stirred over night at 85° C. LCMS analysis showed ca. 40% conversion and thus nitric acid (2.97 g, 2.14 mL, 30.7 mmol) was added and the reaction was stirred 5 h at 85° C. A further portion of nitric acid (2.97 g, 2.14 mL, 30.7 mmol) was added and the reaction was stirred over night at 85° C. After this time, the mixture was poured into ice water and extracted with 250 mL of Et₂O. The combined organic phases were dried over sodium sulfate and concentrated in vacuo. The residue was purified by flash chromatography, eluting with dichloromethane to give the title compound (18% yield). ¹H NMR (400 MHz, CDCl3): 10.32 (s, 1H), 8.82 (s, 1H), 8.30 (s, 1H) ppm.

Step B: 4-amino-6-(trifluoromethyl)pyridin-3-ol

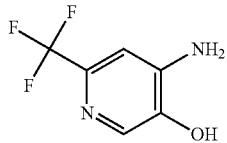 [SMILES: Nc1cc(C(F)(F)F)ncc1O]

To a solution of 4-nitro-6-(trifluoromethyl)pyridin-3-ol (1.15 g, 5.53 mmol) in ethanol (50 mL) and tetrahydrofuran (10 mL) was added Palladium on carbon (0.12 g) under argon. A hydrogen atmosphere was applied (balloon) and the mixture was stirred over night at room temperature. After complete reduction, the mixture was filtered over celite and the cake washed with ethanol. The solvent was removed in vacuo and the residue was purified by flash chromatography (cyclohexane/ethyl acetate) to give the title compound (0.98 g, quantitative) as a red gum. $^1$H NMR (400 MHz, CDCl3): 7.92 (s, 1H), 6.92 (s, 1H), 4.75 (s, 2H) ppm.

Step C: 2-[3-ethylsulfanyl-5-(trifluoromethyl)-2-pyridyl]-6-(trifluoromethyl)oxazolo[5,4-c]pyridine. (Compound A6.006-B1.014)

A6.006-B1.014

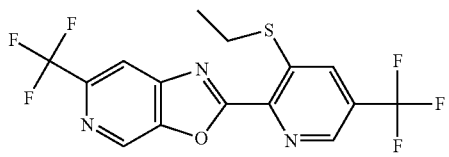

To a solution of 4-amino-6-(trifluoromethyl)pyridin-3-ol (100 mg, 0.56 mmol) and 3-ethylsulfanyl-5-(trifluoromethyl)pyridine-2-carboxylic acid (155 mg, 0.62 mmol, prepared as described in WO 2013018928) in polyphosphoric acid (2 mL) were stirred at 185° C. for 24 hours. The reaction mixture was then poured into water (50 mL) under vigorous stirring, and the pH was adjusted to 8 with NaOH (2N). The aqueous phase was extracted with dichloromethane (×2), and the combined organic phases and dried over sodium sulphate. The solvent was evaporated in vacuo and the residue was purified by flash chromatography (cyclohexane/ethyl acetate) to give the title compound (75 mg, 34%).
$^1$H NMR (400 MHz, CDCl3): 9.20 (s, 1H), 8.82 (s, 1H), 8.32 (s, 1H), 7.98 (s, 1H), 3.14 (q, 2H), 1.54 (t, 3H) ppm. LCMS (method SQD13): Rt: 1.15 min, 394 (M+H).

Step D: 2-[3-ethylsulfonyl-5-(trifluoromethyl)-2-pyridyl]-6-(trifluoromethyl)oxazolo[5,4-c]pyridine (Compound V12.05)

Compound V12.05

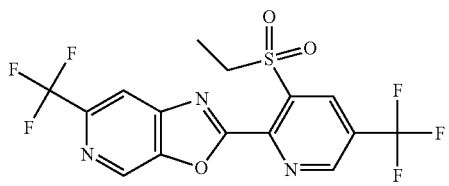

To a solution of 2-[3-ethylsulfanyl-5-(trifluoromethyl)-2-pyridyl]-6-(trifluoromethyl)oxazolo[5,4-c]pyridine (60 mg, 0.153 mmol) in dichloromethane (10 mL) was added m-CPBA (83 mg, 0.34 mmol). The resulting yellow solution was stirred for 1 hour at room temperature and then a further 60 mg of m-CPBA were added. The reaction mixture was stirred for a further 2 h at room temperature and then poured into a saturated solution of potassium carbonate. The aqueous phase was extracted 2 times with dichloromethane and the combined organic phases dried over sodium sulfate and concentrated in vacuo. The residue was purified by flash chromatography (cyclohexane/ethyl acetate) to give the title compound (49 mg, 75%) as a white powder (75%).
$^1$H NMR (400 MHz, CDCl$_3$): 9.28 (s, 1H), 9.22 (s, 1H), 8.84 (s, 1H), 8.24 (s, 1H), 3.98 (q, 2H), 1.48 (t, 3H) ppm. LCMS (method SQD13): Rt. 1.02 min, 426 (M+H+).

Example P14: 2-[3-ethylsulfonyl-5-(trifluoromethyl)-2-pyridyl]-7-(trifluoromethyl)imidazo[1,2-c]pyrimidine (Compound V16.02)

V16.02

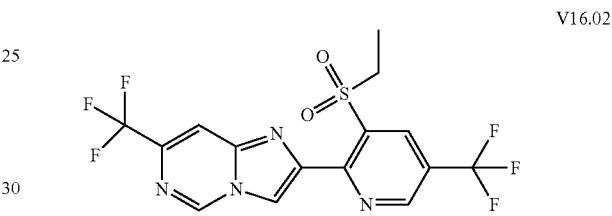

Step A: 1-[3-ethylsulfanyl-5-(trifluoromethyl)-2-pyridyl]ethanone

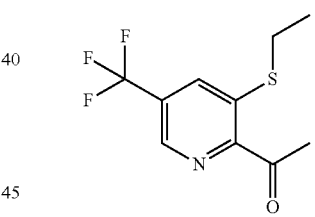

A solution of bromo(methyl)magnesium (1.4 M in THF: Toluen 1:3, 14 Ml, 18.95 mmol) toluene dry (90 mL) was cooled to 0° C. and treated dropwise with a solution of 3-ethylsulfanyl-5-(trifluoromethyl)pyridine-2-carbonitrile (4.00 g, 17.23 mmol, prepared as described in WO 2013018928) dissolved in 30 ml of toluene. The reaction was allowed to stir for 30 min. at 0° C. LCMS analysis after this time showed reaction completion. The reaction mixture was slowly quenched with NH$_4$Cl sat aq (50 ml) and HCl 10% (30 ml) and the resulting mixture vigorously stirred for 15 min at room temperature. The aqueous layer was extracted twice with EtOAc, and the combined organic phases washed successively with 10% HCl aq, water and brine, dried over anhydrous Na$_2$SO$_4$, filtered and concentrated in vacuo. The crude title product (4.335 g, 91%) was used without purification for the next step.
$^1$H NMR (400 MHz, CDCl$_3$): δ (ppm) 8.62 (s, 1H), 7.85 (d, J=1.1 Hz, 1H), 2.96 (q, J=7.3 Hz, 2H), 2.74 (s, 3H), 1.43 (t, J=7.5 Hz, 3H). LCMS (method SQD13): Ret. Time 1.05 min, 250 (M+H).

Step B: 1-[3-ethylsulfonyl-5-(trifluoromethyl)-2-pyridyl]ethanone

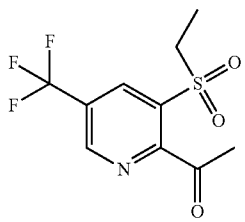 [SMILES: CCS(=O)(=O)c1cc(C(F)(F)F)cnc1C(C)=O]

At 0° C. m-CPBA (24.29 g, 98.53 mmol) was added portionwise to a solution of 1-[3-ethylsulfanyl-5-(trifluoromethyl)-2-pyridyl]ethanone (11.98 g, 48.06 mmol) in chloroform (400 mL) at 0° C. The resulting mixture was allowed to warm up to RT and stirred for 20 h. The reaction mixture was then quenched with 200 mL NaHCO$_3$aq. and 50 mL saturated sodium thiosulfate aqueous solution and extracted with three times with EtOAc. The combined organic phases were washed successively with aqueous NaHCO$_3$ and brine, dried over Na$_2$SO$_4$ and concentrated in vacuo. Purification on a 220 g column on the torrent machine eluting with EtOAc/heptane gave the title compound (8.5 g, 63%) as a white solid.
$^1$H NMR (400 MHz, CDCl$_3$): δ (ppm) 9.07 (d, J=1.1 Hz, 1H), 8.59 (d, J=1.5 Hz, 1H), 3.58 (q, J=7.3 Hz, 2H), 2.74 (s, 3H), 1.38 (t, J=7.5 Hz, 3H). LCMS (method SQD13): Ret. Time 0.87 min, 282 (M+H).

Step C: 2-[3-ethylsulfonyl-5-(trifluoromethyl)-2-pyridyl]-7-(trifluoromethyl)imidazo[1,2-c]pyrimidine

V16.02

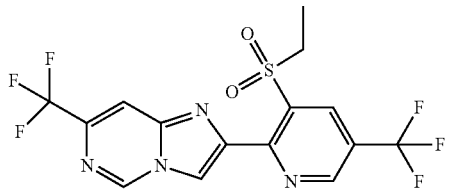

A mixture of 6-(trifluoromethyl)pyrimidin-4-amine (232 mg, 1.0607 mmol, prepared as described in WO2007113558), 1-[3-ethylsulfonyl-5-(trifluoromethyl)-2-pyridyl]ethanone (200 mg, 0.71 mmol), copper(I)iodide (7.0 mg, 0.036 mmol), In(III)triflate (4.0 mg, 0.0071 mmol) and 1-methyl-2-pyrrolidone (4 mL) were stirred for 19 hr at 120° C. LC-MS: desired product and starting material, and thus the reaction was stirred for a further 27 hr at 120° C. Reaction mixture was cooled to ambient temperature and water and ethylacetate were added. Aqueous layer was extracted 2 times with ethylacetate and the combined organic layers were washed with brine, dried over Na2SO4, filtered and concentrated in vacuo. The product was purified by combiflash chromatography with column of 12 g and a gradient of cyclohexane+0-80% ethylacetate, to give the title compound (96 mg, 31%) as a white solid. $^1$H NMR (400 MHz, CDCl$_3$): δ (ppm) 9.20 (s, 1H), 9.14 (s, 1H), 8.80 (d, J=1.5 Hz, 1H), 8.44 (s, 1H), 7.99 (s, 1H), 4.10 (q, J=7.5 Hz, 2H), 1.43 (t, J=7.5 Hz, 3H). LCMS (method SQD13): Rt: 0.98 min, 425 (M+H). Mpt. 180-181° C.

Example P15: 2-[3-ethylsulfonyl-5-(trifluoromethyl)-2-pyridyl]-3-methyl-7-(trifluoromethyl)imidazo[1,2-c]pyrimidine (Compound V16.01)

V16.01

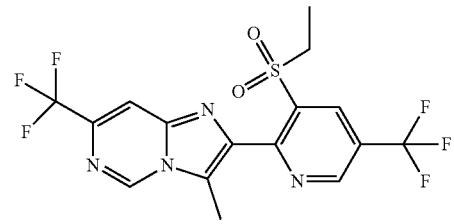

Step A: 3-bromo-2-[3-ethylsulfonyl-5-(trifluoromethyl)-2-pyridyl]-7-(trifluoromethyl)imidazo[1,2-c]pyrimidine

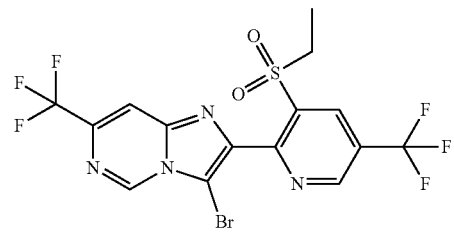 [SMILES: CCS(=O)(=O)c1cc(C(F)(F)F)cnc1-c1nc2cc(C(F)(F)F)ncn2c1Br]

2-[3-ethylsulfonyl-5-(trifluoromethyl)-2-pyridyl]-7-(trifluoromethyl)imidazo[1,2-c]pyrimidine (52 mg, 0.123 mmol) was dissolved in acetonitrile (1 mL) and treated with N-bromosuccinimide (24.5 mg, 0.135 mmol) at ambient temperature. Reaction mixture was stirred over night at room temperature. The reaction mixture was concentrated in vacuo and purified by combiflash chromatography with a column of 4 g and a gradient cyclohexane+0-50% ethylacetate. The title product was obtained as a white solid.
$^1$H NMR (400 MHz, CDCl$_3$): δ (ppm) 9.22 (d, J=0.7 Hz, 1H), 9.20 (s, 1H), 8.77 (d, J=1.5 Hz, 1H), 7.94 (s, 1H), 4.00 (q, J=7.6 Hz, 2H), 1.40-1.47 (t, J=7.6 Hz, 3H). LCMS (method SQD13): Rt: 1.04 min, 503/505 (M+H).

Step B: 3-bromo-2-[3-ethylsulfonyl-5-(trifluoromethyl)-2-pyridyl]-7-(trifluoromethyl)imidazo[1,2-c]pyrimidine (Compound V16.01)

V16.01

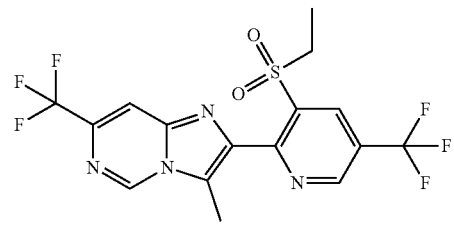

A suspension of 3-bromo-2-[3-ethylsulfonyl-5-(trifluoromethyl)-2-pyridyl]-7-(trifluoromethyl)imidazo[1,2-c]pyrimidine (100 mg, 0.199 mmol) and potassium carbonate (84 mg, 0.60 mmol) in 1,4-dioxane (3 mL) was purged with argon for 10 min and then treated with 2,4,6-trimethyl-1,3,5,2,4,6-trioxatriborinane (30.0 mg, 0.24 mmol, 0.0332 mL) and Pd(Ph3)4 (23 mg, 0.02 mmol). The reaction mixture was heated at 95° C. for 12 hr. LCMS analysis showed the desired product and starting material, and thus the mixture was cooled and purged with argon for 10 min and treated with 2,4,6-trimethyl-1,3,5,2,4,6-trioxatriborinane (30.0 mg, 0.24 mmol, 0.0332 mL) and Pd(Ph3)4 (23 mg, 0.02 mmol). The reaction mixture was heated for a further 5 hr 95° C. until reaction completion. The reaction mixture was diluted with NH₄Cl sat sol, and water, and then extracted three times with ethyl acetate. The combined organic layers were washed with brine, dried over Na2SO4, filtered and concentrated in vacuo. The product was purified by Combiflash chromatography with a column of 12 g and a gradient cyclohexane 0-50% ethylacetate. This gave the title product (51 mg, 59%) as a white solid. $^1$H NMR (400 MHz, CDCl$_3$): δ (ppm) 9.17 (d, J=1.5 Hz, 1H), 9.01 (s, 1H), 8.77 (d, J=1.5 Hz, 1H), 4.10 (q, J=7.6 Hz, 2H), 2.78 (s, 3H), 1.40-1.47 (t, 7.6 Hz, 3H). LCMS (method SQD13): Rt: 1.01 min, 439 (M+H). Mpt. 240-242° C.

Example P16: 2-[3-ethylsulfonyl-5-(trifluoromethyl)-2-pyridyl]-1-methyl-5-(trifluoromethyl)imidazo[4,5-b]pyrazine (Compound A1.026-B1.022)

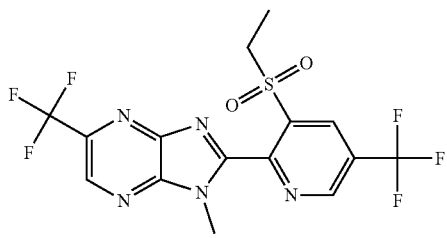 [SMILES: CCS(=O)(=O)c1cc(C(F)(F)F)cnc1-c1nc2nc(C(F)(F)F)cnc2n1C]

Step A: 3,5-diiodo-N-methyl-pyrazin-2-amine

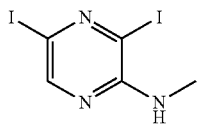

To a stirred solution of N-methylpyrazin-2-amine (1 g, 9.2 mmol) in dimethyl sulfoxide (20 ml)/water (0.4 ml) at 10° C. was added portionwise N-Iodosuccinimide (4.1 g, 18.4 mmol). The reaction mixture was then allowed to warm slowly to room temperature and stirred at that temperature overnight. An additional aliquot of N-Iodosuccinimide (4.1 g, 18.4 mmol) was then added at room temperature. After stirring for 7 hr, the reaction mixture was poured onto ice (20 g). The precipitate was collected, washed with cold water (20 ml), and dried to provide the title compound (2.15 g, 65%). $^1$H NMR (300 MHz, DMSO-d$_6$) δ(ppm): 8.14 (s, 1H), 6.69 (br, 1H), 2.77 (d, 3H, J=4.5 Hz); ESI-MS(−): 360.

Step B: 5-iodo-N2-methyl-pyrazine-2,3-diamine

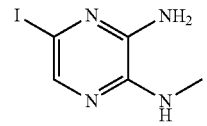

NH$_3$(g) in EtOH (15 ml) was added to 3,5-diiodo-N-methyl-pyrazin-2-amine (2.15 g, 6 mmol) and the mixture was heated to 150° C. in a sealed tube for 18 h. After the solution was cooled, dichloromethane and water (1:1, 200 ml) were added. The aqueous phase was extracted with methylene chloride (50 ml) and the combined organic layers were dried over Na$_2$SO$_4$ and concentrated to give the title compound as a white solid. (1.19 g, 80%). $^1$H NMR (300 MHz, DMSO-d$_6$) δ (ppm): 7.41 (s, 1H) 6.35 (br, 3H), 2.78 (s, 3H); ESI-MS (−): 249, ESI-MS (+): 251.

Step C: 2-[3-ethylsulfonyl-5-(trifluoromethyl)-2-pyridyl]-5-iodo-1-methyl-imidazo[4,5-b]pyrazine

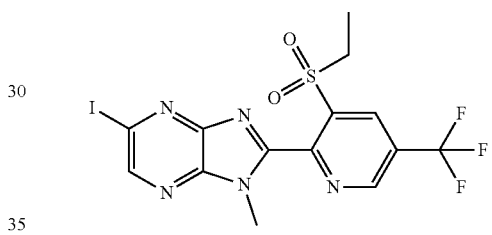

This compound was prepared by methods described in the examples above from 5-iodo-N2-methyl-pyrazine-2,3-diamine and 3-ethylsulfonyl-5-(trifluoromethyl)pyridine-2-carboxylic acid.

Step D: 2-[3-ethylsulfonyl-5-(trifluoromethyl)-2-pyridyl]-1-methyl-5-(trifluoromethyl)imidazo[4,5-b]pyrazine (compound A1.026-B1.022)

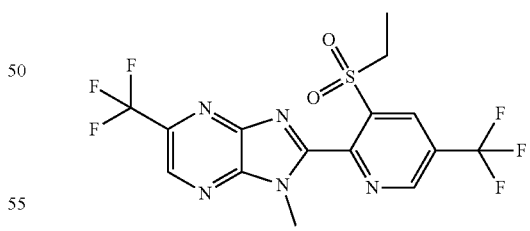

A mixture of compound 2-[3-ethylsulfonyl-5-(trifluoromethyl)-2-pyridyl]-5-iodo-1-methyl-imidazo[4,5-b]pyrazine (497 mg, 1 mmol), FSO$_2$CF$_2$COOMe (384 mg, 2 m mol) and CuI (191 mg, 1 mmol) in 5 ml of DMF was stirred at 120° C. under an nitrogen atmosphere for 24 h. Then the mixture was poured into dilute hydrochloric acid and extracted with ethyl acetate three times. The combined organic layers were dried over sodium sulfate, filtered and concentrated under vacuum. The crude product was purified by column chromatography on silica gel to give the title compound (197.5 mg, Y: 45%). ¹H NMR (300 MHz, CDCl₃) δ (ppm): 9.26 (s, 1H), 8.88 (s, 1H), 8.75 (s, 1H), 3.98 (m, 5H), 1.42 (t, J=6.9 Hz, 3H). ¹⁹F NMR (300 Mz, CDCl₃) δ (ppm): −62.15; −65.18. ESI-MS: 440 (M+H), 462 (M+Na+). Mpt. 162-165° C. LCMS (method SQD13): Rt. 1.04 mins, 440 (M+H).

Example P17: 3-methyl-2-[3-(methylsulfonylmethyl)-5-(trifluoromethyl)-2-pyridyl]-6-(trifluoromethyl)imidazo[4,5-b]pyridine (Compound A.014-B1.106)

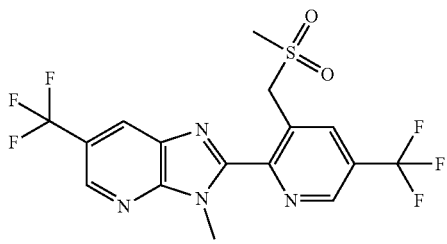

A.014-B1.106

Ethyl 3-methyl-5-(trifluoromethyl)pyridine-2-carboxylate (1.0 g 4.29 mmol, prepared as described in J. Amer. Chem. Soc., 2013, 135, 12122-12134) was dissolved in acetonitrile (40 ml) and treated with N-bromsuccinamide (1.21 g, 6.43 mmol) and benzoyl peroxide (0.150 g, 0.600 mmol). A sunlamp was used to irradiate the reaction mixture which was heated at reflux (75° C. bath temp.) After 10 hr, the mixture was cooled, filtered, and concentrated in vacuo. The crude product (1.27 g), which contained mainly ethyl 3-(bromomethyl)-5-(trifluoromethyl)pyridine-2-carboxylate, was used in the next step without further purification.

Ethyl 3-(bromomethyl)-5-(trifluoromethyl)pyridine-2-carboxylate (0.5 g, 1.6 mmol, prepared as above) was dissolved in DMF, cooled to 0° C., and treated with sodium methanethiolate (0.22 g, 3.2 mmol) The mixture was allowed to warm up to RT and was stirred over night. The reaction mixture was diluted NH₄Cl aq., and extracted with TBME (2×). The remaining aqueous layer was acidified with 6N HCl aq and extracted 3× with dichloromethane. The combined dichloromethane layers were dried over Na₂SO₄, filtered and evaporated to give 0.31 g of a beige solid, which contains the desired 3-(methylsulfanylmethyl)-5-(trifluoromethyl)pyridine-2-carboxylic acid. This was used in the next step without further purification.

N2-methyl-5-(trifluoromethyl)pyridine-2,3-diamine (0.24 g, 1.3 mmol, prepared as described in WO 2012092051), EDC.HCl (0.24 g, 1.3 mmol) and 3-(methylsulfanylmethyl)-5-(trifluoromethyl)pyridine-2-carboxylic acid (0.29 g, crude sample from above) were dissolved in pyridine (15 ml). The brown suspension was stirred at 120° C. for 2 h. The reaction mixture was diluted with water, and extracted EtOAc. The organic layer was separated and washed with brine, dried over Na2SO4 and evaporated. The crude product was purified by chromatography on an RF 200 machine eluting with EtOAc/Cyclohexane gradient, to give 0.35 g of a beige solid, which contained the desired product N-[2-(methylamino)-5-(trifluoromethyl)-3-pyridyl]-3-(methylsulfanylmethyl)-5-(trifluoromethyl)pyridine-2-carboxamide. This product was dissolved in 1-methylpyrrolidin-2-one (5 ml) with toluene-4-sulphonic acid (0.072 g, 0.41 mmol) and heated in the microwave at 160° C. for 1 h. After this time, the reaction mixture was diluted with water, and extracted with EtOAc. The organic layer was washed with water and brine, dried over sodium sulfate and concentrated in vacuo. Purification over a silica gel cartridge (Rf200), eluting with Cyclohexane/EtOAc gave 3-methyl-2-[3-(methylsulfanylmethyl)-5-(trifluoromethyl)-2-pyridyl]-6-(trifluoromethyl)imidazo[4,5-b]pyridine (140 mg) as a white solid. LCMS (method SQD13): Rt. 1.17 mins, 407 (M+H).

A solution of 3-methyl-2-[3-(methylsulfanylmethyl)-5-(trifluoromethyl)-2-pyridyl]-6-(trifluoromethyl)imidazo[4,5-b]pyridine (100 mg, 0.25 mmol) in dichloromethane was cooled to 0° C. and MCPBA (61 mg, 0.25 mmol) was added at 0° C. LC/MS after 1 h showed sulphoxide and sulphone and thus a further 61 mg of MCPBA was added. Upon reaction completion, the mixture was quenched 2M Na₂CO₃ and dichloromethane. The organic layer was separated, washed once with water, dried over Na₂SO₄, filtered and concentrated in vacuo. Purification over a silica gel cartridge (Rf200), eluting with Cyclohexane/EtOAc gave the title compound (80 mg, 70%) as a white solid. LCMS (method SQD13): Rt. 1.02 mins, 439 (M+H). ¹H NMR (400 MHz, CDCl₃): δ (ppm) 9.08 (d, J=1.5 Hz, 1H), 8.79 (d, J=1.5 Hz, 1H), 8.34-8.36 (m, 1H), 8.33 (d, J=1.8 Hz, 1H), 5.25 (s., 2H), 4.13 (s, 3H), 2.93 (s, 3H).

Example P18: 6-bromo-2-[3-ethylsulfonyl-5-(trifluoromethyl)-2-pyridyl]-3-methyl-imidazo[4,5-c]pyridine (Compound V12.20)

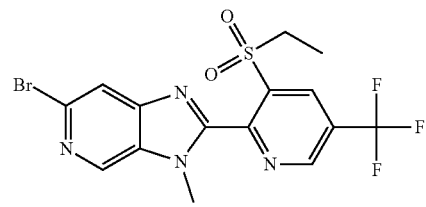

V12.20

Step A: 2-bromo-5-fluoro-1-oxido-pyridin-1-ium

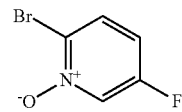

To a stirred solution of 2-bromo-5-fluoropyridine (5.0 g, 28.4 mmol) in TFA (10.0 mL) was added H₂O₂ (30%, 15 mL) dropwise at 0° C., the mixture was stirred under reflux overnight. After cooling, the reaction system was poured onto ice-water, extracted with dichloromethane/methanol (10: 1, 50 mL×3), the organic layer was washed with saturated sodium bicarbonate solution and brine, and dried over anhydrous sodium sulfate. After filtration and concentration in vacuo, the crude product (off white solid, 4.6 g, y: 84%) was used for the next step without further purification.

Step B: 2-bromo-5-fluoro-4-nitro-1-oxido-pyridin-1-ium

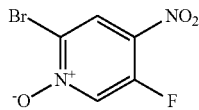

To a solution of 2-bromo-5-fluoro-1-oxido-pyridin-1-ium (4.6 g, 23.9 mmol) in sulphuric acid (conc.) (20 mL) was added fuming nitric acid (10 mL) slowly at 0° C. After the addition the reaction temperature was raised to 120° C., and stirring continued at this temperature for 4 h. After cooling to room temperature, the reaction solution was poured onto ice-water. The pH value was adjusted to 1 with $NH_4OH$. The precipitate was filtered and oven dried to afford the title compound (2.3 g, 40%) as light yellow solid.

Step C: 6-bromo-N-methyl-4-nitro-1-oxido-pyridin-1-ium-3-amine

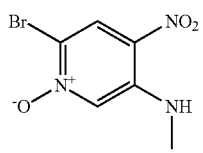

To a solution of 2-bromo-5-fluoro-4-nitro-1-oxido-pyridin-1-ium (1.1 g, 4.6 mmol) in ethanol (10 mL) was added $MeNH_2$/ethanol (4 mL). The reaction mixture was stirred at room temperature for 4 h. The mixture was concentrated in vacuo to give the title compound as a solid which was used for the next step without further purification.

Step D: 6-bromo-N-methyl-4-nitro-pyridin-3-amine

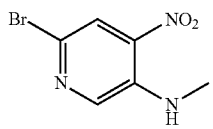

To a solution of 6-bromo-N-methyl-4-nitro-1-oxido-pyridin-1-ium-3-amine (crude from above, 4.6 mmol) in dichloromethane (10 mL) was added $PBr_3$ (1.0 mL). The reaction mixture was stirred at ambient temperature for 1 hour. The mixture was dried under vacuum to give the title compound as a jacinth solid and used for the next step without further purification.

Step E: 6-bromo-N3-methyl-pyridine-3,4-diamine

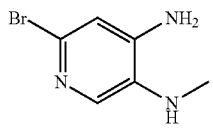

To a solution of 6-bromo-N-methyl-4-nitro-pyridin-3-amine (crude, 4.6 mmol) in methanol (10 mL) was added Raney Ni (20% wt), and hydrazine hydrate (1.0 mL) was added dropwise at 0° C. The reaction mixture was stirred at room temperature for a few minutes. Raney Ni was filtered off through celite; the filtrate was dried in vacuo and purified with chromatography column on silica gel (dichloromethane:methanol, 10: 1) to afford the title compound as a light purple solid (0.6 g, three-step yield, 63%). $^1$H NMR (400 MHz, DMSO-$d_6$): δ (ppm) 7.20 (s, 1H), 6.65 (s, 1H), 6.54 (brs, 2H), 3.34 (s, 1H), 2.69 (d, J=6.4 Hz, 3H). ESI-MS(+): 203 (M+H).

Step F: N-(4-amino-6-bromo-3-pyridyl)-3-ethylsulfonyl-N-methyl-5-(trifluoromethyl)pyridine-2-carboxamide

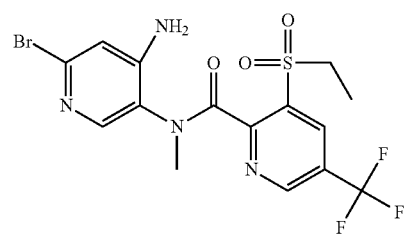 [SMILES: CCS(=O)(=O)c1cc(C(F)(F)F)cnc1C(=O)N(C)c1cnc(Br)cc1N]

To a stirred solution of 6-bromo-N3-methyl-pyridine-3,4-diamine (0.60 g, 2.96 mmol), 3-ethylsulfonyl-5-(trifluoromethyl)pyridine-2-carboxylic acid (0.92 g, 3.26 mmol, prepared as in WO 2013180194) and HATU (1.4 g, 3.68 mmol) in DMF (5.0 mL) was added DIPEA (1.2 ml, 7.26 mmol). The system was stirred at room temperature overnight. The reaction was diluted with EtOAc and $H_2O$, the organic layer was washed with brine and water, dried over anhydrous sodium sulfate. After filtration and concentration in vacuo, the crude title product was used for the next step without further purification.

Step G: 6-bromo-2-[3-ethylsulfonyl-5-(trifluoromethyl)-2-pyridyl]-3-methyl-imidazo[4,5-c]pyridine (Compound V12.20)

(Compound V12.20)

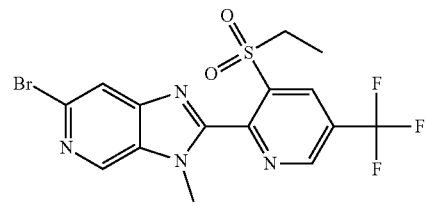

A solution of N-(4-amino-6-bromo-3-pyridyl)-3-ethylsulfonyl-N-methyl-5-(trifluoromethyl)pyridine-2-carboxamide (crude, 2.96 mmol) in acetic acid (5.0 mL) was stirred at 120° C. overnight. The mixture was evaporated to dryness. The residue was purified by chromatography on silica gel (Petroleum ether:EtOAc=4: 1) to afford the title compound as white solid (0.65 g, two-step yield: 48%). $^1$H NMR (400 MHz, DMSO-$d_6$): δ (ppm) 9.53 (s, 1H), 8.94 (s, 1H), 8.74 (s, 1H), 8.01 (s, 1H), 3.83 (q, J=7.6 Hz, 2H), 3.79 (s, 3H), 1.19 (t, J=7.2 Hz, 3H). $^{19}$F NMR (300 MHz, DMSO-d6): δ (ppm) −60.42 (s, 3F). ESI-MS(+): 449 (M+H), 472 (M+Na); ESI-MS(−): 447 (M−H). Mpt. 188-190° C. LCMS (method SQD13): Rt. 0.95 min, 449/451 (M+H).

Example P19: 3-chloro-6-[3-ethylsulfonyl-5-(trifluoromethyl)-2-pyridyl]-7-methyl-imidazo[4,5-c]pyridazine (Compound V12.17)

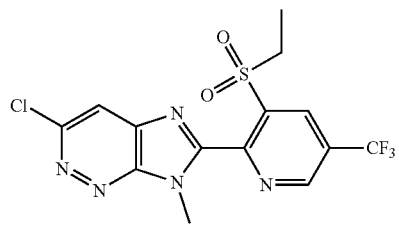

V12.17

Step A: 3,6-dichloropyridazin-4-amine

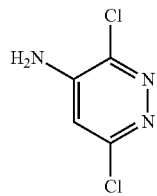

4-Bromo-3,6-dichloro-pyridazine (15.0 g, 65.8 mmol, prepared as described in WO 2008116815) was dissolved in EtOH (73.1 mL) and introduced into an auto clave. At rt, gaseous NH3 (4.48 g, 263 mmol) was introduced, and the reaction mixture was then stirred over night at reflux. The solution was concentrated in vacuo and the residue was triturated with EtOAc, the insoluble part was filtrated off, and the mother liquor evaporated to give the crude product. This was purified by Flash-Chromatography, eluting with cyclohexan/EtOAc 1/1+2.5% Et3N, to give the title compound as a pale brown solid (5.82 g, 53%). LCMS (method ZCQ13): Rt. 0.3 min, 164/166/168 (M+H).

Step B: 6-chloro-N3-methyl-pyridazine-3,4-diamine

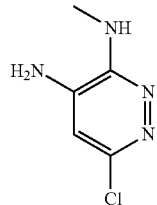

In an auto clave, 3,6-dichloropyridazin-4-amine (2.35 g, 14.3 mmol) was treated with Methylamine dissolved in EtOH (20.2 g, 215 mmol, 26.7 mL) and heated to 100° C. After 48 h at 100° C. LCMS showed no more starting material. The reaction mixture was evaporated to dryness. The crude product was diluted in dichloromethane and 4 ml Et3N was added. The mixture was stirred 5' at rt and evaporated. The residue was diluted with 5 ml water and the insoluble material was filtrated and dried to give the title product 1.35 g, 57%) as a pale brown solid. LCMS (Method ZCQ13): Rt. 0.17 min, 157/159 (M−H).

Step C: N-[6-chloro-3-(methylamino)pyridazin-4-yl]-3-ethylsulfanyl-5-(trifluoromethyl)pyridine-2-carboxamide

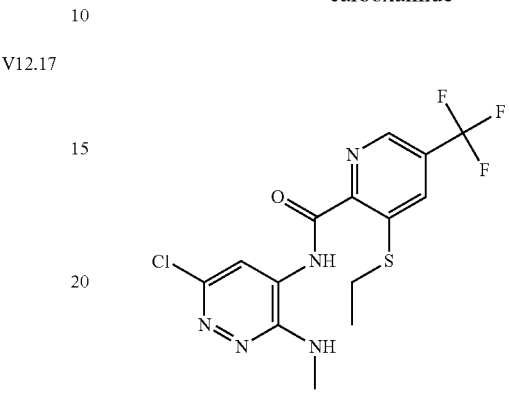

6-Chloro-N3-methyl-pyridazine-3,4-diamine (0.3 g, 1.89 mmol) dissolved in Pyridine (14.6 mL), was treated with 3-Ethylsulfanyl-5-(trifluoromethyl)pyridine-2-carboxylic acid (0.499 g, 1.99 mmol, prepared as described in WO 2013018928) and EDCl.HCl (0.4352 g, 2.27 mmol). The reaction mixtures was stirred 4 h at rt, and then treated with a further portion of EDC.HCl (0.4352 g, 2.27 mmol). The mixture was stirred over night at rt. The reaction mixture was then concentrated in vacuo and the residue taken up in EtOAc and water. The phases were separated and the organic phase washed with brine, dried over Na2SO4, and concentrated in vacuo. The crude product was purified by Flash-Master (Solvent: Cyclohexan/EtOAc 3/1 to give the title compound as a white solid (250 mg, 33%). LCMS (method ZCQ13) Ret. Time 1.01 min, 392/394 (M+H).

Step D: 3-chloro-6-[3-ethylsulfanyl-5-(trifluoromethyl)-2-pyridyl]-7-methyl-imidazo[4,5-c]pyridazine (Compound A6.015-B1.014)

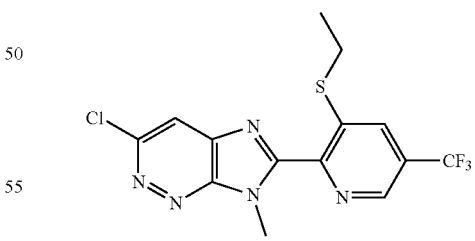

N-[6-chloro-3-(methylamino)pyridazin-4-yl]-3-ethylsulfanyl-5-(trifluoromethyl)pyridine-2-carboxamide (250 mg, 0.64 mmol) was dissolved in DMF (2 mL) and toluene (8 mL). p-toluenesulfonic acid monohydrate (0.123 g, 0.70 mmol) was added. The bombe tube was closed, and heated to 160° C. for 4 hr. This was then cooled to rt and evaporated to dryness. The residue was purified by Flash-Master (Solvent: Cyclohexan/EtOAc 2/1) to give the title compound (172 mg, 72%) as a yellow solid.

$^1$H NMR (400 MHz, CDCl$_3$): δ (ppm) 8.65-8.88 (m, 1H), 7.86-8.05 (m, 2H), 4.13-4.27 (m, 3H), 3.04 (q, J=7.5 Hz, 2H), 1.41 (t, J=7.5 Hz, 3H). LCMS (method ZCQ13): Ret. Time 1.01 min, 374/376 (M+H). Mpt.: 156°-158° C.

Step D: 3-chloro-6-[3-ethylsulfonyl-5-(trifluoromethyl)-2-pyridyl]-7-methyl-imidazo[4,5-c]pyridazine (Compound V12.17)

V12.17

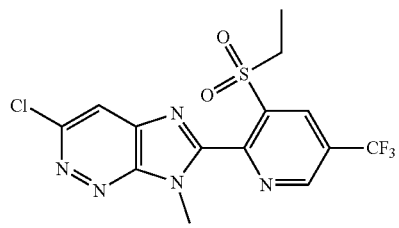

3-chloro-6-[3-ethylsulfanyl-5-(trifluoromethyl)-2-pyridyl]-7-methyl-imidazo[4,5-c]pyridazine (0.14 g, 0.3745 mmol) was dissolved in dichloromethane (8 mL). At 0° C. MCPBA (0.1747 g, 0.7491 mmol) was added, and the mixture was stirred 1 h at 0° C., then 3 h at rt. The reaction was quenched with sat sodium thiosulphate solution. The separated organic phase was washed with aq NaHCO$_3$ and brine, dried over Na$_2$SO$_4$, filtrated and concentrated in vacuo. The crude product was purified by Flash-Master (Solvent: Cyclohexan/EtOAc 1/1) to give the title compound (164 mg, 96%) as a white solid. $^1$H NMR (400 MHz, CDCl$_3$): δ (ppm) 9.28 (d, J=1.5 Hz, 1H), 8.78 (d, J=1.8 Hz, 1H), 7.71-8.03 (m, 1H), 4.02 (s, 3H), 3.84 (q, J=7.6 Hz, 2H), 1.40 (t, J=7.5 Hz, 3H). LCMS (method ZCQ13): Ret. Time 0.91 min, 406/408 (M+H). Mpt. 228-229° C.

Specific examples of compounds of formula (I) are illustrated in the Tables 1 to 130 below, wherein Tables A to K depict the groups B and Tables L to Q depict groups A:

A-B    (I)

TABLE A

Radicals of formula B$_1$ (DB denotes a direct bond, i.e. the sulphur is attached directly to the aromatic ring)

B$_1$

| Radical | R$_3$ | R$_4$ | V$_0$ | V$_1$ | V$_2$ | m | L$_1$ |
|---------|-------|-------|-------|-------|-------|---|-------|
| B1.001 | CH$_3$ | H | C—H | N | C—H | 0 | DB |
| B1.002 | CH$_3$ | H | C—H | N | C—CF$_3$ | 0 | DB |
| B1.003 | CH$_3$ | H | C—H | N | C—Br | 0 | DB |
| B1.004 | CH$_3$ | H | C—H | N | C—Cl | 0 | DB |
| B1.005 | CH$_3$ | H | C—H | N | C—H | 1 | DB |
| B1.006 | CH$_3$ | H | C—H | N | C—CF$_3$ | 1 | DB |
| B1.007 | CH$_3$ | H | C—H | N | C—Br | 1 | DB |
| B1.008 | CH$_3$ | H | C—H | N | C—Cl | 1 | DB |
| B1.009 | CH$_3$ | H | C—H | N | C—H | 2 | DB |
| B1.010 | CH$_3$ | H | C—H | N | C—CF$_3$ | 2 | DB |
| B1.011 | CH$_3$ | H | C—H | N | C—Br | 2 | DB |
| B1.012 | CH$_3$ | H | C—H | N | C—Cl | 2 | DB |
| B1.013 | CH$_2$CH$_3$ | H | C—H | N | C—H | 0 | DB |
| B1.014 | CH$_2$CH$_3$ | H | C—H | N | C—CF$_3$ | 0 | DB |
| B1.015 | CH$_2$CH$_3$ | H | C—H | N | C—Br | 0 | DB |
| B1.016 | CH$_2$CH$_3$ | H | C—H | N | C—Cl | 0 | DB |
| B1.017 | CH$_2$CH$_3$ | H | C—H | N | C—H | 1 | DB |
| B1.018 | CH$_2$CH$_3$ | H | C—H | N | C—CF$_3$ | 1 | DB |
| B1.019 | CH$_2$CH$_3$ | H | C—H | N | C—Br | 1 | DB |
| B1.020 | CH$_2$CH$_3$ | H | C—H | N | C—Cl | 1 | DB |
| B1.021 | CH$_2$CH$_3$ | H | C—H | N | C—H | 2 | DB |
| B1.022 | CH$_2$CH$_3$ | H | C—H | N | C—CF$_3$ | 2 | DB |
| B1.023 | CH$_2$CH$_3$ | H | C—H | N | C—Br | 2 | DB |
| B1.024 | CH$_2$CH$_3$ | H | C—H | N | C—Cl | 2 | DB |
| B1.025 | CH$_3$ | H | C—H | CH | C—H | 0 | DB |
| B1.026 | CH$_3$ | H | C—H | CH | C—CF$_3$ | 0 | DB |
| B1.027 | CH$_3$ | H | C—H | CH | C—Br | 0 | DB |
| B1.028 | CH$_3$ | H | C—H | CH | C—Cl | 0 | DB |
| B1.029 | CH$_3$ | H | C—H | CH | C—H | 1 | DB |
| B1.030 | CH$_3$ | H | C—H | CH | C—CF$_3$ | 1 | DB |
| B1.031 | CH$_3$ | H | C—H | CH | C—Br | 1 | DB |
| B1.032 | CH$_3$ | H | C—H | CH | C—Cl | 1 | DB |
| B1.033 | CH$_3$ | H | C—H | CH | C—H | 2 | DB |
| B1.034 | CH$_3$ | H | C—H | CH | C—CF$_3$ | 2 | DB |
| B1.035 | CH$_3$ | H | C—H | CH | C—Br | 2 | DB |
| B1.036 | CH$_3$ | H | C—H | CH | C—Cl | 2 | DB |
| B1.037 | CH$_2$CH$_3$ | H | C—H | CH | C—H | 0 | DB |
| B1.038 | CH$_2$CH$_3$ | H | C—H | CH | C—CF$_3$ | 0 | DB |
| B1.039 | CH$_2$CH$_3$ | H | C—H | CH | C—Br | 0 | DB |
| B1.040 | CH$_2$CH$_3$ | H | C—H | CH | C—Cl | 0 | DB |
| B1.041 | CH$_2$CH$_3$ | H | C—H | CH | C—H | 1 | DB |
| B1.042 | CH$_2$CH$_3$ | H | C—H | CH | C—CF$_3$ | 1 | DB |
| B1.043 | CH$_2$CH$_3$ | H | C—H | CH | C—Br | 1 | DB |
| B1.044 | CH$_2$CH$_3$ | H | C—H | CH | C—Cl | 1 | DB |
| B1.045 | CH$_2$CH$_3$ | H | C—H | CH | C—H | 2 | DB |
| B1.046 | CH$_2$CH$_3$ | H | C—H | CH | C—CF$_3$ | 2 | DB |
| B1.047 | CH$_2$CH$_3$ | H | C—H | CH | C—Br | 2 | DB |
| B1.048 | CH$_2$CH$_3$ | H | C—H | CH | C—Cl | 2 | DB |
| B1.049 | CH$_2$CH$_3$ | H | N | N | C—H | 0 | DB |
| B1.050 | CH$_2$CH$_3$ | H | N | N | C—CF$_3$ | 0 | DB |
| B1.051 | CH$_2$CH$_3$ | H | N | N | C—Br | 0 | DB |
| B1.052 | CH$_2$CH$_3$ | H | N | N | C—Cl | 0 | DB |
| B1.053 | CH$_2$CH$_3$ | H | N | N | C—H | 1 | DB |
| B1.054 | CH$_2$CH$_3$ | H | N | N | C—CF$_3$ | 1 | DB |
| B1.055 | CH$_2$CH$_3$ | H | N | N | C—Br | 1 | DB |
| B1.056 | CH$_2$CH$_3$ | H | N | N | C—Cl | 1 | DB |
| B1.057 | CH$_2$CH$_3$ | H | N | N | C—H | 2 | DB |
| B1.058 | CH$_2$CH$_3$ | H | N | N | C—CF$_3$ | 2 | DB |
| B1.059 | CH$_2$CH$_3$ | H | N | N | C—Br | 2 | DB |
| B1.060 | CH$_2$CH$_3$ | H | N | N | C—Cl | 2 | DB |
| B1.061 | CH$_3$ | H | N | C—H | C—H | 0 | DB |
| B1.062 | CH$_3$ | H | N | C—H | C—CF$_3$ | 0 | DB |
| B1.063 | CH$_3$ | H | N | C—H | C—Br | 0 | DB |
| B1.064 | CH$_3$ | H | N | C—H | C—Cl | 0 | DB |
| B1.065 | CH$_3$ | H | N | C—H | C—H | 1 | DB |
| B1.066 | CH$_3$ | H | N | C—H | C—CF$_3$ | 1 | DB |
| B1.067 | CH$_3$ | H | N | C—H | C—Br | 1 | DB |
| B1.068 | CH$_3$ | H | N | C—H | C—Cl | 1 | DB |
| B1.069 | CH$_3$ | H | N | C—H | C—H | 2 | DB |
| B1.070 | CH$_3$ | H | N | C—H | C—CF$_3$ | 2 | DB |
| B1.071 | CH$_3$ | H | N | C—H | C—Br | 2 | DB |
| B1.072 | CH$_3$ | H | N | C—H | C—Cl | 2 | DB |
| B1.073 | CH$_2$CH$_3$ | H | N | C—H | C—H | 0 | DB |

TABLE A-continued

Radicals of formula B₁ (DB denotes a direct bond, i.e. the sulphur is attached directly to the aromatic ring)

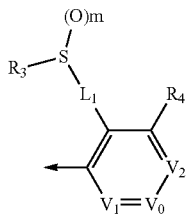

| Radical | $R_3$ | $R_4$ | $V_0$ | $V_1$ | $V_2$ | m | $L_1$ |
|---|---|---|---|---|---|---|---|
| B1.074 | $CH_2CH_3$ | H | N | C—H | C—$CF_3$ | 0 | DB |
| B1.075 | $CH_2CH_3$ | H | N | C—H | C—Br | 0 | DB |
| B1.076 | $CH_2CH_3$ | H | N | C—H | C—Cl | 0 | DB |
| B1.077 | $CH_2CH_3$ | H | N | C—H | C—H | 1 | DB |
| B1.078 | $CH_2CH_3$ | H | N | C—H | C—$CF_3$ | 1 | DB |
| B1.079 | $CH_2CH_3$ | H | N | C—H | C—Br | 1 | DB |
| B1.080 | $CH_2CH_3$ | H | N | C—H | C—Cl | 1 | DB |
| B1.081 | $CH_2CH_3$ | H | N | C—H | C—H | 2 | DB |
| B1.082 | $CH_2CH_3$ | H | N | C—H | C—$CF_3$ | 2 | DB |
| B1.083 | $CH_2CH_3$ | H | N | C—H | C—Br | 2 | DB |
| B1.084 | $CH_2CH_3$ | H | N | C—H | C—Cl | 2 | DB |
| B1.085 | $CH_3$ | H | C—H | C—H | N | 0 | DB |
| B1.086 | $CH_3$ | H | C—H | C—H | N | 1 | DB |
| B1.087 | $CH_3$ | H | C—H | C—H | N | 2 | DB |
| B1.088 | $CH_2CH_3$ | H | C—H | C—H | N | 0 | DB |
| B1.089 | $CH_2CH_3$ | H | C—H | C—H | N | 1 | DB |
| B1.090 | $CH_2CH_3$ | H | C—H | C—H | N | 2 | DB |
| B1.091 | $CH_3$ | H | C—H | N | N | 0 | DB |
| B1.092 | $CH_3$ | H | C—H | N | N | 1 | DB |
| B1.093 | $CH_3$ | H | C—H | N | N | 2 | DB |
| B1.094 | $CH_2CH_3$ | H | C—H | N | N | 0 | DB |
| B1.095 | $CH_2CH_3$ | H | C—H | N | N | 1 | DB |
| B1.096 | $CH_2CH_3$ | H | C—H | N | N | 2 | DB |
| B1.097 | $CH_3$ | H | C—H | N | C—H | 0 | $CH_2$ |
| B1.098 | $CH_3$ | H | C—H | N | C—$CF_3$ | 0 | $CH_2$ |
| B1.099 | $CH_3$ | H | C—H | N | C—Br | 0 | $CH_2$ |
| B1.100 | $CH_3$ | H | C—H | N | C—Cl | 0 | $CH_2$ |
| B1.101 | $CH_3$ | H | C—H | N | C—H | 1 | $CH_2$ |
| B1.102 | $CH_3$ | H | C—H | N | C-$CF_3$ | 1 | $CH_2$ |
| B1.103 | $CH_3$ | H | C—H | N | C—Br | 1 | $CH_2$ |
| B1.104 | $CH_3$ | H | C—H | N | C—Cl | 1 | $CH_2$ |
| B1.105 | $CH_3$ | H | C—H | N | C—H | 2 | $CH_2$ |
| B1.106 | $CH_3$ | H | C—H | N | C—$CF_3$ | 2 | $CH_2$ |
| B1.107 | $CH_3$ | H | C—H | N | C—Br | 2 | $CH_2$ |
| B1.108 | $CH_3$ | H | C—H | N | C—Cl | 2 | $CH_2$ |
| B1.109 | $CH_2CH_3$ | H | C—H | C—H | C—H | 0 | $CH_2$ |
| B1.110 | $CH_2CH_3$ | H | C—H | C—H | C—$CF_3$ | 0 | $CH_2$ |
| B1.111 | $CH_2CH_3$ | H | C—H | C—H | C—Br | 0 | $CH_2$ |
| B1.112 | $CH_2CH_3$ | H | C—H | C—H | C—Cl | 0 | $CH_2$ |
| B1.113 | $CH_2CH_3$ | H | C—H | C—H | C—H | 1 | $CH_2$ |
| B1.114 | $CH_2CH_3$ | H | C—H | C—H | C—$CF_3$ | 1 | $CH_2$ |
| B1.115 | $CH_2CH_3$ | H | C—H | C—H | C—Br | 1 | $CH_2$ |
| B1.116 | $CH_2CH_3$ | H | C—H | C—H | C—Cl | 1 | $CH_2$ |
| B1.117 | $CH_2CH_3$ | H | C—H | C—H | C—H | 2 | $CH_2$ |
| B1.118 | $CH_2CH_3$ | H | C—H | C—H | C—$CF_3$ | 2 | $CH_2$ |
| B1.119 | $CH_2CH_3$ | H | C—H | C—H | C—Br | 2 | $CH_2$ |
| B1.120 | $CH_2CH_3$ | H | C—H | C—H | C—Cl | 2 | $CH_2$ |
| B1.121 | $CH_2CH_3$ | $CH_3$ | C—H | N | C—H | 0 | DB |
| B1.122 | $CH_2CH_3$ | $CH_3$ | C—H | N | C—$CF_3$ | 0 | DB |
| B1.123 | $CH_2CH_3$ | $CH_3$ | C—H | N | C—Br | 0 | DB |
| B1.124 | $CH_2CH_3$ | $CH_3$ | C—H | N | C—Cl | 0 | DB |
| B1.125 | $CH_2CH_3$ | $CH_3$ | C—H | N | C—H | 1 | DB |
| B1.126 | $CH_2CH_3$ | $CH_3$ | C—H | N | C—$CF_3$ | 1 | DB |
| B1.127 | $CH_2CH_3$ | $CH_3$ | C—H | N | C—Br | 1 | DB |
| B1.128 | $CH_2CH_3$ | $CH_3$ | C—H | N | C—Cl | 1 | DB |
| B1.129 | $CH_2CH_3$ | $CH_3$ | C—H | N | C—H | 2 | DB |
| B1.130 | $CH_2CH_3$ | $CH_3$ | C—H | N | C—$CF_3$ | 2 | DB |
| B1.131 | $CH_2CH_3$ | $CH_3$ | C—H | N | C—Br | 2 | DB |
| B1.132 | $CH_2CH_3$ | $CH_3$ | C—H | N | C—Cl | 2 | DB |

TABLE B

Radicals of Formula B2

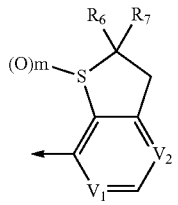

| Radical | $R_6$ | $R_7$ | $V_1$ | $V_2$ | m |
|---|---|---|---|---|---|
| B2.001 | $CH_3$ | H | N | C—H | 0 |
| B2.002 | $CH_3$ | H | N | C—$CF_3$ | 0 |
| B2.003 | $CH_3$ | H | N | C—Br | 0 |
| B2.004 | $CH_3$ | H | N | C—Cl | 0 |
| B2.005 | $CH_3$ | H | N | C—H | 1 |
| B2.006 | $CH_3$ | H | N | C—$CF_3$ | 1 |
| B2.007 | $CH_3$ | H | N | C—Br | 1 |
| B2.008 | $CH_3$ | H | N | C—Cl | 1 |
| B2.009 | $CH_3$ | H | N | C—H | 2 |
| B2.010 | $CH_3$ | H | N | C—$CF_3$ | 2 |
| B2.011 | $CH_3$ | H | N | C—Br | 2 |
| B2.012 | $CH_3$ | H | N | C—Cl | 2 |
| B2.013 | $CH_3$ | H | C—H | C—H | 0 |
| B2.014 | $CH_3$ | H | C—H | C—$CF_3$ | 0 |
| B2.015 | $CH_3$ | H | C—H | C—Br | 0 |
| B2.016 | $CH_3$ | H | C—H | C—Cl | 0 |
| B2.017 | $CH_3$ | H | C—H | C—H | 1 |
| B2.018 | $CH_3$ | H | C—H | C—$CF_3$ | 1 |
| B2.019 | $CH_3$ | H | C—H | C—Br | 1 |
| B2.020 | $CH_3$ | H | C—H | C—Cl | 1 |
| B2.021 | $CH_3$ | H | C—H | C—H | 2 |
| B2.022 | $CH_3$ | H | C—H | C—$CF_3$ | 2 |
| B2.023 | $CH_3$ | H | C—H | C—Br | 2 |
| B2.024 | $CH_3$ | H | C—H | C—Cl | 2 |
| B2.025 | $CH_3$ | $CH_3$ | C—H | C—H | 0 |
| B2.026 | $CH_3$ | $CH_3$ | C—H | C—$CF_3$ | 0 |
| B2.027 | $CH_3$ | $CH_3$ | C—H | C—Br | 0 |
| B2.028 | $CH_3$ | $CH_3$ | C—H | C—Cl | 0 |
| B2.029 | $CH_3$ | $CH_3$ | C—H | C—H | 1 |
| B2.030 | $CH_3$ | $CH_3$ | C—H | C—$CF_3$ | 1 |
| B2.031 | $CH_3$ | $CH_3$ | C—H | C—Br | 1 |
| B2.032 | $CH_3$ | $CH_3$ | C—H | C—Cl | 1 |
| B2.033 | $CH_3$ | $CH_3$ | C—H | C—H | 2 |
| B2.034 | $CH_3$ | $CH_3$ | C—H | C—$CF_3$ | 2 |
| B2.035 | $CH_3$ | $CH_3$ | C—H | C—Br | 2 |
| B2.036 | $CH_3$ | $CH_3$ | C—H | C—Cl | 2 |

TABLE C

Radicals of Formula B₃

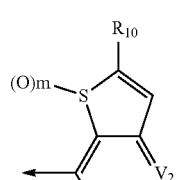

| Radical | $R_{10}$ | $V_1$ | $V_2$ | m |
|---|---|---|---|---|
| B3.001 | $CH_3$ | N | C—H | 0 |
| B3.002 | $CH_3$ | N | C—$CF^3$ | 0 |
| B3.003 | $CH_3$ | N | C—Br | 0 |
| B3.004 | $CH_3$ | N | C—Cl | 0 |
| B3.005 | $CH_3$ | N | C—H | 2 |
| B3.006 | $CH_3$ | N | C—$CF_3$ | 2 |
| B3.007 | $CH_3$ | N | C—Br | 2 |

TABLE C-continued

Radicals of Formula B₃

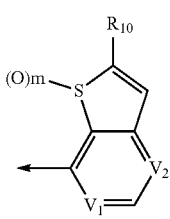

| Radical | $R_{10}$ | $V_1$ | $V_2$ | m |
|---|---|---|---|---|
| B3.008 | $CH_3$ | N | C—Cl | 2 |
| B3.009 | $CH_3$ | C—H | C—H | 0 |
| B3.010 | $CH_3$ | C—H | C—$CF_3$ | 0 |
| B3.011 | $CH_3$ | C—H | C—Br | 0 |
| B3.012 | $CH_3$ | C—H | C—Cl | 0 |
| B3.013 | $CH_3$ | C—H | C—H | 2 |
| B3.014 | $CH_3$ | C—H | C—$CF_3$ | 2 |
| B3.015 | $CH_3$ | C—H | C—Br | 2 |
| B3.016 | $CH_3$ | C—H | C—Cl | 2 |
| B3.017 | $CH_3$ | C—H | C—H | 0 |
| B3.018 | $CH_3$ | C—H | C—$CF_3$ | 0 |
| B3.019 | $CH_3$ | C—H | C—Br | 0 |
| B3.020 | $CH_3$ | C—H | C—Cl | 0 |
| B3.021 | $CH_3$ | C—H | C—H | 2 |
| B3.022 | $CH_3$ | C—H | C—$CF_3$ | 2 |
| B3.023 | $CH_3$ | C—H | C—Br | 2 |
| B3.024 | $CH_3$ | C—H | C—Cl | 2 |

TABLE D

Radicals of formula B₄

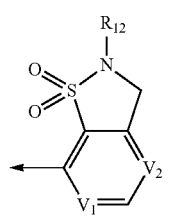

| Radical | $R_{12}$ | $V_1$ | $V_2$ |
|---|---|---|---|
| B4.001 | $CH_3$ | N | C—H |
| B4.002 | $CH_3$ | N | C—$CF_3$ |
| B4.003 | $CH_3$ | N | C—Br |
| B4.004 | $CH_3$ | N | C—Cl |
| B4.005 | $CH_3$ | C—H | C—H |
| B4.006 | $CH_3$ | C—H | C—$CF_3$ |
| B4.007 | $CH_3$ | C—H | C—Br |
| B4.008 | $CH_3$ | C—H | C—Cl |

TABLE E

Radicals of formula B₅

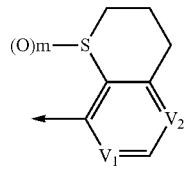

| Radical | $V_1$ | $V_2$ | m |
|---|---|---|---|
| B5.001 | N | C—H | 0 |
| B5.002 | N | C—$CF_3$ | 0 |
| B5.003 | N | C—Br | 0 |
| B5.004 | N | C—Cl | 0 |
| B5.005 | N | C—H | 1 |
| B5.006 | N | C—$CF_3$ | 1 |
| B5.007 | N | C—Br | 1 |
| B5.008 | N | C—Cl | 1 |
| B5.009 | N | C—H | 2 |
| B5.010 | N | C—$CF_3$ | 2 |
| B5.011 | N | C—Br | 2 |
| B5.012 | N | C—Cl | 2 |
| B5.013 | C—H | C—H | 0 |
| B5.014 | C—H | C—$CF_3$ | 0 |
| B5.015 | C—H | C—Br | 0 |
| B5.016 | C—H | C—Cl | 0 |
| B5.017 | C—H | C—H | 1 |
| B5.018 | C—H | C—$CF_3$ | 1 |
| B5.019 | C—H | C—Br | 1 |
| B5.020 | C—H | C—Cl | 1 |
| B5.021 | C—H | C—H | 2 |
| B5.022 | C—H | C—$CF_3$ | 2 |
| B5.023 | C—H | C—Br | 2 |
| B5.024 | C—H | C—Cl | 2 |

TABLE F

Radicals of formula B₆

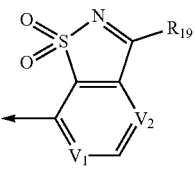

| Radical | $R_{19}$ | $V_1$ | $V_2$ |
|---|---|---|---|
| B6.001 | $C(CH_3)_3$ | N | C—H |
| B6.002 | $C(CH_3)_3$ | N | C—$CF_3$ |
| B6.003 | $C(CH_3)_3$ | N | C—Br |
| B6.004 | $C(CH_3)_3$ | N | C—Cl |
| B6.005 | $C(CH_3)_3$ | C—H | C—H |
| B6.006 | $C(CH_3)_3$ | C—H | C—$CF_3$ |
| B6.007 | $C(CH_3)_3$ | C—H | C—Br |
| B6.008 | $C(CH_3)_3$ | C—H | C—Cl |
| B6.009 | H | N | C—H |
| B6.010 | H | N | C—$CF_3$ |
| B6.011 | H | N | C—Br |
| B6.012 | H | N | C—Cl |
| B6.013 | H | C—H | C—H |
| B6.014 | H | C—H | C—$CF_3$ |
| B6.015 | H | C—H | C—Br |
| B6.016 | H | C—H | C—Cl |

TABLE G

Radicals of formula $B_7$

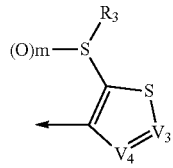

| Radical | $R_3$ | $V_4$ | $V_3$ | m |
|---|---|---|---|---|
| B7.001 | $CH_3$ | C—H | C—H | 0 |
| B7.002 | $CH_3$ | C—H | C—$CF_3$ | 0 |
| B7.003 | $CH_3$ | C—H | C—Br | 0 |
| B7.004 | $CH_3$ | C—H | C—Cl | 0 |
| B7.005 | $CH_3$ | C—H | C—H | 1 |
| B7.006 | $CH_3$ | C—H | C—$CF_3$ | 1 |
| B7.007 | $CH_3$ | C—H | C—Br | 1 |
| B7.008 | $CH_3$ | C—H | C—Cl | 1 |
| B7.009 | $CH_3$ | C—H | C—H | 2 |
| B7.010 | $CH_3$ | C—H | C—$CF_3$ | 2 |
| B7.011 | $CH_3$ | C—H | C—Br | 2 |
| B7.012 | $CH_3$ | C—H | C—Cl | 2 |
| B7.013 | $CH_2CH_3$ | C—H | C—H | 0 |
| B7.014 | $CH_2CH_3$ | C—H | C—$CF_3$ | 0 |
| B7.015 | $CH_2CH_3$ | C—H | C—Br | 0 |
| B7.016 | $CH_2CH_3$ | C—H | C—Cl | 0 |
| B7.017 | $CH_2CH_3$ | C—H | C—H | 1 |
| B7.018 | $CH_2CH_3$ | C—H | C—$CF_3$ | 1 |
| B7.019 | $CH_2CH_3$ | C—H | C—Br | 1 |
| B7.020 | $CH_2CH_3$ | C—H | C—Cl | 1 |
| B7.021 | $CH_2CH_3$ | C—H | C—H | 2 |
| B7.022 | $CH_2CH_3$ | C—H | C—$CF_3$ | 2 |
| B7.023 | $CH_2CH_3$ | C—H | C—Br | 2 |
| B7.024 | $CH_2CH_3$ | C—H | C—Cl | 2 |
| B7.025 | $CH_3$ | N | C—H | 0 |
| B7.026 | $CH_3$ | N | C—$CF_3$ | 0 |
| B7.027 | $CH_3$ | N | C—Br | 0 |
| B7.028 | $CH_3$ | N | C—Cl | 0 |
| B7.029 | $CH_3$ | N | C—H | 1 |
| B7.030 | $CH_3$ | N | C—$CF_3$ | 1 |
| B7.031 | $CH_3$ | N | C—Br | 1 |
| B7.032 | $CH_3$ | N | C—Cl | 1 |
| B7.033 | $CH_3$ | N | C—H | 2 |
| B7.034 | $CH_3$ | N | C—$CF_3$ | 2 |
| B7.035 | $CH_3$ | N | C—Br | 2 |
| B7.036 | $CH_3$ | N | C—Cl | 2 |
| B7.037 | $CH_2CH_3$ | N | C—H | 0 |
| B7.038 | $CH_2CH_3$ | N | C—$CF_3$ | 0 |
| B7.039 | $CH_2CH_3$ | N | C—Br | 0 |
| B7.040 | $CH_2CH_3$ | N | C—Cl | 0 |
| B7.041 | $CH_2CH_3$ | N | C—H | 1 |
| B7.042 | $CH_2CH_3$ | N | C—$CF_3$ | 1 |
| B7.043 | $CH_2CH_3$ | N | C—Br | 1 |
| B7.044 | $CH_2CH_3$ | N | C—Cl | 1 |
| B7.045 | $CH_2CH_3$ | N | C—H | 2 |
| B7.046 | $CH_2CH_3$ | N | C—$CF_3$ | 2 |
| B7.047 | $CH_2CH_3$ | N | C—Br | 2 |
| B7.048 | $CH_2CH_3$ | N | C—Cl | 2 |
| B7.049 | $CH_3$ | N | N | 0 |
| B7.050 | $CH_3$ | N | N | 1 |
| B7.051 | $CH_3$ | N | N | 2 |
| B7.052 | $CH_2CH_3$ | N | N | 0 |
| B7.053 | $CH_2CH_3$ | N | N | 1 |
| B7.054 | $CH_2CH_3$ | N | N | 2 |

TABLE H

Radicals of formula $B_8$

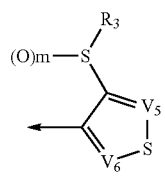

| Radical | $R_3$ | $V_5$ | $V_6$ | m |
|---|---|---|---|---|
| B8.001 | $CH_3$ | C—H | C—H | 0 |
| B8.002 | $CH_3$ | C—H | C—H | 1 |
| B8.003 | $CH_3$ | C—H | C—H | 2 |
| B8.004 | $CH_2CH_3$ | C—H | C—H | 0 |
| B8.005 | $CH_2CH_3$ | C—H | C—H | 1 |
| B8.006 | $CH_2CH_3$ | C—H | C—H | 2 |
| B8.007 | $CH_3$ | C—H | N | 0 |
| B8.008 | $CH_3$ | C—H | N | 1 |
| B8.009 | $CH_3$ | C—H | N | 2 |
| B8.010 | $CH_2CH_3$ | C—H | N | 0 |
| B8.011 | $CH_2CH_3$ | C—H | N | 1 |
| B8.012 | $CH_2CH_3$ | C—H | N | 2 |

TABLE I

Radicals of formula $B_9$

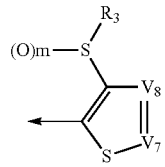

| Radical | $R_3$ | $V_8$ | $V_7$ | m |
|---|---|---|---|---|
| B9.001 | $CH_3$ | C—H | C—H | 0 |
| B9.002 | $CH_3$ | C—H | C—$CF_3$ | 0 |
| B9.003 | $CH_3$ | C—H | C—Br | 0 |
| B9.004 | $CH_3$ | C—H | C—Cl | 0 |
| B9.005 | $CH_3$ | C—H | C—H | 1 |
| B9.006 | $CH_3$ | C—H | C—$CF_3$ | 1 |
| B9.007 | $CH_3$ | C—H | C—Br | 1 |
| B9.008 | $CH_3$ | C—H | C—Cl | 1 |
| B9.009 | $CH_3$ | C—H | C—H | 2 |
| B9.010 | $CH_3$ | C—H | C—$CF_3$ | 2 |
| B9.011 | $CH_3$ | C—H | C—Br | 2 |
| B9.012 | $CH_3$ | C—H | C—Cl | 2 |
| B9.013 | $CH_2CH_3$ | C—H | C—H | 0 |
| B9.014 | $CH_2CH_3$ | C—H | C—$CF_3$ | 0 |
| B9.015 | $CH_2CH_3$ | C—H | C—Br | 0 |
| B9.016 | $CH_2CH_3$ | C—H | C—Cl | 0 |
| B9.017 | $CH_2CH_3$ | C—H | C—H | 1 |
| B9.018 | $CH_2CH_3$ | C—H | C—$CF_3$ | 1 |
| B9.019 | $CH_2CH_3$ | C—H | C—Br | 1 |
| B9.020 | $CH_2CH_3$ | C—H | C—Cl | 1 |
| B9.021 | $CH_2CH_3$ | C—H | C—H | 2 |
| B9.022 | $CH_2CH_3$ | C—H | C—$CF_3$ | 2 |
| B9.023 | $CH_2CH_3$ | C—H | C—Br | 2 |
| B9.024 | $CH_2CH_3$ | C—H | C—Cl | 2 |
| B9.025 | $CH_3$ | C—H | N | 0 |
| B9.026 | $CH_3$ | C—H | N | 1 |
| B9.027 | $CH_3$ | C—H | N | 2 |
| B9.028 | $CH_2CH_3$ | C—H | N | 0 |
| B9.029 | $CH_2CH_3$ | C—H | N | 1 |
| B9.030 | $CH_2CH_3$ | C—H | N | 2 |

TABLE J

Radicals of formula $B_{10}$

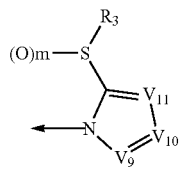

| Radical | $R_3$ | $V_9$ | $V_{10}$ | $V_{11}$ | m |
|---|---|---|---|---|---|
| B10.001 | CH$_2$CH$_3$ | C—H | C—H | C—H | 0 |
| B10.002 | CH$_2$CH$_3$ | C—H | C—H | C—H | 1 |
| B10.003 | CH$_2$CH$_3$ | C—H | C—H | C—H | 2 |
| B10.004 | CH$_2$CH$_3$ | N | C—H | C—H | 0 |
| B10.005 | CH$_2$CH$_3$ | N | C—H | C—H | 1 |
| B10.006 | CH$_2$CH$_3$ | N | C—H | C—H | 2 |
| B10.007 | CH$_2$CH$_3$ | N | C—H | N | 0 |
| B10.008 | CH$_2$CH$_3$ | N | C—H | N | 1 |
| B10.009 | CH$_2$CH$_3$ | N | C—H | N | 2 |
| B10.010 | CH$_2$CH$_3$ | N | N | N | 0 |
| B10.011 | CH$_2$CH$_3$ | N | N | N | 1 |
| B10.012 | CH$_2$CH$_3$ | N | N | N | 2 |

TABLE K

Radicals of formula $B_{11}$

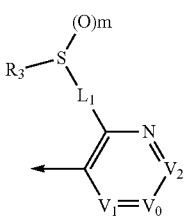

| Radical | $R_3$ | $V_1$ | $V_0$ | $V_2$ | m |
|---|---|---|---|---|---|
| B11.001 | CH$_3$ | C—H | C—H | C—H | 0 |
| B11.002 | CH$_3$ | C—H | C—H | C—CF$_3$ | 0 |
| B11.003 | CH$_3$ | C—H | C—H | C—Br | 0 |
| B11.004 | CH$_3$ | C—H | C—H | C—Cl | 0 |
| B11.005 | CH$_3$ | C—H | C—H | C—H | 1 |
| B11.006 | CH$_3$ | C—H | C—H | C—CF$_3$ | 1 |
| B11.007 | CH$_3$ | C—H | C—H | C—Br | 1 |
| B11.008 | CH$_3$ | C—H | C—H | C—Cl | 1 |
| B11.009 | CH$_3$ | C—H | C—H | C—H | 2 |
| B11.010 | CH$_3$ | C—H | C—H | C—CF$_3$ | 2 |
| B11.011 | CH$_3$ | C—H | C—H | C—Br | 2 |
| B11.012 | CH$_3$ | C—H | C—H | C—Cl | 2 |
| B11.013 | CH$_3$ | N | C—H | C—H | 0 |
| B11.014 | CH$_3$ | N | C—H | C—CF$_3$ | 0 |
| B11.015 | CH$_3$ | N | C—H | C—Br | 0 |
| B11.016 | CH$_3$ | N | C—H | C—Cl | 0 |
| B11.017 | CH$_3$ | N | C—H | C—H | 1 |
| B11.018 | CH$_3$ | N | C—H | C—CF$_3$ | 1 |
| B11.019 | CH$_3$ | N | C—H | C—Br | 1 |
| B11.020 | CH$_3$ | N | C—H | C—Cl | 1 |
| B11.021 | CH$_3$ | N | C—H | C—H | 2 |
| B11.022 | CH$_3$ | N | C—H | C—CF$_3$ | 2 |
| B11.023 | CH$_3$ | N | C—H | C—Br | 2 |
| B11.024 | CH$_3$ | N | C—H | C—Cl | 2 |
| B11.025 | CH$_2$CH$_3$ | C—H | C—H | C—H | 0 |
| B11.026 | CH$_2$CH$_3$ | C—H | C—H | C—CF$_3$ | 0 |
| B11.027 | CH$_2$CH$_3$ | C—H | C—H | C—Br | 0 |
| B11.028 | CH$_2$CH$_3$ | C—H | C—H | C—Cl | 0 |
| B11.029 | CH$_2$CH$_3$ | C—H | C—H | C—H | 1 |
| B11.030 | CH$_2$CH$_3$ | C—H | C—H | C—CF$_3$ | 1 |
| B11.031 | CH$_2$CH$_3$ | C—H | C—H | C—Br | 1 |
| B11.032 | CH$_2$CH$_3$ | C—H | C—H | C—Cl | 1 |
| B11.033 | CH$_2$CH$_3$ | C—H | C—H | C—H | 2 |
| B11.034 | CH$_2$CH$_3$ | C—H | C—H | C—CF$_3$ | 2 |
| B11.035 | CH$_2$CH$_3$ | C—H | C—H | C—Br | 2 |
| B11.036 | CH$_2$CH$_3$ | C—H | C—H | C—Cl | 2 |
| B11.037 | CH$_2$CH$_3$ | N | C—H | C—H | 0 |
| B11.038 | CH$_2$CH$_3$ | N | C—H | C—CF$_3$ | 0 |
| B11.039 | CH$_2$CH$_3$ | N | C—H | C—Br | 0 |
| B11.040 | CH$_2$CH$_3$ | N | C—H | C—Cl | 0 |
| B11.041 | CH$_2$CH$_3$ | N | C—H | C—H | 1 |
| B11.042 | CH$_2$CH$_3$ | N | C—H | C—CF$_3$ | 1 |
| B11.043 | CH$_2$CH$_3$ | N | C—H | C—Br | 1 |
| B11.044 | CH$_2$CH$_3$ | N | C—H | C—Cl | 1 |
| B11.045 | CH$_2$CH$_3$ | N | C—H | C—H | 2 |
| B11.046 | CH$_2$CH$_3$ | N | C—H | C—CF$_3$ | 2 |
| B11.047 | CH$_2$CH$_3$ | N | C—H | C—Br | 2 |
| B11.048 | CH$_2$CH$_3$ | N | C—H | C—Cl | 2 |
| B11.049 | CH$_2$CH$_3$ | C—H | C—H | N | 0 |
| B11.051 | CH$_2$CH$_3$ | C—H | C—H | N | 1 |
| B11.052 | CH$_2$CH$_3$ | C—H | C—H | N | 2 |
| B11.053 | CH$_2$CH$_3$ | C—H | N | C—H | 0 |
| B11.054 | CH$_2$CH$_3$ | C—H | N | C—CF$_3$ | 0 |
| B11.055 | CH$_2$CH$_3$ | C—H | N | C—Br | 0 |
| B11.056 | CH$_2$CH$_3$ | C—H | N | C—Cl | 0 |
| B11.057 | CH$_2$CH$_3$ | C—H | N | C—H | 1 |
| B11.058 | CH$_2$CH$_3$ | C—H | N | C—CF$_3$ | 1 |
| B11.059 | CH$_2$CH$_3$ | C—H | N | C—Br | 1 |
| B11.060 | CH$_2$CH$_3$ | C—H | N | C—Cl | 1 |
| B11.061 | CH$_2$CH$_3$ | C—H | N | C—H | 2 |
| B11.062 | CH$_2$CH$_3$ | C—H | N | C—CF$_3$ | 2 |
| B11.063 | CH$_2$CH$_3$ | C—H | N | C—Br | 2 |
| B11.064 | CH$_2$CH$_3$ | C—H | N | C—Cl | 2 |

TABLE L

Radicals of formula $A_1$

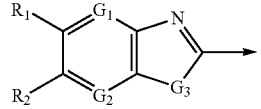

| Radical | $R_1$ | $R_2$ | $G_1$ | $G_2$ | $G_3$ |
|---|---|---|---|---|---|
| A1.001 | CH$_3$ | H | C—H | C—H | N—CH$_3$ |
| A1.002 | CF$_3$ | H | C—H | C—H | N—CH$_3$ |
| A1.003 | Cl | H | C—H | C—H | N—CH$_3$ |
| A1.004 | Br | H | C—H | C—H | N—CH$_3$ |
| A1.005 | CH$_3$ | H | C—H | C—H | O |
| A1.006 | CF$_3$ | H | C—H | C—H | O |
| A1.007 | Cl | H | C—H | C—H | O |
| A1.008 | Br | H | C—H | C—H | O |
| A1.009 | CH$_3$ | H | C—H | C—H | S |
| A1.010 | CF$_3$ | H | C—H | C—H | S |
| A1.011 | Cl | H | C—H | C—H | S |
| A1.012 | Br | H | C—H | C—H | S |
| A1.013 | CH$_3$ | H | C—H | N | N—CH$_3$ |
| A1.014 | CF$_3$ | H | C—H | N | N—CH$_3$ |
| A1.015 | Cl | H | C—H | N | N—CH$_3$ |
| A1.016 | Br | H | C—H | N | N—CH$_3$ |
| A1.017 | CH$_3$ | H | C—H | N | O |

TABLE L-continued

Radicals of formula $A_1$

| Radical | $R_1$ | $R_2$ | $G_1$ | $G_2$ | $G_3$ |
|---|---|---|---|---|---|
| A1.018 | $CF_3$ | H | C—H | N | O |
| A1.019 | Cl | H | C—H | N | O |
| A1.020 | Br | H | C—H | N | O |
| A1.021 | $CH_3$ | H | C—H | N | S |
| A1.022 | $CF_3$ | H | C—H | N | S |
| A1.023 | Cl | H | C—H | N | S |
| A1.024 | Br | H | C—H | N | S |
| A1.025 | $CH_3$ | H | N | N | N—$CH_3$ |
| A1.026 | $CF_3$ | H | N | N | N—$CH_3$ |
| A1.027 | Cl | H | N | N | N—$CH_3$ |
| A1.028 | Br | H | N | N | N—$CH_3$ |
| A1.029 | $CH_3$ | H | N | N | O |
| A1.030 | $CF_3$ | H | N | N | O |
| A1.031 | Cl | H | N | N | O |
| A1.032 | Br | H | N | N | O |
| A1.033 | $CH_3$ | H | N | N | S |
| A1.034 | $CF_3$ | H | N | N | S |
| A1.035 | Cl | H | N | N | S |
| A1.036 | Br | H | N | N | S |

TABLE M

Radicals of formula $A_2$

| Radical | $R_1$ | $R_2$ | $G_1$ | $G_2$ | $G_5$ |
|---|---|---|---|---|---|
| A2.001 | $CH_3$ | H | C—H | C—H | N |
| A2.002 | $CF_3$ | H | C—H | C—H | N |
| A2.003 | Cl | H | C—H | C—H | N |
| A2.004 | Br | H | C—H | C—H | N |
| A2.005 | $CH_3$ | H | C—H | N | N |
| A2.006 | $CF_3$ | H | C—H | N | N |
| A2.007 | Cl | H | C—H | N | N |
| A2.008 | Br | H | C—H | N | N |
| A2.009 | $CH_3$ | H | N | N | N |
| A2.010 | $CF_3$ | H | N | N | N |
| A2.011 | Cl | H | N | N | N |
| A2.012 | Br | H | N | N | N |
| A2.013 | $CH_3$ | H | C—H | C—H | C—$CH_3$ |
| A2.014 | $CF_3$ | H | C—H | C—H | C—$CH_3$ |
| A2.015 | Cl | H | C—H | C—H | C—$CH_3$ |
| A2.016 | Br | H | C—H | C—H | C—$CH_3$ |
| A2.017 | $CH_3$ | H | C—H | N | C—$CH_3$ |
| A2.018 | $CF_3$ | H | C—H | N | C—$CH_3$ |
| A2.019 | Cl | H | C—H | N | C—$CH_3$ |
| A2.020 | Br | H | C—H | N | C—$CH_3$ |
| A2.021 | $CH_3$ | H | N | N | C—$CH_3$ |
| A2.022 | $CF_3$ | H | N | N | C—$CH_3$ |
| A2.023 | Cl | H | N | N | C—$CH_3$ |
| A2.024 | Br | H | N | N | C—$CH_3$ |

TABLE N

Radicals of formula $A_3$

| Radical | $R_1$ | $R_2$ | $G_1$ | $G_2$ | $G_4$ |
|---|---|---|---|---|---|
| A3.001 | $CH_3$ | H | C—H | C—H | N |
| A3.002 | $CF_3$ | H | C—H | C—H | N |
| A3.003 | Cl | H | C—H | C—H | N |
| A3.004 | Br | H | C—H | C—H | N |
| A3.005 | $CH_3$ | H | C—H | N | N |
| A3.006 | $CF_3$ | H | C—H | N | N |
| A3.007 | Cl | H | C—H | N | N |
| A3.008 | Br | H | C—H | N | N |
| A3.009 | $CH_3$ | H | N | N | N |
| A3.010 | $CF_3$ | H | N | N | N |
| A3.011 | Cl | H | N | N | N |
| A3.012 | Br | H | N | N | N |
| A3.013 | $CH_3$ | H | C—H | C—H | C—$CH_3$ |
| A3.014 | $CF_3$ | H | C—H | C—H | C—$CH_3$ |
| A3.015 | Cl | H | C—H | C—H | C—$CH_3$ |
| A3.016 | Br | H | C—H | C—H | C—$CH_3$ |
| A3.017 | $CH_3$ | H | C—H | N | C—$CH_3$ |
| A3.018 | $CF_3$ | H | C—H | N | C—$CH_3$ |
| A3.019 | Cl | H | C—H | N | C—$CH_3$ |
| A3.020 | Br | H | C—H | N | C—$CH_3$ |
| A3.021 | $CH_3$ | H | N | N | C—$CH_3$ |
| A3.022 | $CF_3$ | H | N | N | C—$CH_3$ |
| A3.023 | Cl | H | N | N | C—$CH_3$ |
| A3.024 | Br | H | N | N | C—$CH_3$ |

TABLE O

Radicals of formula $A_4$

| Radical | $J_2$ | $J_3$ | $G_1$ | $G_2$ | $G_3$ |
|---|---|---|---|---|---|
| A4.001 | C—H | O | C—H | C—H | N—$CH_3$ |
| A4.002 | C—$CF_3$ | O | C—H | C—H | N—$CH_3$ |
| A4.003 | C—H | S | C—H | C—H | N—$CH_3$ |
| A4.004 | C—$CF_3$ | S | C—H | C—H | N—$CH_3$ |
| A4.005 | C—H | O | C—H | N | N—$CH_3$ |
| A4.006 | C—$CF_3$ | O | C—H | N | N—$CH_3$ |
| A4.007 | C—H | S | C—H | N | N—$CH_3$ |
| A4.008 | C—$CF_3$ | S | C—H | N | N—$CH_3$ |

TABLE P

Radicals of formula $A_4$

| Radical | $R_1$ | $R_2$ | $G_1$ | $G_2$ | $G_5$ | $G_4$ |
|---|---|---|---|---|---|---|
| A5.001 | $CH_3$ | H | C—H | C—H | N | N |
| A5.002 | $CF_3$ | H | C—H | C—H | N | N |
| A5.003 | Cl | H | C—H | C—H | N | N |
| A5.004 | Br | H | C—H | C—H | N | N |

TABLE P-continued

Radicals of formula $A_4$ $A_5$

| Radical | $R_1$ | $R_2$ | $G_1$ | $G_2$ | $G_5$ | $G_4$ |
|---|---|---|---|---|---|---|
| A5.005 | CH$_3$ | H | C—H | N | N | N |
| A5.006 | CF$_3$ | H | C—H | N | N | N |
| A5.007 | Cl | H | C—H | N | N | N |
| A5.008 | Br | H | C—H | N | N | N |
| A5.009 | CH$_3$ | H | C—H | C—H | C—CH$_3$ | N |
| A5.010 | CF$_3$ | H | C—H | C—H | C—CH$_3$ | N |
| A5.011 | Cl | H | C—H | C—H | C—CH$_3$ | N |
| A5.012 | Br | H | C—H | C—H | C—CH$_3$ | N |
| A5.013 | CH$_3$ | H | C—H | N | C—CH$_3$ | N |
| A5.014 | CF$_3$ | H | C—H | N | C—CH$_3$ | N |
| A5.015 | Cl | H | C—H | N | C—CH$_3$ | N |
| A5.016 | Br | H | C—H | N | C—CH$_3$ | N |

TABLE Q

Radicals of formula $A_6$ $A_6$

| Radical | $R_1$ | $G_1$ | $G_2$ | $G_3$ |
|---|---|---|---|---|
| A6.001 | CH$_3$ | C—H | C—H | N—CH$_3$ |
| A6.002 | CF$_3$ | C—H | C—H | N—CH$_3$ |
| A6.003 | Cl | C—H | C—H | N—CH$_3$ |
| A6.004 | Br | C—H | C—H | N—CH$_3$ |
| A6.005 | CH$_3$ | C—H | C—H | O |
| A6.006 | CF$_3$ | C—H | C—H | O |
| A6.007 | Cl | C—H | C—H | O |
| A6.008 | Br | C—H | C—H | O |
| A6.009 | CH$_3$ | C—H | C—H | S |
| A6.010 | CF$_3$ | C—H | C—H | S |
| A6.011 | Cl | C—H | C—H | S |
| A6.012 | Br | C—H | C—H | S |
| A3.013 | CH$_3$ | C—H | N | N—CH$_3$ |
| A6.014 | CF$_3$ | C—H | N | N—CH$_3$ |
| A6.015 | Cl | C—H | N | N—CH$_3$ |
| A6.016 | Br | C—H | N | N—CH$_3$ |
| A6.017 | CH$_3$ | C—H | N | O |
| A6.018 | CF$_3$ | C—H | N | O |
| A6.019 | Cl | C—H | N | O |
| A6.020 | Br | C—H | N | O |
| A6.021 | CH$_3$ | C—H | N | S |
| A6.022 | CF$_3$ | C—H | N | S |
| A6.023 | Cl | C—H | N | S |
| A6.024 | Br | C—H | N | S |

TABLE R

Radicals of formula $A_{7a}$ $A_{7a}$

| Radical | $R_1$ | $G_1$ | $G_2$ | $G_3$ |
|---|---|---|---|---|
| A7.001 | CH$_3$ | C—H | C—H | C—CH$_3$ |
| A7.002 | CF$_3$ | C—H | C—H | C—CH$_3$ |
| A7.003 | Cl | C—H | C—H | C—CH$_3$ |
| A7.004 | Br | C—H | C—H | C—CH$_3$ |
| A7.005 | CH$_3$ | C—H | C—H | C—H |
| A7.006 | CF$_3$ | C—H | C—H | C—H |
| A7.007 | Cl | C—H | C—H | C—H |
| A7.008 | Br | C—H | C—H | C—H |
| A7.009 | CH$_3$ | C—H | C—H | N |
| A7.010 | CF$_3$ | C—H | C—H | N |
| A7.011 | Cl | C—H | C—H | N |
| A7.012 | Br | C—H | C—H | N |

TABLE S

Radicals of formula $A_{8a}$ $A_{8a}$

| Radical | $R_1$ | $G_1$ | $G_2$ | $G_4$ |
|---|---|---|---|---|
| A8.001 | CH$_3$ | C—H | C—H | C—H |
| A8.002 | CF$_3$ | C—H | C—H | C—H |
| A8.003 | Cl | C—H | C—H | C—H |
| A8.004 | Br | C—H | C—H | C—H |
| A8.005 | CH$_3$ | C—H | C—H | C—CH$_3$ |
| A8.006 | CF$_3$ | C—H | C—H | C—CH$_3$ |
| A8.007 | Cl | C—H | C—H | C—CH$_3$ |
| A8.008 | Br | C—H | C—H | C—CH$_3$ |
| A8.009 | CH$_3$ | C—H | C—H | N |
| A8.010 | CF$_3$ | C—H | C—H | N |
| A8.011 | Cl | C—H | C—H | N |
| A8.012 | Br | C—H | C—H | N |

Table 1: This table discloses 66 compounds of the formula A1.014-B1 wherein the radicals B1 are the radicals B1.049-B1.084, and B1.091-B1.120 shown in table A, and A1.014 is defined in Table L.

Table 2: This table discloses 66 compounds of the formula A1.018-B1 wherein the radicals B1 are the radicals B1.049-B1.084, and B1.091-B1.120 shown in table A, and A1.018 is defined in Table L.

Table 3: This table discloses 66 compounds of the formula A1.022-B1 wherein the radicals B1 are the radicals B1.049-B1.084, and B1.091-B1.120 shown in table A, and A1.022 is defined in Table L.

Table 4: This table discloses 36 compounds of the formula A1.014-B2 wherein the radicals B2 are the radicals B2.001-B2.036 shown in table B, and A1.014 is defined in Table L.

Table 5: This table discloses 36 compounds of the formula A1.018-B2 wherein the radicals B2 are the radicals B2.001-B2.036 shown in table B, and A1.018 is defined in Table L.

Table 6: This table discloses 36 compounds of the formula A1.022-B2 wherein the radicals B2 are the radicals B2.001-B2.036 shown in table B, and A1.022 is defined in Table L.

Table 7: This table discloses 24 compounds of the formula A1.014-B3 wherein the radicals B3 are the radicals B3.001-B3.024 shown in table C, and A1.014 is defined in Table L.

Table 8: This table discloses 24 compounds of the formula A1.018-B3 wherein the radicals B3 are the radicals B3.001-B3.024 shown in table C, and A1.018 is defined in Table L.

Table 9: This table discloses 24 compounds of the formula A1.022-B3 wherein the radicals B3 are the radicals B3.001-B3.024 shown in table C, and A1.022 is defined in Table L.

Table 10: This table discloses 8 compounds of the formula A1.014-B4 wherein the radicals B4 are the radicals B4.001-B4.008 shown in table D, and A1.014 is defined in Table L.

Table 11: This table discloses 8 compounds of the formula A1.018-B4 wherein the radicals B4 are the radicals B4.001-B4.008 shown in table D, and A1.018 is defined in Table L.

Table 12: This table discloses 8 compounds of the formula A1.022-B4 wherein the radicals B4 are the radicals B4.001-B4.008 shown in table D, and A1.022 is defined in Table L.

Table 13: This table discloses 24 compounds of the formula A1.014-B5 wherein the radicals B5 are the radicals B5.001-B5.024 shown in table E, and A1.014 is defined in Table L.

Table 14: This table discloses 24 compounds of the formula A1.018-B5 wherein the radicals B5 are the radicals B5.001-B5.024 shown in table E, and A1.018 is defined in Table L.

Table 15: This table discloses 24 compounds of the formula A1.022-B5 wherein the radicals B5 are the radicals B5.001-B5.024 shown in table E, and A1.022 is defined in Table L.

Table 16: This table discloses 16 compounds of the formula A1.014-B6 wherein the radicals B6 are the radicals B6.001-B6.016 shown in table F, and A1.014 is defined in Table L.

Table 17: This table discloses 16 compounds of the formula A1.018-B6 wherein the radicals B6 are the radicals B6.001-B6.016 shown in table F, and A1.018 is defined in Table L.

Table 18: This table discloses 16 compounds of the formula A1.022-B6 wherein the radicals B6 are the radicals B6.001-B6.016 shown in table F, and A1.022 is defined in Table L.

Table 19: This table discloses 54 compounds of the formula A1.014-B7 wherein the radicals B7 are the radicals B7.001-B7.054 shown in table G, and A1.014 is defined in Table L.

Table 20: This table discloses 54 compounds of the formula A1.018-B7 wherein the B7 are the radicals B7.001-B7.054 shown in table G, and A1.018 is defined in Table L.

Table 21: This table discloses 54 compounds of the formula A1.022-B7 wherein the radicals B7 are the radicals B7.001-B7.054 shown in table G, and A1.022 is defined in Table L.

Table 22: This table discloses 12 compounds of the formula A1.014-B8 wherein the radicals B8 are the radicals B8.001-B8.012 shown in table H, and A1.014 is defined in Table L.

Table 23: This table discloses 12 compounds of the formula A1.018-B8 wherein the radicals B8 are the radicals B8.001-B8.012 shown in table H, and A1.018 is defined in Table L Table 24: This table discloses 12 compounds of the formula A1.022-B8 wherein the radicals B8 are the radicals B8.001-B8.012 shown in table H, and A1.022 is defined in Table L Table 25: This table discloses 30 compounds of the formula A1.014-B9 wherein the radicals B9 are the radicals B9.001-B9.030 shown in table I, and A1.014 is defined in Table L.

Table 26: This table discloses 30 compounds of the formula A1.018-B9 wherein the radicals B9 are the radicals B9.001-B9.030 shown in table I, and A1.018 is defined in Table L.

Table 27: This table discloses 30 compounds of the formula A1.022-B9 wherein the radicals B9 are the radicals B9.001-B9.030 shown in table I, and A1.0122 is defined in Table L.

Table 28: This table discloses 12 compounds of the formula A1.014-B10 wherein the radicals B10 are the radicals B10.001-B10.012 shown in table J, and A1.014 is defined in Table L.

Table 29: This table discloses 12 compounds of the formula A1.018-B10 wherein the radicals B10 are the radicals B10.001-B10.012 shown in table J, and A1.018 is defined in Table L.

Table 30: This table discloses 12 compounds of the formula A1.022-B10 wherein the radicals B10 are the radicals B10.001-B10.012 shown in table J, and A1.022 is defined in Table L.

Table 31: This table discloses 64 compounds of the formula A1.014-B11 wherein the radicals B11 are the radicals B11.001-B11.064 shown in table K, and A1.014 is defined in Table L.

Table 29: This table discloses 64 compounds of the formula A1.018-B11 wherein the radicals B11 are the radicals B11.001-B11.064 shown in table K, and A1.018 is defined in Table L.

Table 30: This table discloses 64 compounds of the formula A1.022-B11 wherein the radicals B11 are the radicals B11.001-B11.064 shown in table K, and A1.022 is defined in Table L.

Table 31: This table discloses 132 compounds of the formula A2.006-B1 wherein the radicals B1 are the radicals B1.001-B1.132 shown in table A, and A2.006 is defined in Table M.

Table 32: This table discloses 132 compounds of the formula A2.018-B1 wherein the radicals B1 are the radicals B1.001-B1.132 shown in table A, and A2.018 is defined in Table M.

Table 33: This table discloses 36 compounds of the formula A2.006-B2 wherein the radicals B2 are the radicals B2.001-B2.0036 shown in table B, and A2.006 is defined in Table M.

Table 34: This table discloses 36 compounds of the formula A2.018-B2 wherein the radicals B2 are the radicals B2.001-B2.0036 shown in table B, and A2.018 is defined in Table M.

Table 35: This table discloses 24 compounds of the formula A2.006-B3 wherein the radicals B3 are the radicals B3.001-B3.0024 shown in table C, and A2.0006 is defined in Table M.

Table 36: This table discloses 24 compounds of the formula A2.018-B3 wherein the radicals B3 are the radicals B3.001-B3.0024 shown in table C, and A2.018 is defined in Table M.

Table 37: This table discloses 8 compounds of the formula A2.006-B4 wherein the radicals B4 are the radicals B4.001-B4.008 shown in table D, and A2.006 is defined in Table M.

Table 38: This table discloses 8 compounds of the formula A2.018-B4 wherein the radicals B4 are the radicals B4.001-B4.008 shown in table D, and A2.018 is defined in Table M.

Table 39: This table discloses 24 compounds of the formula A2.006-B5 wherein the radicals B5 are the radicals B5.001-B5.024 shown in table E, and A2.006 is defined in Table M.

Table 40: This table discloses 24 compounds of the formula A2.018-B5 wherein the radicals B5 are the radicals B5.001-B5.024 shown in table E, and A2.018 is defined in Table M.

Table 42: This table discloses 16 compounds of the formula A2.006-B6 wherein the radicals B6 are the radicals B6.001-B6.016 shown in table F, and A2.006 is defined in Table M.

Table 43: This table discloses 16 compounds of the formula A2.018-B6 wherein the radicals B6 are the radicals B6.001-B6.016 shown in table F, and A2.018 is defined in Table M.

Table 44: This table discloses 54 compounds of the formula A2.006-B7 wherein the radicals B7 are the radicals B7.001-B7.054 shown in table G, and A2.0106 is defined in Table M.

Table 45: This table discloses 54 compounds of the formula A2.018-B7 wherein the B7 are the radicals B7.001-B7.054 shown in table G, and A2.018 is defined in Table M.

Table 46: This table discloses 12 compounds of the formula A2.006-B8 wherein the radicals B8 are the radicals B8.001-B8.012 shown in table H, and A2.006 is defined in Table M.

Table 47: This table discloses 12 compounds of the formula A2.018-B8 wherein the radicals B8 are the radicals B8.001-B8.012 shown in table H, and A2.018 is defined in Table M.

Table 48: This table discloses 30 compounds of the formula A2.006-B9 wherein the radicals B9 are the radicals B9.001-B9.030 shown in table I, and A2.006 is defined in Table M.

Table 49: This table discloses 30 compounds of the formula A2.018-B9 wherein the radicals B9 are the radicals B9.001-B9.030 shown in table I, and A2.018 is defined in Table M.

Table 50: This table discloses 12 compounds of the formula A2.006-B10 wherein the radicals B10 are the radicals B10.001-B10.012 shown in table J, and A2.006 is defined in Table M.

Table 51: This table discloses 12 compounds of the formula A2.018-B10 wherein the radicals B10 are the radicals B10.001-B10.012 shown in table J, and A2.018 is defined in Table M.

Table 52: This table discloses 64 compounds of the formula A2.006-B11 wherein the radicals B11 are the radicals B11.001-B11.064 shown in table K, and A2.006 is defined in Table M.

Table 53: This table discloses 64 compounds of the formula A2.018-B11 wherein the radicals B11 are the radicals B11.001-B11.064 shown in table K, and A2.018 is defined in Table M.

Table 54: This table discloses 132 compounds of the formula A3.006-B1 wherein the radicals B1 are the radicals B1.001-B1.132 shown in table A, and A3.006 is defined in Table N.

Table 55: This table discloses 132 compounds of the formula A3.018-B1 wherein the radicals B1 are the radicals B1.001-B1.132 shown in table A, and A3.018 is defined in Table N.

Table 56: This table discloses 36 compounds of the formula A3.006-B2 wherein the radicals B2 are the radicals B2.001-B2.0036 shown in table B, and A3.006 is defined in Table N.

Table 57: This table discloses 36 compounds of the formula A3.018-B2 wherein the radicals B2 are the radicals B2.001-B2.0036 shown in table B, and A3.018 is defined in Table N.

Table 58: This table discloses 24 compounds of the formula A3.006-B3 wherein the radicals B3 are the radicals B3.001-B3.0024 shown in table C, and A3.006 is defined in Table N.

Table 59: This table discloses 24 compounds of the formula A3.018-B3 wherein the radicals B3 are the radicals B3.001-B3.0024 shown in table C, and A3.018 is defined in Table N.

Table 60: This table discloses 8 compounds of the formula A3.006-B4 wherein the radicals B4 are the radicals B4.001-B4.008 shown in table D, and A3.006 is defined in Table N.

Table 61: This table discloses 8 compounds of the formula A3.018-B4 wherein the radicals B4 are the radicals B4.001-B4.008 shown in table D, and A3.018 is defined in Table N.

Table 62: This table discloses 24 compounds of the formula A3.006-B5 wherein the radicals B5 are the radicals B5.001-B5.024 shown in table E, and A3.006 is defined in Table N.

Table 63: This table discloses 24 compounds of the formula A3.018-B5 wherein the radicals B5 are the radicals B5.001-B5.024 shown in table E, and A3.018 is defined in Table N.

Table 64: This table discloses 16 compounds of the formula A3.006-B6 wherein the radicals B6 are the radicals B6.001-B6.016 shown in table F, and A3.006 is defined in Table N.

Table 65: This table discloses 16 compounds of the formula A3.018-B6 wherein the radicals B6 are the radicals B6.001-B6.016 shown in table F, and A3.018 is defined in Table N.

Table 66: This table discloses 54 compounds of the formula A3.006-B7 wherein the radicals B7 are the radicals B7.001-B7.054 shown in table G, and A3.006 is defined in Table N.

Table 67: This table discloses 54 compounds of the formula A3.018-B7 wherein the B7 are the radicals B7.001-B7.054 shown in table G, and A3.018 is defined in Table N.

Table 68: This table discloses 12 compounds of the formula A3.006-B8 wherein the radicals B8 are the radicals B8.001-B8.012 shown in table H, and A3.006 is defined in Table N.

Table 69: This table discloses 12 compounds of the formula A3.0018-B8 wherein the radicals B8 are the radicals B8.001-B8.012 shown in table H, and A3.018 is defined in Table N.

Table 70: This table discloses 30 compounds of the formula A3.006-B9 wherein the radicals B9 are the radicals B9.001-B9.030 shown in table I, and A3.006 is defined in Table N.

Table 71: This table discloses 30 compounds of the formula A3.018-B9 wherein the radicals B9 are the radicals B9.001-B9.030 shown in table I, and A3.018 is defined in Table N.

Table 72: This table discloses 12 compounds of the formula A3.006-B10 wherein the radicals B10 are the radicals B10.001-B10.012 shown in table J, and A3.006 is defined in Table N.

Table 73: This table discloses 12 compounds of the formula A3.018-B10 wherein the radicals B10 are the radicals B10.001-B10.012 shown in table J, and A3.018 is defined in Table N.

Table 74: This table discloses 64 compounds of the formula A3.006-B11 wherein the radicals B11 are the radicals B11.001-B11.064 shown in table K, and A3.006 is defined in Table N.

Table 75: This table discloses 64 compounds of the formula A3.018-B11 wherein the radicals B11 are the radicals B11.001-B11.064 shown in table K, and A3.018 is defined in Table N.

Table 76: This table discloses 132 compounds of the formula A4.006-B1 wherein the radicals B1 are the radicals B1.001-B1.132 shown in table A, and A4.006 is defined in Table O.

Table 77: This table discloses 132 compounds of the formula A4.008-B1 wherein the radicals B1 are the radicals B1.001-B1.132 shown in table A, and A4.008 is defined in Table O.

Table 78: This table discloses 36 compounds of the formula A4.006-B2 wherein the radicals B2 are the radicals B2.001-B2.0036 shown in table B, and A4.006 is defined in Table O.

Table 79: This table discloses 36 compounds of the formula A4.008-B2 wherein the radicals B2 are the radicals B2.001-B2.0036 shown in table B, and A4.008 is defined in Table O.

Table 80: This table discloses 24 compounds of the formula A4.006-B3 wherein the radicals B3 are the radicals B3.001-B3.0024 shown in table C, and A4.006 is defined in Table O.

Table 81: This table discloses 24 compounds of the formula A4.008-B3 wherein the radicals B3 are the radicals B3.001-B3.0024 shown in table C, and A4.008 is defined in Table O.

Table 82: This table discloses 8 compounds of the formula A4.006-B4 wherein the radicals B4 are the radicals B4.001-B4.008 shown in table D, and A4.006 is defined in Table O.

Table 83: This table discloses 8 compounds of the formula A4.008-B4 wherein the radicals B4 are the radicals B4.001-B4.008 shown in table D, and A4.008 is defined in Table O.

Table 84: This table discloses 24 compounds of the formula A4.006-B5 wherein the radicals B5 are the radicals B5.001-B5.024 shown in table E, and A4.006 is defined in Table O.

Table 85: This table discloses 24 compounds of the formula A4.008-B5 wherein the radicals B5 are the radicals B5.001-B5.024 shown in table E, and A4.008 is defined in Table O.

Table 86: This table discloses 16 compounds of the formula A4.006-B6 wherein the radicals B6 are the radicals B6.001-B6.016 shown in table F, and A4.006 is defined in Table O.

Table 87: This table discloses 16 compounds of the formula A4.008-B6 wherein the radicals B6 are the radicals B6.001-B6.016 shown in table F, and A4.008 is defined in Table O.

Table 88: This table discloses 54 compounds of the formula A4.006-B7 wherein the radicals B7 are the radicals B7.001-B7.054 shown in table G, and A4.006 is defined in Table O.

Table 89: This table discloses 54 compounds of the formula A4.008-B7 wherein the B7 are the radicals B7.001-B7.054 shown in table G, and A4.008 is defined in Table O.

Table 90: This table discloses 12 compounds of the formula A4.006-B8 wherein the radicals B8 are the radicals B8.001-B8.012 shown in table H, and A4.006 is defined in Table O.

Table 91: This table discloses 12 compounds of the formula A4.008-B8 wherein the radicals B8 are the radicals B8.001-B8.012 shown in table H, and A4.008 is defined in Table O.

Table 92: This table discloses 30 compounds of the formula A4.006-B9 wherein the radicals B9 are the radicals B9.001-B9.030 shown in table I, and A4.006 is defined in Table O.

Table 93: This table discloses 30 compounds of the formula A4.008-B9 wherein the radicals B9 are the radicals B9.001-B9.030 shown in table I, and A4.008 is defined in Table O.

Table 94: This table discloses 12 compounds of the formula A4.006-B10 wherein the radicals B10 are the radicals B10.001-B10.012 shown in table J, and A4.006 is defined in Table O.

Table 95: This table discloses 12 compounds of the formula A4.008-B10 wherein the radicals B10 are the radicals B10.001-B10.012 shown in table J, and A4.008 is defined in Table O.

Table 96: This table discloses 64 compounds of the formula A4.006-B11 wherein the radicals B11 are the radicals B11.001-B11.064 shown in table K, and A4.006 is defined in Table O.

Table 97: This table discloses 64 compounds of the formula A4.008-B11 wherein the radicals B11 are the radicals B11.001-B11.064 shown in table K, and A3.008 is defined in Table O.

Table 98: This table discloses 132 compounds of the formula A5.006-B1 wherein the radicals B1 are the radicals B1.001-B1.132 shown in table A, and A5.006 is defined in Table P.

Table 99: This table discloses 36 compounds of the formula A5.006-B2 wherein the radicals B2 are the radicals B2.001-B2.0036 shown in table B, and A5.006 is defined in Table P.

Table 100: This table discloses 24 compounds of the formula A5.006-B3 wherein the radicals B3 are the radicals B3.001-B3.0024 shown in table C, and A5.006 is defined in Table P.

Table 101: This table discloses 8 compounds of the formula A5.006-B4 wherein the radicals B4 are the radicals B4.001-B4.008 shown in table D, and A4.006 is defined in Table P.

Table 102: This table discloses 24 compounds of the formula A5.006-B5 wherein the radicals B5 are the radicals B5.001-B5.024 shown in table E, and A5.006 is defined in Table P.

Table 103: This table discloses 16 compounds of the formula A5.006-B6 wherein the radicals B6 are the radicals B6.001-B6.016 shown in table F, and A5.006 is defined in Table P.

Table 104: This table discloses 54 compounds of the formula A5.006-B7 wherein the radicals B7 are the radicals B7.001-B7.054 shown in table G, and A5.006 is defined in Table P.

Table 105: This table discloses 12 compounds of the formula A5.006-B8 wherein the radicals B8 are the radicals B8.001-B8.012 shown in table H, and A5.006 is defined in Table P.

Table 106: This table discloses 30 compounds of the formula A5.006-B9 wherein the radicals B9 are the radicals B9.001-B9.030 shown in table I, and A5.006 is defined in Table P.

Table 107: This table discloses 12 compounds of the formula A5.006-B10 wherein the radicals B10 are the radicals B10.001-B10.012 shown in table J, and A5.006 is defined in Table P.

Table 108: This table discloses 64 compounds of the formula A5.006-B11 wherein the radicals B11 are the radicals B11.001-B11.064 shown in table K, and A5.006 is defined in Table P.

Table 109: This table discloses 132 compounds of the formula A6.002-B1 wherein the radicals B1 are the radicals B1.001-B1.132 shown in table A, and A6.002 is defined in Table Q.

Table 110: This table discloses 132 compounds of the formula A6.014-B1 wherein the radicals B1 are the radicals B1.001-B1.132 shown in table A, and A6.014 is defined in Table Q.

Table 111: This table discloses 36 compounds of the formula A6.002-B2 wherein the radicals B2 are the radicals B2.001-B2.0036 shown in table B, and A6.002 is defined in Table Q.

Table 112: This table discloses 36 compounds of the formula A6.014-B2 wherein the radicals B2 are the radicals B2.001-B2.0036 shown in table B, and A6.014 is defined in Table Q.

Table 113: This table discloses 24 compounds of the formula A6.002-B3 wherein the radicals B3 are the radicals B3.001-B3.0024 shown in table C, and A6.002 is defined in Table Q.

Table 114: This table discloses 24 compounds of the formula A6.014-B3 wherein the radicals B3 are the radicals B3.001-B3.0024 shown in table C, and A6.014 is defined in Table Q.

Table 115: This table discloses 8 compounds of the formula A6.002-B4 wherein the radicals B4 are the radicals B4.001-B4.008 shown in table D, and A6.002 is defined in Table Q.

Table 116: This table discloses 8 compounds of the formula A6.014-B4 wherein the radicals B4 are the radicals B4.001-B4.008 shown in table D, and A6.014 is defined in Table Q.

Table 117: This table discloses 24 compounds of the formula A6.002-B5 wherein the radicals B5 are the radicals B5.001-B5.024 shown in table E, and A6.002 is defined in Table Q.

Table 118: This table discloses 24 compounds of the formula A6.014-B5 wherein the radicals B5 are the radicals B5.001-B5.024 shown in table E, and A4.014 is defined in Table Q.

Table 119: This table discloses 16 compounds of the formula A6.002-B6 wherein the radicals B6 are the radicals B6.001-B6.016 shown in table F, and A6.002 is defined in Table Q.

Table 120: This table discloses 16 compounds of the formula A6.014-B6 wherein the radicals B6 are the radicals B6.001-B6.016 shown in table F, and A6.014 is defined in Table Q.

Table 121: This table discloses 54 compounds of the formula A6.002-B7 wherein the radicals B7 are the radicals B7.001-B7.054 shown in table G, and A6.002 is defined in Table Q.

Table 122: This table discloses 54 compounds of the formula A6.014-B7 wherein the B7 are the radicals B7.001-B7.054 shown in table G, and A6.014 is defined in Table Q.

Table 123: This table discloses 12 compounds of the formula A6.002-B8 wherein the radicals B8 are the radicals B8.001-B8.012 shown in table H, and A6.002 is defined in Table Q.

Table 124: This table discloses 12 compounds of the formula A6.0014-B8 wherein the radicals B8 are the radicals B8.001-B8.012 shown in table H, and A6.014 is defined in Table Q.

Table 125: This table discloses 30 compounds of the formula A6.002-B9 wherein the radicals B9 are the radicals B9.001-B9.030 shown in table I, and A6.002 is defined in Table Q.

Table 126: This table discloses 30 compounds of the formula A6.014-B9 wherein the radicals B9 are the radicals B9.001-B9.030 shown in table I, and A6.014 is defined in Table Q.

Table 127: This table discloses 12 compounds of the formula A6.002-B10 wherein the radicals B10 are the radicals B10.001-B10.012 shown in table J, and A6.002 is defined in Table Q.

Table 128: This table discloses 12 compounds of the formula A6.014-B10 wherein the radicals B10 are the radicals B10.001-B10.012 shown in table J, and A6.014 is defined in Table Q.

Table 129: This table discloses 64 compounds of the formula A6.002-B11 wherein the radicals B11 are the radicals B11.001-B11.064 shown in table K, and A6.002 is defined in Table Q.

Table 130: This table discloses 64 compounds of the formula A6.014-B11 wherein the radicals B11 are the radicals B11.001-B11.064 shown in table K, and A6.014 is defined in Table Q.

Table 131: This table discloses 132 compounds of the formula A7.002-B1 wherein the radicals B1 are the radicals B1.001-B1.132 shown in table A, and A7.002 is defined in Table R Table 132: This table discloses 132 compounds of the formula A7.006-B1 wherein the radicals B1 are the radicals B1.001-B1.132 shown in table A, and A7.006 is defined in Table R.

Table 133: This table discloses 132 compounds of the formula A7.010-B1 wherein the radicals B1 are the radicals B1.001-B1.132 shown in table A, and A7.010 is defined in Table R.

Table 134: This table discloses 54 compounds of the formula A7.002-B7 wherein the radicals B7 are the radicals B7.001-B7.054 shown in table G, and A7.002 is defined in Table R.

Table 135: This table discloses 54 compounds of the formula A7.006-B7 wherein the B7 are the radicals B7.001-B7.054 shown in table G, and A7.006 is defined in Table R.

Table 136: This table discloses 54 compounds of the formula A7.010-B7 wherein the B7 are the radicals B7.001-B7.054 shown in table G, and A7.010 is defined in Table R.

Table 137: This table discloses 12 compounds of the formula A7.002-B8 wherein the radicals B8 are the radicals B8.001-B8.012 shown in table H, and A7.002 is defined in Table R.

Table 138: This table discloses 12 compounds of the formula A7.006-B8 wherein the radicals B8 are the radicals B8.001-B8.012 shown in table H, and A7.006 is defined in Table R.

Table 139: This table discloses 12 compounds of the formula A7.010-B8 wherein the radicals B8 are the radicals B8.001-B8.012 shown in table H, and A7.010 is defined in Table R.

Table 140: This table discloses 30 compounds of the formula A7.002-B9 wherein the radicals B9 are the radicals B9.001-B9.030 shown in table I, and A7.002 is defined in Table R.

Table 142: This table discloses 30 compounds of the formula A7.006-B9 wherein the radicals B9 are the radicals B9.001-B9.030 shown in table I, and A7.006 is defined in Table R.

Table 143: This table discloses 30 compounds of the formula A7.010-B9 wherein the radicals B9 are the radicals B9.001-B9.030 shown in table I, and A7.010 is defined in Table R.

Table 144: This table discloses 12 compounds of the formula A7.002-B10 wherein the radicals B10 are the radicals B10.001-B10.012 shown in table J, and A7.002 is defined in Table R.

Table 145: This table discloses 12 compounds of the formula A7.006-B10 wherein the radicals B10 are the radicals B10.001-B10.012 shown in table J, and A7.006 is defined in Table R.

Table 146: This table discloses 12 compounds of the formula A7.010-B10 wherein the radicals B10 are the radicals B10.001-B10.012 shown in table J, and A7.010 is defined in Table R.

Table 147: This table discloses 64 compounds of the formula A7.002-B11 wherein the radicals B11 are the radicals B11.001-B11.064 shown in table K, and A7.002 is defined in Table R.

Table 148: This table discloses 64 compounds of the formula A7.006-B11 wherein the radicals B11 are the radicals B11.001-B11.064 shown in table K, and A7.006 is defined in Table R.

Table 149: This table discloses 64 compounds of the formula A7.010-B11 wherein the radicals B11 are the radicals B11.001-B11.064 shown in table K, and A7.010 is defined in Table R.

Table 150: This table discloses 132 compounds of the formula A8.002-B1 wherein the radicals B1 are the radicals B1.001-B1.132 shown in table A, and A8.002 is defined in Table R Table 151: This table discloses 132 compounds of the formula A8.006-B1 wherein the radicals B1 are the radicals B1.001-B1.132 shown in table A, and A8.006 is defined in Table S.

Table 152: This table discloses 132 compounds of the formula A8.010-B1 wherein the radicals B1 are the radicals B1.001-B1.132 shown in table A, and A8.010 is defined in Table S.

Table 153: This table discloses 54 compounds of the formula A8.002-B7 wherein the radicals B7 are the radicals B7.001-B7.054 shown in table G, and A8.002 is defined in Table S.

Table 154: This table discloses 54 compounds of the formula A8.006-B7 wherein the B7 are the radicals B7.001-B7.054 shown in table G, and A8.006 is defined in Table R.

Table 155: This table discloses 54 compounds of the formula A8.010-B7 wherein the B7 are the radicals B7.001-B7.054 shown in table G, and A8.010 is defined in Table R.

Table 156: This table discloses 12 compounds of the formula A8.002-B8 wherein the radicals B8 are the radicals B8.001-B8.012 shown in table H, and A8.002 is defined in Table S.

Table 157: This table discloses 12 compounds of the formula A8.006-B8 wherein the radicals B8 are the radicals B8.001-B8.012 shown in table H, and A8.006 is defined in Table S.

Table 158: This table discloses 12 compounds of the formula A8.010-B8 wherein the radicals B8 are the radicals B8.001-B8.012 shown in table H, and A8.010 is defined in Table S.

Table 159: This table discloses 30 compounds of the formula A8.002-B9 wherein the radicals B9 are the radicals B9.001-B9.030 shown in table I, and A8.002 is defined in Table S.

Table 160: This table discloses 30 compounds of the formula A4.006-B9 wherein the radicals B9 are the radicals B9.001-B9.030 shown in table I, and A8.006 is defined in Table S.

Table 161: This table discloses 30 compounds of the formula A8.010-B9 wherein the radicals B9 are the radicals B9.001-B9.030 shown in table I, and A8.010 is defined in Table S.

Table 162: This table discloses 12 compounds of the formula A8.002-B10 wherein the radicals B10 are the radicals B10.001-B10.012 shown in table J, and A8.002 is defined in Table S.

Table 164: This table discloses 12 compounds of the formula A8.006-B10 wherein the radicals B10 are the radicals B10.001-B10.012 shown in table J, and A8.006 is defined in Table S.

Table 165: This table discloses 12 compounds of the formula A8.010-B10 wherein the radicals B10 are the radicals B10.001-B10.012 shown in table J, and A8.010 is defined in Table S.

Table 166: This table discloses 64 compounds of the formula A8.002-B11 wherein the radicals B11 are the radicals B11.001-B11.064 shown in table K, and A8.002 is defined in Table S.

Table 167: This table discloses 64 compounds of the formula A8.006-B11 wherein the radicals B11 are the radicals B11.001-B11.064 shown in table K, and A8.006 is defined in Table S.

Table 168: This table discloses 64 compounds of the formula A8.010-B11 wherein the radicals B11 are the radicals B11.001-B11.064 shown in table K, and A8.010 is defined in Table S.

TABLE T

Physical-chemical data for compounds of formula I:

| Entry No. | Compound | Ret. Time (min) | (M + H) Measured | Method | Mpt. ° C. |
| --- | --- | --- | --- | --- | --- |
| T.1 | A1.014-B2.023 | | | | 199-200 |
| T.2 | A1.014-B3.012 | 1.2 | 384/386 | SQD13 | 169-170 |
| T.3 | A1.014-B2.036 | | | | 150-160 |
| T.4 | A2.014-B1.022 | | | | 194-195 |
| T.5 | A1.014-B3.016 | | | | 197-198 |
| T.6 | A1.028-B1.022 | | | | 140-141 |
| T.7 | A1.028-B1.013 | | | | 122-123 |
| T.8 | A1.014-B1.098 | 1.13 | 369 | ZCQ13 | |
| T.9 | A1.014-B1.106 | | | | 101-103.5 |
| T.10 | A2.018-B1.045 | | | | 185-185 |
| T.11 | A2.022-B1.022 | | | | 167-168 |

TABLE T-continued

Physical-chemical data for compounds of formula I:

| Entry No. | Compound | Ret. Time (min) | (M + H) Measured | Method | Mpt. ° C. |
|---|---|---|---|---|---|
| T.12 | A1.014-B7.038 | | | | 161-163 |
| T.13 | A1.026-B1.022 | | | | 190-192 |
| T.14 | A1.014-B7.014 | | | | 79-80 |
| T.15 | A1.014-B7.022 | | | | 139-141 |
| T.16 | A1.026-B1.014 | 1.51 | 370 | ZCQ13 | |
| T.17 | A1.014-B11.014 | | | | 143-145 |
| T.18 | A1.014-B11.022 | | | | 181-183 |
| T.19 | A1.028-B1.014 | 1.11 | 418/420 | ZQD13 | 159-162 |
| T.20 | A1.014-B7.038 | 1.27 | 413 | ZQD13 | 206-209 |
| T.21 | A1.014-B7.046 | 1.14 | 445 | ZQD13 | 107-109 |
| T.22 | A1.026-B1.022 | 1.04 | 440 | SQD13 | 162-165 |
| T.23 | A6.02-B1.014 | 1.08 | 406 | SQD13 | 137-140 |
| T.24 | A1.014-B7.014 | 1.21 | 412 | ZQD13 | 135-137 |
| T.25 | A1.014-B7.022 | 1.08 | 444 | ZQD13 | 152-154 |
| T.26 | A1.026-B1.014 | 1.13 | 408 | ZQD13 | 172-175 |
| T.27 | A1.014-B8.10 | | | | 188-189 |
| T.28 | A1.014-B8.012 | | | | 144-146 |
| T.29 | A6.02-B1.038 | | | | 136-138 |
| T.30 | A6.02-B9.014 | | | | 82-84 |
| T.31 | A6.02-B7.037 | | | | 167-169 |
| T.32 | A1.014-B11.014 | | | | 122-124 |
| T.33 | A6.015-B1.014 | 1.01 | 374/376 | ZCQ13 | 156°-158° C. |
| T.34 | A1.014-B1.050 | 1.12 | 408 | SQD13 | 149-150 |
| T.35 | A1.014-B1.058 | 1.06 | 440 | ZCQ13 | 172-174 |

TABLE U

Physical-chemical data of especially preferred compounds of formula I and its intermediates:

| Entry No. | COMPOUND (IUPAC name) | RT (min) | [M + H] (measured) | Method | Mpt. ° C. |
|---|---|---|---|---|---|
| U.1 | 2-(3-ethylsulfonyl-2-pyridyl)-7-(trifluoromethyl)imidazo[1,2-b]pyridazine | | | | 208-209 |
| U.2 | 2-(3-ethylsulfonyl-2-pyridyl)-5-(trifluoromethyl)-1H-imidazo[4,5-b]pyridine | 0.82 | 357 | SQD13 | |
| U.3 | 2-(3-Ethylsulfanyl-5-trifluoro-methyl-pyridin-2-yl)-3,5-dimethyl-6-trifluoromethyl-3,5-dihydro-diimidazo[4,5-b; 4',5'-e]pyridine | 1.15 | 461 | SQD13 | 191-193 |
| U.4 | 2-(3-Ethylsulfanyl-pyridin-2-yl)-3,5-dimethyl-6-trifluoromethyl-3,5-dihydro-diimidazo[4,5-b; 4',5'-e]pyridine | 0.97 | 393 | SQD13 | 129-131 |
| U.5 | 2-[3-ethylsulfanyl-5-(trifluoromethyl)-2-pyridyl]-6-(trifluoromethyl)-3H-imidazo[4,5-c]pyridine | 1.09 | 393 | SQD13 | 222-224 |
| U.6 | 2-[3-ethylsulfanyl-5-(trifluoromethyl)-2-pyridyl]-1-methyl-6-(trifluoromethyl)imidazo[4,5-c]pyridine | 1.08 | 407 | SQD13 | 119-121 |
| U.7 | 4-ethylsulfanyl-5-[3-methyl-6-(trifluoromethyl)imidazo[4,5-b]pyridin-2-yl]-2-(trifluoromethyl)thiazole | 1.22 | 413 | SQD13 | 100-102 |
| U.8 | 4-ethylsulfonyl-5-[3-methyl-6-(trifluoromethyl)imidazo[4,5-b]pyridin-2-yl]-2-(trifluoromethyl)thiazole | 1.02 | 445 | SQD13 | 172-174 |
| U.9 | 6-(3-ethylsulfonyl-2-pyridyl)-3-(trifluoromethyl)imidazo[1,2-b][1,2,4]triazine | | | | 199-201 |
| U.10 | 3-methyl-2-[3-(oxiran-2-ylmethylsulfonyl)-5-(trifluoromethyl)-2-pyridyl]-6-(trifluoromethyl)imidazo[4,5-b]pyridine | 1.03 | 467 | ZQD13 | |
| U.11 | 3-methyl-2-[3-(oxetan-3-ylmethylsulfonyl)-5-(trifluoromethyl)-2-pyridyl]-6-(trifluoromethyl)imidazo[4,5-b]pyridine | 1.01 | 481 | ZQD13 | |
| U.12 | 3-methyl-2-[3-(tetrahydrofuran-3-ylmethylsulfonyl)-5-(trifluoromethyl)-2-pyridyl]-6-(trifluoromethyl)imidazo[4,5-b]pyridine | 1.05 | 495 | ZQD13 | |

TABLE U-continued

Physical-chemical data of especially preferred compounds of formula I and its intermediates:

| Entry No. | COMPOUND (IUPAC name) | RT (min) | [M + H] (measured) | Method | Mpt. ° C. |
|---|---|---|---|---|---|
| U.13 | 3-methyl-2-[3-(tetrahydrofuran-2-ylmethylsulfonyl)-5-(trifluoromethyl)-2-pyridyl]-6-(trifluoromethyl)imidazo[4,5-b]pyridine | 1.11 | 495 | ZQD13 | |
| U.14 | 2-[6-chloro-3-ethylsulfonyl-5-(trifluoromethyl)-2-pyridyl]-3-methyl-6-(trifluoromethyl)imidazo[4,5-b]pyridine | 1.14 | 473/475 | ZQD13 | |
| U.15 | 5-ethylsulfonyl-6-[3-methyl-6-(trifluoromethyl)imidazo[4,5-b]pyridin-2-yl]-3-(trifluoromethyl)pyridin-2-ol | 0.91 | 455 | ZQD13 | |
| U.16 | 2-(3-ethylsulfanyl-5-methyl-2-pyridyl)-3-methyl-5-(trifluoromethyl)imidazo[4,5-b]pyridine | 1.17 | 407 | ZQD13 | 141-143 |
| U.17 | 2-[3-cyclobutylsulfonyl-5-(trifluoromethyl)-2-pyridyl]-3-methyl-6-(trifluoromethyl)imidazo[4,5-b]pyridine | 1.12 | 465 | SQD13 | 149-150 |
| U.18 | 3-methyl-2-[3-pyrimidin-2-ylsulfonyl-5-(trifluoromethyl)-2-pyridyl]-6-(trifluoromethyl)imidazo[4,5-b]pyridine | 1.64 | 489.00 | ZQ2000 | |
| U.19 | 3-methyl-2-[3-(4-pyridylsulfonyl)-5-(trifluoromethyl)-2-pyridyl]-6-(trifluoromethyl)imidazo[4,5-b]pyridine | 1.50 | 488 | ZQ2000 | |
| U.20 | 2-[3-cyclohexylsulfonyl-5-(trifluoromethyl)-2-pyridyl]-3-methyl-6-(trifluoromethyl)imidazo[4,5-b]pyridine | 2.02 | 493 | ZQ2000 | |
| U.21 | 2-[3-cyclopentylsulfonyl-5-(trifluoromethyl)-2-pyridyl]-3-methyl-6-(trifluoromethyl)imidazo[4,5-b]pyridine | 1.91 | 479 | ZQ2000 | |
| U.22 | 2-[[2-[3-methyl-6-(trifluoromethyl)imidazo[4,5-b]pyridin-2-yl]-5-(trifluoromethyl)-3-pyridyl]sulfonyl]-1,3,4-thiadiazole | 1.66 | 495 | ZQ2000 | |
| U.23 | 3-methyl-2-[3-(2-thienylsulfonyl)-5-(trifluoromethyl)-2-pyridyl]-6-(trifluoromethyl)imidazo[4,5-b]pyridine | 1.76 | 493 | ZQ2000 | |
| U.24 | 3-methyl-2-[3-(2-thienylsulfinyl)-5-(trifluoromethyl)-2-pyridyl]-6-(trifluoromethyl)imidazo[4,5-b]pyridine | 1.94 | 477 | ZQ2000 | |
| U.25 | 2-[3-(cyclobutylmethylsulfonyl)-5-(trifluoromethyl)-2-pyridyl]-3-methyl-6-(trifluoromethyl)imidazo[4,5-b]pyridine | 1.18 | 479 | ZQD13 | 110-111 |
| U.26 | 2-[3-[2-(1,3-dioxan-2-yl)ethylsulfanyl]-5-(trifluoromethyl)-2-pyridyl]-3-methyl-6-(trifluoromethyl)imidazo[4,5-b]pyridine | 1.16 | 493 | ZQD13 | 100-101 |
| U.27 | 2-[3-[2-(1,3-dioxolan-2-yl)ethylsulfanyl]-5-(trifluoromethyl)-2-pyridyl]-3-methyl-6-(trifluoromethyl)imidazo[4,5-b]pyridine | 1.1 | 465 | ZQD13 | 104-105 |
| U.28 | 2-[3-[2-(1,3-dioxan-2-yl)ethylsulfonyl]-5-(trifluoromethyl)-2-pyridyl]-3-methyl-6-(trifluoromethyl)imidazo[4,5-b]pyridine | | | | 144-145 |
| U.29 | 2-[3-[2-(1,3-dioxolan-2-yl)ethylsulfonyl]-5-(trifluoromethyl)-2-pyridyl]-3-methyl-6-(trifluoromethyl)imidazo[4,5-b]pyridine | | | | 140-141 |
| U.30 | 2-[3-(1,3-dioxolan-2-ylmethylsulfonyl)-5-(trifluoromethyl)-2-pyridyl]-3-methyl-6-(trifluoromethyl)imidazo[4,5-b]pyridine | | | | 149-150 |
| U.31 | 2-[3-ethylsulfanyl-5-(trifluoromethyl)-2-pyridyl]-6-(trifluoromethyl)pyrazolo[1,5-a]pyrimidine | | | | 124-126 |
| U.32 | 2-[3-ethylsulfonyl-5-(trifluoromethyl)-2-pyridyl]-6-(trifluoromethyl)pyrazolo[1,5-a]pyrimidine | | | | 189-191 |
| U.33 | 4-bromo-5-[3-methyl-6-(trifluoromethyl)imidazo[4,5-c]pyridin-2-yl]-2-(trifluoromethyl)thiazole | 1.03 | 431/433 | ZQD13 | |
| U.34 | 4-ethylsulfanyl-5-[3-methyl-6-(trifluoromethyl)imidazo[4,5-c]pyridin-2-yl]-2-(trifluoromethyl)thiazole | | | | 92-94 |
| U.35 | 2-[3-ethylsulfanyl-6-(trifluoromethyl)pyrazin-2-yl]-3-methyl-6-(trifluoromethyl)imidazo[4,5-b]pyridine | | | | 206-208 |
| U.36 | 2-[3-ethylsulfonyl-6-(trifluoromethyl)pyrazin-2-yl]-3-methyl-6-(trifluoromethyl)imidazo[4,5-b]pyridine | | | | 214-216 |

TABLE U-continued

Physical-chemical data of especially preferred compounds of formula I and its intermediates:

| Entry No. | COMPOUND (IUPAC name) | RT (min) | [M + H] (measured) | Method | Mpt. ° C. |
|---|---|---|---|---|---|
| U.37 | 2-[5-(difluoromethoxy)-3-ethylsulfanyl-2-pyridyl]-3-methyl-6-(trifluoromethyl)imidazo[4,5-b]pyridine | | | | 82-83 |
| U.38 | 2-[5-(difluoromethoxy)-3-ethylsulfonyl-2-pyridyl]-3-methyl-6-(trifluoromethyl)imidazo[4,5-b]pyridine | | | | 115-117 |
| U.39 | 2-[2-ethylsulfanyl-4-(trifluoromethyl)phenyl]-1-methyl-6-(trifluoromethyl)imidazo[4,5-c]pyridine | | | | 120-122 |
| U.40 | 2-[2-ethylsulfonyl-4-(trifluoromethyl)phenyl]-1-methyl-6-(trifluoromethyl)imidazo[4,5-c]pyridine | | | | 237-239 |
| U.41 | 5-bromo-2-[3-ethylsulfonyl-5-(trifluoromethyl)-2-pyridyl]-1-methyl-imidazo[4,5-b]pyridine | | | | 94-97 |
| U.42 | 2-[3-ethylsulfonyl-5-(trifluoromethyl)-2-pyridyl]-1-methyl-5-(trifluoromethyl)imidazo[4,5-b]pyridine | | | | 202-204 |
| U.43 | 5-bromo-2-(3-ethylsulfonyl-2-pyridyl)-1-methyl-imidazo[4,5-b]pyridine | | | | 183-186 |
| U.44 | 2-[3-ethylsulfonyl-5-(trifluoromethyl)-2-pyridyl]-7-(trifluoromethyl)imidazo[1,2-a]pyridine | | | | 191-192 |
| U.45 | 3-chloro-2-[3-ethylsulfonyl-5-(trifluoromethyl)-2-pyridyl]-7-(trifluoromethyl)imidazo[1,2-a]pyridine | | | | 195-197 |
| U.46 | 3-bromo-2-[3-ethylsulfonyl-5-(trifluoromethyl)-2-pyridyl]-7-(trifluoromethyl)imidazo[1,2-a]pyridine | | | | 202-204 |
| U.47 | 3-bromo-2-[3-ethylsulfonyl-5-(trifluoromethyl)-2-pyridyl]-7-(trifluoromethyl)imidazo[1,2-c]pyrimidine | | | | 180-182 |
| U.48 | 2-[3-(1,3-dioxan-2-ylmethylsulfonyl)-5-(trifluoromethyl)-2-pyridyl]-3-methyl-6-(trifluoromethyl)imidazo[4,5-b]pyridine | 1.09 | 511 | SQD13 | |
| U.49 | 3-bromo-2-(3-ethylsulfonyl-2-pyridyl)-7-(trifluoromethyl)imidazo[1,2-c]pyrimidine | | | | 174-175 |
| U.50 | 2-[3-(4-methoxyphenyl)sulfinyl-5-(trifluoromethyl)-2-pyridyl]-3-methyl-6-(trifluoromethyl)imidazo[4,5-b]pyridine | | | | 156-158 |
| U.51 | 3-bromo-2-[3-ethylsulfonyl-5-(trifluoromethyl)-2-pyridyl]-6-(trifluoromethyl)imidazo[1,2-a]pyrazine | | | | 223-224 |
| U.52 | 6-bromo-2-[3-ethylsulfonyl-5-(trifluoromethyl)-2-pyridyl]imidazo[1,2-a]pyrazine | | | | 221-223 |
| U.53 | 3-bromo-2-(3-ethylsulfonyl-2-pyridyl)-6-(trifluoromethyl)imidazo[1,2-a]pyrazine | | | | 200-212 |
| U.54 | 6-bromo-2-(3-ethylsulfonyl-2-pyridyl)imidazo[1,2-a]pyrazine | | | | 219-220 |
| U.55 | 2-(3-Ethylsulfanyl-5-trifluoromethyl-thiophen-2-yl)-3,5-dimethyl-6-trifluoromethyl-3,5-dihydro-diimidazo[4,5-b; 4',5'-e]pyridine | | | | 164-166 |
| U.56 | 2-(5-Ethylsulfanyl-thiazol-4-yl)-3,5-dimethyl-6-trifluoromethyl-3,5-dihydro-diimidazo[4,5-b; 4',5'-e]pyridine | | | | 200-202 |
| U.57 | 2-[2-ethylsulfanyl-6-(trifluoromethyl)-3-pyridyl]-3-methyl-6-(trifluoromethyl)imidazo[4,5-c]pyridine | | | | 115-117 |
| U.58 | 2-[2-ethylsulfanyl-6-(trifluoromethyl)-3-pyridyl]-7-(trifluoromethyl)imidazo[1,2-a]pyridine | | | | 117-119 |
| U.59 | 2-[5-(difluoromethoxy)-3-ethylsulfanyl-2-pyridyl]-3-methyl-6-(trifluoromethyl)imidazo[4,5-c]pyridine | | | | 146-148 |
| U.60 | 3-ethylsulfanyl-4-[3-methyl-6-(trifluoromethyl)imidazo[4,5-b]pyridin-2-yl]isothiazole | | | | 163-165 |
| U.61 | 2-[3-ethylsulfanyl-5-(trifluoromethyl)-2-thienyl]-7-(trifluoromethyl)imidazo[1,2-a]pyridine | | | | 98-100 |

TABLE U-continued

Physical-chemical data of especially preferred compounds of formula I and its intermediates:

| Entry No. | COMPOUND (IUPAC name) | RT (min) | [M + H] (measured) | Method | Mpt. °C. |
|---|---|---|---|---|---|
| U.62 | 4-bromo-2-(trifluoromethyl)-5-[7-(trifluoromethyl)imidazo[1,2-a]pyridin-2-yl]thiazole | | | | 152-154 |
| U.63 | 2-(4-Ethylsulfanyl-2-trifluoromethyl-thiazol-5-yl)-3,5-dimethyl-6-trifluoromethyl-3,5-dihydro-diimidazo[4,5-b; 4',5'-e]pyridine | | | | 196-198 |
| U.64 | 2-(2-Ethylsulfanyl-6-trifluoromethyl-pyridin-3-yl)-3,5-dimethyl-6-trifluoromethyl-3,5-dihydro-diimidazo[4,5-b; 4',5'-e]pyridine | | | | 154-156 |
| U.65 | 2-[3-ethylsulfonyl-5-(trifluoromethyl)-2-pyridyl]-3-methyl-7-(trifluoromethyl)imidazo[1,2-a]pyrimidine | 1.56 | 439 | ZCQ13 | |
| U.66 | 4-ethylsulfanyl-2-(trifluoromethyl)-5-[7-(trifluoromethyl)imidazo[1,2-a]pyridin-2-yl]thiazole | 1.25 | 398 | SQD13 | 115-117 |
| U.67 | 3-bromo-2-[3-ethylsulfonyl-5-(trifluoromethyl)-2-thienyl]-7-(trifluoromethyl)imidazo[1,2-a]pyridine | 1.13 | 507/509 | SQD13 | 176-178 |
| U.68 | 2-[3-ethylsulfanyl-5-(trifluoromethyl)-2-thienyl]-7-(trifluoromethyl)-[1,2,4]triazolo[1,5-a]pyridine | 1.22 | 398 | SQD13 | 94-96 |
| U.69 | 4-bromo-2-(trifluoromethyl)-5-[7-(trifluoromethyl)-[1,2,4]triazolo[1,5-a]pyridin-2-yl]thiazole | 1.15 | 417/419 | SQD13 | 90-91 |
| U.70 | 4-ethylsulfanyl-2-(trifluoromethyl)-5-[7-(trifluoromethyl)-[1,2,4]triazolo[1,5-a]pyridin-2-yl]thiazole | 1.24 | 399 | SQD13 | 102-103 |
| U.71 | 2-[3-ethylsulfanyl-5-(trifluoromethyl)-2-thienyl]-6-(trifluoromethyl)-[1,2,4]triazolo[1,5-a]pyridine | 1.22 | 398 | SQD13 | 121-123 |
| U.72 | 2-(2-Ethylsulfanyl-5-trifluoromethyl-thiophen-3-yl)-3,5-dimethyl-6-trifluoromethyl-3,5-dihydro-diimidazo[4,5-b; 4',5'-e]pyridine | 1.18 | 466 | SQD13 | 121-123 |
| U.73 | 2-(2-Ethylsulfanyl-4-trifluoromethyl-phenyl)-3,5-dimethyl-6-trifluoromethyl-3,5-dihydro-diimidazo[4,5-b; 4',5'-e]pyridine | 1.13 | 460 | SQD13 | 201-203 |
| U.74 | 2-[2-ethylsulfanyl-5-(trifluoromethyl)-3-thienyl]-3-methyl-6-(trifluoromethyl)imidazo[4,5-c]pyridine | 1.12 | 412 | SQD13 | 148-150 |

Preference is given to a group of compounds of formula I defined as embodiments (1) to (7) which are illustrated below:

An especially preferred group of compounds of formula I according to the invention is defined as embodiment (1) and comprises combinations of (1): Radical A2 with radicals B selected from B7, B9 and B11;

wherein A2 is preferably represented by the radical A2.1

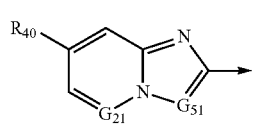

(A2.1)

wherein $R_{40}$ is halogen, $C_1$-$C_4$haloalkyl, $C_1$-$C_4$haloalkylthio, $C_1$-$C_4$haloalkylsulfonyl, O($C_1$-$C_4$haloalkyl), $SF_5$, phenylcarbonylthio, mercapto or $C_1$-$C_4$alkoxycarbonyl;

$G_{21}$ is nitrogen, CH, C—$C_1$-$C_6$ alkyl, C—$C_1$-$C_6$haloalkyl, C-halogen, C—CN, C—O—$C_1$-$C_4$alkyl, C—S—$C_1$-$C_4$alkyl, C—$SO_2$—$C_1$-$C_4$alkyl, C—S-phenyl, C—$SO_2$-phenyl or C—$SO_2$—$C_1$-$C_4$haloalkyl; and $G_{51}$ is nitrogen, CH, C—$C_1$-$C_6$ alkyl, C—$C_1$-$C_6$haloalkyl, C-halogen, C—CN, C—O—$C_1$-$C_4$alkyl, C—S—$C_1$-$C_4$alkyl, C—$SO_2$—$C_1$-$C_4$alkyl, C—S-phenyl, C—$SO_2$-phenyl or C—$SO_2$—$C_1$-$C_4$haloalkyl; and the radicals B7, B9 and B11 are preferably represented by the radicals selected from B7.1, B9.1 and B11.1

(B7.1)

wherein m is 0, 1 or 2;

$V_{82}$ is nitrogen or methine;

$R_{41}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{42}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

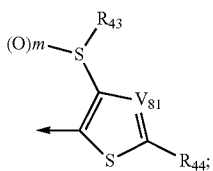
(B9.1)

wherein m is 0, 1 or 2;

$V_{81}$ is nitrogen or methine, $R_{43}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{44}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and

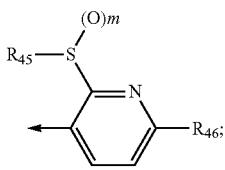
(B11.1)

wherein m is 0, 1 or 2;

$R_{45}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{46}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl.

Especially preferred compounds according to embodiment (1) are represented by embodiment (1.1), wherein (1.1) in the radical A2.1

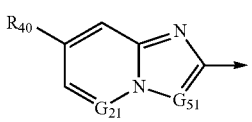
(A2.1)

$R_{40}$ is $C_1$-$C_4$haloalkyl, in particular trifluoromethyl;

$G_{21}$ is nitrogen or CH; and $G_{51}$ is nitrogen or C—$C_1$-$C_6$ alkyl, in particular nitrogen or C-methyl;

and in the radicals B7.1, B9.1 and B11.1

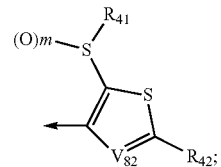
(B7.1)

m is 2;

$V_{82}$ is nitrogen or methine;

$R_{41}$ is $C_1$-$C_4$alkyl, preferably ethyl; and $R_{42}$ is $C_1$-$C_4$haloalkyl, preferably trifluoromethyl;

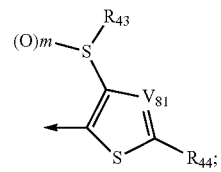
(B9.1)

m is 2;

$V_{81}$ is nitrogen or methine, $R_{43}$ is $C_1$-$C_4$alkyl, preferably ethyl; and $R_{44}$ is $C_1$-$C_4$haloalkyl, preferably trifluoromethyl;

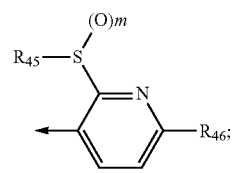
(B11.1)

m is 2;

$R_{45}$ is $C_1$-$C_4$alkyl, preferably ethyl; and $R_{46}$ is $C_1$-$C_4$haloalkyl, preferably trifluoromethyl.

A further especially preferred group of compounds of formula I according to the invention is defined as embodiment (2) and comprises combinations of (2): Radical A3 with radicals B selected from B7, B9 and B11;

wherein A3 is preferably represented by the radical A3.1

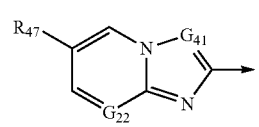
(A3.1)

wherein $R_{47}$ is halogen, $C_1$-$C_4$haloalkyl, $C_1$-$C_4$haloalkylthio, $C_1$-$C_4$haloalkylsulfonyl, O($C_1$-$C_4$haloalkyl), $SF_5$, phenylcarbonylthio, mercapto or $C_1$-$C_4$alkoxycarbonyl;

$G_{41}$ is nitrogen, CH, C—$C_1$-$C_6$ alkyl, C—$C_1$-$C_6$haloalkyl, C-halogen, C—CN, C—O—$C_1$-$C_4$alkyl, C—S—$C_1$-$C_4$alkyl, C—SO$_2$—$C_1$-$C_4$alkyl, C—S-phenyl, C—SO$_2$-phenyl or C—SO$_2$—$C_1$-$C_4$halolakyl; and $G_{22}$ is nitrogen, CH, C—$C_1$-$C_6$ alkyl, C—$C_1$-$C_6$haloalkyl, C-halogen, C—CN, C—O—$C_1$-$C_4$alkyl, C—S—$C_1$-$C_4$alkyl, C—$SO_2$—$C_1$-$C_4$alkyl, C—S-phenyl, C—$SO_2$-phenyl or C—$SO_2$—$C_1$-$C_4$halolakyl; and the radicals B7, B9 and B11 are preferably represented by the radicals selected from B7.1, B9.1 and B11.1

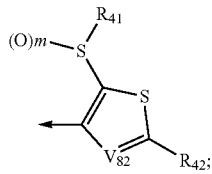
(B7.1)

wherein m is 0, 1 or 2;

$V_{82}$ is nitrogen or methine;

$R_{41}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{42}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

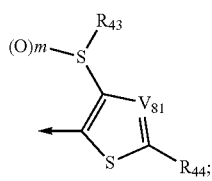
(B9.1)

wherein m is 0, 1 or 2;

$V_{81}$ is nitrogen or methine, $R_{43}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{44}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and

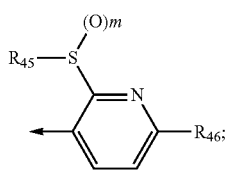
(B11.1)

wherein m is 0, 1 or 2;

$R_{45}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{46}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl.

Especially preferred compounds according to embodiment (2) are represented by embodiment (2.1), wherein (2.1) in the radical A3.1

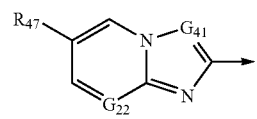
(A3.1)

$R_{47}$ is $C_1$-$C_4$haloalkyl, in particular trifluoromethyl;

$G_{22}$ is nitrogen or CH; and $G_{41}$ is nitrogen, or C—$C_1$-$C_6$ alkyl, in particular nitrogen or C-methyl;

and in the radicals B7.1, B9.1 and B11.1

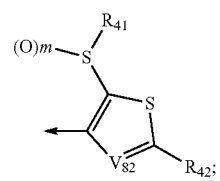
(B7.1)

m is 2;

$V_{82}$ is nitrogen or methine;

$R_{41}$ is $C_1$-$C_4$alkyl, preferably ethyl; and $R_{42}$ is $C_1$-$C_4$haloalkyl, preferably trifluoromethyl;

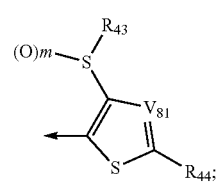
(B9.1)

m is 2;

$V_{81}$ is nitrogen or methine, $R_{43}$ is $C_1$-$C_4$alkyl, preferably ethyl; and $R_{44}$ is $C_1$-$C_4$haloalkyl, preferably trifluoromethyl;

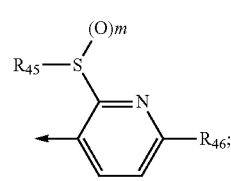
(B11.1)

m is 2;

$R_{45}$ is $C_1$-$C_4$alkyl, preferably ethyl; and $R_{46}$ is $C_1$-$C_4$haloalkyl, preferably trifluoromethyl.

A further especially preferred group of compounds of formula I according to the invention is defined as embodiment (3) and comprises combinations of (3): Radical A4 with radical $B_1$, wherein A4 is preferably represented by the radical A4.1

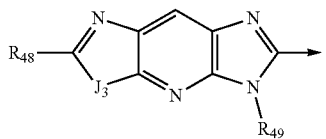
(A4.1)

wherein $R_{48}$ is halogen, $C_1$-$C_4$haloalkyl, $C_1$-$C_4$haloalkylthio, $C_1$-$C_4$haloalkylsulfonyl, O($C_1$-$C_4$haloalkyl), $SF_5$, phenylcarbonylthio, mercapto or $C_1$-$C_4$alkoxycarbonyl;

$J_3$ is sulfur oxygen or N-methyl; and $R_{49}$ is hydrogen, $C_1$-$C_6$ alkyl, $C_1$-$C_6$haloalkyl, halogen, CN, O—$C_1$-$C_4$alkyl, S—$C_1$-$C_4$alkyl, $SO_2$—$C_1$-$C_4$alkyl, S-phenyl, $SO_2$-phenyl or $SO_2$—$C_1$-$C_4$halolakyl;

and the radical $B_1$ is

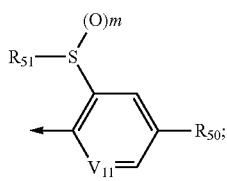
(B1.1)

wherein m is 0, 1 or 2;

$R_{51}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{50}$ is hydrogen, $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

Preferred compounds according to embodiment (3) are also represented by embodiment (3.1), wherein (3.1) in the radical A4.1

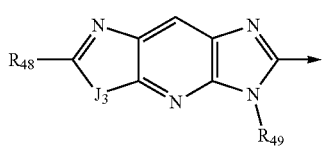
(A4.1)

$R_{48}$ is $C_1$-$C_4$haloalkyl, in particular trifluoromethyl;

$J_3$ is oxygen, sulphur or N-methyl; and $R_{49}$ is hydrogen or $C_1$-$C_6$ alkyl, in particular hydrogen or methyl;

and the radicals B1, B7, B9 and B11 are preferably represented by the radicals selected from B1.1, B7.1, B9.1 and B11.1

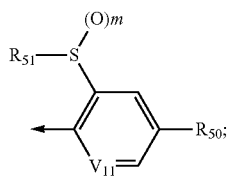
(B1.1)

wherein m is 0, 1 or 2;

$R_{51}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{50}$ is hydrogen, $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

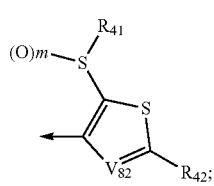
(B7.1)

wherein m is 0, 1 or 2;

$V_{82}$ is nitrogen or methine;

$R_{41}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{42}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

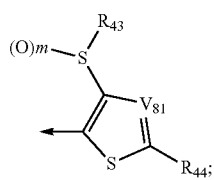
(B9.1)

wherein m is 0, 1 or 2;

$V_{81}$ is nitrogen or methine, $R_{43}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{44}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and

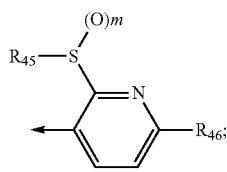
(B11.1)

wherein m is 0, 1 or 2;
R<sub>45</sub> is C<sub>1</sub>-C<sub>4</sub>alkyl, C<sub>1</sub>-C<sub>4</sub>haloalkyl, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl; and
R<sub>46</sub> is C<sub>1</sub>-C<sub>4</sub>alkyl, C<sub>1</sub>-C<sub>4</sub>haloalkyl, C<sub>1</sub>-C<sub>3</sub>haloalkoxy, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl.

Further especially preferred compounds according to embodiment (3) are represented by embodiment (3.2), wherein (3.2) in the radical A4.1

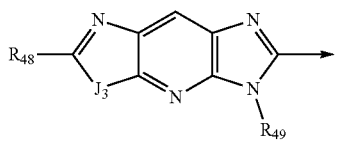
(A4.1)

R<sub>48</sub> is C<sub>1</sub>-C<sub>4</sub>haloalkyl, in particular trifluoromethyl;
J<sub>3</sub> is oxygen, sulphur or N-methyl; and
R<sub>49</sub> is hydrogen or C<sub>1</sub>-C<sub>6</sub> alkyl, in particular hydrogen or methyl;
and in the radical B1.1

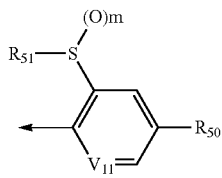
(B1.1)

m is 2;
V<sub>11</sub> is nitrogen or methine;
R<sub>51</sub> is C<sub>1</sub>-C<sub>4</sub>alkyl, preferably ethyl; and
R<sub>50</sub> is hydrogen or C<sub>1</sub>-C<sub>4</sub>haloalkyl, preferably hydrogen or trifluoromethyl.

A further especially preferred group of compounds of formula I according to the invention is defined as embodiment (4) and comprises combinations of
(4): Radical A5 with radicals B selected from B1, B7, B9 and B11;
wherein A5 is preferably represented by the radical A5.1

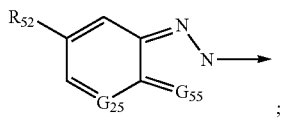
(A5.1)

wherein
G<sub>55</sub> is nitrogen or C—R<sub>53</sub>;
R<sub>53</sub> is C<sub>1</sub>-C<sub>4</sub>alkyl;
G<sub>25</sub> is nitrogen or methine; and
R<sub>52</sub> is halogen, C<sub>1</sub>-C<sub>4</sub>haloalkyl, C<sub>1</sub>-C<sub>4</sub>haloalkylthio, C<sub>1</sub>-C<sub>4</sub>haloalkylsulfonyl, O(C<sub>1</sub>-C<sub>4</sub>haloalkyl), SF<sub>5</sub>, phenylcarbonylthio, mercapto or C<sub>1</sub>-C<sub>4</sub>alkoxycarbonyl;
and the radicals B1, B7, B9 and B11 are preferably represented by the radicals selected from B1.1, B7.1, B9.1 and B11.1

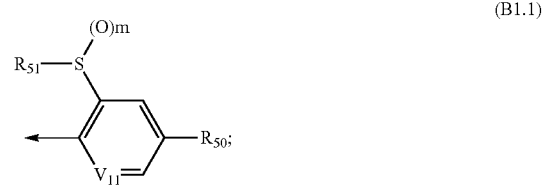
(B1.1)

wherein m is 0, 1 or 2;
R<sub>51</sub> is C<sub>1</sub>-C<sub>4</sub>alkyl, C<sub>1</sub>-C<sub>4</sub>haloalkyl, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl; and
R<sub>50</sub> is hydrogen, C<sub>1</sub>-C<sub>4</sub>alkyl, C<sub>1</sub>-C<sub>4</sub>haloalkyl, C<sub>1</sub>-C<sub>3</sub>haloalkoxy, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl;

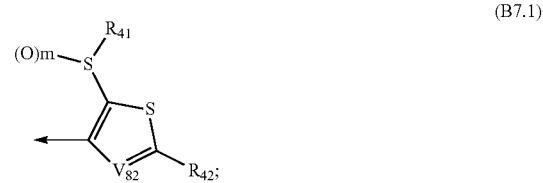
(B7.1)

wherein m is 0, 1 or 2;
V<sub>82</sub> is nitrogen or methine;
R<sub>41</sub> is C<sub>1</sub>-C<sub>4</sub>alkyl, C<sub>1</sub>-C<sub>4</sub>haloalkyl, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl; and
R<sub>42</sub> is C<sub>1</sub>-C<sub>4</sub>alkyl, C<sub>1</sub>-C<sub>4</sub>haloalkyl, C<sub>1</sub>-C<sub>3</sub>haloalkoxy, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl;

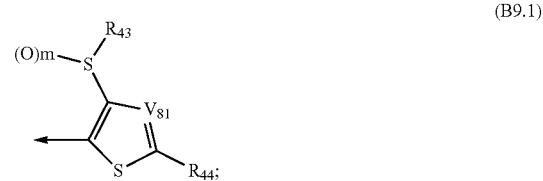
(B9.1)

wherein m is 0, 1 or 2;
V<sub>81</sub> is nitrogen or methine,
R<sub>43</sub> is C<sub>1</sub>-C<sub>4</sub>alkyl, C<sub>1</sub>-C<sub>4</sub>haloalkyl, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl; and
R<sub>44</sub> is C<sub>1</sub>-C<sub>4</sub>alkyl, C<sub>1</sub>-C<sub>4</sub>haloalkyl, C<sub>1</sub>-C<sub>3</sub>haloalkoxy, C<sub>3</sub>-C<sub>6</sub>cycloalkyl, C<sub>3</sub>-C<sub>6</sub>cycloalkyl-C<sub>1</sub>-C<sub>4</sub>alkyl, C<sub>3</sub>-C<sub>6</sub>halocycloalkyl, C<sub>2</sub>-C<sub>6</sub>alkenyl, C<sub>2</sub>-C<sub>6</sub>haloalkenyl or C<sub>2</sub>-C<sub>6</sub>alkynyl; and

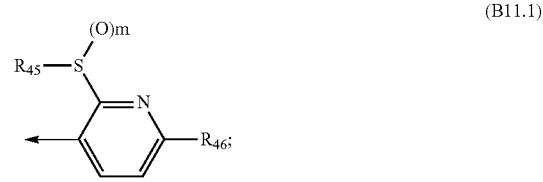
(B11.1)

wherein m is 0, 1 or 2;
$R_{45}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and
$R_{46}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl.

Especially preferred compounds according to embodiment (4) are represented by embodiment (4.1), wherein
(4.1) in the radical A5.1

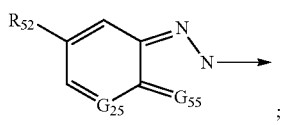

(A5.1)

$R_{52}$ is $C_1$-$C_4$haloalkyl, in particular trifluoromethyl;
$G_{55}$ is nitrogen or C—$C_1$-$C_4$alkyl, preferably nitrogen or methyl; and
$G_{25}$ is nitrogen or methine;
and in the radical B1.1

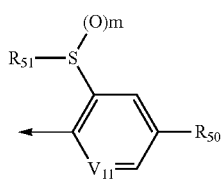

(B1.1)

m is 2;
$V_{11}$ is nitrogen or methine;
$R_{51}$ is $C_1$-$C_4$alkyl, preferably ethyl; and
$R_{50}$ is hydrogen or $C_1$-$C_4$haloalkyl, preferably hydrogen or trifluoromethyl;
in the radical B7.1

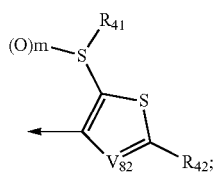

(B7.1)

m is 2;
$V_{82}$ is nitrogen or methine;
$R_{41}$ is $C_1$-$C_4$alkyl, preferably ethyl; and
$R_{42}$ is $C_1$-$C_4$haloalkyl, preferably trifluoromethyl;
in the radical B9.1

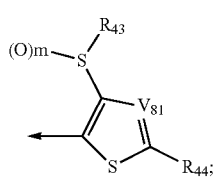

(B9.1)

m is 2;
$V_{81}$ is nitrogen or methine,
$R_{43}$ is $C_1$-$C_4$alkyl, preferably ethyl; and
$R_{44}$ is $C_1$-$C_4$haloalkyl, preferably trifluoromethyl;
and in the radical B11.1

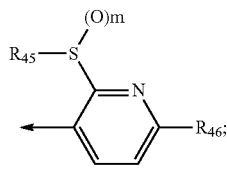

(B11.1)

m is 2;
$R_{45}$ is $C_1$-$C_4$alkyl, preferably ethyl; and
$R_{46}$ is $C_1$-$C_4$haloalkyl, preferably trifluoromethyl.

A further especially preferred group of compounds of formula I according to the invention is defined as embodiment (5) and comprises combinations of
(5): Radical A6 with radicals B selected from B1, B7, B9 and B11;
wherein $A_6$ is preferably represented by the radical A6.1

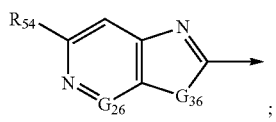

A6.1)

wherein
$G_{36}$ is N—$R_{55}$, oxygen or sulfur;
$R_{55}$ is $C_1$-$C_4$alkyl;
$G_{26}$ is nitrogen or methine; and
$R_{54}$ is halogen, $C_1$-$C_4$haloalkyl, $C_1$-$C_4$haloalkylthio, $C_1$-$C_4$haloalkylsulfonyl, O($C_1$-$C_4$haloalkyl), SF$_5$, phenylcarbonylthio, mercapto or $C_1$-$C_4$alkoxycarbonyl;
and the radicals B1, B7, B9 and B11 are preferably represented by the radicals selected from B1.1, B7.1, B9.1 and B11.1

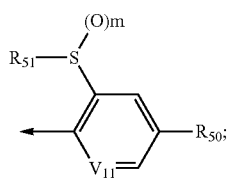

(B1.1)

wherein m is 0, 1 or 2;
$R_{51}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and
$R_{50}$ is hydrogen, $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

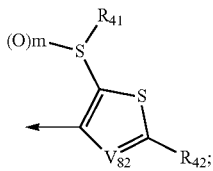

(B7.1)

wherein m is 0, 1 or 2;
$V_{82}$ is nitrogen or methine;
$R_{41}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and
$R_{42}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

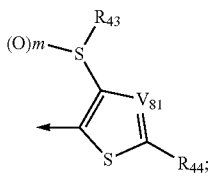

(B9.1)

wherein m is 0, 1 or 2;
$V_{81}$ is nitrogen or methine,
$R_{43}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and
$R_{44}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and

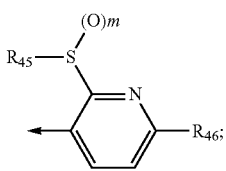

(B11.1)

wherein m is 0, 1 or 2;
$R_{45}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and
$R_{46}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl.

Especially preferred compounds according to embodiment (5) are represented by embodiment (5.1), wherein
(5.1) in the radical A6.1

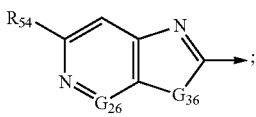

(A6.1)

$R_{54}$ is $C_1$-$C_4$haloalkyl, in particular trifluoromethyl;
$G_{36}$ is N—$C_1$-$C_4$alkyl, oxygen or sulfur; preferably N—$CH_3$, oxygen or sulfur; and
$G_{26}$ is nitrogen or methine;
and in the radical B1.1

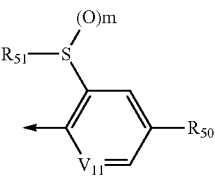

(B1.1)

m is 2;
$V_{11}$ is nitrogen or methine;
$R_{51}$ is $C_1$-$C_4$alkyl, preferably ethyl; and
$R_{50}$ is hydrogen or $C_1$-$C_4$haloalkyl, preferably hydrogen or trifluoromethyl;
in the radical B7.1

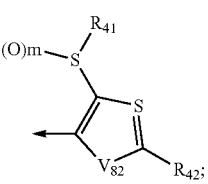

(B7.1)

m is 2;
$V_{82}$ is nitrogen or methine;
$R_{41}$ is $C_1$-$C_4$alkyl, preferably ethyl; and
$R_{42}$ is $C_1$-$C_4$haloalkyl, preferably trifluoromethyl;
in the radical B9.1

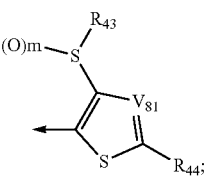

(B9.1)

m is 2;
$V_{81}$ is nitrogen or methine,
$R_{43}$ is $C_1$-$C_4$alkyl, preferably ethyl; and
$R_{44}$ is $C_1$-$C_4$haloalkyl, preferably trifluoromethyl;
and in the radical B11.1

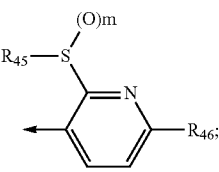

(B11.1)

m is 2;
$R_{45}$ is $C_1$-$C_4$alkyl, preferably ethyl; and
$R_{46}$ is $C_1$-$C_4$haloalkyl, preferably trifluoromethyl.

A further especially preferred group of compounds of formula I according to the invention is defined as embodiment (6) and comprises combinations of (6): Radical A7 with radicals B selected from B1, B7, B9 and B11;

wherein $A_7$ is preferably represented by the radical A7.1

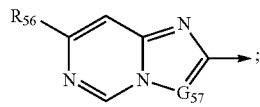
(A7.1)

wherein $G_{57}$ is nitrogen or C—$R_{57}$;

$R_{57}$ is hydrogen or $C_1$-$C_4$alkyl; and $R_{56}$ is halogen, $C_1$-$C_4$haloalkyl, $C_1$-$C_4$haloalkylthio, $C_1$-$C_4$haloalkylsulfonyl, O($C_1$-$C_4$haloalkyl), $SF_5$, phenylcarbonylthio, mercapto or $C_1$-$C_4$alkoxycarbonyl;

and the radicals B1, B7, B9 and B11 are preferably represented by the radicals selected from B1.1, B7.1, B9.1 and B11.1

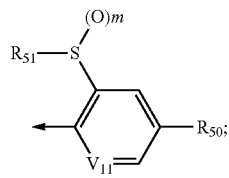
(B1.1)

wherein m is 0, 1 or 2;

$R_{51}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{50}$ is hydrogen, $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

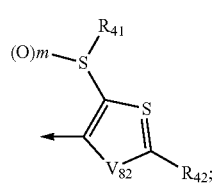
(B7.1)

wherein m is 0, 1 or 2;

$V_{82}$ is nitrogen methine;

$R_{41}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{42}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

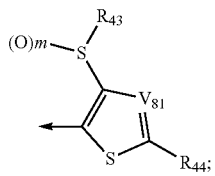
(B9.1)

wherein m is 0, 1 or 2;

$V_{81}$ is nitrogen or methine, $R_{43}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{44}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and

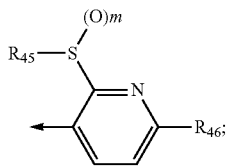
(B11.1)

wherein m is 0, 1 or 2;

$R_{45}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{46}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl.

Especially preferred compounds according to embodiment (6) are represented by embodiment (6.1), wherein (6.1) in the radical A7.1

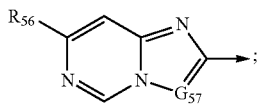
(A7.1)

$R_{56}$ is $C_1$-$C_4$haloalkyl, in particular trifluoromethyl; and
$G_{57}$ is nitrogen, C—H or C—$C_1$-$C_4$alkyl; preferably nitrogen, C—H or C—$CH_3$;
and in the radical B1.1

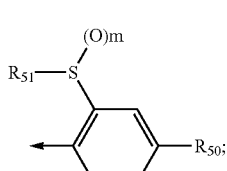
(B1.1)

m is 2;
$V_{11}$ is nitrogen or methine;
$R_{51}$ is $C_1$-$C_4$alkyl, preferably ethyl; and $R_{50}$ is hydrogen or $C_1$-$C_4$haloalkyl, preferably hydrogen or trifluoromethyl;

in the radical B7.1

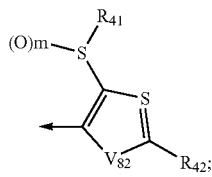
(B7.1)

m is 2;
$V_{82}$ is nitrogen or methine;
$R_{41}$ is $C_1$-$C_4$alkyl, preferably ethyl; and
$R_{42}$ is $C_1$-$C_4$haloalkyl, preferably trifluoromethyl;

in the radical B9.1

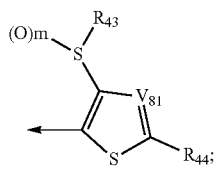
(B9.1)

m is 2;
$V_{81}$ is nitrogen or methine,
$R_{43}$ is $C_1$-$C_4$alkyl, preferably ethyl; and
$R_{44}$ is $C_1$-$C_4$haloalkyl, preferably trifluoromethyl;

and in the radical B11.1

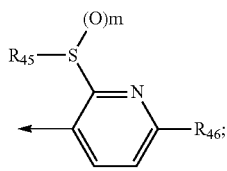
(B11.1)

m is 2;
$R_{45}$ is $C_1$-$C_4$alkyl, preferably ethyl; and
$R_{46}$ is $C_1$-$C_4$haloalkyl, preferably trifluoromethyl.

A further especially preferred group of compounds of formula I according to the invention is defined as embodiment (7) and comprises combinations of (7): Radical A8 with radicals B selected from B1, B7, B9 and B11;

wherein $A_8$ is preferably represented by the radical A8.1

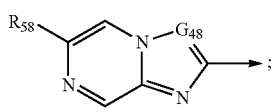
(A8.1)

wherein
$G_{48}$ is nitrogen or C—$R_{59}$;
$R_{59}$ is hydrogen or $C_1$-$C_4$alkyl; and
$R_{58}$ is halogen, $C_1$-$C_4$haloalkyl, $C_1$-$C_4$haloalkylthio, $C_1$-$C_4$haloalkylsulfonyl, O($C_1$-$C_4$haloalkyl), $SF_5$, phenylcarbonylthio, mercapto or $C_1$-$C_4$alkoxycarbonyl;

and the radicals B1, B7, B9 and B11 are preferably represented by the radicals selected from B1.1, B7.1, B9.1 and B11.1

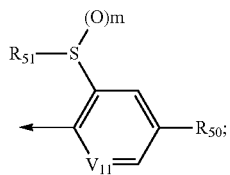
(B1.1)

wherein m is 0, 1 or 2;

$R_{51}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{50}$ is hydrogen, $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

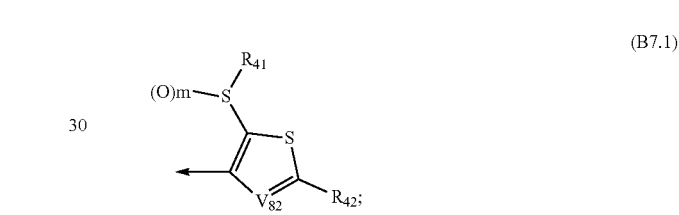
(B7.1)

wherein m is 0, 1 or 2;

$V_{82}$ is nitrogen or methine;

$R_{41}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{42}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

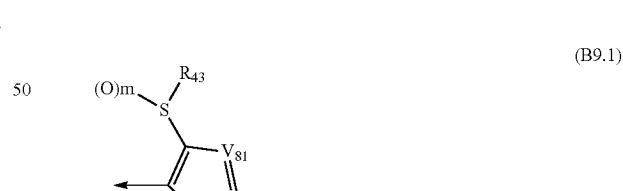
(B9.1)

wherein m is 0, 1 or 2;

$V_{81}$ is nitrogen or methine, $R_{43}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{44}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and

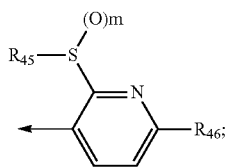

(B11.1)

wherein m is 0, 1 or 2;

$R_{45}$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl; and $R_{46}$ is $C_1$-$C_4$alkyl, $C_1$-$C_4$haloalkyl, $C_1$-$C_3$haloalkoxy, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl.

Especially preferred compounds according to embodiment (7) are represented by embodiment (7.1), wherein (7.1) in the radical A8.1

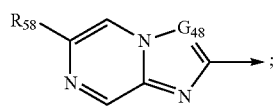

(A8.1)

$R_{58}$ is $C_1$-$C_4$haloalkyl, in particular trifluoromethyl; and $G_{48}$ is nitrogen, C—H or C—$C_1$-$C_4$alkyl; preferably nitrogen, C—H or C—$CH_3$;

and in the radical B1.1

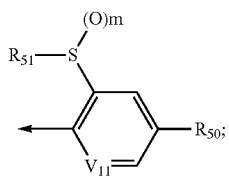

(B1.1)

m is 2;

$V_{11}$ is nitrogen or methine;

$R_{51}$ is $C_1$-$C_4$alkyl, preferably ethyl; and $R_{50}$ is hydrogen or $C_1$-$C_4$haloalkyl, preferably hydrogen or trifluoromethyl;

in the radical B7.1

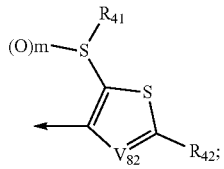

(B7.1)

m is 2;

$V_{82}$ is nitrogen or methine;

$R_{41}$ is $C_1$-$C_4$alkyl, preferably ethyl; and $R_{42}$ is $C_1$-$C_4$haloalkyl, preferably trifluoromethyl;

in the radical B9.1

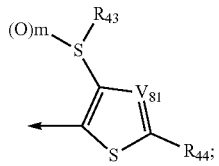

(B9.1)

m is 2;

$V_{81}$ is nitrogen or methine, $R_{43}$ is $C_1$-$C_4$alkyl, preferably ethyl; and $R_{44}$ is $C_1$-$C_4$haloalkyl, preferably trifluoromethyl;

and in the radical B11.1

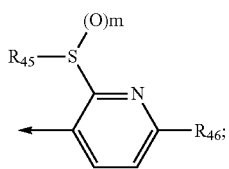

(B11.1)

m is 2;

$R_{45}$ is $C_1$-$C_4$alkyl, preferably ethyl; and $R_{46}$ is $C_1$-$C_4$haloalkyl, preferably trifluoromethyl.

Especially preferred compounds of formula I of the invention are listed in the following tables V1 to V26. The tables V1 to V26 represent further embodiments of the invention: In these tables Et is $CH_2CH_3$, Me is $CH_3$, NMe is N—CH3, CMe is C-Me etc.

TABLE V1

Compounds of the formula A2.1-B7.1:

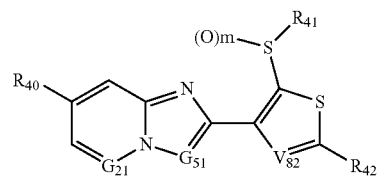

(A2.1-B7.1)

| No. | $R_{40}$ | $R_{41}$ | $R_{42}$ | m | $G_{21}$ | $G_{51}$ | $V_{82}$ | Mpt. °C. | Ret. time (mins) | (M + H) | Method |
|---|---|---|---|---|---|---|---|---|---|---|---|
| V1.01 | $CF_3$ | Et | $CF_3$ | 2 | CH | N | CH | 160-161 | | | |
| V1.02 | $CF_3$ | Et | $CF_3$ | 2 | N | N | CH | 156-159 | | | |
| V1.03 | $CF_3$ | Et | $CF_3$ | 2 | CH | CMe | CH | | | | |

TABLE V1-continued

| | | | | | | | |
|---|---|---|---|---|---|---|---|
| V1.04 | CF$_3$ | Et | CF$_3$ | 2 | N | CMe | CH | |
| V1.05 | CF$_3$ | Et | CF$_3$ | 2 | CH | CH | CH | |
| V1.06 | CF$_3$ | Et | CF$_3$ | 2 | N | CH | CH | 187-190 |
| V1.07 | CF$_3$ | Et | CF$_3$ | 2 | CH | CH | N | |
| V1.08 | CF$_3$ | Et | H | 2 | CH | CH | N | |

TABLE V2

Compounds of the formula A2.1-B9.1:

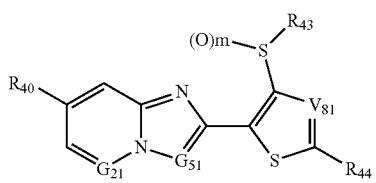

(A2.1-B9.1)

| No. | R$_{40}$ | R$_{43}$ | R$_{44}$ | V$_{81}$ | m | G$_{21}$ | G$_{51}$ | Mpt. °C. | Ret. time (mins) | (M + H) | Method |
|---|---|---|---|---|---|---|---|---|---|---|---|
| V2.01 | CF$_3$ | Et | CF$_3$ | CH | 2 | CH | N | 136-138 | 1.08 | 430 | SQD13 |
| V2.02 | CF$_3$ | Et | CF$_3$ | CH | 2 | N | N | 109-111 | | | |
| V2.03 | CF$_3$ | Et | CF$_3$ | CH | 2 | CH | CMe | 190-192 | 1.08 | 443 | SQD13 |
| V2.04 | CF$_3$ | Et | CF$_3$ | CH | 2 | N | CMe | 92-94 | 1.11 | 444 | SQD13 |
| V2.05 | CF$_3$ | Et | CF$_3$ | CH | 2 | CH | CH | 174-176 | 1.13 | 429 | SQD13 |
| V2.06 | CF$_3$ | Et | CF$_3$ | CH | 2 | N | CH | 209-211 | 1.11 | 430 | SQD13 |
| V2.07 | CF$_3$ | Et | CF$_3$ | N | 2 | CH | N | 129-130 | 1.10 | 431 | SQD13 |
| V2.08 | CF$_3$ | Et | CF$_3$ | N | 2 | N | N | 119-120 | | | |
| V2.09 | CF$_3$ | Et | CF$_3$ | N | 2 | CH | CMe | | | | |
| V2.10 | CF$_3$ | Et | CF$_3$ | N | 2 | N | CMe | | | | |
| V2.11 | CF$_3$ | Et | CF$_3$ | N | 2 | CH | CH | 126-128 | | | |
| V2.12 | CF$_3$ | Et | CF$_3$ | N | 2 | N | CH | 192-194 | | | |

TABLE V3

Compounds of the formula A2.1-B11.1:

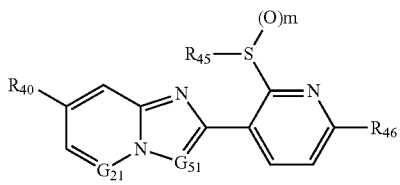

(A2.1-B11.1)

| No. | R$_{40}$ | R$_{45}$ | R$_{46}$ | m | G$_{21}$ | G$_{51}$ | Mpt. °C. | Ret. time (mins) | (M + H) | Method |
|---|---|---|---|---|---|---|---|---|---|---|
| V3.01 | CF$_3$ | Et | CF$_3$ | 2 | CH | N | 133-134 | 0.95 | 425 | SQD13 |
| V3.02 | CF$_3$ | Et | CF$_3$ | 2 | N | N | 158-159 | 0.93 | 426 | SQD13 |
| V3.03 | CF$_3$ | Et | CF$_3$ | 2 | CH | CMe | | | | |
| V3.04 | CF$_3$ | Et | CF$_3$ | 2 | N | CMe | 106-108 | 1.01 | 439 | SQD13 |
| V3.05 | CF$_3$ | Et | CF$_3$ | 2 | CH | CH | 188-190 | 1.07 | 424 | SQD13 |
| V3.06 | CF$_3$ | Et | CF$_3$ | 2 | N | CH | 135-137 | 1.03 | 425 | SQD13 |

TABLE V4

Compounds of the formula A3.1-B7.1:

(A3.1-B7.1)

| No. | $R_{47}$ | $R_{41}$ | $R_{42}$ | m | $G_{22}$ | $G_{41}$ | $V_{82}$ | Mpt. °C. | Ret. time (mins) | (M + H) | Method |
|---|---|---|---|---|---|---|---|---|---|---|---|
| V4.01 | $CF_3$ | Et | $CF_3$ | 2 | CH | N | CH | 198-199 | | | |
| V4.02 | $CF_3$ | Et | $CF_3$ | 2 | N | N | CH | 195-197 | | | |
| V4.03 | $CF_3$ | Et | $CF_3$ | 2 | CH | CMe | CH | | | | |
| V4.04 | $CF_3$ | Et | $CF_3$ | 2 | N | CMe | CH | | | | |
| V4.05 | $CF_3$ | Et | $CF_3$ | 2 | CH | CH | CH | | | | |
| V4.06 | $CF_3$ | Et | $CF_3$ | 2 | N | CH | CH | | | | |

TABLE V5

Compounds of the formula A3.1-B9.1:

(A3.1-B9.1)

| No. | $R_{47}$ | $R_{43}$ | $R_{44}$ | m | $G_{22}$ | $G_{41}$ | $V_{81}$ | Mpt. °C. | Ret. time (mins) | (M + H) | Method |
|---|---|---|---|---|---|---|---|---|---|---|---|
| V5.01 | $CF_3$ | Et | $CF_3$ | 2 | CH | N | CH | 147-149 | 1.08 | 430 | SQD13 |
| V5.02 | $CF_3$ | Et | $CF_3$ | 2 | N | N | CH | 156-158 | | | |
| V5.03 | $CF_3$ | Et | $CF_3$ | 2 | CH | CMe | CH | | | | |
| V5.04 | $CF_3$ | Et | $CF_3$ | 2 | N | CMe | CH | | | | |
| V5.05 | $CF_3$ | Et | $CF_3$ | 2 | CH | CH | CH | | | | |
| V5.06 | $CF_3$ | Et | $CF_3$ | 2 | N | CH | CH | | | | |
| V5.07 | $CF_3$ | Et | $CF_3$ | 2 | CH | N | N | 127-128 | 1.0 | 431 | SQD13 |
| V5.08 | $CF_3$ | Et | $CF_3$ | 2 | N | N | N | 130-131 | | | |
| V5.09 | $CF_3$ | Et | $CF_3$ | 2 | CH | CMe | N | | | | |
| V5.010 | $CF_3$ | Et | $CF_3$ | 2 | N | CMe | N | | | | |
| V5.011 | $CF_3$ | Et | $CF_3$ | 2 | CH | CH | N | | | | |
| V5.012 | $CF_3$ | Et | $CF_3$ | 2 | N | CH | N | | | | |

TABLE V6

Compounds of the formula A3.1-B11.1:

(A3.1-B11.1)

| No. | $R_{47}$ | $R_{45}$ | $R_{46}$ | m | $G_{22}$ | $G_{41}$ | Mpt. °C. | Ret. time (mins) | (M + H) | Method |
|---|---|---|---|---|---|---|---|---|---|---|
| V6.01 | $CF_3$ | Et | $CF_3$ | 2 | CH | N | 155-156 | 0.95 | 425 | SQD13 |
| V6.02 | $CF_3$ | Et | $CF_3$ | 2 | N | N | 201-203 | 0.89 | 426 | SQD13 |
| V6.03 | $CF_3$ | Et | $CF_3$ | 2 | CH | CMe | | | | |
| V6.04 | $CF_3$ | Et | $CF_3$ | 2 | N | CMe | | | | |
| V6.05 | $CF_3$ | Et | $CF_3$ | 2 | CH | CH | | | | |
| V6.06 | $CF_3$ | Et | $CF_3$ | 2 | N | CH | | | | |

TABLE V7

Compounds of the formula A4.1-B1.1:

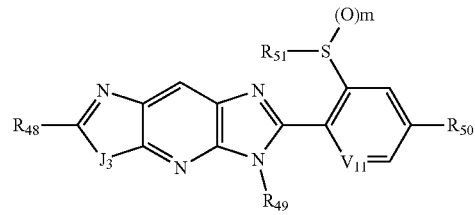

(A4.1-B1.1)

| No. | R$_{48}$ | R$_{51}$ | R$_{50}$ | m | J$_3$ | R$_{49}$ | V$_{11}$ | Mpt. °C. | Ret. time (mins) | (M + H) | Method |
|---|---|---|---|---|---|---|---|---|---|---|---|
| V7.01 | CF$_3$ | Et | CF$_3$ | 2 | O | Me | N | | | | |
| V7.02 | CF$_3$ | Et | CF$_3$ | 2 | S | Me | N | | | | |
| V7.03 | CF$_3$ | Et | CF$_3$ | 2 | O | Me | CH | | | | |
| V7.04 | CF$_3$ | Et | CF$_3$ | 2 | S | Me | CH | | | | |
| V7.05 | CF$_3$ | Et | H | 2 | O | Me | N | | | | |
| V7.06 | CF$_3$ | Et | H | 2 | S | Me | N | | | | |
| V7.07 | CF$_3$ | Et | H | 2 | O | Me | CH | | | | |
| V7.08 | CF$_3$ | Et | H | 2 | S | Me | CH | | | | |
| V7.09 | CF$_3$ | Et | CF$_3$ | 2 | NMe | Me | N | 206-208 | 1.04 | 493 | SQD13 |
| V7.10 | CF$_3$ | Et | CF$_3$ | 2 | NMe | Me | CH | 210-212 | 1.02 | 492 | SDQ13 |
| V7.11 | CF$_3$ | Et | H | 2 | NMe | Me | N | 152-154 | 0.87 | 425 | ZQD13 |
| V7.12 | CF$_3$ | Et | H | 2 | NMe | Me | CH | 234-236 | 0.90 | 424 | SQD13 |

TABLE V8

Compounds of the formula A5.1-B1.1:

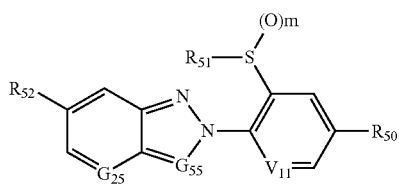

(A5.1-B1.1)

| No. | R$_{52}$ | R$_{51}$ | R$_{50}$ | m | G$_{25}$ | G$_{55}$ | V$_{11}$ | Mpt. | Ret. time (mins) | (M + H) | Method |
|---|---|---|---|---|---|---|---|---|---|---|---|
| V8.01 | CF$_3$ | Et | CF$_3$ | 2 | CH | N | N | | | | |
| V8.02 | CF$_3$ | Et | CF$_3$ | 2 | CH | N | CH | | | | |
| V8.03 | CF$_3$ | Et | H | 2 | CH | N | N | | | | |
| V8.04 | CF$_3$ | Et | H | 2 | CH | N | CH | | | | |
| V8.05 | CF$_3$ | Et | CF$_3$ | 2 | N | N | N | | | | |
| V8.06 | CF$_3$ | Et | CF$_3$ | 2 | N | N | CH | | | | |
| V8.07 | CF$_3$ | Et | H | 2 | N | N | N | | | | |
| V8.08 | CF$_3$ | Et | H | 2 | N | N | CH | | | | |
| V8.09 | CF$_3$ | Et | CF$_3$ | 2 | CH | CMe | N | | | | |
| V8.10 | CF$_3$ | Et | CF$_3$ | 2 | CH | CMe | CH | | | | |
| V8.11 | CF$_3$ | Et | H | 2 | CH | CMe | N | | | | |
| V8.12 | CF$_3$ | Et | H | 2 | CH | CMe | CH | | | | |

TABLE V9

Compounds of the formula A5.1-B7.1:

(A5.1-B7.1)

| No. | $R_{52}$ | $R_{41}$ | $R_{42}$ | m | $G_{25}$ | $G_{55}$ | $V_{82}$ | Mpt. °C. | Ret. time (mins) | (M + H) | Method |
|---|---|---|---|---|---|---|---|---|---|---|---|
| V9.01 | $CF_3$ | Et | $CF_3$ | 2 | CH | N | CH | | | | |
| V9.02 | $CF_3$ | Et | $CF_3$ | 2 | N | N | CH | | | | |
| V9.03 | $CF_3$ | Et | $CF_3$ | 2 | N | CMe | CH | | | | |

TABLE V10

Compounds of the formula A5.1-B9.1:

(A5.1-B9.1)

| No. | $R_{52}$ | $R_{43}$ | $R_{44}$ | m | $G_{25}$ | $G_{55}$ | $V_{81}$ | Mpt. °C. | Ret. time (mins) | (M + H) | Method |
|---|---|---|---|---|---|---|---|---|---|---|---|
| V10.01 | $CF_3$ | Et | $CF_3$ | 2 | CH | N | CH | | | | |
| V10.02 | $CF_3$ | Et | $CF_3$ | 2 | N | N | CH | | | | |
| V10.03 | $CF_3$ | Et | $CF_3$ | 2 | N | CMe | CH | | | | |
| V10.04 | $CF_3$ | Et | $CF_3$ | 2 | CH | N | N | | | | |
| V10.05 | $CF_3$ | Et | $CF_3$ | 2 | N | N | N | | | | |
| V10.06 | $CF_3$ | Et | $CF_3$ | 2 | N | CMe | N | | | | |

TABLE V11

Compounds of the formula A5.1-B11.1:

(A5.1-B11.1)

| No. | $R_{52}$ | $R_{45}$ | $R_{46}$ | m | $G_{25}$ | $G_{55}$ | Mpt. °C. | Ret. time (mins) | (M + H) | Method |
|---|---|---|---|---|---|---|---|---|---|---|
| V11.01 | $CF_3$ | Et | $CF_3$ | 2 | CH | N | | | | |
| V11.02 | $CF_3$ | Et | $CF_3$ | 2 | N | N | | | | |
| V11.03 | $CF_3$ | Et | $CF_3$ | 2 | N | CMe | | | | |

TABLE V12

Compounds of the formula A6.1-B1.1:

(A6.1-B1.1)

| No. | $R_{54}$ | $R_{51}$ | $R_{50}$ | m | $G_{26}$ | $G_{36}$ | $V_{11}$ | Mpt. °C. | Ret. time (mins) | (M + H) | Method |
|---|---|---|---|---|---|---|---|---|---|---|---|
| V12.01 | $CF_3$ | Et | $CF_3$ | 2 | CH | NMe | N | 214-216 | 0.99 | 439 | ZQD13 |
| V12.02 | $CF_3$ | Et | $CF_3$ | 2 | CH | NMe | CH | 168-170 | 0.98 | 438 | ZQD13 |
| V12.03 | $CF_3$ | Et | H | 2 | CH | NMe | N | 211-213 | 0.81 | 371 | ZQD13 |
| V12.04 | $CF_3$ | Et | H | 2 | CH | NMe | CH | 192-195 | | | |
| V12.05 | $CF_3$ | Et | $CF_3$ | 2 | CH | O | N | | 1.02 | 426 | SQD13 |
| V12.06 | $CF_3$ | Et | $CF_3$ | 2 | CH | O | CH | | 1.04 | 423 | SQD13 |
| V12.07 | $CF_3$ | Et | H | 2 | CH | O | N | | 0.87 | 358 | SQD13 |
| V12.08 | $CF_3$ | Et | H | 2 | CH | O | CH | | | | |
| V12.09 | $CF_3$ | Et | $CF_3$ | 2 | CH | S | N | | | | |
| V12.10 | $CF_3$ | Et | $CF_3$ | 2 | CH | S | CH | | | | |
| V12.11 | $CF_3$ | Et | H | 2 | CH | S | N | | | | |
| V12.12 | $CF_3$ | Et | H | 2 | CH | S | CH | | | | |
| V12.13 | $CF_3$ | Et | $CF_3$ | 2 | N | NMe | N | | | | |
| V12.14 | $CF_3$ | Et | $CF_3$ | 2 | N | NMe | CH | | | | |
| V12.15 | $CF_3$ | Et | H | 2 | N | NMe | N | | | | |
| V12.16 | $CF_3$ | Et | H | 2 | N | NMe | CH | | | | |
| V12.17 | Cl | Et | $CF_3$ | 2 | N | NMe | N | 228-229 | 0.91 | 406/408 | ZCQ13 |
| V12.18 | $CF_3$ | Me | $CF_3$ | 2 | CH | NMe | N | 234-236 | 0.93 | 425 | SQD13 |
| V12.19 | $CF_3$ | Et | $OCHF_2$ | 2 | CH | NMe | N | 146-148 | 1.03 | 405 | SQD13 |
| V12.20 | Br | Et | $CF_3$ | 2 | CH | NMe | N | 188-190 | 0.95 | 449/451 | SQD13 |

TABLE V13

Compounds of the formula A6.1-B7.1:

(A6.1-B7.1)

| NO. | $R_{54}$ | $R_{41}$ | $R_{42}$ | m | $G_{26}$ | $G_{36}$ | $V_{82}$ | MPt. °C. | Ret. time (mins) | (M +H) | Method |
|---|---|---|---|---|---|---|---|---|---|---|---|
| V13.01 | $CF_3$ | Et | $CF_3$ | 2 | CH | NMe | CH | 188-191 | | | |
| V13.02 | $CF_3$ | Et | $CF_3$ | 2 | CH | O | CH | | | | |
| V13.03 | $CF_3$ | Et | $CF_3$ | 2 | N | NMe | CH | | | | |
| V13.04 | $CF_3$ | Et | $CF_3$ | 2 | CH | S | CH | | | | |
| V13.05 | $CF_3$ | Et | H | 2 | CH | NMe | N | 178-179 | 0.85 | 377 | SQD13 |

TABLE V14:

Compounds of the formula A6.1-B9.1:

(A6.1-B9.1)

| No. | $R_{54}$ | $R_{43}$ | $R_{44}$ | m | $G_{26}$ | $G_{36}$ | $V_{81}$ | MPt. °C. | Ret. time (mins) | (M + H) | Method |
|---|---|---|---|---|---|---|---|---|---|---|---|
| V14.01 | $CF_3$ | Et | $CF_3$ | 2 | CH | NMe | CH | 115-117 | 1.09 | 407 | SQD13 |
| V14.02 | $CF_3$ | Et | $CF_3$ | 2 | CH | O | CH | | | | |
| V14.03 | $CF_3$ | Et | $CF_3$ | 2 | N | NMe | CH | | | | |
| V14.04 | $CF_3$ | Et | $CF_3$ | 2 | CH | S | CH | | | | |
| V14.05 | $CF_3$ | Et | $CF_3$ | 2 | CH | NMe | N | 168-170 | 0.95 | 445 | SQD13 |
| V14.06 | $CF_3$ | Et | $CF_3$ | 2 | CH | O | N | | | | |
| V14.07 | $CF_3$ | Et | $CF_3$ | 2 | N | NMe | N | | | | |
| V14.08 | $CF_3$ | Et | $CF_3$ | 2 | CH | S | N | | | | |

TABLE V15

Compounds of the formula A6.1-B11.1:

(A6.1-B11.1)

| No. | $R_{54}$ | $R_{45}$ | $R_{46}$ | m | $G_{26}$ | $G_{36}$ | Mpt. °C. | Ret. time (mins) | (M + H) | Method |
|---|---|---|---|---|---|---|---|---|---|---|
| V15.01 | $CF_3$ | Et | $CF^3$ | 2 | CH | NMe | 209-211 | 1.09 | 407 | SQD13 |
| V15.02 | $CF_3$ | Et | $CF_3$ | 2 | CH | O | | | | |
| V15.03 | $CF_3$ | Et | $CF_3$ | 2 | N | NMe | | | | |
| V15.04 | $CF_3$ | Et | $CF_3$ | 2 | CH | S | | | | |

TABLE V16

Compounds of the formula A7.1-B1.1:

(A7.1-B1.1)

| No. | $R_{56}$ | $R_{51}$ | $R_{50}$ | m | $G_{57}$ | $V_{11}$ | Mpt. °C. | Ret. time (mins) | (M + H) | Method |
|---|---|---|---|---|---|---|---|---|---|---|
| V16.01 | $CF_3$ | Et | $CF_3$ | 2 | CMe | N | 240-242° | 1.01 | 439 | SQD13 |
| V16.02 | $CF_3$ | Et | $CF_3$ | 2 | CH | N | 180-181 | 0.98 | 425 | SQD13 |
| V16.03 | $CF_3$ | Et | $CF_3$ | 2 | N | N | 190-192 | 0.94 | 426 | SQD13 |
| V16.04 | $CF_3$ | Et | $CF_3$ | 2 | CMe | CH | | | | |
| V16.05 | $CF_3$ | Et | $CF_3$ | 2 | CH | CH | | 1.02 | 424 | SQD13 |
| V16.06 | $CF_3$ | Et | $CF_3$ | 2 | N | CH | 148-150 | 0.87 | 357 | SQD13 |
| V16.07 | $CF_3$ | Et | H | 2 | CMe | N | | 0.81 | 371 | SQD13 |
| V16.08 | $CF_3$ | Et | H | 2 | CH | N | 216-217 | 0.79 | 357 | SQD13 |

TABLE V16-continued

Compounds of the formula A7.1-B1.1:

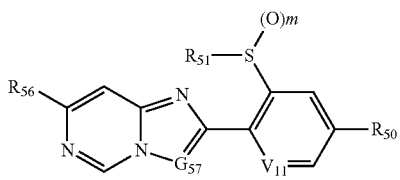

(A7.1-B1.1)

| No. | R$_{56}$ | R$_{51}$ | R$_{50}$ | m | G$_{57}$ | V$_{11}$ | Mpt. °C. | Ret. time (mins) | (M + H) | Method |
|---|---|---|---|---|---|---|---|---|---|---|
| V16.09 | CF$_3$ | Et | H | 2 | N | N | | 0.76 | 358 | SQD13 |
| V16.10 | CF$_3$ | Et | H | 2 | CMe | CH | | | | |
| V16.11 | CF$_3$ | Et | H | 2 | CH | CH | 166-167 | 0.88 | 356 | SQD13 |
| V16.12 | CF$_3$ | Et | H | 2 | N | CH | 193-195 | 1.01 | 425 | SQD13 |

TABLE V17

Compounds of the formula A7.1-B7.1:

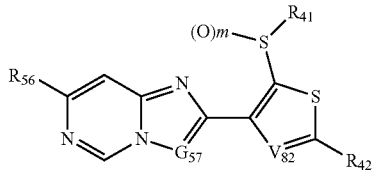

(A7.1-B7.1)

| No. | R$_{56}$ | R$_{41}$ | R$_{42}$ | m | G$_{57}$ | V$_{82}$ | Mpt. °C. | Ret. time (mins) | (M + H) | Method |
|---|---|---|---|---|---|---|---|---|---|---|
| V17.01 | CF$_3$ | Et | CF$_3$ | 2 | CMe | CH | | | | |
| V17.02 | CF$_3$ | Et | CF$_3$ | 2 | H | CH | | | | |
| V17.03 | CF$_3$ | Et | CF$_3$ | 2 | N | CH | | | | |
| V17.04 | CF$_3$ | Et | H | 2 | H | N | | | | |

TABLE V18

Compounds of the formula A7.1-B9.1:

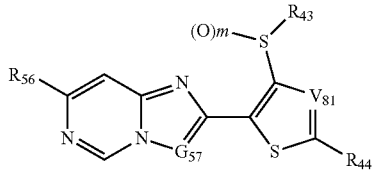

(A7.1-B9.1)

| No. | R$_{56}$ | R$_{43}$ | R$_{44}$ | m | G$_{57}$ | V$_{81}$ | Mpt. °C. | Ret. time (mins) | (M + H) | Method |
|---|---|---|---|---|---|---|---|---|---|---|
| V18.01 | CF$_3$ | Et | CF$_3$ | 2 | CMe | CH | | | | |
| V18.02 | CF$_3$ | Et | CF$_3$ | 2 | H | CH | 201-202° C. | 1.08 | 430 | SQD13 |
| V18.03 | CF$_3$ | Et | CF$_3$ | 2 | N | CH | 161-162 | 1.04 | 431 | SQD13 |
| V18.04 | CF$_3$ | Et | CF$_3$ | 2 | CMe | N | | | | |
| V18.05 | CF$_3$ | Et | CF$_3$ | 2 | H | N | 163-165 | 1.06 | 431 | SQD13 |
| V18.06 | CF$_3$ | Et | CF$_3$ | 2 | N | N | 157-158 | 0.97 | 432 | SQD13 |

TABLE V19

Compounds of the formula A7.1-B11.1:

(A7.1-B11.1)

| No. | $R_{56}$ | $R_{45}$ | $R_{46}$ | m | $G_{57}$ | Mpt. °. | Ret. time (mins) | (M + H) | Method |
|---|---|---|---|---|---|---|---|---|---|
| V19.01 | $CF_3$ | Et | $CF_3$ | 2 | CMe | | | | |
| V19.02 | $CF_3$ | Et | $CF_3$ | 2 | CH | | 0.99 | 425 | SQD13 |
| V19.03 | $CF_3$ | Et | $CF_3$ | 2 | N | | 0.94 | 426 | SQD13 |

TABLE V20

Compounds of the formula A8.1-B1.1:

(A8.1-B1.1)

| No. | $R_{58}$ | $R_{51}$ | $R_{50}$ | m | $G_{48}$ | $V_{11}$ | Mpt ° C. | Ret. time (mins) | (M + H) | Method |
|---|---|---|---|---|---|---|---|---|---|---|
| V20.01 | $CF_3$ | Et | $CF_3$ | 2 | CMe | N | 245-246 | 1...00 | 439 | SQD13 |
| V20.02 | $CF_3$ | Et | $CF_3$ | 2 | CH | N | 197-203 | 0.97 | 425 | SQD13 |
| V20.03 | $CF_3$ | Et | $CF_3$ | 2 | N | N | | | | |
| V20.04 | $CF_3$ | Et | $CF_3$ | 2 | CMe | CH | | | | |
| V20.05 | $CF_3$ | Et | $CF_3$ | 2 | CH | CH | | 1.00 | 424 | SQD13 |
| V20.06 | $CF_3$ | Et | $CF_3$ | 2 | N | CH | | | | |
| V20.07 | $CF_3$ | Et | H | 2 | CMe | N | 272-273 | 0.80 | 371 | SQD13 |
| V20.08 | $CF_3$ | Et | H | 2 | CH | N | 208-218 | 0.77 | 357 | ZCQ13 |
| V20.09 | $CF_3$ | Et | H | 2 | N | N | | | | |
| V20.10 | $CF_3$ | Et | H | 2 | CMe | CH | | | | |
| V20.11 | $CF_3$ | Et | H | 2 | CH | CH | | | | |
| V20.12 | $CF_3$ | Et | H | 2 | N | CH | | | | |

TABLE V21

Compounds of the formula A8.1-B7.1:

(A8.1-B7.1)

| No. | $R_{58}$ | $R_{41}$ | $R_{42}$ | m | $G_{48}$ | $V_{82}$ | Mpt. ° C. | Ret. time (mins) | (M + H) | Method |
|---|---|---|---|---|---|---|---|---|---|---|
| V21.01 | $CF_3$ | Et | $CF_3$ | 2 | CMe | CH | | | | |
| V21.02 | $CF_3$ | Et | $CF_3$ | 2 | CH | CH | | | | |
| V21.03 | $CF_3$ | Et | $CF_3$ | 2 | N | CH | | | | |

TABLE V22

Compounds of the formula A8.1-B9.1:

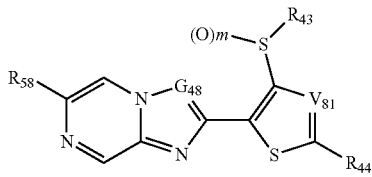
(A8.1-B9.1)

| No. | $R_{58}$ | $R_{43}$ | $R_{44}$ | m | $G_{48}$ | $V_{81}$ | Mpt. °C. | Ret. time (mins) | (M + H) | Method |
|---|---|---|---|---|---|---|---|---|---|---|
| V22.01 | $CF_3$ | Et | $CF_3$ | 2 | C—Me | CH | | | | |
| V22.02 | $CF_3$ | Et | $CF_3$ | 2 | CH | CH | 204-205 | 1.07 | 430 | SQD13 |
| V22.03 | $CF_3$ | Et | $CF_3$ | 2 | N | CH | | | | |
| V22.04 | $CF_3$ | Et | $CF_3$ | 2 | CMe | N | | | | |
| V22.05 | $CF_3$ | Et | $CF_3$ | 2 | CH | N | | | | |
| V22.06 | $CF_3$ | Et | $CF_3$ | 2 | N | N | | | | |

TABLE V23

Compounds of the formula A8.1-B11.1:

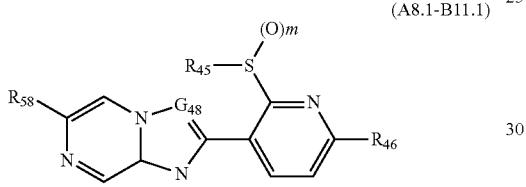
(A8.1-B11.1)

| No. | $R_{58}$ | $R_{45}$ | $R_{46}$ | m | $G_{48}$ | Mpt °C. | Ret. time (mins) | (M + H) | Method |
|---|---|---|---|---|---|---|---|---|---|
| V23.01 | $CF_3$ | Et | $CF_3$ | 2 | CMe | | | | |
| V23.02 | $CF_3$ | Et | $CF_3$ | 2 | CH | | 0.98 | 425 | SQD13 |
| V23.03 | $CF_3$ | Et | $CF_3$ | 2 | N | | | | |

TABLE V24

Compounds of the formula A4.1-B7.1:

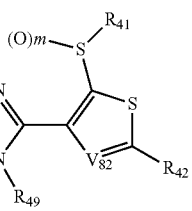
(A4.1-B7.1)

| No. | $R_{48}$ | $R_{41}$ | m | $J_3$ | $R_{49}$ | $R_{42}$ | $V_{82}$ | Mpt. °C. | Ret. time (mins) | (M + H) | Method |
|---|---|---|---|---|---|---|---|---|---|---|---|
| V24.01 | $CF_3$ | Et | 2 | O | Me | $CF_3$ | CH | | | | |
| V24.02 | $CF_3$ | Et | 2 | S | Me | $CF_3$ | CH | | | | |
| V24.03 | $CF_3$ | Et | 2 | NMe | Me | $CF_3$ | CH | | | | |
| V24.04 | $CF_3$ | Et | 2 | NMe | Me | $CF_3$ | CH | 185-187 | 1.06 | 498 | SQD13 |
| V24.05 | $CF_3$ | Et | 2 | Me | Me | H | N | 214-216 | 0.90 | 431 | SQD13 |

TABLE V25

Compounds of the formula A4.1-B9.1:

(A4.1-B9.1)

| No. | $R_{48}$ | $R_{43}$ | $R_{44}$ | m | $J_3$ | $R_{49}$ | $V_{81}$ | Mpt. °C. | Ret. time (mins) | (M + H) | Method |
|---|---|---|---|---|---|---|---|---|---|---|---|
| V25.01 | $CF_3$ | Et | $CF_3$ | 2 | O | Me | CH | | | | |
| V25.02 | $CF_3$ | Et | $CF_3$ | 2 | S | Me | CH | | | | |
| V25.03 | $CF_3$ | Et | $CF_3$ | 2 | NMe | Me | CH | 158-160 | 1.03 | 498 | SQD13 |
| V25.04 | $CF_3$ | Et | $CF_3$ | 2 | O | Me | N | | | | |
| V25.05 | $CF_3$ | Et | $CF_3$ | 2 | S | Me | N | | | | |
| V25.06 | $CF_3$ | Et | $CF_3$ | 2 | NMe | Me | N | 170-172 | 0.99 | 499 | SQ13 |

TABLE V26

Compounds of the formula A4.1-B11.1:

(A4.1-B11.1)

| No. | $R_{48}$ | $R_{45}$ | $R_{46}$ | m | $J_3$ | $R_{49}$ | Mpt. °C. | Ret. time (mins) | (M + H) | Method |
|---|---|---|---|---|---|---|---|---|---|---|
| V26.01 | $CF_3$ | Et | $CF_3$ | 2 | O | Me | | | | |
| V26.02 | $CF_3$ | Et | $CF_3$ | 2 | S | Me | | | | |
| V26.03 | $CF_3$ | Et | $CF_3$ | 2 | NMe | Me | 197-199 | 0.95 | 493 | SQD13 |

FORMULATION EXAMPLES (%=PERCENT BY WEIGHT)

Example F1: Emulsion Concentrates

| | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

| | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|                       | a)  | b)  | c)  | d)  |
|-----------------------|-----|-----|-----|-----|
| Active ingredient     | 5%  | 10% | 8%  | 21% |
| Kaolin                | 94% | —   | 79% | 54% |
| Highly disperse silica| 1%  | —   | 13% | 7%  |
| Attapulgite           | —   | 90% | —   | 18% |

The active ingredient is dissolved in dichloromethane, the solution is sprayed onto the carrier(s), and the solvent is subsequently evaporated in vacuo.

Example F4: Dusts

|                        | a)  | b)  |
|------------------------|-----|-----|
| Active ingredient      | 2%  | 5%  |
| Highly disperse silica | 1%  | 5%  |
| Talc                   | 97% | —   |
| Kaolin                 | —   | 90% |

Ready-to-use dusts are obtained by intimately mixing the carriers and the active ingredient.

Example F5: Wettable Powders

|                                                       | a)  | b)  | c)  |
|-------------------------------------------------------|-----|-----|-----|
| Active ingredient                                     | 25% | 50% | 75% |
| Sodium lignosulfonate                                 | 5%  | 5%  | —   |
| Sodium lauryl sulfate                                 | 3%  | —   | 5%  |
| Sodium diisobutyl-naphthalenesulfonate                | —   | 6%  | 10% |
| Octylphenoxypolyethylene glycol ether (7-8 mol of EO) | —   | 2%  | —   |
| Highly disperse silica                                | 5%  | 10% | 10% |
| Kaolin                                                | 62% | 27% | —   |

The active ingredient is mixed with the additives and the mixture is ground thoroughly in a suitable mill. This gives wettable powders, which can be diluted with water to give suspensions of any desired concentration.

Example F6: Extruder Granules

| Active ingredient     | 10% |
|-----------------------|-----|
| Sodium lignosulfonate | 2%  |
| Carboxymethylcellulose| 1%  |
| Kaolin                | 87% |

The active ingredient is mixed with the additives, and the mixture is ground, moistened with water, extruded, granulated and dried in a stream of air.

Example F7: Coated Granules

| Active ingredient           | 3%  |
|-----------------------------|-----|
| Polyethylene glycol (MW 200)| 3%  |
| Kaolin                      | 94% |

In a mixer, the finely ground active ingredient is applied uniformly to the kaolin, which has been moistened with the polyethylene glycol. This gives dust-free coated granules.

Example F8: Suspension Concentrate

| Active ingredient                                   | 40%  |
|-----------------------------------------------------|------|
| Ethylene glycol                                     | 10%  |
| Nonylphenoxypolyethylene glycol ether (15 mol of EO)| 6%   |
| Sodium lignosulfonate                               | 10%  |
| Carboxymethylcellulose                              | 1%   |
| 37% aqueous formaldehyde solution                   | 0.2% |
| Silicone oil (75% aqueous emulsion)                 | 0.8% |
| Water                                               | 32%  |

The finely ground active ingredient is mixed intimately with the additives. Suspensions of any desired concentration can be prepared from the thus resulting suspension concentrate by dilution with water.

Example F9: Powders for Dry Seed Treatment

|                          | a)  | b)  | c)  |
|--------------------------|-----|-----|-----|
| active ingredient        | 25% | 50% | 75% |
| light mineral oil        | 5%  | 5%  | 5%  |
| highly dispersed silicic acid | 5%  | 5%  | —   |
| Kaolin                   | 65% | 40% | —   |
| Talcum                   | —   | —   | 20% |

The combination is thoroughly mixed with the adjuvants and the mixture is thoroughly ground in a suitable mill, affording powders that can be used directly for seed treatment.

Example F10: Emulsifiable Concentrate

| active ingredient                                | 10% |
|--------------------------------------------------|-----|
| octylphenol polyethylene glycol ether (4-5 mol of ethylene oxide) | 3%  |
| calcium dodecylbenzenesulfonate                  | 3%  |
| castor oil polyglycol ether (35 mol of ethylene oxide) | 4%  |
| Cyclohexanone                                    | 30% |
| xylene mixture                                   | 50% |

Emulsions of any required dilution, which can be used in plant protection, can be obtained from this concentrate by dilution with water.

Example F11: Flowable Concentrate for Seed Treatment

| active ingredients                                  | 40%   |
|-----------------------------------------------------|-------|
| propylene glycol                                    | 5%    |
| copolymer butanol PO/EO                             | 2%    |
| Tristyrenephenole with 10-20 moles EO               | 2%    |
| 1,2-benzisothiazolin-3-one (in the form of a 20% solution in water) | 0.5%  |
| monoazo-pigment calcium salt                        | 5%    |
| Silicone oil (in the form of a 75% emulsion in water)| 0.2%  |
| Water                                               | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 168 and V1 to V26 of the present invention"):

an adjuvant selected from the group of substances consisting of petroleum oils (alternative name) (628)+TX, an acaricide selected from the group of substances consisting of acequinocyl ([57960-19-7] [CCN])+TX, fenpyroximate [134098-61-6][CCN]+TX, flucythrinate [70124-77-5][CCN]+TX, 1,1-bis(4-chlorophenyl)-2-ethoxyethanol (IUPAC name) (910)+TX, hexythiazox [78587-05-0] [CCN]+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen [400882-07-7]+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin 11 (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhiodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of momfluorothrin [609346-29-4]+TX, pyrafluprole [315208-17-4]+TX, flometoquin [875775-74-9]+TX, flupyradifuron [951659-40-8]+TX, 1-dichloro-1-nitroethane (IUPAC/Chemical Abstracts name) (1058)+TX, 1,1-dichloro-2,2-bis (4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl) phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanato ethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IU- PAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin 11 (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX and a compound of the formula B1

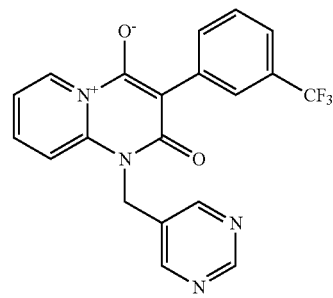

(B1)

with the common name triflumezopyrim (disclosed in WO 2012/092115)+TX;

a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, decliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-

0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, mandestrobin [173662-97-0]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, 3-[5-(4-chlorophenyl)-2,3-dimethyl-3-isoxazolidinyl]pyridine (SYP-Z048), mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, and SDHI inhibitors selected from the group consisting of penflufen ([494793-67-8], U.S. Pat. No. 7,538,073 (N-[2-(1,3-dimethylbutyl)phenyl]-5-fluoro-1,3-dimethyl-1H-pyrazole-4-carboxamide)+TX, furametpyr ([123572-88-3] (5-chloro-N-(1,3-dihydro-1,1,3-trimethyl-4-isobenzofuranyl)-1,3-dimethyl-1H-pyrazole-4-carboxamide)+TX, penthiopyrad (U.S. Pat. No. 5,747,518, [183675-82-3], (N-[2-(1,3-dimethylbutyl)-3-thienyl]-1-methyl-3-(trifluoromethyl)-1H-pyrazole-4-carboxamide)+TX, bixafen (U.S. Pat. No. 7,329,633, [581809-46-3], (N-(3',4'-dichloro-5-fluoro[1,1'-biphenyl]-2-yl)-3-(difluoromethyl)-1-methyl-1H-pyrazole-4-carboxamide)+TX, isopyrazam (U.S. Pat. No. 7,598,395, [881685-58-1] (mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1 RS,4SR,9SR)-1,2,3,4-tetrahydro-9-isopropyl-1,4-methanonaphthalen-5-yl]pyrazole-4-carboxamide)+TX, sedaxane (EP 1480955B1, [874967-67-6] (mixture of 2 cis-isomers 2'-[(1RS,2RS)-1,1'-bicycloprop-2-yl]-3-(difluoromethyl)-1-methylpyrazole-4-carboxanilide and 2 trans-isomers 2'-[(1RS,2SR)-1,1'-bicycloprop-2-yl]-3-(difluoromethyl)-1-methylpyrazole-4-carboxanilide)+TX, fluxapyroxad (U.S. Pat. No. 8,008,232, [907204-31-3] (3-(difluoromethyl)-1-methyl-N-(3',4',5'-trifluoro[1,1'-biphenyl]-2-yl)-1H-pyrazole-4-carboxamide)+TX, solatenol (WO 2007/048556 (3-difluoromethyl-1-methyl-1H-pyrazole-4-carboxylic acid (9-dichloromethylene-1,2,3,4-tetrahydro-1,4-methanonaphthalen-5-yl)-amide,)+TX, the compound 3-(difluoromethyl)-N-methoxy-1-methyl-N-[1-methyl-2-(2,4,6-trichlorophenyl)ethyl]pyrazole-4-carboxamide (described in WO 2010/063700)+TX, thifluzamide (U.S. Pat. No. 5,045,554, [130000-40-7] (N-[2,6-dibromo-4-(trifluoromethoxy)phenyl]-2-methyl-4-(trifluoromethyl)-5-thiazolecarboxamide)+TX, boscalid (U.S. Pat. No. 5,589,493, [188425-85-6 (2-chloro-N-(4'-chloro[1,1'-biphenyl]-2-yl)-3-pyridinecarboxamide)+TX, oxycarboxin ([5259-88-1] (5,6-dihydro-2-methyl-N-phenyl-1,4-oxathiin-3-carboxamide 4,4-dioxide,)+TX, carboxin ([5234-68-4] (5,6-dihydro-2-methyl-N-phenyl-1,4-oxathiin-3-carboxamide)+TX, fluopyram (U.S. Pat. No. 7,572,818, [658066-35-4], (N-[2-[3-chloro-5-(trifluoromethyl)-2-pyridinyl]ethyl]-2-(trifluoromethyl)benzamide)+TX, flutolanil ([24691-80-3], (2-methyl-N-phenyl-3-furancarboxamide, fenfuram), U.S. Pat. No. 4,093,743, CA Reg. No. 66332-96-5 (N-[3-(1-methylethoxy)phenyl]-2-(trifluoromethyl)benzamide)+TX, mepronil ([55814-41-0], (2-methyl-N-[3-(1-methylethoxy)phenyl]benzamide)+TX and benodanil ([15310-01-7], (2-iodo-N-phenylbenzamide)+TX;

and the compounds [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX, 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX and 4-oxo-4-[(2-phenylethyl)amino]-butyric acid (disclosed in WO 2010/137677)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2013]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed.

The active ingredient mixture of the compounds of formula I selected from Tables 1 to 168 and V1 to V26 with active ingredients described above comprises a compound selected from Tables 1 to 130 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are ratios by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 168 and V1 to V26 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 168 and V1 to V26 and the active ingredients as described above is not essential for working the present invention.

BIOLOGICAL EXAMPLES

Example B1: *Spodoptera littoralis* (Egyptian Cotton Leaf Worm)

Test compounds were applied by pipette from 10,000 ppm DMSO stock solutions into 24-well plates and mixed with agar. Lettuce seeds were placed on the agar and the multi well plate was closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples were assessed for mortality, anti-feedant effect and growth inhibition in comparison to untreated samples 6 days after infestation.

The following compounds gave an effect of at least 80% in at least one of the three categories (mortality, anti-feedancy, or growth inhibition) at a test rate of 12.5 ppm:

V20.02, V20.01, V16.02, V12.02, V16.01, V12.01, and V12.03

Example B2: *Spodoptera littoralis* (Egyptian Cotton Leaf Worm)

Cotton leaf discs were placed on agar in 24-well microtiter plates and sprayed with aqueous test solutions prepared from 10,000 ppm DMSO stock solutions. After drying the leaf discs were infested with five L1 larvae. The samples were assessed for mortality 3 days after infestation. The following compounds resulted in at least 80% mortality at an application rate of 200 ppm: The following compounds resulted in at least 80% control at an application rate of 200 ppm:

V14.01, V12.18, V16.08, V20.02, V16.02, V12.20, V12.02, V16.01, V12.01, V7.11, V12.03, V25.03 and V7.09

Example B3: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality 5 days after infestation.

The following compounds resulted in at least 80% mortality at an application rate of 200 ppm:

V14.01, V16.08, V20.08, V20.02, V16.09, V16.03, V16.07, V16.02, V12.02, V16.01, V12.01, V7.11, V12.03, V13.05, V25.03 and V7.09

Example B4: *Diabrotica balteata* (Corn Root Worm)

24-well microtiter plates with artificial diet were treated with aqueous test solutions prepared from 10,000 ppm DMSO stock solutions by pipetting. After drying, the plates were infested with L2 larvae (6 to 10 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

V14.01, V12.18, V16.08, V20.02, V16.09, V16.03, V16.07, V16.02, V12.20, V12.02, V12.01, V7.11, V12.03, V13.05, V25.03 and V7.09.

Example B5: *Myzus persicae* (Green Peach Aphid)

Sunflower leaf discs were placed on agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
V14.01, V16.08, V20.08, V16.09, V16.03, V16.07, V16.02, V12.20, V12.02, V14.05, V16.01, V12.17, V12.01, V7.11, V12.03, V25.03 and V7.09.

Example B6: *Myzus persicae* (Green Peach Aphid)

Roots of pea seedlings infested with an aphid population of mixed ages were placed directly in the aqueous test solutions prepared from 10,000 DMSO stock solutions. The samples were assessed for mortality 6 days after placing seedlings in test solutions.

The following compounds resulted in at least 80% mortality at a test rate of 24 ppm:
V16.08, V20.08, V16.09, V16.03, V16.07, V12.20, V12.02, V14.05, V12.17, V12.01, and V12.03.

Example B7: *Myzus persicae* (Green Peach Aphid)

Test compounds from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:
V12.20, V12.02, V14.05, V16.01, V12.17, V12.01, V7.11, V12.03, and V7.09

Example B8: *Thrips tabaci* (Onion Thrips)

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm:
V12.01, V12.03, and V7.09

Example B9: *Frankliniella occidentalis* (Western Flower Thrips)

Sunflower leaf discs were placed on agar in 24-well microtiter plates and sprayed with aqueous test solutions prepared from 10,000 ppm DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:
V12.02

Example B10: *Bemisia tabaci* (Cotton White Fly)

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation. The following compounds resulted in at least 80% mortality at an application rate of 200 ppm:
V12.20, V12.02, V12.01, V13.05, V25.03 and V7.09.

Example B11: *Tetranychus urticae* (Two-Spotted Spider Mite)

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
V14.01, V12.18, V20.08, and V16.02.

Example B12: *Aedes aegypti* (Yellow Fever Mosquito)

Larvicide, Contact/Feeding Activity, Curative 10 to 15 *Aedes* larvae (L2) together with a nutrition mixture were placed in 96-well microtiter plates. Test compounds were pipetted into the wells. After an incubation period of 2 days insects were assessed for mortality and growth inhibition.

The following compounds gave an effect of at least 80% in at least one of the two categories (mortality or growth inhibition) at a test rate of 5 ppm:
V12.01

What is claimed is:
1. A method, comprising:
applying a compound of formula I,

$$A\text{-}B \qquad (I),$$

wherein A is

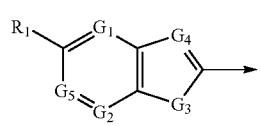

wherein the arrow denotes the point of attachment to the radical B; and
B is

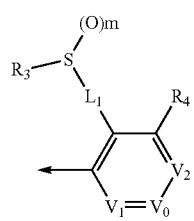

wherein the arrow denotes the point of attachment to the radical A;
wherein
$L_1$ is a direct bond;
$V_0$ is $CR_5$;

$V_1$ is nitrogen;
$V_2$ is $CR_{21}$,
$G_1$ is $CR_{31}$;
$G_2$ is $CR_{32}$, wherein $R_{32}$ is H;
$G_3$ is —$NR_{35}$;
$G_4$ is nitrogen;
$G_5$ is nitrogen;
$R_1$ represents hydrogen, halogen, $C_1$-$C_6$alkyl or $C_1$-$C_6$haloalkyl;
$R_3$ is a $C_1$-$C_6$alkyl, $C_2$-$C_6$ alkenyl or $C_2$-$C_6$ alkynyl group which can be mono- or polysubstituted by substituents selected from the group consisting of $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen, $C_3$-$C_6$cycloalkyl, said $C_3$-$C_6$cycloalkyl itself can be mono- or polysubstituted by substituents selected from halogen and $C_1$-$C_3$alkyl; and by a 5- or 6-membered heterocyclic group, which can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano and nitro;
or $R_3$ is $C_3$-$C_6$cycloalkyl, which can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy and halogen;
or $R_3$ is a 5- or 6-membered heterocyclic group, which can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano and nitro;
or $R_3$ is —$CO_2R_{36}$, —$C(O)R_{36}$ or hydrogen;
$R_{35}$ is hydrogen, $C_1$-$C_6$alkyl which can be mono- or polysubstituted by substituents selected from the group consisting of $C_1$-$C_6$alkoxy, $C_1$-$C_6$haloalkoxy, $C_2$-$C_6$alkenyloxy, $C_2$-$C_6$haloalkenyloxy, $C_2$-$C_6$ alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_2$-$C_6$alkylcarbonyl, $C_2$-$C_6$alkoxycarbonyl, cyano, hydroxy, halogen and $C_3$-$C_6$cycloalkyl, said $C_3$-$C_6$cycloalkyl itself can be mono- or polysubstituted by substituents selected from halogen and $C_1$-$C_3$alkyl; or an N-oxide thereof;

$R_4$, $R_5$, and $R_{21}$ are the same or different and represents cyano, nitro, halogen, hydroxy, $C_1$-$C_6$alkenyloxy, $C_1$-$C_6$-haloalkoxy, $C_3$-$C_6$cycloalkyl, —$C(O)R_{36}$ or hydrogen; or
$C_1$-$C_6$alkyl which can be mono- or polysubstituted by substituents selected from the group consisting of cyano, halogen, hydroxy, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$ alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl, said cycloalkyl itself can be substituted by substituents selected from the group consisting of halogen and $C_1$-$C_3$alkyl; or represents
a phenyl group which can be mono or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro;
$R_7$ represents $C_1$-$C_6$ alkyl, $C_1$-$C_6$ haloalkyl, or hydrogen;
$R_{31}$ represents $C_1$-$C_6$alkyl, $C_1$-$C_6$haloalkyl, —$OR_7$, —$S(O)_nR_{36}$, —$NR_{36}R_{37}$, —$CO_2R_{36}$, —$C(O)R_{36}$, cyano, nitro, halogen or hydrogen;
$R_{36}$ and $R_{37}$ are the same or different and represents hydrogen, $C_1$-$C_6$alkyl which can be mono- or polysubstituted by substituents selected from $C_1$-$C_6$alkoxy, $C_1$-$C_6$haloalkoxy, $C_2$-$C_6$ alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$ cycloalkyl, wherein said $C_3$-$C_6$ cycloalkyl can be mono- or polysubstituted by substituents selected from the group consisting of halogen and $C_1$-$C_3$alkyl; or
$R_{36}$ and $R_{37}$ are the same or different and represents
a phenyl group which can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro;
each m independently represents 0, 1 or 2, and n represents 0, 1 or 2, with the proviso that:
in —$S(O)_nR_{36}$, $R_{36}$ is hydrogen when n is 0;
or an agrochemically acceptable salt, enantiomer, diastereomer, tautomer, or N-oxide thereof, or a composition comprising the compound of formula (I), to an insect, a locus of an insect, or a plant susceptible to attack by an insect.

2. The method of claim 1, wherein the applying is of the composition comprising the compound of formula (I).

3. The method of claim 1, wherein the applying is a pesticidally effective amount.

4. The method of claim 3, wherein the pesticidally effective amount is an insecticidally effective amount.

5. The method of claim 4, wherein the applying is to the insect.

6. The method of claim 4, wherein the applying is to the locus of the insect.

7. The method of claim 4, wherein the applying is to the plant susceptible to attack by the insect.

8. The method of claim 1, wherein the applying is of the composition comprising the compound of formula (I) wherein the composition further comprises a suitable carrier or diluent therefor.

9. The method of claim 1, wherein $R_1$ is $C_1$-$C_6$haloalkyl and $R_{21}$ is a phenyl group which can be mono or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, $C_1$-$C_6$alkylamino, $C_1$-$C_6$haloalkylamino, $C_2$-$C_8$dialkylamino, $C_2$-$C_8$halodialkylamino, halogen, cyano, and nitro.

10. The method of claim 1, wherein $R_1$ is $C_1$-$C_6$haloalkyl and $R_{21}$ is $C_1$-$C_6$alkyl which can be mono- or polysubstituted by substituents selected from the group consisting of cyano, halogen, hydroxy, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl, said cycloalkyl itself can be substituted by substituents selected from the group consisting of halogen and $C_1$-$C_3$alkyl.

11. The method of claim 1, wherein $R_3$ is $C_1$-$C_6$alkyl.

12. The method of claim 1, wherein $R_{35}$ is $C_1$-$C_6$alkyl.

13. The method of claim 1, wherein m is 2.

14. The method of claim 1, wherein $R_1$ is $C_1$-$C_6$alkyl and $R_{21}$ is $C_1$-$C_6$alkyl which can be mono- or polysubstituted by substituents selected from the group consisting of cyano, halogen, hydroxy, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl.

15. The method of claim 1, wherein $R_5$ is hydrogen.

16. The method of claim 1, wherein $R_5$ is hydrogen, $R_3$ is $C_1$-$C_6$alkyl, and $R_{35}$ is H or $C_1$-$C_6$alkyl.

17. The method of claim 1, wherein $R_3$ is $C_1$-$C_6$alkyl, $R_{35}$ is H or $C_1$-$C_6$alkyl, and $R_{21}$ is $C_1$-$C_6$alkyl which can be mono- or polysubstituted by substituents selected from the group consisting of cyano, halogen, hydroxy, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl, said cycloalkyl itself can be substituted by substituents selected from the group consisting of halogen and $C_1$-$C_3$alkyl.

18. The method of claim 1, wherein $R_4$ is hydrogen.

19. The method of claim 1, wherein $R_4$ is hydrogen, $R_5$ is hydrogen, $R_3$ is $C_1$-$C_6$alkyl, and $R_{35}$ is H or $C_1$-$C_6$alkyl.

20. The method of claim 19, wherein $R_{35}$ is methyl.

21. The method of claim 20, wherein $R_{31}$ is hydrogen.

22. The method of claim 21, wherein $R_1$ is $C_1$-$C_6$haloalkyl and $R_{21}$ is $C_1$-$C_6$alkyl which can be mono- or polysubstituted by substituents selected from the group consisting of cyano, halogen, hydroxy, $C_1$-$C_6$alkoxy, $C_1$-$C_6$haloalkoxy, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulphanyl, $C_1$-$C_6$haloalkylsulphanyl, $C_1$-$C_6$alkylsulphinyl, $C_1$-$C_6$haloalkylsulphinyl, $C_1$-$C_6$alkylsulphonyl, $C_1$-$C_6$haloalkylsulphonyl, $C_2$-$C_6$alkylcarbonyl, $C_2$-$C_6$haloalkylcarbonyl, $C_2$-$C_6$alkoxycarbonyl, $C_2$-$C_6$haloalkoxycarbonyl, cyano, hydroxy, halogen and $C_3$-$C_6$cycloalkyl, said cycloalkyl itself can be substituted by substituents selected from the group consisting of halogen and $C_1$-$C_3$alkyl.

* * * * *